United States Patent
Borrell et al.

(10) Patent No.: US 10,590,431 B2
(45) Date of Patent: Mar. 17, 2020

(54) DROUGHT TOLERANT PLANTS PRODUCED BY MODIFICATION OF THE STAY-GREEN STGX LOCUS

(71) Applicants: The State of Queensland acting through the Department of Agriculture, Fisheries and Forestry, Brisbane (AU); The Texas A&M University System, College Station, TX (US); Grains Research and Development Corporation, Barton (AU)

(72) Inventors: Andrew Kenneth Borrell, Warwick (AU); David Robert Jordan, Warwick (AU); John Mullet, College Station, TX (US); Patricia Klein, College Station, TX (US)

(73) Assignees: The State of Queensland, Brisbane (AU); The Texas A&M University System, College Station, TX (US); Grains Research and Development Corporation, Barton (AU)

( * ) Notice: Subject to any disclaimer, the term of this patent is extended or adjusted under 35 U.S.C. 154(b) by 141 days.

(21) Appl. No.: 14/358,725

(22) PCT Filed: Nov. 16, 2012

(86) PCT No.: PCT/AU2012/001423
§ 371 (c)(1),
(2) Date: May 15, 2014

(87) PCT Pub. No.: WO2013/071366
PCT Pub. Date: May 23, 2013

(65) Prior Publication Data
US 2014/0331347 A1    Nov. 6, 2014

Related U.S. Application Data

(60) Provisional application No. 61/560,763, filed on Nov. 16, 2011.

(51) Int. Cl.
| | |
|---|---|
| *C12N 15/82* | (2006.01) |
| *A01H 1/02* | (2006.01) |
| *A01H 5/10* | (2018.01) |
| *C12Q 1/6895* | (2018.01) |
| *C12N 15/01* | (2006.01) |

(52) U.S. Cl.
CPC ........... *C12N 15/8273* (2013.01); *A01H 1/02* (2013.01); *A01H 5/10* (2013.01); *C12N 15/01* (2013.01); *C12Q 1/6895* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 7,638,681 B2 | 12/2009 | Orozco, Jr. et al. | |
| 2003/0236208 A1* | 12/2003 | Kmiec | C12N 15/102 514/44 R |
| 2009/0094717 A1 | 4/2009 | Maxim et al. | |

FOREIGN PATENT DOCUMENTS

| WO | WO 2003/008540 | 1/2003 |
|---|---|---|
| WO | WO 2004/050873 | 6/2004 |
| WO | WO 2007/011771 | 1/2007 |
| WO | WO 2012/065219 | 5/2012 |

OTHER PUBLICATIONS

Harris et al., 2007, Journal of Experimental Botany 58: 327-338.*
Shirzadian-Khorramabad et al., 2008, Agronomy Society of New Zealand Special Publication No. 13 / Grassland Research and Practice Series No. 14: 119-129.*
Sorghum bicolor protein SORBIDRAFT_03g029320, GenBank Accession No. XP_ 002456039.1, published Jul. 13, 2009.*
Srinivas et al., 2008, Theor. Appl. Genet. 117: 283-296.*
Kyndt et al., 2015, Proceedings of the Natural Academy of Sciences USA 112: 5844-5849.*
Conley et al., 2001, New Phytologist 151: 407-412.*
Kohli et al., 2006, Plant Signaling & Behavior 1: 185-195.*
Borrell et al., 2015, Identifying the Function of Sorghum's Drought Tolerance Stay-Green QTL, In: Plant and Animal Genome XXIII Conference, published Jul. 6, 2015, at http://era.daf.qld.gov.au/id/eprint/4728/, accessed on Feb. 9, 2018.*
Křeček et al., 2009, Genome Biology 10: 249, pp. 1-11.*
Lee et al., 2006, The Plant Cell 18: 1604-1616.*
Mace and Jordan, 2010, Theor. Appl. Genet. 121: 1339-1356.*
Shen et al., 2010, FEBS Journal 277: 2954-2969.*
Partial Supplementary European Search Report for PCT/AU2012001423, dated Mar. 4, 2015.
Borrell etas., "Stay-green alleles individually enhance grain yield in sorghum under drought by modifying canopy development and water uptake patterns," *New Phytologist* 203:817-830, 2014.
Andrade et al., "Kernel number prediction in maize under nitrogen or water stress," *Crop Sci.*, 42:1173-1179, 2002.
Borrell et al., "Does maintaining green leaf area in sorghum improve yield under drought? I. Leaf growth and senescence," *Crop Sci.*, 40:1026-1037, 2000.
Borrell et al., "Does maintaining green leaf area in sorghum improve yield under drought? II. Dry matter production and yield," *Crop Sci.*, 40:1037-1048, 2000.

(Continued)

*Primary Examiner* — Bratislav Stankovic
(74) *Attorney, Agent, or Firm* — Dentons US LLP

(57) ABSTRACT

The present disclosure teaches the generation of drought tolerant plants. The present disclosure enables manipulation of a phenotypic characteristic referred to as "stay-green" to facilitate drought adaptation in plants by recombinant, mutagenic and/or breeding and selection methods. Plant management practice systems to increase crop yield and harvest efficiency in water-limited environments are also taught herein.

3 Claims, 59 Drawing Sheets

(56) References Cited

OTHER PUBLICATIONS

Borrell et al., "Nitrogen dynamics and the physiological basis of stay-green in sorghum," *Crop Sci.*, 40:1295-1307, 2000.
Borrell et al., "Discovering stay-green drought tolerance genes in sorghum: a multidisciplinary approach," in Fisher, T., et al. eds. New Directions for a Diverse Planet: Proceedings of the 4th International Crop Science Congress. The Regional Institute Ltd., Brisbane, Australia, September-October, pp. 1-6, 2004.
Buchanan et al., "*Sorghum bicolor's* transcriptome response to dehydration, high salinity and ABA," *Plant Mol Biol.*, 58:699-720, 2005.
Buell et al., "Sequence, annotation, and analysis of synteny between rice chromosome 3 and diverged grass species," *Genome Research*, 15(9):1284-1291, 2005.
Christopher et al., "Developmental and physiological traits associated with high yield and stay-green phenotype in wheat," *Aust. J. Agric. Res.*, 59:354-364, 2008.
Crasta et al., "Mapping of post-flowering drought resistance traits in grain sorghum: association between QTLs influencing premature senescence and maturity," *Molecular and General Genetics*, 262(3):579-588, 1999.
Domagalska et al., "Signal integration in the control of shoot branching," *Nat Rev Mol Cell Biol.*, 12(4):211-221, 2011.
Forestan et al., "ZmPIN1-Mediated auxin transport is related to cellular differentiation during maize embryogenesis and endosperm development," *Plant Physiology*, 152:1373-1390, 2010.
Friml et al., "Auxin transport—shaping the plant," *Current Opinion in Plant Biology*, 6(1):7-12, 2003.
Galyuon et at., "Functioning under drought stress of stay-green sorghum developed by marker-assisted selection," Comparative Biochemistry and Physiology Part A Molecular & Integrative Physiology, 141:S314, Annual Meeting of the Society for Experimental Biology, 2005 (abstract).
Hammer et al., "On the extent of genetic variation for transpiration efficiency in sorghum," *Aust. J. Agric. Res.*, 48:649-655, 1997.
Hammer, "Pathways to prosperity: breaking the yield barrier in sorghum," *Agric Sci.*,19:16-22, 2006.
Harris et al., "Sorghum stay-green QTL individually reduce post-flowering drought-induced leaf senescence," *J. Exp. Bot.*, 58:327-338, 2007.
Hausmann et al., "QTL mapping of stay-green in two sorghum recombinant inbred populations," *Theoretical and Applied Genetics*, 106:133-142, 2002.
Henderson et al., "Correlation between carbon isotope discrimination and transpiration efficiency in lines of the C4 species *Sorghum bicolour* in the glasshouse and the field," *Aust. J. Plant Physiol.*, 25:111-123, 1998.
Henzell et al., "Research on drought resistance in grain sorghum in Australia," *International Sorghum and Millets Newsletter*, 38:1-9, 1997.
Jiao et al., "Regulation of OsSPL14 by OsmiR156 defines ideal plant architecture in rice," *Nature Genetics*, 42:541-544, 2010.
Kashiwagi et al., "Locus pr15 improves lodging resistance of rice by delaying senescence and increasing carbohydrate reaccumulation," *Plant Physiol Biochem*, 44:152-157, 2006.
Kassahun et al., "Stay-green expression in early generation sorghum [*Sorghum bicolor* (L.) Moench] QTL introgression lines," *Euphytica*, 172:351-362, 2010.
Kebede et al., "Quantitative trait loci influencing drought tolerance in grain sorghum (*Sorghum bicolor* L. Moench)," *Theor Appl Genet.*, 103(2):266-276, 2001.
Luo et al., "Control of tiller growth of rice by OsSPL14 and strigolactones, which work in two independent pathways," *Plant Cell Physiol.*, 53(10):1793-1801, 2012.
Mace et al., "A consensus genetic map of sorghum that integrates multiple component maps and high-throughput diversity array technology (DArT) markers," *BMC Plant Biology*, 9:13, 2009.
Manschadi et al., "The role of root architectural traits in adaptation of wheat to water-limited environments," *Funct. Plant Biol.*, 33(9):823-837, 2006.
Menz et al., "A high-density genetic map of *Sorghum bicolor* (L.) Moench based on 2926 AFLP, RFLP and SSR markers," *Plant Molecular Biology*, 48:483-499, 2002.
Miura et al., "OsSPL14 promotes panicle branching and higher grain productivity in rice," *Nature Genetics*, 42:545-549, 2010.
Mortlock et al., "Genotype and water limitation effects on transpiration efficiency in sorghum," *J. Crop. Prod.*, 2:265-286, 1999.
Mravec et al., "Subcellular homeostasis of phytohormone auxin is mediated by the ER-localized PIN5 transporter," *Nature*, 459:1136-1140, 2009.
Passioura, "Grain yield, harvest index, and water use of wheat," *J Aust Inst Agri Sci*, 43:117-121, 1977.
Rashotte et al., "Genetic and chemical reductions in protein phosphatase activity alter auxin transport, gravity response, and lateral root growth," *Plant Cell*, 13:1683-1697, 2001.
Reddy et al., "Evaluation of sorghum genotypes for the stay-green trait and grain yield," *SAT eJournal*, 3:1-4, 2007.
Rosenow et al., "Drought tolerant sorghum and cotton germplasm," *Agric. Water Manag.*, 7:207-222, 1983.
Sadras et al., "Physiological basis of the response of harvest index to the fraction of water transpired after anthesis. a simple model to estimate harvest index for determinate species," *Field Crops Research*, 26:227-239, 1991.
Shen et al., "Expression profile of PIN, AUX/LAX and PGP auxin transporter gene families in *Sorghum bicolor* under phytohormone and abiotic stress," *FEBS Journal*, 277(14):2954-2969, 2010.
Spano et al., "Physiological characterization of 'stay green' mutants in durum wheat," *J Exp Bot.*, 54:1415-1420, 2003.
Srinivas et al., "Exploration and mapping of microsatellite markers from subtracted drought stress ESTs in *Sorghum bicolor* (L.) Moench," *Theor Appl. Genet*, 118:703-717, 2009.
Subudhi et al., "Quantitative trait loci for the stay green trait in sorghum (*Sorghum bicolor* L. Moench): consistency across genetic backgrounds and environments," *Theor. Appl. Genet.*, 101:733-741, 2000.
Tao et al., "Identification of genomic regions associated with stay green in sorghum by testing RILs in multiple environments," *Theor Appl Genet.*, 100:1225-1232, 2000.
Turner, "Agronomic options for improving rainfall-use efficiency of crops in dryland farming systems," *J Exp Bot.*, 55:2413-2425, 2004.
Van Oosterom et al., "Determination of grain number in sorghum," *Field Crops Res.*, 108(3):259-268, 2008.
Van Oosterom et al., "Functional dynamics of the nitrogen balance of sorghum: I. N demand of vegetative plant parts," *Field Crops Res.*, 115(1):19-28, 2010.
Van Oosterom et al., "Functional dynamics of the nitrogen balance of sorghum: II. Grain filing period," *Field Crops Res.*, 115(1):29-38, 2010.
Wang et al., "Expression of PIN Genes in Rice (*Oryza sativa* L.): Tissue specificity and regulation by hormones," *Molecular Plant*, 2(4):823-831, 2009.
Xin et al., "Genetic diversity of transpiration efficiency in sorghum," *Field Crops Res.*, 111(1):74-80, 2009.
Xu et al., "Molecular mapping of QTLs conferring stay-green in grain sorghum (*Sorghum bicolor* L. Moench)," *Genome*, 43(3):461-469, 2000.
Zheng et al., "QTL mapping of maize (*Zea mays*) stay-green traits and their relationship to yield," *Plant Breed*, 128:54-62, 2009.
International Search Report for PCT/AU2012/001423, dated Mar. 5, 2013.
Benkova et al., "Local, Efflux-Dependent Auxin Gradients as a Common Module for Plant Organ Formation," *Cell* 115:591-602, 2003.
Carraro et al., "ZmPIN1a and ZmPIN1b Encode Two Novel Putative Candidates for Polar Auxin Transport and Plant Architecture Determination of Maize," *Plant Physiology* 142:254-264, 2006.
Garud etal., "Usefulness of Non-senescent Parents for Charcoal Rot Resistance Breeding in Sorghum," *Sorghum and Millets Newsletter* 43:63-65, 2002.

(56) References Cited

OTHER PUBLICATIONS

Jordan et al., "Prediction of hybrid performance in grain sorghum using RFLP markers," *Theor. Appl. Genet.* 106:559-567, 2003.

Leyser, "Dynamic Integration of Auxin Transport and Signalling," *Current Biology* 16:R424-R433, 2001.

Reddy et al., "Molecular mapping of genomic regions harboring QTLs for stalk rot resistance in sorghum," *Euphytica* 159:191-198, 2008.

Reinhardt et al., "Auxin Regulates the Initiation and Radial Position of Plant Lateral Organs," *The Plant Cell* 12:507-518, 2000.

Spano et al., "Physiological characterization of 'stay green' mutants in durum wheat," *Journal of Experimental Botany* 54(386):1415-1420, 2003.

Springer, "Shaping a better rice plant," *Nature Genetics* 46(6):475-476, 2010.

Tenkouano et al., "Genetics of nonsenescence and charcoal rot resistance in sorghum," *Theor. Appl. Genet.* 85:644-648, 1993.

Van Oosterom et al., "Determination of grain number in sorghum," *Field Crops Research* 108:259-268, 2008.

Innan et al., "Microsatellite Polymorphism in Natural Populations of the Wild Plant *Arabidopsis thaliana*," *Genetics* 146:1441-1452, 1997.

Bedo et al., "Precision-mapping and statistical validation of quantitative trait loci by machine learning," *BMC Genetics* 9:35, 2008.

Billou et al., "The PIN auxin efflux facilitator network controls growth and patterning in *Arabidopsis* roots," *Nature* 433:39-44, 2005.

Feltus et al., "Alignment of genetic maps and QTLs between inter- and intra-specific sorghum populations," *Theor. Appl. Genet.* 112:1295-1305, 2006.

Guo et al., "Protein tolerance to random amino acid change," *PNAS* 101(25):9205-9210, 2004.

Krecek et al., "The PIN-Formed (PIN) protein family of auxin transporters," *Genome Biology* 10:249.1-249.11, 2009.

Latha et al., "Development of transgenic pearl millet (*Pennisetum glaucum* (L.) R. Br.) plants resistant to downy mildew," *Plant Cell Rep.* 25:927-935, 2006.

Sharp et al., "Root growth maintenance during water deficis: physiology to functional genomics," *Journal of Experimental Botany* 55(407):2343-2351, 2004.

Xu et al., "A *PIN1* Family Gene, *OsPIN1*, involved in Auxin-dependent Adventitious Root Emergence and Tillering in Rice," *Plant Cell Physiol.* 46(10):1674-1681, 2005.

\* cited by examiner

| | Tx7000 | NiL10877-5 | NiL10975-4 | NiL10604-4 | 6078-1 | NiL10382-1 | NiL10604-2 | NiL10604-5 | NiL10564-1 | NiL10568-2 | NiL10620-4 | NiL10704-1 | NiL10564-2 | NiL10620-2 | NiL10703-2 | NiL10822-2 | NiL10762-4 | NiL10896-4 | NiL10580-1 |
|---|---|---|---|---|---|---|---|---|---|---|---|---|---|---|---|---|---|---|---|
| txa2506 | TT | TT | TT | TT | TT | TT | BB | BB | BB | BB | BB | TT | BB | BB | TT | BB | BB | BB | TT |
| txa2179 | TT | TT | TT | BB | BB | BB | BB | BB | BB | BB | BB | BB | BB | BB | BB | BB | BB | BB | TT |
| txp114 | TT | TT | TT | BB | BB | BB | BB | BB | BB | BB | BB | BB | BB | BB | BB | BB | BB | BB | BB |
| CORN031 | TT | TT | BB | BB | BB | BB | BB | BB | BB | BB | BB | BB | BB | BB | BB | BB | BB | BB | TT |
| TS196 | TT | TT | BB | BB | BB | BB | BB | BB | BB | BB | BB | BB | BB | BB | BB | BB | BB | BB | TT |
| txp196 | TT | TT | BB | BB | BB | BB | BB | BB | BB | BB | BB | BB | BB | BB | TT | BB | BB | BB | TT |
| txa2961 | TT | TT | BB | BB | BB | BB | BB | BB | BB | BB | BB | BB | BB | BB | BB | BB | BB | BB | TT |
| BH245191 | TT | BB | BB | BB | BB | BB | BB | BB | BB | BB | BB | BB | BB | BB | BB | TT | TT | TT | TT |
| BG411222 | TT | BB | BB | BB | BB | BB | BB | BB | BB | BB | BB | BB | BB | BB | BB | TT | TT | TT | TT |
| txp439 | TT | BB | BB | BB | BB | BB | BB | BB | BB | BB | x | BB | x | BB | TT | TT | TT | TT | TT |
| txp440 | TT | BB | BB | BB | BB | BB | BB | BB | BB | BB | x | BB | x | x | TT | TT | TT | TT | TT |
| txp542 | TT | BB | BB | BB | BB | BB | BB | BB | TT | BB | x | BB | x | TT | TT | TT | TT | TT | TT |
| txp563 | TT | BB | BB | BB | BB | BB | BB | BB | BB | BB | x | x | x | x | TT | x | TT | TT | TT | TT |
| txa3676 | TT | BB | BB | BB | BB | BB | BB | BB | BB | TT | TT | TT | TT | TT | BB | TT | TT | TT | TT |
| txa2986 | TT | BB | BB | BB | BB | BB | BB | BB | BB | TT | TT | TT | TT | TT | BB | TT | TT | TT | TT |
| txp581 | TT | BB | BB | BB | BB | BB | BB | BB | TT | TT | TT | TT | TT | TT | TT | TT | TT | TT | TT |
| txp587 | TT | BB | BB | BB | BB | BB | BB | BB | TT | TT | TT | TT | TT | TT | TT | TT | TT | TT | TT |
| txp446 | TT | BB | BB | BB | BB | BB | BB | BB | BB | TT | TT | TT | TT | TT | TT | TT | TT | TT | TT |
| txp442 | TT | BB | BB | BB | BB | BB | BB | BB | BB | TT | TT | TT | TT | TT | TT | TT | TT | TT | TT |
| Sb03QGM106 | TT | BB | BB | BB | BB | BB | BB | BB | TT | TT | TT | TT | TT | TT | TT | TT | TT | TT | TT |
| Sb03QGM109 | TT | BB | BB | BB | BB | BB | BB | BB | TT | TT | TT | TT | TT | TT | TT | TT | TT | TT | TT |
| Sb03QGM110 | TT | BB | BB | BB | BB | BB | BB | BB | TT | TT | TT | TT | TT | TT | TT | TT | TT | TT | TT |
| Sb03QGM121 | TT | BB | BB | BB | BB | BB | BB | BB | TT | TT | TT | TT | TT | TT | TT | TT | TT | TT | TT |
| txp580 | TT | BB | BB | BB | BB | BB | BB | BB | TT | TT | TT | TT | TT | TT | TT | TT | TT | TT | TT |
| txp564 | TT | BB | BB | BB | BB | BB | BB | BB | TT | TT | TT | TT | TT | TT | TT | TT | TT | TT | TT |
| txp565 | TT | BB | BB | BB | BB | BB | BB | BB | TT | TT | TT | TT | TT | TT | TT | TT | TT | TT | TT |
| txa3390 | TT | BB | BB | TT | BB | BB | TT | TT | TT | TT | TT | TT | TT | TT | TT | TT | TT | TT | TT |
| txp572 | TT | BB | BB | TT | BB | BB | TT | TT | TT | TT | TT | TT | TT | TT | TT | TT | TT | TT | TT |
| txp583 | TT | BB | BB | TT | BB | BB | BT | BT | TT | TT | TT | TT | TT | TT | TT | TT | TT | TT | TT |
| Sb03QGM116 | TT | BB | BB | TT | BB | BB | TT | TT | TT | TT | TT | TT | TT | TT | TT | TT | TT | TT | TT |
| txp447 | TT | BB | BB | TT | BB | BB | TT | TT | TT | TT | TT | TT | TT | TT | TT | TT | TT | TT | TT |
| txp38 | TT | BB | BB | TT | BB | BB | TT | TT | TT | TT | TT | TT | TT | TT | TT | TT | TT | TT | TT |
| txa3008 | TT | TT | TT | TT | TT | TT | TT | TT | TT | TT | TT | TT | TT | TT | TT | TT | TT | TT | TT |
| txa422 | TT | TT | TT | TT | TT | TT | TT | TT | TT | TT | TT | TT | TT | TT | TT | TT | TT | TT | TT |

Figure 4

| | Tx7000 | NIL10709-5 | 6078-1 | NIL10604-5 | NIL10568-2 |
|---|---|---|---|---|---|
| txa2506 | TT | TT | TT | BB | BB |
| txa2179 | TT | TT | BB | BB | BB |
| txp114 | TT | TT | BB | BB | BB |
| CORN031 | TT | TT | BB | BB | BB |
| TS196 | TT | TT | BB | BB | BB |
| txp196 | TT | TT | BB | BB | BB |
| txa2961 | TT | TT | BB | BB | BB |
| BH245191 | TT | TT | BB | BB | BB |
| BG411222 | TT | TT | BB | BB | BB |
| txp439 | TT | TT | BB | BB | BB |
| txp440 | TT | TT | BB | BB | BB |
| txp542 | TT | TT | BB | BB | BB |
| txp563 | TT | TT | BB | BB | x |
| txa3676 | TT | TT | BB | BB | TT |
| txa2986 | TT | TT | BB | BB | TT |
| txp581 | TT | TT | BB | BB | TT |
| txp587 | TT | TT | BB | BB | TT |
| txp446 | TT | TT | BB | BB | TT |
| txp442 | TT | TT | BB | BB | TT |
| Sb03QGM106 | TT | x | BB | BB | TT |
| Sb03QGM109 | TT | BB | BB | BB | TT |
| Sb03QGM110 | TT | BB | BB | BB | TT |
| Sb03QGM121 | TT | BT | BB | BB | TT |
| txp580 | TT | BT | BB | BB | TT |
| txp564 | TT | x | BB | BB | TT |
| txp565 | TT | x | BB | BB | TT |
| txa3390 | TT | BB | BB | TT | TT |
| txp572 | TT | x | BB | TT | TT |
| txp583 | TT | x | BB | BT | TT |
| Sb03QGM116 | TT | BT | BB | TT | TT |
| txp447 | TT | x | BB | TT | TT |
| txp38 | TT | BB | BB | TT | TT |
| txa3008 | TT | TT | TT | TT | TT |
| txa422 | TT | TT | TT | TT | TT |

|  | NIL10604-1-502-11-2 | NIL10604-1-502-142-1 | NIL10604-1-110-2 | NIL10604-1-157-5 | NIL10604-1-359-3 | NIL10604-1-318-1 | NIL10604-1-8-1 | NIL10604-1-222-1 |
|---|---|---|---|---|---|---|---|---|
| txa2506 | x | x | x | x | x | x | x | x |
| txa2179 | x | x | TT | TT | TT | TT | TT | TT |
| txp114 | BB | BB | TT | TT | TT | TT | TT | TT |
| CORN031 | x | x | TT | TT | TT | TT | TT | TT |
| TS196 | x | x | TT | TT | TT | TT | TT | TT |
| txp196 | TT | TT | TT | TT | TT | TT | TT | TT |
| txa2961 | TT | TT | TT | TT | TT | TT | TT | TT |
| BH245191 | TT | TT | TT | TT | TT | TT | TT | TT |
| BG411222 | TT | TT | TT | TT | TT | TT | TT | TT |
| txp439 | TT | TT | TT | TT | TT | TT | TT | TT |
| txp440 | TT | TT | TT | TT | TT | TT | TT | TT |
| txp542 | TT | TT | TT | TT | TT | TT | TT | BB |
| txp563 | TT | TT | TT | TT | TT | TT | BB | BB |
| txa3676 | TT | TT | TT | TT | x | x | BB | BB |
| txa2986 | TT | TT | TT | TT | x | x | BB | BB |
| txp581 | TT | TT | TT | TT | BB | BB | BB | BB |
| txp587 | TT | TT | TT | BB | BB | BB | BB | BB |
| txp446 | TT | TT | BB | BB | BB | BB | BB | BB |
| txp442 | TT | BT | BB | BB | BB | BT | BB | BB |
| Sb03QGM106 | TT | BB | BB | BB | BB | BB | BB | BB |
| Sb03QGM109 | BB | BB | BB | BB | BB | BB | BB | BB |
| Sb03QGM110 | BB | BB | BB | BB | BB | BB | BB | BB |
| Sb03QGM121 | BB | BB | BB | BB | BB | BB | BB | BB |
| txp580 | BB | BB | BB | BB | BB | BB | BB | BB |
| txp564 | BB | BB | BB | BB | BB | BB | BB | BB |
| txp565 | BB | BB | BB | BB | BB | BB | BB | BB |
| txa3390 | x | x | x | x | x | x | x | x |
| txp572 | TT | TT | TT | TT | TT | TT | TT | TT |
| txp583 | TT | TT | TT | TT | TT | TT | TT | TT |
| Sb03QGM116 | TT | TT | TT | TT | TT | TT | TT | TT |
| txp447 | TT | TT | TT | TT | TT | TT | TT | TT |
| txp38 | TT | TT | TT | TT | TT | TT | TT | TT |

Figure 12

| | Tx7000 | NIL10709-5 | 6078-1 | NIL10604-5 | NIL10568-2 |
|---|---|---|---|---|---|
| txa2506 | TT | TT | TT | BB | BB |
| txa2179 | TT | TT | BB | BB | BB |
| txp114 | TT | TT | BB | BB | BB |
| CORN031 | TT | TT | BB | BB | BB |
| TS196 | TT | TT | BB | BB | BB |
| txp196 | TT | TT | BB | BB | BB |
| txa2961 | TT | TT | BB | BB | BB |
| BH245191 | TT | TT | BB | BB | BB |
| BG411222 | TT | TT | BB | BB | BB |
| txp439 | TT | TT | BB | BB | BB |
| txp440 | TT | TT | BB | BB | BB |
| txp542 | TT | TT | BB | BB | BB |
| txp563 | TT | TT | BB | BB | x |
| txa3676 | TT | TT | BB | BB | TT |
| txa2986 | TT | TT | BB | BB | TT |
| txp581 | TT | TT | BB | BB | TT |
| txp587 | TT | TT | BB | BB | TT |
| txp446 | TT | TT | BB | BB | TT |
| txp442 | TT | TT | BB | BB | TT |
| Sb03QGM106 | TT | x | BB | BB | TT |
| Sb03QGM109 | TT | BB | BB | BB | TT |
| Sb03QGM110 | TT | BB | BB | BB | TT |
| Sb03QGM121 | TT | BT | BB | BB | TT |
| txp580 | TT | BT | BB | BB | TT |
| txp564 | TT | x | BB | BB | TT |
| txp565 | TT | x | BB | BB | TT |
| txa3390 | TT | BB | BB | TT | TT |
| txp572 | TT | x | BB | TT | TT |
| txp583 | TT | x | BB | BT | TT |
| Sb03QGM116 | TT | BT | BB | TT | TT |
| txp447 | TT | x | BB | TT | TT |
| txp38 | TT | BB | BB | TT | TT |
| txa3008 | TT | TT | TT | TT | TT |
| txa422 | TT | TT | TT | TT | TT |

Figure 15

| | Tx7000 | NIL10604-1-157-5 | NIL10604-1-318-1 | NIL10604-1-222-1 | 6078-1 |
|---|---|---|---|---|---|
| txa2506 | TT | x | x | x | TT |
| txa2179 | TT | TT | TT | TT | BB |
| txp114 | TT | TT | TT | TT | BB |
| CORN031 | TT | TT | TT | TT | BB |
| TS196 | TT | TT | TT | TT | BB |
| txp196 | TT | TT | TT | TT | BB |
| txa2961 | TT | TT | TT | TT | BB |
| BH245191 | TT | TT | TT | TT | BB |
| BG411222 | TT | TT | TT | TT | BB |
| txp439 | TT | TT | TT | TT | BB |
| txp440 | TT | TT | TT | TT | BB |
| txp542 | TT | TT | TT | BB | BB |
| txp563 | TT | TT | TT | BB | BB |
| txa3678 | TT | TT | x | BB | BB |
| txa2986 | TT | TT | x | BB | BB |
| txp581 | TT | TT | BB | BB | BB |
| txp587 | TT | BB | BB | BB | BB |
| txp446 | TT | BB | BB | BB | BB |
| txp442 | TT | BB | BT | BB | BB |
| Sb03QGM106 | TT | BB | BB | BB | BB |
| Sb03QGM109 | TT | BB | BB | BB | BB |
| Sb03QGM110 | TT | BB | BB | BB | BB |
| Sb03QGM121 | TT | BB | BB | BB | BB |
| txp580 | TT | BB | BB | BB | BB |
| txp564 | TT | BB | BB | BB | BB |
| txp565 | TT | BB | BB | BB | BB |
| txa3390 | TT | x | x | x | BB |
| txp572 | TT | TT | TT | TT | BB |
| txp583 | TT | TT | TT | TT | BB |
| Sb03QGM116 | TT | TT | TT | TT | BB |
| txp447 | TT | TT | TT | TT | BB |
| txp38 | TT | TT | TT | TT | BB |

Figure 22

| markers | Culms per plant (Field 2004-06) Breakpoint analysis | Culms per plant (ROS 2006) Breakpoint analysis | Total tiller number (Igloo 2008 L11 harvest) Marker x trait analysis | Tiller biomass (Igloo 2008 L11 harvest) Marker x trait analysis | Tiller green leaf mass (Igloo 2008 L11 harvest) Marker x trait analysis | Tiller stem mass (Igloo 2008 L11 harvest) Marker x trait analysis | Tiller green leaf area (Igloo 2008 L11 harvest) Marker x trait analysis | T2 presence (Igloo 2008) Breakpoint analysis | Culms per plant (Igloo 2010) Breakpoint analysis | Leaf size distribution (ROS 2006) breakpoint analysis | L9 area (Igloo 2008) Marker x trait analysis | L10 area (Igloo 2008) Marker x trait analysis | L11 area (Igloo 2008) Marker x trait analysis | L9 length (Igloo 2010) breakpoint analysis | L10 length (Igloo 2010) breakpoint analysis |
|---|---|---|---|---|---|---|---|---|---|---|---|---|---|---|---|
| | | | | low-tillering gene | | | | | | | | small-leaf gene | | | |
| txa2506 | | | | | | | | | | | | | | | |
| txa2179 | | | | | | | | | | | | | | | |
| txp114 | | | | | | | | | | | | | | | |
| CORN031 | | | | | | | | | | | | | | | |
| TS196 | | | | | | | | | | | | | | | |
| txp196 | | | | | | | | | | | | | | | |
| txa2961 | | | | | | | | | | | | | | | |
| BH245191 | | | | | | | | | | | | | | | |
| BG411222 | | | | | | | | | | | | | | | |
| txp439 | | | | | | | | | | | | | | | |
| txp440 | | | | | | | | | | | | | | | |
| txp542 | | | | | | | | | | ▓ | | | | ▓ | ▓ |
| txp563 | ▓ | | | | | | | | | | ▓ | ▓ | ▓ | | |
| txa3676 | ▓ | | | | | | | | | | ▓ | ▓ | ▓ | | |
| txa2988 | ▓ | | | | | | | | | | ▓ | ▓ | ▓ | | |
| txp581 | | | | | | | | | | | ▓ | ▓ | ▓ | | |
| txp587 | | | | | | | | | | | ▓ | ▓ | ▓ | | |
| txp446 | | | | | | | | | | | ▓ | ▓ | ▓ | | |
| txp442 | | | | | | | | | | | ▓ | ▓ | ▓ | | |
| Sb03QGM106 | | ▓ | | | | | | | | | ▓ | | | | |
| Sb03QGM109 | | | | | | | | | | | | | | | |
| Sb03QGM110 | | | | | | | | | | | | | | | |
| Sb03QGM121 | | | | | | | | | | | | | | | |
| txp580 | | | | | | | | | | | | | | | |
| txp564 | | | | | | | | | | | | | | | |
| txp565 | | | | | | | | | | | | | | | |
| txa3390 | | | | | | | | | | | | | | | |
| txp572 | | | | | | | | | | | | | | | |
| txp583 | | | | | | | | | | | | | | | |
| Sb03QGM116 | | | | | | | | | | | | | | | |
| txp447 | | | | | | | | | | | | | | | |
| txp38 | | | | | | | | | | | | | | | |
| txa3008 | | | | | | | | | | | | | | | |
| txa422 | | | | | | | | | | | | | | | |

Figure 23

Increased water availability at anthesis

A

Increased water accessibility during grain filling

B

| | Tx7000 | NIL10709-5 | 6078-1 | NIL10604-5 | NIL10568-2 |
|---|---|---|---|---|---|
| txa2506 | TT | TT | TT | BB | BB |
| txa2179 | TT | TT | BB | BB | BB |
| txp114 | TT | TT | BB | BB | BB |
| CORN031 | TT | TT | BB | BB | BB |
| TS196 | TT | TT | BB | BB | BB |
| txp196 | TT | TT | BB | BB | BB |
| txa2961 | TT | TT | BB | BB | BB |
| BH245191 | TT | TT | BB | BB | BB |
| BG411222 | TT | TT | BB | BB | BB |
| txp439 | TT | TT | BB | BB | BB |
| txp440 | TT | TT | BB | BB | BB |
| txp542 | TT | TT | BB | BB | BB |
| txp563 | TT | TT | BB | BB | x |
| txa3676 | TT | TT | BB | BB | TT |
| txa2986 | TT | TT | BB | BB | TT |
| txp581 | TT | TT | BB | BB | TT |
| txp587 | TT | TT | BB | BB | TT |
| txp446 | TT | TT | BB | BB | TT |
| txp442 | TT | TT | BB | BB | TT |
| Sb03QGM106 | TT | x | BB | BB | TT |
| Sb03QGM109 | TT | BB | BB | BB | TT |
| Sb03QGM110 | TT | BB | BB | BB | TT |
| Sb03QGM121 | TT | BT | BB | BB | TT |
| txp580 | TT | BT | BB | BB | TT |
| txp564 | TT | x | BB | BB | TT |
| txp565 | TT | x | BB | BB | TT |
| txa3390 | TT | BB | BB | TT | TT |
| txp572 | TT | x | BB | TT | TT |
| txp583 | TT | x | BB | BT | TT |
| Sb03QGM116 | TT | BT | BB | TT | TT |
| txp447 | TT | x | BB | TT | TT |
| txp38 | TT | BB | BB | TT | TT |
| txa3008 | TT | TT | TT | TT | TT |
| txa422 | TT | TT | TT | TT | TT |

Figure 46

DROUGHT TOLERANT PLANTS PRODUCED BY MODIFICATION OF THE STAY-GREEN STGX LOCUS

FILING DATA

This application is a 371 National Stage Entry of PCT/AU2012/01423, filed Nov. 16, 2012, which claims priority from U.S. Provisional Patent Application No. 61/560,763, filed on 16 Nov. 2011 entitled "Drought tolerant plants", the entire contents of which, are incorporated herein by reference.

FIELD

The present disclosure teaches the generation of drought tolerant plants. The present disclosure enables manipulation of a phenotypic characteristic referred to as "stay-green" to facilitate drought adaptation in plants by recombinant, mutagenic, breeding and/or selection methods. Plant management practice systems to increase crop yield and harvest efficiency in water-limited environments are also taught herein.

BACKGROUND

Bibliographic details of the publications referred to by author in this specification are collected alphabetically at the end of the description.

Reference to any prior art in this specification is not, and should not be taken as, an acknowledgment or any form of suggestion that this prior art forms part of the common general knowledge in any country.

An increasing human population necessitates improvements in crop productivity. This has been a major goal for plant breeders and geneticists. One approach to improving crop productivity involves the selection of plant traits which facilitate higher grain yield and stability (Springer (2010) *Nature Genetics* 42:475-476). This approach has been referred to as the "Green Revolution". Other approaches include the development of ideal plant architectures which have, for example, led to the identification of a quantitative trait locus (QTL) which encodes squamosa promoter binding protein-like 14 (OsSPL14) in rice and which facilitates improved rice yield (Jiao et al. (2010) *Nature Genetics* 42:541-544; Miura et al. (2010) *Nature Genetics* 42:545-549).

Drought is the single most important constraint to cereal production worldwide. Sorghum is a repository of drought resistance mechanisms, which include $C_4$ photosynthesis, deep roots and thick leaf wax which enable growth in hot and dry environments. Drought tolerance makes sorghum especially important in dry regions such as sub-Saharan Africa, western-central India, north-eastern Australia, and the southern plains of the US. With increasing pressure on the availability of scarce water resources, the identification of traits associated with grain yield under drought conditions becomes more important.

The drought adaptation mechanism identified in sorghum which results in the retention of green leaves for longer periods during grain filling under drought is known as 'stay-green'. Stay-green has been associated with high grain yield under post-anthesis drought in sorghum (Borrell et al. (200b) *Crop Sci.* 40:1037-1048; Kassahun et al. (2010) *Euphytica* 72:351-362), wheat (*Triticum aestivum* L.) [Spano et al. (2003) *J. Exp. Bot.* 54:1415-1420; Christopher et al. (2008) *Aust. J. Agric. Res.* 59:354-364], rice (*Oryza sativa* L.) [Kashiwagi et al. (2006) *Plant Physiology and Biochemistry* 44:152-157] and maize (*Zea mays* L.) [Zheng et al. (2009) *Plant Breed* 128:54-62]. In addition, it may indirectly affect grain yield under drought by improving charcoal rot (*Macrophomina phaseolina* [Tassi] Goid.) resistance (Tenkouano et al. (1993) *Theor. Appl. Genet.* 85:644-648; Garud et al. (2002) *Int. Sorghum and Millets Newsl.* 43:63-65). This reduces lodging (Reddy et al. (2008) *Euphytica* 159:191-198), allowing plant breeders to exploit the positive association between plant height and grain yield (Jordan et al. (2003) *Theor. Appl. Genet.* 106:559-567). Stay-green has been an important selection criterion for sorghum breeding programs targeting drought adaptation in both the US (Rosenow et al. (1983) *Agric. Water Manag.* 7:207-222) and Australia (Henzell et al. (1997) *Australia Int. Sorghum and Millets Newsl.* 38:1-9).

A considerable body of physiological evidence is mounting in support of this trait (Borrell et al. (2000a) *Crop Sci.* 40:1026-1037; Borrell and Hammer (2000) *Crop Sci.* 40:1295-1307; Harris et al. (2007) *J. Exp. Bot.* 58:327-338; Christopher et al. (2008) supra; Van Oosterom et al. (2010a) *Field Crops Res.* 115:19-28 and Van Oosterom et al. (2010b) *Field Crops Res.* 115:29-38). Although this drought resistance mechanism has been utilized by sorghum breeders in the US and Australia for over 25 years, and the broad physiological basis of the trait is becoming better understood, the causal mechanisms and the genetic loci involved have hitherto been unknown.

Under water limiting conditions, grain yield is a function of transpiration (T), transpiration efficiency (TE), and harvest index (HI) [Passioura (1977) *J. Aust. Inst. Agric. Sci.* 43:117-120]. Within this framework, grain yield is linked to post-anthesis T (Turner (2004) *J. Exp. Bot.* 55:2413-2425; Manschadi et al. (2006) *Funct. Plant. Biol.* 33:823-837), because HI increases with the fraction of total crop T used after anthesis (Passioura, (1977) supra; Sadras and Connor (1991) *Field Crops Res.* 26:227-239; Hammer (2006) *Agric. Sci.* 19:16-22). Increased post-anthesis T is associated with reduced drought stress around anthesis, which can positively affect crop growth rate at anthesis of cereals and hence grain number (Andrade et al. (2002) *Crop Sci.* 42:1173-1179; Van Oosterom and Hammer (2008) *Field Crops Res.* 108:259-268). If the total amount of available water is limited, post-anthesis T can be increased by restricting pre-anthesis T. This can be achieved by restricting canopy size, either genetically or through crop management. However, a smaller canopy will only reduce total T if its TE is not compromised. Significant genotypic differences in TE have been reported for sorghum (Hammer et al. (1997) *Aust. J. Agric. Res.* 48:649-655; Henderson et al. (1998) *Aust. J. Plant Physiol.* 25:111-123; Mortlock and Hammer (1999) *J. Crop Prod.* 2:265-286; Xin et al. (2009) *Field Crops Res.* 111:74-80). Alternatively, post-anthesis water use can be increased by increasing the total amount of water accessed by the crop, either through deeper rooting or reduced lower limit of water extraction (Manschadi et al. (2006) supra).

The stay-green trait affects a number of the above processes in sorghum. First, stay-green reduces water use during the pre-anthesis period by restricting canopy size (via reduced tillering and smaller leaves).

Second, stay-green improves water accessibility by increasing the root:shoot ratio. There is some experimental evidence for better water extraction in stay-green lines, although more research is required. These root responses could also be explained by enhanced auxin transport (Wang et al. (2009) *Molecular Plant* 2(4):823-831). Third, stay-green increases the greenness of leaves at anthesis, effectively increasing photosynthetic capacity, and, therefore. TE (providing that photosynthesis increases proportionately more than conductance). The increase in leaf greenness is an indirect affect of reduced leaf mass, i.e. nitrogen is concentrated in the leaf.

Producing more food with less water is one of the major challenges currently facing humanity. There is a real and urgent need in both developing and developed countries to identify the genes and gene networks controlling drought adaptation in crop plants. This enables increased drought adaptation in a wide range of crop species grown in water-limited environments worldwide.

SUMMARY

Quantitative trait loci (QTLs) are used to identify genomic regions in sorghum associated with and/or which otherwise facilitate the stay-green phenotype. The QTLs identify stay-green (Stg) X wherein X is a numeral increasing from 1 which represents the region on a chromosome comprising loci associated with the stay-green phenotype. A region within StgX is referred to as StgXm wherein in is an alphabetical designation such as Stg3a and Stg3b. In one embodiment, X is 1 and the region is Stg1 on chromosome 3 between markers txp581 and txp38 of sorghum or its equivalent in another plant genome. In another embodiment, X is 2 and the region is Stg2 on chromosome 3 between markers txp530 and txp31 of sorghum or its equivalent in another plant genome. In yet another embodiment, X is 3 and the region is Stg3 on chromosome 2 between markers txp471 and txp179 of sorghum or its equivalent in another plant genome. Stg3 is divided into Stg3a (region between txp298 and sPb-2568) and Stg3b (region between sPb-2568 and txp179). In still another embodiment, X is 4 and the region is Stg4 on chromosome 5 between markers txp283 and txp15 of sorghum or its equivalent in another plant genome.

A list of genes associated with the stay-green phenotype is provided in Tables 1A through 1C. FIG. 68 provides a diagram of how many of the genes in Stg1, Stg2, Stg3a, Stg3b and Stg4 affect the stay-green phenotype.

As taught herein, StgX comprise loci which encode proteins or regulatory agents such as microRNAs, the level of expression of which, facilitate the stay-green phenotype. Selection of a genetic locus or genetic region at StgX in a crop plant including elevating or reducing expression of an indigenous locus or loci is proposed to shift water use by the plant to the post-anthesis period or increase accessibility of water during crop growth or increase transpiration efficiency thereby increasing harvest index (HI) and grain yield under water-limited conditions. It is further proposed that StgX is part of a genetic and physiological network associated with drought adaptation. Polymorphic variants of loci within an StgX may also affect levels of expression. Hence, the present disclosure teaches the selection of plant breeding parents which express a particular polymorphism as well as introducing an StgX to a plant by any number of means including recombinant means or via standard breeding protocols. Mutagenesis of existing (i.e. indigenous) loci is also contemplated herein.

Taught herein is a method for generating a genetically modified plant which uses water more efficiently than a non-genetically modified plant of the same species, said method comprising modulating the level of expression of an existing or introduced StgX locus or loci in all or selected tissue in plant, the StgX corresponding to the location on a chromosome within a sorghum plant or its equivalent in another plant, which StgX encodes a product, the level of which, is associated with or facilitates a stay-green phenotype which phenotype includes a shift in water use to the post-anthesis period or increased accessibility of water during crop growth or increased transpiration efficiency resulting in increased harvest index and grain yield under water-limited conditions, and wherein StgX is identified by fine structure mapping.

Enabled herein is a method for generating a genetically modified plant which uses water more efficiently than a non-genetically modified plant of the same species, the method comprising introducing into the plant or a parent of the plant an agent selected form the list consisting of: (i) a genetic agent comprising one or more loci, located in a region selected from Stg1 on chromosome 3 between txp581 and txp38; Stg2 on chromosome 3 between txp530 and txp31; Stg3a (region between txp298 and sPb-2568); Stg3b (region between sPb-2568 and txp179); and Stg4 on chromosome 5 between txp283 and txp15 of sorghum or its equivalent in another plant, the level of expression of which, is associated with or facilitates a stay-green phenotype, which phenotype includes a shift in water use to the post-anthesis period or increased accessibility of water during crop growth or increased transpiration efficiency resulting in increased harvest index and grain yield under water-limited conditions; and (ii) an agent which up-regulates or down-regulates an indigenous form of the locus or loci. Reference to "Stg3" includes Stg3a located between txp298 and sPb-2568 and Stg3b located between sPb-2568 and txp179.

This aspect encompasses using recombinant techniques to introduce one or more loci into a plant as well as using breeding protocols to select plants having a particular expression profile of the one or more loci. Mutagenesis followed by selection may also be used to alter expression profiles or patterns in indigenous loci.

Further taught herein is a method for generating a genetically modified plant which uses water more efficiently than a non-genetically modified plant of the same species, the method comprising modulating the level of expression of an existing or introduced StgX locus or loci in all or selected tissue in a plant, which locus or loci corresponding to a locus or loci located at Stg1, Stg2, Stg3 (including Stg3a and Stg3b) and/or Stg4 on a chromosome within a sorghum plant or its equivalent in another plant which encodes a product, the level of which, is associated with or facilitates a stay-green phenotype, which phenotype includes a shift in water use to the post-anthesis period or increased accessibility of water during crop growth or increased transpiration efficiency resulting in increased harvest index and grain yield under water-limited conditions, and wherein StgX is identified by fine structure mapping.

It is taught herein that a the level of expression of one or more loci in an StgX region facilitates inter alia a particular plant canopy architecture which enables a plant to become more water efficient. The locus or loci in StgX, therefore, is/are referred to herein as a "drought adaptation gene(s)" or "drought adaption locus/loci". Examples of loci are listed in Tables 1A through 1C. In an example, a locus is selected from Table 1B. In another example, the locus encodes a protein associated with auxin such as a pin-like inflorescence (PIN) protein. PIN proteins are auxin efflux carriers which contain transmembrane domains and are mainly localized in the plasma membranes. The locus encoding a PIN protein is represented herein as PIN. Other examples of a genetic loci are IPA-1 (Ideal Plant Architecture1), WFP (Wealthy Farmers Panicle), squamosa Spl (promoter binding protein-like) and CCD7/8.

The present disclosure teaches introducing one or more stay-green loci into a plant or introducing a functional equivalent such as a cDNA or up-regulating or down regulating expression of an indigenous locus or loci. This includes recombinant techniques, breeding, hybridization and selection protocols and mutagenesis methods.

Enabled herein is a set of stay-green genes as listed in Table 1B (and Table 1C) for use in generating drought insensitive plants by recombinant DNA technology and/or by breeding, crossing and hybridization methods. This includes up-regulating or down-regulating the genes in one or more of Stg1, Stg2, Stg3a, Stg3b and/or Stg4 (as exemplified in Tables 1B and 1C).

Enabled herein is a set of stay-green genes as listed in Table 1A for use in generating drought insensitive plants by recombinant DNA technology and/or by breeding, crossing and hybridization methods.

The term "SbPINn" is used to describe a SbPIN protein produced in sorghum wherein n is a numeral defining the auxin efflux carrier component and n is 1 through 11. Reference to "SbPINn" includes its homologs and orthologs in other plants. Examples of SbPINn loci are those which encode SbPIN4 and SbPIN2 and their equivalents in other plants. The level or location of expression of a PIN or level of expression of a PIN with a particular polymorphic variation is proposed herein to facilitate expression of the stay-green phenotype. The PIN may be introduced or its level of expression altered by recombinant means, standard breeding protocols and mutagenesis methods. SbPIN4 corresponds to the OsPIN5 and SbPIN2 corresponds to OsPIN3a. The term "Os" refers to rice (refer to Table 1A).

In another embodiment, the locus is IPA-1. The level of expression of IPA-1 or level or location of expression of IPA-1 with a particular polymorphic variation is proposed herein to facilitate the stay-green phenotype In another embodiment, the locus is WFP. The level or location of expression of WFP or level of expression of WFP with a particular polymorphic variation is proposed herein to facilitate the stay-green phenotype In another embodiment, the locus is Spl. The level or location of expression of Spl or level of expression of Spl with a particular polymorphic variation is proposed herein to facilitate the level of the stay-green phenotype. In another embodiment, the locus is CCD7/8. The level or location of expression of CCD7/8 or level of expression of CCD7/8 with a particular polymorphic variation is proposed herein to facilitate expression of the stay-green phenotype.

The stay-green loci may be expressed in all plant tissue or in selected tissue. Differential expression may also be selected.

Taught herein s a method for generating a genetically modified plant which uses water more efficiently than a non-genetically modified plant of the same species, the method comprising introducing into a plant or parent of the plant a one or more loci corresponding to a locus located at Stg1, Stg2, Stg3a, Stg3b or Stg4 as listed in Tables 1A through 1C or a functional equivalent thereof or an agent which modulates expression of an indigenous form of one or more of these loci wherein the level and/or location of expression of the one or more loci causes a shift in water use to the post-anthesis period or increased accessibility of water during crop growth or increased transpiration efficiency resulting in increased harvest index and grain yield under water limiting conditions.

Taught herein s a method for generating a genetically modified plant which uses water more efficiently than a non-genetically modified plant of the same species, the method comprising introducing into a plant or parent of the plant a one or more loci corresponding to a locus located at Stg1, Stg2, Stg3a, Stg3b or Stg4 as listed in Table 1B or a functional equivalent thereof or an agent which modulates expression of an indigenous form of one or more of these loci wherein the level and/or location of expression of the one or more loci causes a shift in water use to the post-anthesis period or increased accessibility of water during crop growth or increased transpiration efficiency resulting in increased harvest index and grain yield under water limiting conditions.

In an embodiment, SbPIN2 (for Sorghum bicolor member of the auxin efflux carrier component 2 family), is at Stg2 on chromosome 3, fine-mapped to a region between markers txp512 and txp530 and SbPIN4 is at Stg1, on chromosome 3, fine-mapped to a region between markers txp563 and txp442 are taught herein to be responsible for the stay-green trait in sorghum resulting in a range of phenotypes that confer drought adaptation via increased water use at anthesis (due to reduced tillering and smaller leaves), increased water accessibility (due to enhanced root:shoot ratio), increased transpiration efficiency under mild water deficit (due to higher leaf nitrogen concentration), increased biomass per leaf area under terminal water deficit (due to increased transpiration per leaf area) and increased grain yield, grain size and lodging resistance. Reference to the txp markers in sorghum extends to the equivalent markers in the genome of other plants.

Another aspect taught herein is a method for generating a genetically modified plant which uses water more efficiently than a non-genetically modified plant of the same species, the method comprising introducing into a plant or parent of the plant a one or more loci corresponding to SbPIN1 to 11, IPA-1, WFP, Spl and/or CCD7/8 or a functional equivalent thereof or an agent which modulates expression of an indigenous form of one or more of these loci wherein the level and/or location of expression of the one or more loci causes a shift in water use to the post-anthesis period or increased accessibility of water during crop growth or increased transpiration efficiency resulting in increased harvest index and grain yield under water limiting conditions.

A "functional equivalent" of a locus includes a cDNA molecule or a homolog from another plant species. This aspect includes a recombinant approach to introduce a locus or a breeding protocol to introduce or select a locus with a particular expression profile.

The present disclosure further teaches a method for generating a genetically modified plant which uses water more efficiently than a non-genetically modified plant of the same species, the method comprising introducing into a plant or parent of the plant a locus or cDNA encoding a locus located in Stg1 or a molecule which modulates expression of an indigenous locus. Examples are listed in Tables 1A through 1C, such as Table 1B.

The present disclosure further teaches a method for generating a genetically modified plant which uses water more efficiently than a non-genetically modified plant of the same species, the method comprising introducing into a plant or parent of the plant a locus or cDNA encoding a locus located in Stg2 or a molecule which modulates expression of an indigenous locus. Examples are listed in Tables 1A through 1C, such as Table 1B.

The present disclosure further teaches a method for generating a genetically modified plant which uses water more efficiently than a non-genetically modified plant of the same species, the method comprising introducing into a plant or parent of the plant a locus or cDNA encoding a locus located in Stg3a or a molecule which modulates expression of an indigenous locus. Examples are listed in Tables 1A through 1C, such as Table 1B.

The present disclosure further teaches a method for generating a genetically modified plant which uses water more efficiently than a non-genetically modified plant of the same species, the method comprising introducing into a plant or parent of the plant a locus or cDNA encoding a locus located in Stg3b or a molecule which modulates expression of an indigenous locus. Examples are listed in Tables 1A through 1C, such as Table 1B.

The present disclosure further teaches a method for generating a genetically modified plant which uses water more efficiently than a non-genetically modified plant of the same species, the method comprising introducing into a plant or parent of the plant a locus or cDNA encoding a locus located in Stg4 or a molecule which modulates expression of an indigenous locus. Examples are listed in Tables 1A through 1C, such as Table 1B.

The present disclosure further teaches a method for generating a genetically modified plant which uses water more efficiently than a non-genetically modified plant of the same species, the method comprising introducing into a plant or parent of the plant a locus or cDNA encoding a PIN protein, or a molecule which modulates expression of an indigenous PIN locus. Examples of PINs are SbPIN1 to 11 which include SbPIN4 and SbPIN2 and other SbPINs listed in Table 1A as well as their equivalent in other plants.

In another embodiment, the present disclosure teaches a method for generating a genetically modified plant which uses water more efficiently than a non-genetically modified plant of the same species, the method comprising introducing into a plant or parent of the plant a locus or cDNA which encodes IPA-1 or a functional homolog or ortholog thereof or an agent which modulates the level of expression of an indigenous IPA-1 to cause a shift in water use to the post-anthesis period or increased accessibility of water during crop growth or increased transpiration efficiency resulting in increased harvest index and grain yield under water limiting conditions.

In another embodiment, the present disclosure teaches a method for generating a genetically modified plant which uses water more efficiently than a non-genetically modified plant of the same species, the method comprising introducing into a plant or parent of the plant a locus or cDNA which encodes WFP or a functional homolog or ortholog thereof or an agent which modulates the level of expression of an indigenous WFP to cause a shift in water use to the post-anthesis period or increased accessibility of water during crop growth or increased transpiration efficiency resulting in increased harvest index and grain yield under water limiting conditions.

In another embodiment, the present disclosure teaches a method for generating a genetically modified plant which uses water more efficiently than a non-genetically modified plant of the same species, the method comprising introducing into a plant or parent of the plant a locus or cDNA which encodes Spl or a functional homolog or ortholog thereof or an agent which modulates the level of expression of an indigenous Spl to cause a shift in water use to the post-anthesis period or increased accessibility of water during crop growth or increased transpiration efficiency resulting in increased harvest index and grain yield under water limiting conditions.

In another embodiment, the present disclosure teaches a method for generating a genetically modified plant which uses water more efficiently than a non-genetically modified plant of the same species, the method comprising introducing into a plant or parent of the plant a locus or cDNA which encodes CCD7/8 or a functional homolog or ortholog thereof or an agent which modulates the level of expression of an indigenous CCD7/8 to cause a shift in water use to the post-anthesis period or increased accessibility of water during crop growth or increased transpiration efficiency resulting in increased harvest index and grain yield under water limiting conditions.

In an embodiment, the plants are modified or selected to change the level of expression of two or more of loci listed in Tables 1B or 1C.

In an embodiment, the plants are modified or selected to change the level of expression of two or more of PIN, IPA-1, WFP, Spl and/or CCD7/8 and/or two or more PINs.

Genetically modified plants and their progeny exhibiting the stay-green trait are also enabled herein as well as seeds, fruit and flowers and other reproductive or propagating material. Such "genetically modified plants" include plants modified by recombinant means as well as plants selected through breeding protocols and/or plants subjected to mutagenesis and selection.

Genetic material is enabled herein which encodes a product which is associated with or facilitates a stay-green phenotype which phenotype includes a shift in water use to the post-anthesis period or increased accessibility of water during crop growth or increased transpiration efficiency resulting in increased harvest index and grain yield under water-limited conditions, and encoded by a locus in the StgX region wherein X is a numeral corresponding to the location on the chromosome and wherein StgX is identified by fine structure mapping is enabled thereon as in a functional equivalent of the StgX. The genetic material is useful for generating a genetically modified plant which uses water more efficiently than a non-genetically modified plant of the same species as well as for developing markers for selection of traits during breeding protocol.

Genetic material contemplated herein includes cDNA, genomic DNA and germplasm encoding one or more of a locus listed in Tables 1A through 1C, such as Table 1B.

Genetic material contemplated herein includes cDNA, genomic DNA and germplasm encoding one or more of a PIN, IPA-1, WFP, Spl and/or CCD7/8. Reference to a "PIN" includes one or more PINs.

Taught herein is a plant management system to reduce crop reliance on water or to otherwise improve water use efficiency and to enhance grain or product yield. The plant management system includes the generation of a drought adapted crop including cereal plants using the selection and expression of an StgX locus or a functional equivalent thereof alone or in combination with the introduction of other useful traits such as grain size, root size, salt tolerance, herbicide resistance, pest resistance and the like. Alternatively or in addition, the plant management system comprises generation of drought adapted plants and agricultural procedures such as irrigation, nutrient requirements, crop density and geometry, weed control, insect control, soil aeration, reduced tillage, raised beds and the like. Examples of a StgX locus in sorghum include SbPIN1 to 11, IPA-1, WFP, Spl and CCD7/8 and their equivalents in other plants. Examples of loci include located in Stg1, Stg2, Stg3a, Stg3b and/or Stg4 (see Tables 1A through 1C such as Table 1B).

A business model is also taught herein for improved economic returns on crop yield, the model comprising generating crop plants having a selected StgX trait or elevated or reduced StgX trait resulting in the crop plant having a shift in water use by the plant to the post-anthesis period thereby increasing HI and grain yield under water-limited conditions, obtaining seed from the generated crop plant and distributing the seed to grain producers to enhance yield and profit.

The present disclosure further teaches markers for the stay-green phenotype for use in breeding programs for drought tolerant plants, the markers comprising a stay-green X (StgX) locus, wherein X is a numeral corresponding to the location on a chromosome within a sorghum plant or its equivalent in another plant which encodes a product which is associated with or facilitates a stay-green phenotype which phenotype includes a shift in water use to the post-anthesis period or increased accessibility of water during crop growth or increased transpiration efficiency resulting in increased harvest index and grain yield under water-limited conditions. Examples of suitable markers include Stg1 on chromosome 3 between txp581 and txp38; Stg2 on chromosome 3 between txp530 and txp31; Stg3 is divided into Stg3a (region between txp298 and sPb-2568) and Stg3b (region between sPb-2568 and txp179) and Stg4 on chromosome 5 between txp283 and txp15. Examples include those listed in Tables 1B and 1C. These markers are based on the sorghum genome but extend to the equivalents in another plant genome. Furthermore, marker adjacent or proximal to the genomic locations given above may also be used to screen for particular progeny in a breeding program.

Hence, a set of biomarkers is taught herein including Stg1 on chromosome 3 between txp581 and txp38; Stg2 on chromosome 3 between txp530 and txp31; Stg3 is divided into Stg3a (region between txp298 and sPb-2568) and Stg3b (region between sPb-2568 and txp179) and Stg4 on chromosome 5 between txp283 and txp15 on chromosome 5 of sorghum, or the equivalent in the genome of another plant. Such markers are useful in breeding protocols designed to generate plants exhibiting the stay-green phenotype. Examples of loci are listed in Tables 1A through 1C. Particular examples are in Table 1B.

In an embodiment, the locus is in Stg1 selected from PINS, GID1L2, P45098A1, indole-3-acetate and brassinosteroid insensitive.

In an embodiment, the locus is in Stg2 and is auxin efflux carrier component 3a (PIN3a).

In an embodiment, the locus is in Stg3a selected from leaf senescence protein-like (Sb02g023510), leaf senescence protein-like (Sb02g023520), RAMOSA1 C2H2 zinc-finger transcription factor (Sb02g024410), putative auxin-independent growth promoter (Sb02g024540), similar to dehydration-responsive protein-like (Sb02g024670), similar to glucose transporter (Sb02g024690), WRKY transcription factor 76 (Sb02g024760), glutamine synthetase-like protein (Sb02g025100), senescence-associated protein DH (Sb02g025180), putative alanine aminotransferase (Sb02g025480), auxin-induced protein-like (Sb02g025610), auxin-induced protein-like (Sb02g025620), putative far-red impaired response protein (Sb02g025670), similar to cytochrome P450 monooxygenase CYP92A (Sb02g025820), auxin-independent growth promoter (Sb02g025960), asparate aminotransferase (Sb02g026430), similar to abscisic acid 8'-hydroxylase 3 (Sb02g026600) similar to ethylene-binding protein-like (Sb02g026630) and putative auxin-induced protein family (Sb02g027150).

In an embodiment, the locus is in Stg3b selected from putative auxin-independent growth promoter (Sb02g027470), squamosa promoter-binding-like protein 17 (Sb02g028420), similar to Os09g0505400 (OsPIN9) protein (Sb02g029210), squamosa promoter-binding-like protein 17 (Sb02g029300) similar to auxin-induced protein-like (Sb02g029630).

In an embodiment, the locus is in Stg4 selected from brassinosteroid LRR receptor (Sb05g006842), brassinosteroid LRR receptor (Sb05g006860), putative far-red impaired response protein (Sb05g007130), cytochrome P450 84A1 (Sb05g007210), gibberellin receptor GID1L2 (Sb05g007270), gibberellin receptor GID1L2 (Sb05g007290), sucrose-phosphate synthase (Sb05g007310), aquaporin SIP1-1 (Sb05g007520), gibberellin 20 oxidase 2 (Sb05g008460), OsIAA29-auxin-responsive (Sb05g008510), OsIAA29-auxin-responsive (Sb05g008512), protein gibberellin receptor GID1L2 (Sb05g008610), similar to aminotransferase, putative (Sb05g009410), indole-3-acetic acid-amido (Sb05g010310), indole-3-acetic acid-amido (Sb05g010320), indole-3-acetic acid-amido (Sb05g010326), cytochrome P450 86A2 (Sb05g010360), cytochrome P450 51, putative (Sb05g011296), cytochrome P450 51, putative (Sb05g011430), triacylglycerol lipase, leaf senescence, jasmonic acid biosynthetic process_GO (Sb05g013160), growth regulator like (Sb05g015590), cytochrome P450 78A4 (Sb05g016750), similar to ABC transporter family protein, expressed (Sb05g017120) and squamosa promoter-binding-like protein 19 (Sb05g017510).

The following abbreviations are used in the subject specification:

CCD7/8, gene conferring a stay-green phenotype
CI, confidence interval
CWU, crop water use
DW, dry weight
GLA, green leaf area
HD, high density
HI, harvest index
HT, high tillering
HW, high water
HWHD, high water, high density (intermediate water stress)
HWLD, high water, low density (least water stressed)
IPA-1, Ideal Plant Architecture1
LA, leaf area
LD, low density
LT, low tillering
LW, low water
LWHD, low water, high density (most water stressed)
LWLD, low water, low density (intermediate water stress)
NIL, Near-isogenic line
OsPIN, PIN from rice
PAB, post-anthesis biomass
PASM, post-anthesis stem mass
PIN, pin-like inflorescence
PPBR, pre:post anthesis biomass ratio
QTL, quantitative trait locus
ROS, rain-out shelter
RWC, relative water content
SbPIN, PIN from sorghum
SLW, specific leaf weight
SML, statistical machine learning
Spl, squamosa promoter binding protein-like
Stg, stay-green
Stg1, Fine-mapped region between txp563 and txp581 containing 60 annotated genes
  Larger middle region between txp440 and txp580 containing 307 annotated genes
  Candidates in tail between txp580 and txp38 containing 178 annotated genes Stg2, Fine-mapped region between txp512 and txp2 containing 15 annotated genes
  Larger region between txp31 and txp530 containing 241 annotated genes
Stg3a, Entire region between txp298 and sPb-2568 containing 520 annotated genes
Stg3b, Entire region between sPb-2568 and txp179 containing 291 annotated genes
Stg4, Entire region defined by txp283 and txp15 containing 306 annotated genes
T, transpiration
T2, tiller in the axil of leaf 2
T3, tiller in the axil of leaf 3
T4, tiller in the axil of leaf 4
T5, tiller in the axil of leaf 5
T6, tiller in the axil of leaf 6
TE, transpiration efficiency
TS, terminal stress
VPD, vapor pressure deficit
WPA, Wealthy Farmer's Panicle
WW, well watered Table 1A provides information on PIN's from sorghum and rice.

TABLE 1A

*Sorghum* Stg QTL details

| *Sorghum* Gene ID | Rice homologue | *Sorghum* | Chromosome | bp (start) | bp (end) | Length (bp) | predicted cM |
|---|---|---|---|---|---|---|---|
| Sb02g029210 | OsPIN6 | SbPIN1 | SBI-02 | 64347327 | 64350341 | 3014 | 144.3023044 |
| Sb03g029320 | OsPIN3a | SbPIN2 | SBI-03 | 57449784 | 57453744 | 3960 | 88.78882569 |
| Sb03g032850 | OsPIN1 | SbPIN3 | SBI-03 | 61297480 | 61299969 | 2489 | 115.1215502 |
| Sb03g037350 | OsPIN5 | SbPIN4 | SBI-03 | 65310051 | 65313194 | 3143 | 129.5972557 |
| Sb03g043960 | OsPIN6 | SbPIN5 | SBI-03 | 71204119 | 71206483 | 2364 | 152.8989678 |
| Sb04g028170 | OsPIN1 | SbPIN6 | SBI-04 | 58261350 | 58264959 | 3609 | 107.0875147 |
| Sb05g002150 | OsPIN1b | SbPIN7 | SBI-05 | 2304407 | 2307630 | 3223 | 17.31415415 |
| Sb07g026370 | OsPIN4 | SbPIN8 | SBI-07 | 61560708 | 61563133 | 2425 | 123.616344 |
| Sb10g004430 | OsPIN1 | SbPIN9 | SBI-10 | 3915101 | 3917519 | 2418 | 32.96657613 |
| Sb10g008290 | OsPIN1c | SbPIN10 | SBI-10 | 8438481 | 8441508 | 3027 | 45.84731059 |
| Sb10g026300 | OsPIN2 | SbPIN11 | SBI-10 | 55747009 | 55751104 | 4095 | 82.37617984 |

| *Sorghum* Gene ID | LOD | R2 | Pop | Publication | Source of allele | Published symbol | Stg QTL summary |
|---|---|---|---|---|---|---|---|
| Sb02g029210 | 1.9 | 10.7 | B35/Tx7000 | Subudhi et al 2000 | B35 | stg3 | Stg3B |
|  | 2.5 | 4.9 | N13/E36-1 | Hausmann et al 2002 | N13 | % GL15 #3 |  |
|  | 3 | 5.8 | N13/E36-1 | Hausmann et al 2002 | N13 | % GL30 #5 |  |
|  | 4.9 | 9.5 | N13/E36-1 | Hausmann et al 2002 | N13 | % GL45 #4 |  |
| Sb03g029320 | 2.63 | 10.2 | SC56/Tx7000 | Kebede et al 2001 | SC56 | Stg A | Stg2 |
|  | 2.65 | 14 | B35/Tx7000 | Subudhi et al 2000 | B35 | stg2 |  |
|  | 2.65 | 6.1 | 296B/IS18551 | Srinivas et al 2009 | 296B | QGlaa-sbi03 |  |
|  | 2.9 | 7.5 | 296B/IS18551 | Srinivas et al 2009 | 296B | QPglam-sbi03 |  |
|  | 3.66 | 19.9 | B35/Tx7000 | Subudhi et al 2000 | B35 | Stg2 |  |
|  | 5.52 | 29.2 | B35/Tx7000 | Subudhi et al 2000 | B35 | Stg2 |  |
|  | 5.44 | 22.6 | B35/Tx7000 | Subudhi et al 2000 | Tx7000 | Stg2 |  |
|  | 5.6 | 24.8 | B35/Tx7000 | Xu et al 2000 | Tx7000 | Chl2 |  |
|  | 6.23 | 30.3 | B35/Tx7000 | Xu et al 2000 | B35 | Stg2 |  |
|  | 6.6 | 28.6 | B35/Tx430 | Crasta et al 1999 | B35 | SGA |  |
|  | 2.8 | 5.6 | N13/E36-1 | Hausmann et al 2002 | E36-1 | % GL45 #5 |  |
| Sb03g032850 | 2.69 | 12 | B35/Tx7000 | Xu et al 2000 | Tx7000 | Chl1 | Stg1 (broader QTL) |
|  | 4.59 | 19.6 | B35/Tx7000 | Xu et al 2000 | B35 | Stg1 |  |
|  | 3.18 | 15.4 | B35/Tx7000 | Subudhi et al 2000 | B35 | Stg1 |  |
|  | 3.61 | 18.1 | B35/Tx7000 | Subudhi et al 2000 | B35 | Stg1 |  |
|  | 14.9 | 26.3 | IS9830/E36-1 | Hausmann et al 2002 | IS9830 | % GL15 #1 |  |
|  | 6.5 | 12.4 | IS9830/E36-1 | Hausmann et al 2002 | IS9830 | % GL30 #2 |  |

TABLE 1A-continued

Sorghum Stg QTL details

| | | | | | | | |
|---|---|---|---|---|---|---|---|
| Sb03g037350 | Stg1 (fine-mapped QTL) | | | | | | Stg1 (fine-mapped QTL) |
| Sb03g043960 | | | | | | | — |
| Sb04g028170 | 3.63 | 13.4 | SC56/Tx7000 | Kebede et al 2001 | SC56 | Stg C.1 | smlQTL and near StgC.1 |
| | 3.1 | 6.1 | IS9830/E36-1 | Hausmann et al 2002 | IS9830 | % GL15 #2 | |
| | 2.8 | 5.5 | IS9830/E36-1 | Hausmann et al 2002 | IS9830 | % GL30 #3 | |
| | 2.6 | 5.1 | IS9830/E36-1 | Hausmann et al 2002 | IS9830 | % GL45 #4 | |
| | 4.11 | 15.1 | SC56/Tx7000 | Kebede et al 2001 | Tx7000 | Stg C.2 | |
| Sb05g002150 | sml QTL only | | | | | | smlQTL |
| Sb07g026370 | 2.8 | 5.6 | N13/E36-1 | Hausmann et al 2002 | N13 | % GL15 #5 | Hausmann QTL and smlQTL |
| | 3.4 | 6.7 | N13/E36-1 | Hausmann et al 2002 | N13 | % GL30 #7 | |
| | 2.9 | 5.8 | N13/E36-1 | Hausmann et al 2002 | N13 | % GL45 #8 | |
| Sb10g004430 | 3.65 | 13.8 | SC56/Tx7000 | Kebede et al 2001 | Tx7000 | Stg B | Kebede QTL |
| Sb10g008290 | 2.76 | 11.2 | QL39/QL41 | Tao et al 2000 | QL141 | Stg1 | Stg1 |
| Sb10g026300 | 2.7 | 5.5 | N13/E36-1 | Hausmann et al 2002 | E36-1 | % GL30 #8 | Hausmann & Crasta QTL |
| | 2.6 | 5.2 | N13/E36-1 | Hausmann et al 2002 | E36-1 | % GL45 #9 | |

TABLE 1B

Stg regions

Stg1 region
Fine-mapped region (region between txp563 and txp581 containing 60 annotated genes):

probable auxin efflux carrier component 5, PIN5 (Sb03g037350), primary candidate
protein gibberellin receptor GID1L2 (Sb03g037296)
protein cytochrome P450 98A1 (Sb03g037380)
protein indole-3-acetate (Sb03g037450)
protein BRASSINOSTEROID INSENSITIVE (Sb03g037580)
Larger middle region (region between txp440 and txp580 containing 307 annotated genes):

protein cytokinin dehydrogenase 5 (Sb03g036160)
protein D-erythro-sphingosine kinase_ABA (Sb03g036460)
protein caltractin_response to auxin_GO (Sb03g036610)
protein indole-3-acetic acid-amido (Sb03g036680)
ethylene-responsive factor-like transcription factor ERFL1c (Sb03g037080)
ethylene-responsive factor-like transcription factor ERFL1c (Sb03g037085)
protein Leucine Rich Repeat family (Sb03g037140)
protein transcription factor GAMYB_gibberellinn TF (Sb03g037680)
protein auxin hydrogen symporter (Sb03g038030)
protein transcription factor LAX (Sb03g038820)
protein gibberellin 20 oxidase 2 (Sb03g038880)
Candidates in tail (region between txp580 and txp38 containing 178 annotated genes):

protein cytokinin dehydrogenase 5 (Sb03g036160)
protein protein phosphatase 2C_ABA stomata (Sb03g039630)
protein delta_proline biosyn_ABA_water_GO (Sb03g039820)
protein auxin transporter-like_root cap_GO (Sb03g040320)
protein ABA response element binding (Sb03g040510)
Stg2 region
Fine-mapped region (region between txp512 and txp2 containing 15 annotated genes):

Probable auxin efflux carrier component 3a PIN3a (Sb03g029320), primary candidate
Larger region (region between txp31 and txp530 containing 241 annotated genes):

protein auxin-induced protein (Sb03g028020)
protein auxin-induced protein (Sb03g028050)
protein auxin-induced protein (Sb03g028060)
protein indole-3-acetic acid-amido (Sb03g028240)
protein cytochrome P450 72A1 (Sb03g028560)
protein BRASSINOSTEROID INSENSITIVE (Sb03g028800)
protein (ABA glucosyl transferase_GO) (Sb03g029060)
protein (ABA glucosyl transferase_GO) (Sb03g029070)
protein (ABA glucosyl transferase_GO) (Sb03g029080)
protein DELLA protein RGA, putative (Sb03g029470)
protein BRASSINOSTEROID INSENSITIVE (Sb03g029550)
Stg3 region
Stg3a entire region (region between txp298 and sPb-2568 containing 520 annotated genes):

Leaf senescence protein-like (Sb02g023510)
Leaf senescence protein-like (Sb02g023520)
RAMOSA1 C2H2 zinc-finger transcription factor (Sb02g024410)
Putative auxin-independent growth promoter (Sb02g024540)
similar to Dehydration-responsive protein-like (Sb02g024670)
similar to Glucose transporter (Sb02g024690)
WRKY transcription factor 76 (Sb02g024760)
Glutamine synthetase-like protein (Sb02g025100)

TABLE 1B-continued

Stg regions

Senescence-associated protein DH (Sb02g025180)
Putative alanine aminotransferase (Sb02g025480)
Auxin-induced protein-like (Sb02g025610)
Auxin-induced protein-like (Sb02g025620)
weakly similar to Putative far-red impaired response protein (Sb02g025670)
similar to Cytochrome P450 monooxygenase CYP92A1 (Sb02g025820)
auxin-independent growth promoter (Sb02g025960)
asparate aminotransferase (Sb02g026430)
similar to Abscisic acid 8'-hydroxylase 3 (Sb02g026600)
similar to Ethylene-binding protein-like (Sb02g026630)
weakly similar to Putative auxin-induced protein family (Sb02g027150)
Stg3b entire region (region between sPb-2568 and txp179 containing 291 annotated genes):

similar to Putative auxin-independent growth promoter (Sb02g027470)
Squamosa promoter-binding-like protein 17 (Sb02g028420)
similar to Os09g0505400 (OsPIN9) protein (Sb02g029210)
Squamosa promoter-binding-like protein 17 (Sb02g029300)
similar to Auxin-induced protein-like (Sb02g029630)
Stg4 region
Entire Stg4 region (region defined by txp283 and txp15 containing 306 annotated genes):

protein brassinosteroid LRR receptor (Sb05g006842)
protein brassinosteroid LRR receptor (Sb05g006860)
weakly similar to Putative far-red impaired response protein (Sb05g007130)
protein cytochrome P450 84A1 (Sb05g007210)
protein gibberellin receptor GID1L2 (Sb05g007270)
protein gibberellin receptor GID1L2 (Sb05g007290)
protein sucrose-phosphate synthase (Sb05g007310)
Aquaporin SIP1-1 (Sb05g007520)
protein gibberellin 20 oxidase 2 (Sb05g008460)
protein OsIAA29 - Auxin-responsive (Sb05g008510)
protein OsIAA29 - Auxin-responsive (Sb05g008512)
protein gibberellin receptor GID1L2 (Sb05g008610)
similar to Aminotransferase, putative (Sb05g009410)
protein indole-3-acetic acid-amido (Sb05g010310)
protein indole-3-acetic acid-amido (Sb05g010320)
protein indole-3-acetic acid-amido (Sb05g010326)
protein cytochrome P450 86A2 (Sb05g010360)
protein cytochrome P450 51, putative (Sb05g011296)
protein cytochrome P450 51, putative (Sb05g011430)
protein triacylglycerol lipase, leaf senescence, jasmonic acid biosynthetic process_GO (Sb05g013160)
protein growth regulator like (Sb05g015590)
protein cytochrome P450 78A4 (Sb05g016750)
similar to ABC transporter family protein, expressed (Sb05g017120)
squamosa promoter-binding-like protein 19 (Sb05g017510)

TABLE 1C

Potential mechanism to confer stay-green phenotype

| Stg QTL | Gene ID | Annotation | Link in pathway | Potential mechanism to confer stay-green phenotype |
|---|---|---|---|---|
| Stg1 | Sb03g037350 | probable auxin efflux carrier component 5, PIN5 | axillary bud growth, polar auxin transport | Overexpression of this gene might lead to increased uptake of IAA into lumen of ER and decreased availability of IAA in cytosol (Mravec 2009) might lead to decreased polar auxin transport which would increase competition between buds (Domagalska 2011) (ie one bud grows out and suppresses others). |
| Stg1 | Sb03g037296 | protein gibberellin receptor GID1L2 | cell elongation | Gibberellins destabilise DELLA proteins which are suppressors of elongation. This gene could have an effect on leaf size. |
| Stg1 | Sb03g037380 | protein cytochrome P450 98A1 | axillary bud growth, strigolactone pathway | This gene might alter the biosynthesis of strigolactones. Strigolactones in turn are down-regulators of tillering. |
| Stg1 | Sb03g037450 | protein indole-3-acetate | axillary bud growth, leaf size, auxin biosynthesis | This gene might encode auxin biosynthesis. |
| Stg1 | Sb03g037580 | protein BRASSINOSTEROID INSENSITIVE | axillary bud growth, senescence, auxin transport | Brassinosteroids up-regulate auxin efflux carriers ABCB/PGP19 and have been associated with senescence. |
| Stg1 | Sb03g036160 | protein cytokinin dehydrogenase 5 | axillary bud growth, cytokinin synthesis | cytokinins up-regulate bud growth |
| Stg1 | Sb03g036460 | protein D-erythro-sphingosine kinase_ABA | stress signalling, stomata control | ABA is associated with growth regulation and stomata closure as response to stress. |
| Stg1 | Sb03g036610 | protein caltractin_response to auxin_GO | auxin signalling | This gene might change perception of auxin. |
| Stg1 | Sb03g036680 | protein indole-3-acetic acid-amido | axillary bud growth, leaf size, auxin biosynthesis | This gene might encode auxin biosynthesis. |
| Stg1 | Sb03g037080 | ethylene-responsive factor-like transcription factor ERFL1c | senescence, root growth | Ethylene affects root growth and senescence. A mutation in this gene changes sensitivity to ethylene. |
| Stg1 | Sb03g037085 | ethylene-responsive factor-like transcription factor ERFL1c | senescence, root growth | Ethylene affects root growth and senescence. A mutation in this gene changes sensitivity to ethylene. |
| Stg1 | Sb03g037140 | protein Leucine Rich Repeat family | axillary bud growth, strigolactone pathway | MAX2 which is a locus in the strigolactone pathway is in the family of Leucine Rich Repeat proteins. |
| Stg1 | Sb03g037680 | protein transcription factor GAMYB_gibberellin TF | cell elongation | Gibberellins destabilise DELLA proteins which are suppressors of elongation. This gene could have an effect on leaf size. |
| Stg1 | Sb03g038030 | protein auxin hydrogen symporter | axillary bud growth, auxin transport | This gene might have an effect on auxin transport. Auxins are associated with shoot and root growth. |

TABLE 1C-continued

Potential mechanism to confer stay-green phenotype

| Stg QTL | Gene ID | Annotation | Link in pathway | Potential mechanism to confer stay-green phenotype |
|---|---|---|---|---|
| Stg1 | Sb03g038820 | protein transcription factor LAX | auxin transport | LAX encodes an auxin influx carrier. Auxins are associated with shoot or root growth. |
| Stg1 | Sb03g036160 | protein cytokinin dehydrogenase 5 | axillary bud growth, cytokinin synthesis | Cytokinins up-regulate bud growth. |
| Stg1 | Sb03g039630 | protein protein phosphatase 2C_ABA stomata | stress signalling, stomata control | ABA is associated with growth regulation and stomata closure as response to stress. |
| Stg1 | Sb039039820 | protein delta_proline biosyn_ABA_water_GO | stress signalling, stomata control | ABA is associated with growth regulation and stomata closure as response to stress. |
| Stg1 | Sb03g040320 | protein auxin transporter-like_root cap_GO | auxing transport | Auxins are associated with shoot or root growth. |
| Stg1 | Sb03g040510 | protein ABA response element binding | stress signalling, stomata control | ABA is associated with growth regulation and stomata closure as response to stress. |
| Stg2 | Sb03g029320 | Probable auxin efflux carrier component 3a PIN3a | axillary bud growth, polar auxin transport | Overexpression of this gene might lead to increased export of IAA (Mravec 2009) and might lead to increased polar auxin transport which could suppress bud outgrowth through increased apical dominance (Domagalska 2011). |
| Stg2 | Sb03g028020 | protein auxin-induced protein | auxing pathway | Auxins are associated with shoot or root growth. |
| Stg2 | Sb03g028050 | protein auxin-induced protein | auxing pathway | Auxins are associated with shoot or root growth. |
| Stg2 | Sb03g028060 | protein auxin-induced protein | auxing pathway | Auxins are associated with shoot or root growth. |
| Stg2 | Sb03g028240 | protein indole-3-acetic acid-amido | axillary bud growth, leaf size, auxin biosynthesis | This gene might encode auxin biosynthesis. |
| Stg2 | Sb03g028560 | protein cytochrome P450 72A1 | axillary bud growth, strigolactone pathway | This gene might alter the biosynthesis of strigolactones. Strigolactones in turn are down-regulators of tillering. |
| Stg2 | Sb03g028800 | protein BRASSINOSTEROID INSENSITIVE | axillary bud growth, senescence, auxin transport | Brassinosteroids up-regulate auxin efflux carriers ABCB/PGP19 and have been associated with senescence. |
| Stg2 | Sb03g029060 | protein (ABA glucosyl transferase_GO) | stress signalling, stomata control | ABA is associated with growth regulation and stomata closure as response to stress. |
| Stg2 | Sb03g029070 | protein (ABA glucosyl transferase_GO) | stress signalling, stomata control | ABA is associated with growth regulation and stomata closure as response to stress. |
| Stg2 | Sb03g029080 | protein (ABA glucosyl transferase_GO) | stress signalling, stomata control | ABA is associated with growth regulation and stomata closure as response to stress. |
| Stg2 | Sb03g029470 | protein DELLA protein RGA, putative | cell elongation, growth | DELLA protein are growth suppressors that interact with gibberellins to control cell elongation. This gene could control leaf size. |
| Stg2 | Sb03g029550 | protein BRASSINOSTEROID INSENSITIVE | axillary bud growth, senescence, auxin transport | Brassinosteroids up-regulate auxin efflux carriers ABCB/PGP19 and have been associated with senescence. |
| Stg3a | Sb02g023510 | Leaf senescence protein-like | senescence | This gene could directly affect green leaf area after flowering. |
| Stg3a | Sb02g023520 | Leaf senescence protein-like | senescence | This gene could directly affect green leaf area after flowering. |
| Stg3a | Sb02g024410 | RAMOSA1 C2H2 zinc-finger transcription factor | axillary bud growth | RAMOSUS1 is a homolog of MAX4 which encodes CCD8 in the strigolactone pathway. This transcription factor could affect tillering via the locus RMS1. |
| Stg3a | Sb02g024540 | Putative auxin-independent growth promoter | growth | This locus might affect leaf size. |
| Stg3a | Sb02g024670 | similar to Dehydration-responsive protein-like | stress signalling | Could affect any growth processes in response to water stress. |
| Stg3a | Sb02g024690 | similar to Glucose transporter | glucose pathway | Glucose is required for growth, might be involved in osmotic adjustment and therefore dehydration avoidance. |
| Stg3a | Sb02g024760 | WRKY transcription factor 76 | gene regulation | WRKY transcription factors have been associated with various stress responses. |
| Stg3a | Sb02g025100 | Glutamine synthetase-like protein | nitrogen assimilation | This gene could affect the maintenance of green leaf area. |
| Stg3a | Sb02g025180 | Senescence-associated protein DH | senescence | This gene could directly affect green leaf area after flowering. |
| Stg3a | Sb02g025480 | Putative alanine aminotransferase | nitrogen assimilation | This gene could affect the maintenance of green leaf area. |
| Stg3a | Sb02g025610 | Auxin-induced protein-like | auxin signalling | This gene could affect growth processes. |
| Stg3a | Sb02g025620 | Auxin-induced protein-like | auxin signalling | This gene could affect growth processes. |
| Stg3a | Sb02g025670 | weakly similar to Putative far-red impaired response protein | axillary bud growth | This gene could affect perception of neighbours and have an impact on tiller number. |

TABLE 1C-continued

Potential mechanism to confer stay-green phenotype

| Stg QTL | Gene ID | Annotation | Link in pathway | Potential mechanism to confer stay-green phenotype |
|---|---|---|---|---|
| Stg3a | Sb02g025820 | similar to Cytochrome P450 monooxygenase CYP92A1 | axillary bud growth, strigolactone pathway | This gene might alter the biosynthesis of strigolactones. Strigolactones in turn are down-regulators of tillering. |
| Stg3a | Sb02g025960 | Putative auxin-independent growth promoter | growth | This locus might affect leaf size. |
| Stg3a | Sb02g026430 | asparate aminotransferase | nitrogen assimilation | This gene could affect the maintenance of green leaf area. |
| Stg3a | Sb02g026600 | similar to Abscisic acid 8'-hydroxylase 3 | stress signalling, stomata control | ABA is associated with growth regulation and stomata closure as response to stress. |
| Stg3a | Sb02g026630 | similar to Ethylene-binding protein-like | senescence, root growth | Ethylene affects root growth and senescence. A mutation in this gene changes sensitivity to ethylene. |
| Stg3a | Sb02g027150 | weakly similar to Putative auxin-induced protein family | auxin signalling | This gene could affect growth processes. |
| Stg3b | Sb02g027470 | similar to Putative auxin-independent growth promoter | growth | This locus might affect leaf size. |
| Stg3b | Sb02g028420 | Squamosa promoter-binding-like protein 17 | growth | SPL transcription factors are involved in growth processes, eg temporal regulation of shoot develompment. SPL14 is also known as WEALTHY FARMERS PANICLE which reduces tiller number, but increases spikelet number in rice (Luo 2012). |
| Stg3b | Sb02g029210 | similar to Os0990505400 (OsPIN9) protein | root growth | OsPIN9 has a role in adventitious root growth (Wang 2009) |
| Stg3b | Sb02g029300 | Squamosa promoter-binding-like protein 17 | axillary bud growth, spikelet architecture (grain number) | SPL transcription factors are involved in growth processes, eg temporal regulation of shoot develompment. SPL14 is also known as WEALTHY FARMERS PANICLE which reduces tiller number, but increases spikelet number in rice (Luo 2012). |
| Stg3b | Sb02g029630 | similar to Auxin-induced protein-like | auxin signalling | This gene could affect growth processes. |
| Stg4 | Sb05g006842 | protein brassinosteroid LRR receptor | axillary bud growth, senescence, auxin transport | Brassinosteroids up-regulate auxin efflux carriers ABCB/PGP19 and have been associated with senescence. |
| Stg4 | Sb05g006860 | protein brassinosteroid LRR receptor | axillary bud growth, senescence, auxin transport | Brassinosteroids up-regulate auxin efflux carriers ABCB/PGP19 and have been associated with senescence. |
| Stg4 | Sb05g007130 | weakly similar to Putative far-red impaired response protein | axillary bud growth | This gene could affect perception of neighbours and have an impact on tiller number. |
| Stg4 | Sb05g007210 | protein cytochrome P450 84A1 | axillary bud growth, strigolactone pathway | This gene might alter the biosynthesis of strigolactones. Strigolactones in turn are down-regulators of tillering. |
| Stg4 | Sb05g007270 | protein gibberellin receptor GID1L2 | cell elongation | Gibberellins destabilise DELLA proteins which are suppressors of elongation. This gene could have an effect on leaf size. |
| Stg4 | Sb05g007290 | protein gibberellin receptor GID1L2 | cell elongation | Gibberellins destabilise DELLA proteins which are suppressors of elongation. This gene could have an effect on leaf size. |
| Stg4 | Sb05g007310 | protein sucrose-phosphate synthase | assimilation | Sucrose is a photoassimilate and required for growth. |
| Stg4 | Sb05g007520 | Aquaporin SIP1-1 | transpiration | aquaporins have been associated with transport of water molecules. |
| Stg4 | Sb05g008460 | protein gibberellin 20 oxidase 2 | cell elongation | Gibberellins destabilise DELLA proteins which are suppressors of elongation. This gene could have an effect on leaf size. |
| Stg4 | Sb05g008510 | protein OsIAA29 - Auxin-responsive | auxin signalling | This gene could affect growth processes. |
| Stg4 | Sb05g008512 | protein OsIAA29 - Auxin-responsive | auxin signalling | This gene could affect growth processes. |
| Stg4 | Sb05g008610 | protein gibberellin receptor GID1L2 | cell elongation | Gibberellins destabilise DELLA proteins which are suppressors of elongation. This gene could have an effect on leaf size. |
| Stg4 | Sb05g009410 | similar to Aminotransferase, putative | nitrogen assimilation | This gene could affect the maintenance of green leaf area. |
| Stg4 | Sb05g010310 | protein indole-3-acetic acid-amido | axillary bud growth, leaf size, auxin biosynthesis | This gene might encode auxin biosynthesis. |
| Stg4 | Sb05g010320 | protein indole-3-acetic acid-amido | axillary bud growth, leaf size, auxin biosynthesis | This gene might encode auxin biosynthesis. |
| Stg4 | Sb05g010326 | protein indole-3-acetic acid-amido | axillary bud growth, leaf size, auxin biosynthesis | This gene might encode auxin biosynthesis. |
| Stg4 | Sb05g010360 | protein cytochrome P450 86A2 | axillary bud growth, strigolactone pathway | This gene might alter the biosynthesis of strigolactones. Strigolactones in turn are down-regulators of tillering. |
| Stg4 | Sb05g011296 | protein cytochrome P450 51, putative | axillary bud growth, strigolactone pathway | This gene might alter the biosynthesis of strigolactones. Strigolactones in turn are down-regulators of tillering. |

TABLE 1C-continued

Potential mechanism to confer stay-green phenotype

| Stg QTL | Gene ID | Annotation | Link in pathway | Potential mechanism to confer stay-green phenotype |
|---|---|---|---|---|
| Stg4 | Sb05g011430 | protein cytochrome P450 51, putative | axillary bud growth, strigolactone pathway | This gene might alter the biosynthesis of strigolactones. Strigolactones in turn are down-regulators of tillering. |
| Stg4 | Sb05g013160 | protein triacylglycerol lipase, leaf senescence, jasmonic acid biosynthetic process_GO | senescence, stress response | Jasmonic acid has been associated with stress response. |
| Stg4 | Sb05g015590 | protein growth regulator like | growth | This gene could affect leaf size or tiller number. |
| Stg4 | Sb05g016750 | protein cytochrome P450 78A4 | axillary bud growth, strigolactone pathway | This gene might alter the biosynthesis of strigolactones. Strigolactones in turn are down-regulators of tillering. |
| Stg4 | Sb05g017120 | similar to ABC transporter family protein, expressed | auxin efflux | ABC transporters are also know as PGP or MDR transporters and have a role in auxin efflux. They have been associated with stem length and some of these transporters interact with PINs and could therefore have an effect on axillary bud growth. |
| Stg4 | Sb05g017510 | squamosa promoter-binding-like protein 19 | axillary bud growth, spikelet architecture (grain number) | SPL transcription factors are involved in growth processes, eg temporal regulation of shoot develompment. SPL14 is also known as WEALTHY FARMERS PANICLE which reduces tiller number, but increases spikelet number in rice (Luo 2012): |

BRIEF DESCRIPTION OF THE FIGURES

Some figures contain color representations or entities. Color photographs are available from the Patentee upon request or from an appropriate Patent Office. A fee may be imposed if obtained from a Patent Office.

FIG. 4 is a tabulated representation showing the marker data (BB/TT) for the Stg1 fine-mapping population. BB designates both alleles are like the allele of the stay-green parent, TT designates both alleles are like the allele of the senescent parent, x designates no marker data available. Black and red font color for markers designate actual and inferred marker status, respectively. Green and brown shading for genotypes across the top designate a stay-green (low tillering) and senescent (high tillering) phenotype, respectively. Markers highlighted in pink indicate the likely location of a "low-tillering" gene.

FIG. 6 is a tabulated representation showing marker data (BB/TT) for a subset of the Stg1 fine-mapping population. BB designates both alleles are like the allele of the stay-green parent, TT designates both alleles are like the allele of the senescent parent, BT designates one allele is like the allele of the stay-green parent, the other is like the allele of the senescent parent, x designates no marker data available. Green and brown shading for genotypes across the top designate a stay-green (low tillering) and senescent (high tillering) phenotype, respectively. Markers highlighted in pink indicate the likely location of a "low-tillering" gene.

FIG. 10 is a tabulated representation showing marker data (BB/TT) for the Stg1 fine-mapping population. BB designates both alleles are like the allele of the stay-green parent, TT designates both alleles are like the allele of the senescent parent, BT designates one allele is like the allele of the stay-green parent, the other is like the allele of the senescent parent, x designates no marker data available. Black and red font color for markers designated actual and inferred marker status, respectively. Green and brown shading for genotypes across the top designate a stay-green (low-tillering) and senescent (high-tillering) phenotype, respectively. Markers highlighted in pink indicate the likely location of a "low-tillering" gene.

FIG. 12 is a tabulated representation showing marker data (BB/TT) for the Stg1 fine-mapping population. BB designates both alleles are like the allele of the stay-green parent, TT designates both alleles are like the allele of the senescent parent, BT designates one allele is like the allele of the stay-green parent, the other is like the allele of the senescent parent, x designates no marker data available. Black and red font color for markers designate actual and inferred marker status, respectively. Green and brown shading for genotypes across the top designate a stay-green (low-tillering) and senescent (high-tillering) phenotype, respectively. Markers highlighted in pink indicate the likely location of a "low-tillering" gene.

FIG. 15 is a tabulated representation showing marker data (BB/TT) for the Stg1 fine-mapping population. BB designates both alleles are like the allele of the stay-green parent, TT designates both alleles are like the allele of the senescent parent, BT designates one allele is like the allele of the stay-green parent, the other is like the allele of the senescent parent, x designates no marker data available. Black and red font color for markers designate actual and inferred marker status, respectively. Green and brown shading for genotypes across the top designate a stay-green (small leaf) and senescent (large leaf) phenotype, respectively. Markers highlighted in pink indicate the likely location of a "small leaf size" gene.

FIG. 22 is a tabulated representation showing marker data (BB/TT) for a subset of the Stg1 fine-mapping population. BB designates both alleles are like the allele of the stay-green parent, TT designates both alleles are like the allele of the senescent parent, BT designates one allele is like the allele of the stay-green parent, the other is like the allele of the senescent parent, x designates no marker data available. Black and red font color for markers designate actual and inferred marker status, respectively. Green and brown shading for genotypes cross the top designate a stay-green (short leaf) and senescent (long leaf) phenotype, respectively. Markers highlighted in pink indicate the likely location of a "small leaf size" gene.

FIG. 23 is a schematic representation showing the likely marker location (pink shading) of a gene conferring both "low-tillering" and "small-leaf size" phenotypes in the Stg1 region.

FIG. 46 is a tabulated representation-showing marker data (BB/TT) for RTx7000 (recurrent parent), 6078-1 (NIL containing complete Stg1 region), 10709-5 (NIL containing lower 1/3 of the Stg1 region), 10604-5 (NIL containing upper 3/4 of the Stg1 region), and 10568-2 (NIL containing upper 1/2 of the Stg1 region). BB designates both alleles are like the allele of the stay-green parent, TT designates both alleles are like the allele of the senescent parent, BT designates one allele is like the allele of the stay-green parent, the other is like the allele of the senescent parent, x designates no marker data available. Black and red font color for markers designate actual and inferred marker status, respectively.

FIG. 64 A shows simulated leaf area index (LAI) over time (0-120 days after sowing). FIG. 64 B shows simulated extractable soil water (EWS) over time (0-120 days after sowing). FIG. 64 C shows simulated biomass and grain yield (kg/ha) over time (0-120 days after sowing).

DETAILED DESCRIPTION

Figure 1:
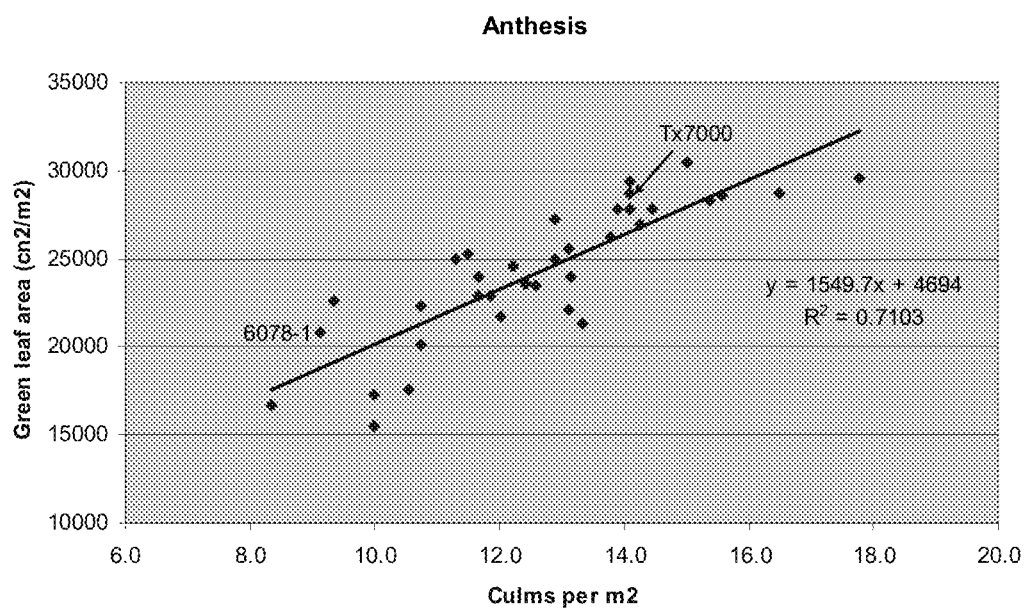
FIG. 1 is a graphical representation showing the relation between culms per $m^2$ and green leaf area at anthesis in a range of NILs containing various Stg introgressions.

Throughout this specification, unless the context requires otherwise, the word "comprise", or variations such as "comprises" or "comprising", will be understood to imply the inclusion of a stated element or integer or method step or group of elements or integers or method steps but not the exclusion of any other element or integer or method step or group of elements or integers or method steps.

As used in the subject specification, the singular forms "a", "an" and "the" include plural aspects unless the context clearly dictates otherwise. Thus, for example, reference to "a locus" includes a single locus, as well as two or more loci; reference to "an auxin" includes a single auxin, as well as two or more auxins; reference to "the disclosure" includes a single and multiple aspects taught by the disclosure. Aspects taught, described and/or claimed is herein are encompassed by the term "invention". All aspects taught herein are enabled within the width of the disclosure and its claims.

The present disclosure teaches loci associated with and which facilitate the stay-green phenotype in crop including cereal plants. The loci are referred generically as StgX wherein X is a numeral from 1 and above corresponding to a genetic locus or genetic loci region on a particular chromosome in a crop plant. A sub-region is referred to as StgXm where m is an alphabetical designation of a region within StgX. The level and/or location of expression of an StgX locus is taught herein to facilitate a physiological and genetic network which induces or promotes a shift in water use by the crop plant to the post-arithesis period or increased accessibility of water during crop growth or increased transpiration efficiency thereby increasing harvest index (HI) and grain yield under water-limited conditions. "Expression" of an StgX includes up-regulating or down-regulating expression levels as well as selection of a polymorphic variant which is expressed at a higher level or which encodes a more active or efficient product. An example of a "physiological network" includes a plant canopy architecture which induces or promotes a shift in water use by the crop plant to the post-anthesis period or increased accessibility of water during crop growth or increased transpiration efficiency thereby increasing harvest index (HI) and grain yield under water-limited conditions. The locus may itself confer this phenotype or a functional equivalent thereof such as a eDNA encoding a protein encoded by the locus. Hence, manipulation of the stay-green phenotype may be by recombinant engineering, breeding and selection as well as by chemical, radioactive or genetic mutagenesis followed by selection.

In an embodiment, X is 1 and the region is Stg1 on, chromosome 3 between markers txp581 and txp38 of sorghum or its equivalent in another plant genome. In another embodiment, X is 2 and the region is Stg2 on chromosome 3 between markers txp530 and txp31 of sorghum or its equivalent in another plant genome. In yet another embodiment, X is 3 and the region is Stg3 is divided into Stg3a (region between txp298 and sPb-2568) and Stg3b (region between sPb-2568 and txp179) of sorghum or its equivalent in another plant genome. In still another embodiment, X is 4 and the region is Stg4 on chromosome 5 between markers txp583 and txp15 of sorghum or its equivalent in another plant genome. These markers or markers adjacent or proximal thereto are also useful in breeding programs to generate plants which exhibit the stay-green phenotype in sorghum or other plants.

Accordingly, enabled herein is a method for generating a genetically modified plant which uses water more efficiently than a non-genetically modified plant of the same species, the method comprising introducing into the plant or a parent of the plant an agent selected form the list consisting of: (i) a genetic agent comprising one or more loci, located in a region selected from Stg1 on chromosome 3 between txp581 and txp38; Stg2 on chromosome 3 between txp530 and txp31; Stg3a (region between txp298 and sPb-2568); Stg3b (region between sPb-2568 and txp179); and Stg4 on chromosome 5 between txp283 and txp15 of sorghum or its equivalent in another plant, the level of expression of which, is associated with or facilitates a stay-green phenotype, which phenotype includes a shift in water use to the post-anthesis period or increased accessibility of water during crop growth or increased transpiration efficiency resulting in increased harvest index and grain yield under water-limited conditions; and (ii) an agent which up-regulates or down-regulates an indigenous form of the locus or loci.

In an embodiment, the StgX regions are defined as follows Stg1: Fine-mapped region between txp563 and txp581 containing 60 annotated genes, Larger middle region between txp440 and txp580 containing 307 annotated genes, Candidates in tail between txp580 and txp38 containing 178 annotated genes; Stg2: Fine-mapped region between txp512 and txp2 containing 15 annotated genes, Larger region between txp31 and txp530 containing 241 annotated genes; Stg3a: Entire region between txp298 and sPb-2568 containing 520 annotated genes; Stg3b: Entire region between sPb-2568 and txp179 containing 291 annotated genes; Stg4: Entire region defined by txp283 and txp15 containing 306 annotated genes. These markers or markers adjacent or proximal thereto are also useful in breeding programs to generate plants which exhibit the stay-green phenotype in sorghum or other plants.

Accordingly, enabled herein is a method for generating a genetically modified plant which uses water more efficiently than a non-genetically modified plant of the same species, the method comprising introducing into the plant or a parent of the plant an agent selected form the list consisting of Stg1: Fine-mapped region between txp563 and txp581 containing 60 annotated genes, Larger middle region between txp440 and txp580 containing 307 annotated genes, Candidates in tail between txp580 and txp38 containing 178 annotated genes; Stg2: Fine-mapped region between txp512 and txp2 containing 15 annotated genes, Larger region between txp31 and txp530 containing 241 annotated genes; Stg3a: Entire region between txp298 and sPb-2568 containing 520 annotated genes; Stg3b: Entire region between sPb-2568 and txp179 containing 291 annotated genes; Stg4: Entire region defined by txp283 and txp15 containing 306 annotated genes; sorghum or its equivalent in another plant, the level of expression of which, is associated with or facilitates a stay-green phenotype, which phenotype includes a shift in water use to the post-anthesis period or increased accessibility of water during crop growth or increased transpiration efficiency resulting in increased harvest index and grain yield under water-limited conditions; and an agent which up-regulates or down-regulates an indigenous form of the locus or loci.

Accordingly, enabled herein is a method for generating a genetically modified plant which uses water more efficiently than a non-genetically modified plant of the same species, the method comprising introducing into the plant or a parent of the plant an agent selected form the list consisting of a locus selected from Table 1B of sorghum or its equivalent in another plant, the level of expression of which, is associated with or facilitates a stay-green phenotype, which phenotype includes a shift in water use to the post-anthesis period or increased accessibility of water during crop growth or increased transpiration efficiency resulting in increased harvest index and grain yield under water-limited conditions; and an agent which up-regulates or down-regulates an indigenous form of the locus or loci.

Accordingly, enabled herein is a method for generating a genetically modified plant which uses water more efficiently than a non-genetically modified plant of the same species, the method comprising introducing into the plant or a parent of the plant an agent selected form the list consisting of a locus selected from Table 1A of sorghum or its equivalent in another plant, the level of expression of which, is associated with or facilitates a stay-green phenotype, which phenotype includes a shift in water use to the post-anthesis period or increased accessibility of water during crop growth or increased transpiration efficiency resulting in increased harvest index and grain yield under water-limited conditions; and an agent which up-regulates or down-regulates an indigenous form of the locus or loci.

Without intending to limit the present teachings to any one theory or mode of action, the level of expression of StgX alone or in combination with the operation of a genetic or physiological network alters plant architecture including plant canopy architecture to enhance or otherwise promote efficient water use. In one aspect, the modified architecture is modified plant canopy architecture.

The term "progeny" includes immediate progeny as well as distant relatives of the plant, as long as it stably expresses the StgX trait first introduced to an earlier parent:

Reference to a "crop plant" includes a cereal plant. The crop plants enabled herein include sorghum, wheat, oats, maize, barley, rye and rice, abaca, alfalfa, almond, apple, asparagus, banana, bean-phaseolus, blackberry, broad bean, canola, cashew, cassava, chick pea, citrus, coconut, coffee, corn, cotton, fig, flax, grapes, groundnut, hemp, kenaf, lavender, mano, mushroom, olive, onion, pea, peanut, pear, pearl millet, potato, ramie, rapeseed, ryegrass, soybean, strawberry, sugarbeet, sugarcane, sunflower, sweetpotato, taro, tea, tobacco, tomato, triticale, truffle and yarn. In an example, the drought tolerance mechanisms of sorghum are used to promote drought tolerance in sorghum as well as other crop plants. In an example, the genetically modified plant uses water more efficiently than a non-genetically modified plant of the same species. A "genetically modified plant" may be produced by recombinant DNA means, selected via a breeding protocol and/or selected following a mutagenesis procedure.

By "drought tolerance" includes drought escape, drought adaptation, drought resistance, reduced sensitivity to drought conditions, drought insensitive, enhanced water use efficiency as well as an ability to shift water use to the post-anthesis period or increased accessibility of water during crop growth or increased transpiration efficiency, thereby increasing HI and grain yield under water-limited conditions. Plants exhibiting drought tolerance are described as "drought adapted plants" or "plants exhibiting reduced sensitivity to water-limited conditions". It is taught herein that drought tolerance is induced, facilitated by or otherwise associated with the stay-green phenotype.

By "genetically modified", in relation to a plant, includes an originally derived genetically modified plant as well as any progeny, immediate or distant which stably express the stay-green trait. Hence, the present disclosure teaches both classical breeding techniques to introduce the genetic agent, i.e. a stay-green locus or loci or a functional equivalent thereof such as cDNA or a genomic fragment or an agent which alters expression of the locus or the protein encoded thereby as well as genetic engineering technology. The latter is encompassed by the terms "genetic engineering means" and "recombinant means". Markers defining StgX can also be screened during breeding protocols to monitor transfer of particular genetic regions. Furthermore, a specific StgX or StgX region can be genetically inserted by recombinant means into a plant cell or plant callus and a plantlet regenerated. A "genetically modified" plant includes a parent or any progeny as well as any products of the plant such as grain, seed, propagating material, pollen and ova. Regions defining StgX in sorghum are located at Stg1 on chromosome 3 between txp581 and txp38; Stg2 on chromosome 3 between txp530 and txp31; Stg3 is divided into Stg3a (region between txp298 and sPb-2568) and Stg3b (region between sPb-2568 and txp179) and Stg4 on chromosome 5 between txp283 and txp15. In particular, regions defining Stg in sorghum are located at Stg1: Fine-mapped region between txp563 and txp581 containing 60 annotated genes, Larger middle region between txp440 and txp580 containing 307 annotated genes, Candidates in tail between txp580 and txp38 containing 178 annotated genes; Stg2: Fine-mapped region between txp512 and txp2 containing 15 annotated genes, Larger region between txp31 and txp530 containing 241 annotated genes; Stg3a: Entire region between txp298 and sPb-2568 containing 520 annotated genes; Stg3b: Entire region between sPb-2568 and txp179 containing 291 annotated genes; Stg4: Entire region defined by txp283 and txp15 containing 306 annotated genes. The present disclosure extends to equivalent regions or equivalent loci located in these regions in non-sorghum plants.

Reference to the "stay-green phenotype" includes characteristics selected from enhanced canopy architecture plasticity, reduced canopy size, enhanced biomass per unit leaf area at anthesis, higher transpiration efficiency, increased water use during grain filling, increased plant water status during grain filling, reduced pre:post anthesis biomass ratio, delayed senescence, increased grain yield, larger grain size, and reduced lodging.

By "StgX" includes QTLs at Stg 1, 2, 3 (including Stg3a and Stg3b), 4, etc which represent a particular locus or group or region of loci associated with drought adaptation. In an embodiment StgX is Stg1 located on chromosome 3 between markers txp581 and txp38 of sorghum. In another embodiment, the StgX is Stg2 located on chromosome 3 between markers txp530 and txp31 of sorghum. In still another embodiment, the StgX is Stg3a (region between txp298 and sPb-2568) or Stg3b (region between sPb-2568 and txp179) of sorghum. In yet another embodiment, the StgX is Stg4 located on chromosome 5 between markers txp283 and txp15 of sorghum. In an embodiment defined is Stg1: Fine-mapped region between txp563 and txp581 containing 60 annotated genes, Larger middle region between txp440 and txp580 containing 307 annotated genes, Candidates in tail between txp580 and txp38 containing 178 annotated genes; Stg2: Fine-mapped region between txp512 and txp2 containing 15 annotated genes, Larger region between txp31 and txp530 containing 241 annotated genes; Stg3a: Entire region between txp298 and sPb-2568 containing 520 annotated genes; Stg3b: Entire region between sPb-2568 and txp179 containing 291 annotated genes; Stg4: Entire region defined by txp283 and txp15 containing 306 annotated genes. The StgX contemplated for use herein may be an isolated naturally occurring genetic element or a particular variation may be artificially induced or selected through classical or recombinant breeding practices. For example, a particular polymorphic variant may result in high expression levels or a more stable expression product or a product which is more or less pleiotropic within a genetic or physiological network. Reference to an StgX includes a cDNA encoding a product as well as a genomic locus or region which may or may not include a promoter region, 5' and 3' untranslated regions, introns, exons and the like. A "cDNA" is an example of a functional equivalent of an StgX.

The present disclosure further teaches markers for the stay-green phenotype for use in breeding programs for drought tolerant plants, the markers comprising a quantitative trait locus (QTL), stay-green X (StgX), wherein X is a numeral corresponding to the location on a chromosome within a sorghum plant or its equivalent in another plant which encodes a product which is associated with or facilitates a stay-green phenotype which phenotype includes a shift in water use to the post-anthesis period or increased accessibility of water during crop growth or increased transpiration efficiency resulting in increased harvest index and grain yield under water-limited conditions. Examples of suitable markers include Stg1 on chromosome 3 between txp581 and txp38; Stg2 on chromosome 3 between txp530 and txp31; Stg3 which is divided into Stg3a (region between txp298 and sPb-2568) and Stg3b (region between sPb-2568 and txp179) and Stg4 on chromosome 5 between txp283 and txp15. These markers are based on the sorghum genome but extend to the equivalents in another plant genome. Examples of suitable markers include Stg1: Fine-mapped region between txp563 and txp581 containing 60 annotated genes, Larger middle region between txp440 and txp580 containing 307 annotated genes, Candidates in tail between txp580 and txp38 containing 178 annotated genes; Stg2: Fine-mapped region between txp512 and txp2 containing 15 annotated genes, Larger region between txp31 and txp530 containing 241 annotated genes; Stg3a: Entire region between txp298 and sPb-2568 containing 520 annotated genes; Stg3b: Entire region between sPb-2568 and txp179 containing 291 annotated genes; Stg4: Entire region defined by txp283 and txp15 containing 306 annotated genes.

Examples of suitable markers include a locus listed in Tables 1A through 1C.

Examples of suitable markers include a locus listed in Table 1B.

Hence, a set of biomarkers is enabled herein including txp581 to txp38 on chromosome 3 of sorghum; txp530 to txp31 on chromosome 3 of sorghum; txp298 to sPb-2568 and sPb-2568 to txp179 on chromosome 2 of sorghum; and txp283 to txp15 on chromosome 5 of sorghum, or the equivalent in the genome of another plant. A set of biomarkers is further enabled herein including Stg1: Fine-mapped region between txp563 and txp581 containing 60 annotated genes, Larger middle region between txp440 and txp580 containing 307 annotated genes, Candidates in tail between txp580 and txp38 containing 178 annotated genes; Stg2: Fine-mapped region between txp512 and txp2 containing 15 annotated genes, Larger region between txp31 and txp530 containing 241 annotated genes; Stg3a: Entire region between txp298 and sPb-2568 containing 520 annotated genes; Stg3b: Entire region between sPb-2568 and txp179 containing 291 annotated genes; Stg4: Entire region defined by txp283 and txp15, containing 306 annotated genes. A set of biomarkers is further taught as listed in Table 1B. Such markers are useful in breeding protocols designed to generate plants exhibiting the stay-green phenotype. Alternatively, markers adjacent or proximal to these regions may be used in the breeding protocol.

The present disclosure teaches the use of genetic material corresponding to an StgX or genetic material which alters expression of an indigenous StgX locus or a genetic equivalent thereof to facilitate the stay-green phenotype. An "indigenous" locus means a locus present in a parent plant prior to breeding, recombinant intervention or mutagenesis. By "alters" includes "modulates".

The present disclosure enables plants genetically modified according to the methods taught herein as well as seeds, fruit, flowers and other reproductive or other propagating material. The present disclosure also teaches use of root stock and propagating stock. This is based on the premise that the seeds, fruit, flowers, reproductive and propagating material exhibit or can pass on the stay-green phenotype introduced into the ultimate parent(s).

Reference to an "agent which up-regulates StgX" includes promoters, microRNAs, genes and chemical compounds which facilitate increased expression of StgX or increased activity of a StgX product. An agent may also be an intron of a genomic StgX which is part of an natural genetic network to facilitate expression. An agent may also be a functional equivalent of a StgX (or QTL) such as a cDNA.

Figure 68:
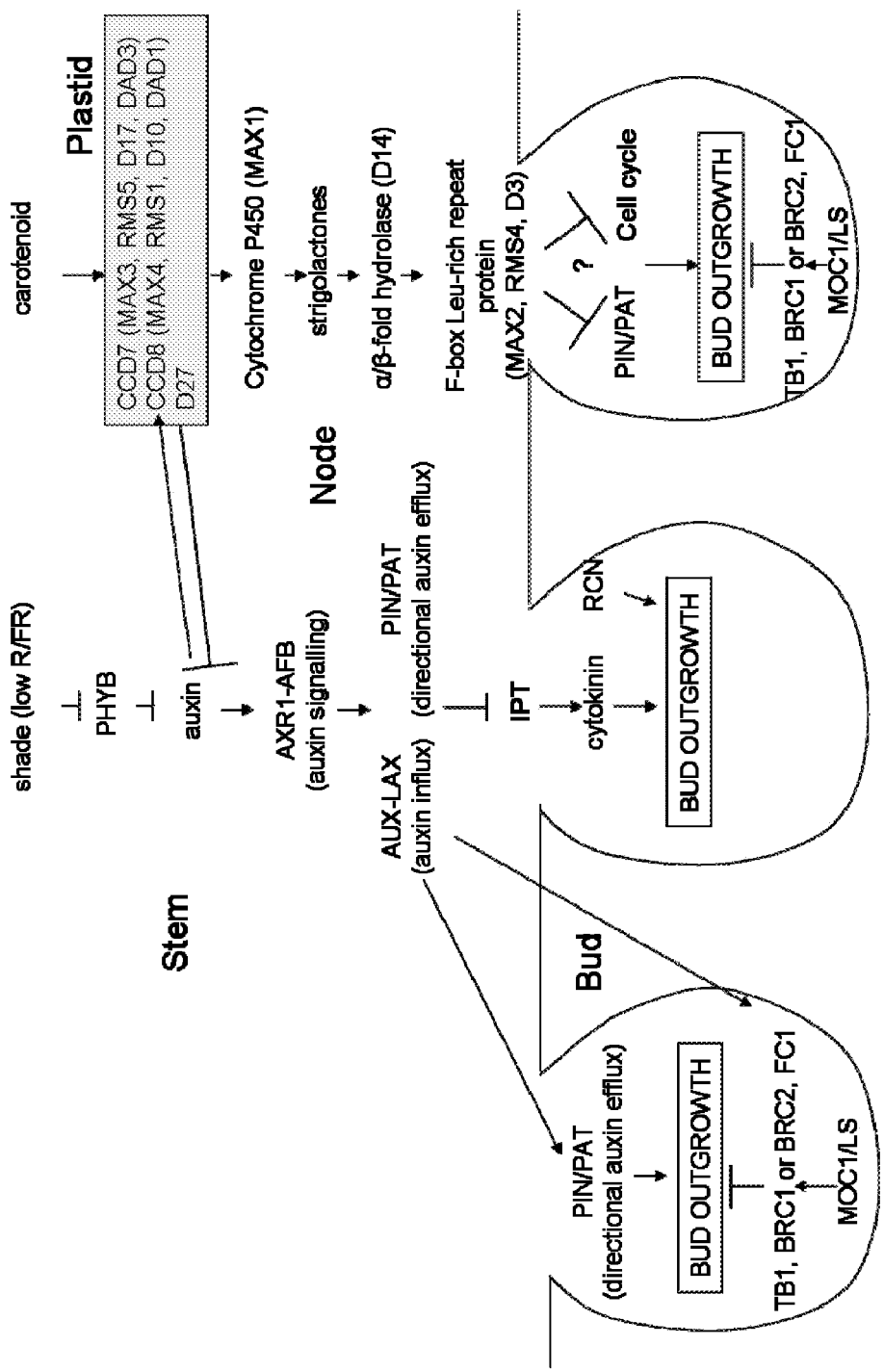
FIG. 68 is a diagrammatic representation of the network of genes identified at Stg1, Stg2, Stg3a, Stg3b and Stg4 and the proposed affect on the stay-green phenotype.

In an embodiment, the StgX encodes a locus selected from Stg1, Stg2, Stg3a, Stg3b and Stg4 as listed in Table 1B (and Table 1A). The interaction of some of these loci in various networking pathways is shown in FIG. 68.

In an embodiment, the StgX encodes a locus selected from Stg1, Stg2, Stg3a. Stg3b and Stg4 as listed in Table 1B (and Table 1C).

In an embodiment, the StgX encodes a PIN protein.

A PIN protein produces an auxin gradient in cells and contains transmembrane domain and is mainly localized in the plasma membrane. PIN proteins are the rate limiting factors of auxin transport and provide vectorial direction for the auxin flows. Taught herein is that an StgX encodes a PIN protein. Introduction of a StgX de novo in a plant or elevation of its expression or the expression of its homolog or ortholog facilitates exhibition of one or more features or sub-features associated with the stay-green phenotype.

As indicated above, PIN proteins are efflux carriers of auxin which mediate polar auxin transport (PAT) from cell to cell as opposed to the transport of auxin through the xylem (Rashotte et al. (2000) *Plant Cell* 13:1683-1697; Friml et al. (2003) *Current Opinion in Plant Biology* 6:7-12). The term 'PIN' is derived from the PIN-like inflorescence which develops in *Arabidopsis* when auxin transport is defective. A number of PIN proteins are known (see Forestan and Varotto (2009) *Plant Physiology*; and Wang et al. (2009) supra). The present disclosure teaches SbPINn, where n is a numeral from 1 through 11 (Table 1A). However, the instant disclosure teaches equivalent or homolog PINs from other plants.

In an embodiment, SbPIN2 (for Sorghum bicolor auxin efflux carrier component 2), is at Stg2 on chromosome 3, fine-mapped to a region between markers txp512 and txp530 and SbPIN4 is at Stg1, on chromosome 3, fine-mapped to a region between markers txp563 and txp 442 are taught herein to be responsible for the stay-green trait in sorghum resulting in a range of phenotypes that confer drought adaptation via increased water use at anthesis (due to reduced tillering and smaller leaves), increased water accessibility (due to enhanced root:shoot ratio), increased transpiration efficiency under mild water deficit (due to higher leaf nitrogen concentration), increased biomass per leaf area under terminal water deficit (due to increased transpiration per leaf area) and increased grain yield, grain size and lodging resistance. Reference to the txp markers in sorghum extends to the equivalent markers in the genome of other plants. SbPIN4 corresponds to the OsPIN5 and SbPIN2 corresponds to OsPIN3a. The term "Os" refers to rice (refer to Table 1A).

Another aspect taught herein is a method for generating a genetically modified plant which uses water more efficiently than a non-genetically modified plant of the same species, the method comprising introducing into a plant or parent of the plant a one or more loci of a functional equivalent thereof or an agent which modulates expression of an indigenous one or more loci wherein the level of expression of the one or more loci causes a shift in water use to the post-anthesis period or increased accessibility of water during crop growth or increased transpiration efficiency resulting in increased harvest index and grain yield under water limiting conditions.

The present disclosure further teaches a method for generating a genetically modified plant which uses water more efficiently than a non-genetically modified plant of the same species, the method comprising introducing into a plant or parent of the plant a locus selected from the list provided in Table 1B or a molecule which modulates expression of an indigenous locus.

The present disclosure further teaches a method for generating a genetically modified plant which uses water more efficiently than a non-genetically modified plant of the same species, the method comprising introducing into a plant or parent of the plant a locus or cDNA encoding a PIN protein, or a molecule which modulates expression of an indigenous PIN locus. Examples of PINs include SbPN4 and SbPIN2 and other SbPINs listed in Table 1A as well as their equivalent in other plants.

It is taught by the present disclosure that sorghum SbPIN4 and SbPIN2 are major drought adaptation genes which have been fine-mapped in multiple studies to a region between markers txp536 and txp442 on chromosone3 (Stg1) and a region between makers txp512 and txp530 on chromosome 3 (Stg2). Differences in auxin signalling explain all of the multiple phenotypes observed in plants containing SbPIN4 or 2. Another gene is SbPIN5. Phenotypes exhibited by SbPIN4 and SbPIN2 plants are explained directly by changes in auxin efflux and include reduced tillering, smaller leaves (both length and width), reduced leaf mass and increased root:shoot ratio. Phenotypes exhibited by SbPIN4 and SbPIN2 plants can also be explained indirectly (or as emergent consequences of these direct effects) and include increased availability of water at anthesis, higher leaf N concentration at anthesis, increased transpiration and biomass per unit leaf area, higher transpiration efficiency, retention of green leaf area during grain filling, increased harvest index, higher grain yield, larger grain size and increased lodging resistance. Enabled herein is that SbPIN4 or 2 is operative alone or together across other major cereal and crop species to enhance drought adaptation in localities worldwide where water limits crop growth post-anthesis.

In accordance with the teachings of the present specification, the level of expression of an StgX such as Stg1, Stg2, Stg3a, Stg3b and/or Stg4 (as defined in Table 1B), (SbPIN4) and/or Stg2 (SbPIN2) [see Table 1A] in all or certain plant tissue confers or confer drought adaptation both directly, and indirectly, ultimately leading to higher grain yield, larger grain size, and lodging resistance under water-limited conditions.

In accordance with the teachings of the present specification, the level of expression of an StgX such as Stg1 (SbPIN4) and/or Stg2 (SbPIN2) in all or certain plant tissue confers or confer drought adaptation both directly, and indirectly, ultimately leading to higher grain yield, larger grain size, and lodging resistance under water-limited conditions. This aspect extends to OsPIN5 which corresponds to SbPIN4 and OsPIN3a which corresponds to SbPIN2.

Other PIN proteins taught herein include those listed in Table 1A and their equivalents in other plants.

In yet another embodiment, StgX encodes a Spl (squamosa promoter binding protein-like) such as but not limited to Spl14.

An Spl controls shoot branching and higher grain yield (see Jiao et al. (2010) supra; Miura et al. (2010) supra).

In another embodiment, the present disclosure teaches a method for generating a genetically modified plant which uses water more efficiently than a non-genetically modified plant of the same species, the method comprising introducing into a plant or parent of the plant a locus or cDNA which encodes CCD7/8 or a functional homolog or ortholog thereof or an agent which modulates the level of expression of an indigenous CCD7/8 to cause a shift in water use to the post-anthesis period or increased accessibility of water during crop growth or increased transpiration efficiency resulting in increased harvest index and grain yield under water limiting conditions.

In another embodiment, the present disclosure teaches a method for generating a genetically modified plant which uses water more efficiently than a non-genetically modified plant of the same species, the method comprising introducing into a plant or parent of the plant a locus or cDNA which encodes WFP or a functional homolog or ortholog thereof or an agent which modulates the level of expression of an indigenous WFP to cause a shift in water use to the post-anthesis period or increased accessibility of water during crop growth or increased transpiration efficiency resulting in increased harvest index and grain yield under water limiting conditions.

In another embodiment, the present disclosure teaches a method for generating a genetically modified plant which uses water more efficiently than a non-genetically modified plant of the same species, the method comprising introducing into a plant or parent of the plant a locus or cDNA which encodes Spl or a functional homolog or ortholog thereof or an agent which modulates the level of expression of an indigenous Spl to cause a shift in water use to the post-anthesis period or increased accessibility of water during crop growth or increased transpiration efficiency resulting in increased harvest index and grain yield under water limiting conditions.

In another embodiment, the present disclosure teaches a method for generating a genetically modified plant which uses water more efficiently than a non-genetically modified plant of the same species, the method comprising introducing into a plant or parent of the plant a locus or cDNA which encodes CCD7/8 or a functional homolog or ortholog thereof or an agent which modulates the level of expression of an indigenous CCD7/8 to cause a shift in water use to the post-anthesis period or increased accessibility of water during crop growth or increased transpiration efficiency resulting in increased harvest index and grain yield under water limiting conditions.

In an embodiment, the plants are modified or selected to change the level of expression of two or more of SbPIN1 to 11, IPA-1, WFP, Spl and/or CCD7/8. This includes two or more SbPINs. By "two or more" includes 2, 3, 4, 5, 6, 7, 8, 9, 10 and 11.

Increased water availability at anthesis is achieved via reduced water use due to two mechanisms (reduced tillering and smaller leaves) in plants containing the Stg1 or Stg2 regions. Both mechanisms, individually, appear to reduce canopy size by about 9%, on average. The 'low-tillering' mechanism dominates in low density environments when tillering potential is high. The 'small-leaf' mechanism dominates in high density environments when tillering potential is low. Combined, these two mechanisms provide crop plants with considerable plasticity to modify canopy architecture in response to the severity of water limitation.

Stay-green enhances canopy architecture plasticity via constitutive and adaptive responses. Canopy size in Stg1 or Stg2 is reduced by about 5%, even when water is not limiting (constitutive response). Canopy size is further reduced (adaptive response) in a mild drought (~10%) and more severe drought (~15%). Low tillering is primarily a constitutive response. Small leaf size is both a constitutive and adaptive response.

Furthermore, it is proposed herein that the Stg1 or Stg2 regions confer drought adaptation by reducing canopy size (via reduced tillering and smaller leaves) and reducing crop water use at anthesis. This is shown by a high correlation (r2=0.9) between canopy size and crop water use in artificial drought (rain-out shelter [ROS]) and lysimeter studies.

Increased water availability at anthesis may also be achieved via increased water accessibility (better water extraction and deeper or greater lateral spread).

Stay-green enhances biomass per unit leaf area at anthesis. Assuming root mass is equivalent (or at least not significantly less), these differences could be explained by differences in transpiration (T) per unit leaf area [LA](T/LA) and/or transpiration efficiency (TE). Lysimetry studies indicate that increases in T/LA, rather than TE, drive the observed increases in biomass per leaf area. Note that increased T/LA only occurred when water deficit was sufficient to reduce leaf area. When water deficit was less severe (i.e. not enough to reduce leaf area), then T/LA decreased, resulting in higher TE.

Higher TE in StgX lines such as Stg1 or Stg2 lines is also observed when water deficit is less severe. Increased TE via introgressing Stg1 or Stg2 is proposed to be due to a) proportionally higher photosynthetic capacity compared with stomatal conductance, due to smaller, thinner and greener leaves, and/or b) a decrease in transpiration while maintaining biomass. Lysimetry studies indicate that both of these mechanisms contribute to higher TE in Stg1 or Stg2 lines, with the reduction in transpiration the primary mechanism.

Changes in transpiration per unit leaf area is proposed to be due to a) number of stomata, b) size of stomatal aperture, c) changes in the timing of stomatal opening and closing relative to VPD, and/or d) the number of hair base cells (which affects the boundary layer and hence T/LA). Introgressing Stg1, for example, into RTx7000 modified leaf anatomy by increasing the number of bundle sheath cells surrounding the vascular bundle.

Differences in the morphology of leaves are apparent between RTx7000 and Stg1 or Stg2. In this case, there were more and smaller bundle sheaths surrounding the vascular bundle in Stg1 or Stg2. Also, there were fewer stomata and more hair base cells per unit leaf area (leaves 7 and 10) in Stg1 or Stg2 compared with RTx7000.

Increased water use during grain filling is achieved via (i) increased water availability at anthesis and (ii) increased water accessibility (better water extraction and deeper or greater lateral spread) during grain filling.

Crop water use (CWU) before anthesis was negatively correlated with CWU after anthesis in an artificial drought (rain-out shelter [ROS]) experiment. Overall, a 25% increase in water use after anthesis (80 vs 60 mm) resulted in a 25% increase in grain yield (400 vs 300 g/m2). This translated to 50 kg/ha of grain for every additional mm of water available.

Increased water use during the grain filling period was exhibited by Stg1 and Stg2 under both low and high density treatments in a rain-out shelter (ROS) experiment. This was due primarily to (i) reduced water use at anthesis under high density, and (ii) increased water accessibility during grain filling under low density.

As taught herein, StgX such as Stg1 or Stg2 confers drought adaptation by being associated with pre- and post-anthesis biomass production. The Stg1 or Stg2 region, for example, reduce the pre:post anthesis biomass ratio below a critical level, increasing grain yield and lodging resistance.

In accordance with the present teachings, the level and location of expression of StgX such as Stg1, Stg2, Stg3 (including Stg3a and Stg3b) and/or Stg4 (e.g. as defined in Table 1B) facilitates one or more of the following phenotypes:

(i) delayed leaf senescence (stay-green), higher grain yield and lodging resistance are consequences of higher plant water status during grain filling (due to increased water use during grain filling);

(ii) introgressing StgX into a, for example, RTx7000 background increases plant water status at mid-grain filling, as indicated by a) higher relative water content (RWC), and b) lower leaf water potential (LWP);

(iii) higher grain yield and larger grain size are consequences of increased water availability during grain filling;

(iv) higher grain yield, larger grain size and increased lodging resistance are not mutually exclusive (i.e. all three traits are exhibited by StgX);
(v) yield and grain size advantage are relatively higher under severe terminal drought than mild terminal drought;
(vi) the benefit of the stay-green genes in a, for example, RTx7000 background (inbreds) occurs in the yield range of 1-3 t/ha (12-22%), followed by a lesser but still significant benefit in the 3-4 t/ha yield range (8-10%). There was, however, a small penalty associated with these regions (2-4%) at higher yield levels (5-8 t/ha) due to wetter conditions. Note that these yield ranges would be considerably higher in hybrids. Since the average sorghum grain yield for hybrids in the northern grain belt is about 2.5 t/ha, the benefit of the stay-green genes should be significant. No reduction in grain yield under wetter conditions (water not limiting) due to stay-green has been observed in hybrids;
(vii) introgressing StgX into, for example, RTx7000 also increases grain size by 11%, on average, under severe terminal drought. There was no impact of the StgX QTL on grain size under a mild terminal drought or under no drought; and
(viii) each of the key StgX mechanisms maps to a defined region, suggesting that the action of a single gene has multiple pleiotrophic effects.

The present invention further contemplates a business model to enhance economic returns from crop production. According to this embodiment, there is provided a business model is also taught herein for improved economic returns on crop yield, the model comprising generating crop plants having a selected StgX trait or elevated or reduced StgX trait resulting in the crop plant having a shift in water use by the plant to the post-anthesis period thereby increasing HI and grain yield under water-limited conditions, obtaining seed from the generated crop plant and distributing the seed to grain producers to enhance yield and profit.

Taught herein is a plant management system to reduce crop reliance on water or to otherwise improve water use efficiency and to enhance grain or product yield. The plant management system includes the generation of a drought adapted crop including cereal plants using the selection and expression of an StgX locus or a functional equivalent thereof alone or in combination with the introduction of other useful traits such as grain size, root size, salt tolerance, herbicide resistance, pest resistance and the like. Alternatively or in addition, the plant management system comprises generation of drought adapted plants and agricultural procedures such as irrigation, nutrient requirements, crop density and geometry, weed control, insect control, soil aeration, reduced tillage, raised beds and the like. Examples of a StgX include Stg1: Fine-mapped region between txp563 and txp581 containing 60 annotated genes, Larger middle region between txp440 and txp580 containing 307 annotated genes, Candidates in tail between txp580 and txp38 containing 178 annotated genes; Stg2: Fine-mapped region between txp512 and txp2 containing 15 annotated genes, Larger region between txp31 and txp530 containing 241 annotated genes; Stg3a: Entire region between txp298 and sPb-2568 containing 520 annotated genes; Stg3b: Entire region between sPb-2568 and txp179 containing 291 annotated genes; Stg4: Entire region defined by txp283 and txp15 containing 306 annotated genes. Examples of loci in these regions are listed in Table 1B (and Table 1C). Examples of a StgX locus include SbPIN1 to 11, IPA-1, WFP, Sp1 and CCD7/8 and their equivalents in other plants.

The disclosure teaches a means to induce or enhance drought adaptation capacity in a plant by introducing do novo one or more features of the stay-green phenotype or elevating expression of an existing one or more StgX loci in a plant and/or selecting an StgX polymorphic variant with improved or enhanced expression or product activity. The manipulation of the stay-green phenotype may be done alone or as part of an integrated plant management system which may include further trait selection and/or improved agronomical techniques. The resulting crops use water more efficiently and have a higher yield of grain and increased grain size.

The business model extends to collecting seed from drought adapted or enhanced crop plants for distribution to growers to ultimately increase grain yield.

The present disclosure further teaches the use of a genetic agent selected from (i) a StgX locus; (ii) a functional equivalent of the StgX locus; and (iii) an agent which modulates expression of an indigenous StgX locus in the manufacture of a drought adapted plant. A "functional equivalent" includes a cDNA.

As taught herein, StgX loci are identified encoding one or more of a locus listed in Table 1B which, when expressed or up-regulated or down-regulated in all or selected tissues in a plant or when a particular polymorphic variant of any one or more is selected in breeding or by genetic engineering, promotes a stay-green phenotype.

As taught herein, StgX loci are identified encoding one or more of SbPIN1 to 11, IPA-1, WFP, SPL and/or CCD7/8 which, when expressed or up-regulated or down-regulated in all or selected tissues in a plant or when a particular polymorphic variant of any one or more is selected in breeding or by genetic engineering, promotes a stay-green phenotype.

Genetically modified plants and their progeny exhibiting the stay-green trait are also enabled herein as well as seeds, fruit and flowers and other reproductive or propagating material.

In an embodiment, the locus is in Stg1 selected from PIN5, GID1L2, P45098A1, indole-3-acetate and brassinosteroid insensitive.

In an embodiment, the locus is in Stg2 and is auxin efflux carrier component 3a (PIN3a).

In an embodiment, the locus is in Stg3a selected from leaf senescence protein-like (Sb02g023510), leaf senescence protein-like (Sb02g023520), RAMOSA1 C2H12 zinc-finger transcription factor (Sb02g024410), putative auxin-independent growth promoter (Sb02g024540), similar to dehydration-responsive protein-like (Sb02g024670), similar to glucose transporter (Sb02g024690), WRKY transcription factor 76 (Sb02g024760), glutamine synthetase-like protein (Sb02g025100), senescence-associated protein DH (Sb02g025180), putative alanine aminotransferase (Sb02g025480), auxin-induced protein-like (Sb02g025610), auxin-induced protein-like (Sb02g025620), putative far-red impaired response protein (Sb02g025670), similar to cytochrome P450 monooxygenase CYP92A1 (Sb02g025820), auxin-independent growth promoter (Sb02g025960), asparate aminotransferase (Sb02g026430), similar to abscisic acid 8'-hydroxylase 3 (Sb02g026600) similar to ethylene-binding protein-like (Sb02g026630) and putative auxin-induced protein family (Sb02g027150).

In an embodiment, the locus is in Stg3b selected from putative auxin-independent growth promoter (Sb02g027470), squamosa promoter-binding-like protein 17 (Sb02g028420), similar to Os09g0505400 (OsPIN9) protein (Sb02g029210), squamosa promoter-binding-like protein 17 (Sb02g029300) similar to auxin-induced protein-like (Sb02g029630).

In an embodiment, the locus is in Stg4 selected from brassinosteroid LRR receptor (Sb05g006842), brassinosteroid LRR receptor (Sb05g006860), putative far-red impaired response protein (Sb05g007130), cytochrome P450 84A1 (Sb05g007210), gibberellin receptor GID1L2 (Sb05g007270), gibberellin receptor GID1L2 (Sb05g007290), sucrose-phosphate synthase (Sb05g007310), aquaporin SIP1-1 (Sb05g007520), gibberellin 20 oxidase 2 (Sb05g008460), OsIAA29-auxin-responsive (Sb05g008510), OsIAA29-auxin-responsive (Sb05g008512), protein gibberellin receptor GID1L2 (Sb05g008610), similar to aminotransferase, putative (Sb05g009410), indole-3-acetic acid-amido (Sb05g010310), indole-3-acetic acid-amido (Sb05g010320), indole-3-acetic acid-amido (Sb05g010326), cytochrome P450 86A2 (Sb05g010360), cytochrome P450 51, putative (Sb05g011296), cytochrome P450 51, putative (Sb05g011430), triacylglycerol lipase, leaf senescence, jasmonic acid biosynthetic process_GO (Sb05g013160), growth regulator like (Sb05g015590), cytochrome P450 78A4 (Sb05g016750), similar to ABC transporter family protein, expressed (Sb05g017120) and squamosa promoter-binding-like protein 19 (Sb05g017510).

EXAMPLES

Aspects taught and enabled herein are further described by the following non-limiting Examples.

Example 1

Identification of an StgX Gene

A quantitative trait locus (QTL) referenced to as Stg1 which is an example of an StgX has been identified which increases or enhances water use efficiency by sorghum plants, Stg1 encodes a sorghum bicolor member of the auxin efflux carrier component 4 family, PIN4 (or SbPIN4).

This major drought adaptation gene has been fine-mapped in multiple studies to a 152 gene block between markers txp563 and txp442. Changes in auxin efflux explains all of the multiple phenotypes observed in plants containing SbPIN4. The candidate gene (and promoter region) is sequenced in the two parents of the fine-mapping population (RTx7000 and Tx642) to identify a single nucleotide polymorphism. RNA expression profiling of the Stg1 fine-mapping population is also conducted for a subset of lines, times and organs. Phenotypes exhibited by SbPIN4 plants that could be explained directly by enhanced auxin availability include reduced tillering, smaller leaves (both length and width), reduced leaf mass and increased root:shoot ratio. Phenotypes exhibited by SbPIN4 plants that could be explained indirectly (or as emergent consequences of these direct effects) include increased availability of water at anthesis, higher leaf N concentration at anthesis, increased transpiration and biomass per unit leaf area, reduced pre:post anthesis biomass ratio, higher transpiration efficiency, retention of green leaf area during grain filling, increased harvest index, higher grain yield, larger grain size and increased lodging resistance. It is proposed that SbPIN4 works across other major cereal and crop species to enhance drought adaptation in localities worldwide where water limits crop growth post-anthesis.

Stg1 (SbPIN4) confers drought adaptation both directly, and indirectly, ultimately leading to higher grain yield, larger grain size, and lodging resistance under water-limited conditions.

Other StgX regions are defined as follows: Stg1: Fine-mapped region between txp563 and txp581 containing 60 annotated genes, Larger middle region between txp440 and txp580 containing 307 annotated genes, Candidates in tail between txp580 and txp38 containing 178 annotated genes; Stg2: Fine-mapped region between txp512 and txp2 containing 15 annotated genes, Larger region between txp31 and txp530 containing 241 annotated genes; Stg3a: Entire region between txp298 and sPb-2568 containing 520 annotated genes; Stg3b: Entire region between sPb-2568 and txp179 containing 291 annotated genes; Stg4: Entire region defined by txp283 and txp15 containing 306 annotated genes.

Examples of loci are listed in Tables 1B and 1C and the interaction of some of these genes in networking pathways is shown in FIG. 68.

Increased water availability at anthesis is achieved via reduced water use due to two mechanisms (reduced tillering and smaller leaves) in plants containing the Stg1 region. Both mechanisms, individually, appear to reduce canopy size by about 9%, on average. The 'low-tillering' mechanism dominates in low density environments when tillering potential is high. The 'small-leaf' mechanism dominates in high density environments when tillering potential is low. Combined, these two mechanisms provide crop plants with considerable plasticity to modify canopy architecture in response to the severity of water limitation.

Stay-green enhances canopy architecture plasticity via constitutive and adaptive responses. Canopy size in Stg1 is reduced by about 5%, even when water is not limiting (constitutive response). Canopy size is further reduced (adaptive response) in a mild drought (~10%) and more severe drought (~15%). Low tillering is primarily a constitutive response. Small leaf size is both a constitutive and adaptive response.

There is a link between reduced canopy size (via reduced tillering and smaller leaves) and reduced crop water use at anthesis. High correlation (r2=0.9) between canopy size and crop water use in ROS and lysimeter studies.

Increased water availability at anthesis is also achieved via increased water accessibility (better water extraction and deeper or greater lateral spread).

Stay-green enhances biomass per unit leaf area at anthesis. Assuming root mass is equivalent (or at least not significantly less), these differences could be explained by differences in transpiration per unit leaf area (T/LA) and/or transpiration efficiency (TE). Lysimetry studies indicate that increases in T/LA, rather than TE, drive the observed increases in biomass per leaf area. Note that increased T/LA only occurred under low VPD conditions; T/LA was actually reduced under high VPD conditions, presumably as a water conservation mechanism.

Higher TE in Stg1 lines was also observed under higher VPD conditions. Increased TE via introgressing Stg1 may be due to a) proportionally higher photosynthetic capacity compared with stomatal conductance, due to smaller, thinner and greener leaves, and/or b) a decrease in transpiration while maintaining biomass. Lysimetry studies indicate that both of these mechanisms contribute to higher TE in Stg1 lines, with the reduction in transpiration the primary mechanism.

Changes in transpiration per unit leaf area could be due to a) number of stomata, b) size of stomatal aperture, c) changes in the timing of stomatal opening and closing relative to VPD, and/or d) the number of hair base cells (which affects the boundary layer and hence T/LA). Introgressing Stg1 into RTx7000 reduced the number of stomata and increased the number of hair base cells per unit leaf area in leaves 7 and 10; both mechanisms can conserve water by reducing T/LA.

Introgressing Stg1 into RTx7000 modified leaf anatomy by increasing the number of bundle sheath cells surrounding the vascular bundle. The increased number of cells in the bundle sheath might also contribute to increased photosynthetic assimilation and hence TE.

Differences in the morphology of leaves (e.g. Leaves 7 and 10) are apparent between Tx7000 and Stg1. In this case, there were more and smaller bundle sheaths surrounding the vascular bundle in Stg1. The increased number of cells in the bundle sheath might also contribute to increased photosynthetic assimilation and hence TE.

Increased water use during grain filling is achieved via (i) increased water availability at anthesis and (ii) increased water accessibility (better water extraction and deeper or greater lateral spread) during grain filling.

a) Increased Water Availability at Anthesis

Crop water use (CWU) before anthesis was negatively correlated with CWU after anthesis in an ROS experiment. Overall, a 25% increase in water use after anthesis (80 vs 60 mm) resulted in a 25% increase in grain yield (400 vs 300 g/m2). This translated to 50 kg/ha of grain for every additional mm of water available.

b) Increased Water Accessibility during Grain Filling

Increased water use during the grain filling period was exhibited by Stg1 under both low and high density treatments in an ROS experiment. This was due primarily to (i) reduced water use at anthesis under high density, and (ii) increased water accessibility during grain filling under low density.

Stg1 region confers drought adaptation via a link between pre- and post-anthesis biomass production. The Stg1 region reduces the pre:post anthesis biomass ratio below a critical level, increasing grain yield and lodging resistance.

Delayed leaf senescence (stay-green), higher grain yield and lodging resistance are consequences of higher plant water status during grain filling (due to increased water use during grain filling).

Introgressing Stg1 into a RTx7000 background increased plant water status at mid-grain filling, as indicated by a) higher relative water content (RWC), and b) lower leaf water potential (LWP).

Higher grain yield and larger grain size are consequences of increased water availability during grain filling.

Higher grain yield, larger grain size and increased lodging resistance are not mutually exclusive (i.e. all three traits are exhibited by Stg1).

Yield and grain size advantage are relatively higher under severe terminal drought than mild terminal drought.

Studies indicate that the greatest benefit of the stay-green genes in a RTx7000 background (inbreds) occurs in the yield range of 1-3 t/ha (12-22%), followed by a lesser but still significant benefit in the 3-4 t/ha yield range (8-10%). There was, however, a small penalty associated with these regions (2-4%) at higher yield levels (5-8 t/ha) due to wetter conditions. Note that these yield ranges would be considerably higher in hybrids. Since the average sorghum grain yield for hybrids in the northern grain belt is about 2.5 t/ha, the benefit of the stay-green genes should be significant. No reduction in grain yield under wetter conditions (water not limiting) due to stay-green has been observed in hybrids.

Introgressing Stg1 into RTx7000 also increased grain size by 11%, on average, under severe terminal drought. There was no impact of this QTL on grain size under a mild terminal drought or under no drought.

Each of the key Stg1 mechanisms maps to the same region, indicating the action of a single gene with multiple pleiotrophic effects.

Example 2

Reduced Tillering (Physiological Studies of NILs in the Field)

Data show the impact of Stg1 on tillering under both high water (HW) and low water (LW) conditions. Differences in canopy development before flowering were largely a consequence of variation in tillering among lines. Culm number per m2 at anthesis was the best overall measure of the effect of tillering on canopy dynamics. Culm numbers per m2 were equivalent under both water regimes (12.89), indicating that reduced tillering is a constitutive trait. Genotypes varied significantly (P<0.001) in this parameter, ranging from 8.59 to 16.67. However, genotype and treatment did not interact significantly for this parameter.

Culm numbers per m2 were analyzed in terms of their Stg status and category means are presented in Table 2. RTx7000 produced 41% more (P<0.05) culms/m2 than B35 (14.07 vs. 10.00). Introgression of the Stg1 region alone into RTx7000 (6078-1) reduced culms/m2 significantly (P<0.05) compared with RTx7000 (9.40 vs. 14.07). Compared with Stg1 only, additional introgressions of either Stg2 or Stg4 increased culm numbers to 10.49 (1,2 combination) and 10.74 (1,4 combination). Note that the three near-isolines containing no Stg regions (2212-3, 2235-11 and 6120-16) also exhibited high tillering equivalent to Tx7000. Hence the overall ranking of tillering in these lines is Stg1<B35<Stg4<Stg2<Stg3<none <RTx7000.

At anthesis, culm numbers were highly correlated ($r2=0.71$) with total green leaf area (GLAA; FIG. 1).

TABLE 2

| Stg status | No of lines | Culms/m2A |
| --- | --- | --- |
| Stg1 region | | |
| 1 | 1 | 9.40 |
| 1, 2 | 2 | 10.49 |
| 1, 4 | 1 | 10.74 |
| RTx7000 | 7 | 14.07 |
| LSD (0.05) | | 4.06 |

Culms per m2 in the recurrent parent (RTx7000) and various lines containing introgressions of the Stg1 QTL, both alone and in combination with other Stg QTL.

Differences in green leaf area at anthesis (GLAA) were primarily due to differences in tiller green leaf area at anithesis (GLAAt), since GLAAt was highly correlated with GLAA ($r2=0.78$), yet mainstem leaf area was not.

Tiller green leaf area at anthesis was analyzed in terms of Stg status and category means are presented in Table 3. RTx7000 produced almost eight-fold more (P<0.05) GLAAt than B35 (15460 vs. 1980). Introgression of the Stg1 region alone into RTx7000 (6078-1) reduced GLAAt significantly (P<0.05) compared with RTx7000 (3121 vs 15460). Compared with Stg1 only, additional introgressions of either Stg2 or Stg4 increased GLAAt to 4187 (1,2 combination) and 4797 (1,4 combination). All lines containing Stg1 (in any combination) were not significantly different (P<0.05) in GLAAt from Stg1 alone. Note that GLAAt in the three near-isolines containing no Stg regions (2212-3, 2235-11 and 6120-16) was not significantly different from RTx7000. Hence the significantly different (P<0.05) rankings of GLAAt in these lines are B35=Stg1=Stg4<Stg2=Stg3<none=RTx7000.

TABLE 3

| Stg status | No of lines | Tiller green leaf area at anthesis (cm2/m2) |
|---|---|---|
| Stg1 region | | |
| 1 | 1 | 3121 |
| 1, 2 | 2 | 4187 |
| 1, 4 | 1 | 4797 |
| RTx7000 | 7 | 15460 |
| LSD (0.05) | | 5282 |

Tiller green leaf area at anthesis in the recurrent parent (RTx7000) and various lines containing introgressions of the Stg1 QTL, both alone and in combination with other Stg QTL.

Figure 2:
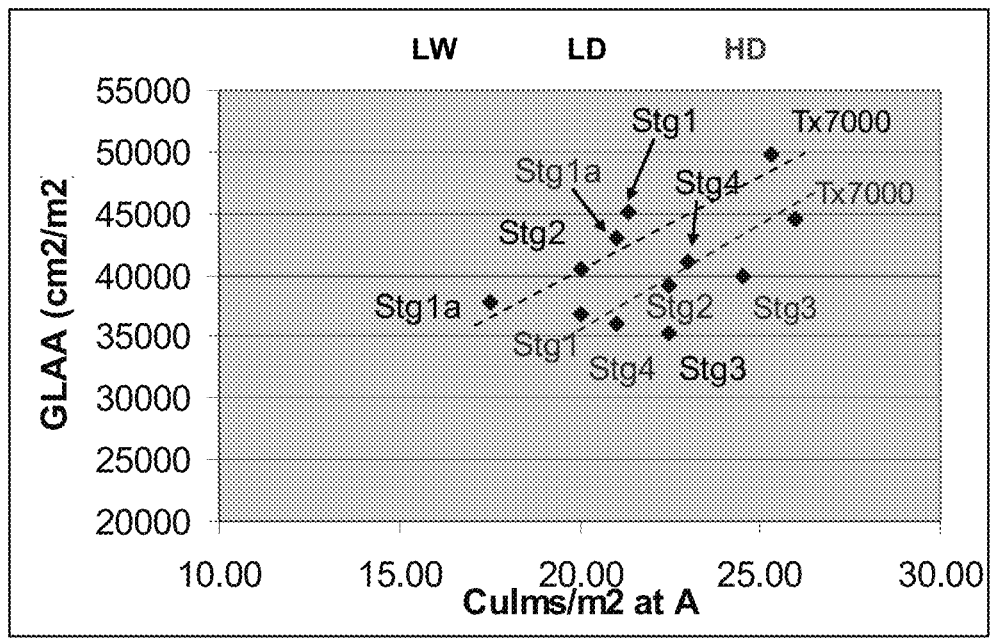
FIG. 2 is a graphical representation showing the relation between culms per $m^2$ and green leaf area at anthesis for a range of Stg introgressions in a RTx7000 background grown under two crop densities (LD=10 plants/$m^2$; HD=20 plants/$m^2$).

Green leaf area and culms per m2 at anthesis were highly correlated under high (HD) and low (LD) density treatments in the rainout shelter experiment (FIG. 2). Introgressing the Stg1 or Stg1a regions into RTx7000 reduced culms per m2 and GLAA under both densities.

Example 3

Reduced Tillering-fine Mapping Studies

Figure 3:
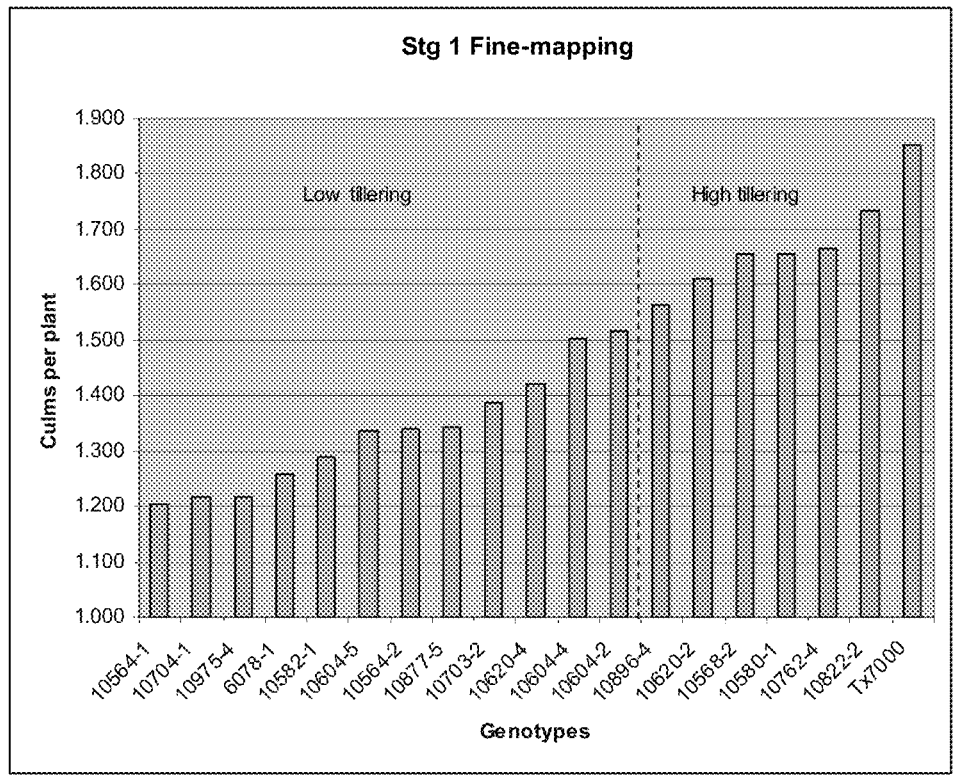
FIG. 3 is a graphical representation showing the histogram of predicted values for culms per plant in the Stg1 fine-mapping population averaged over three seasons.

A Stg1 fine-mapping population was grown in the field under high and low density conditions in three consecutive years. The number of culms per plant was measured at anthesis in each year and a combined analysis was undertaken across years. Overall, RTx7000 produced 47% more culms per plant than 6078-1 (1.85 vs. 1.26; FIG. 3).

In these field studies, the trait (culm number per plant) mapped to a 60 gene block between markers txp563 and txp581 (FIG. 4). An arbitrary value of 1.54 culms per plant gave the optimal separation between high and low tillering for mapping purposes (i.e. recombinants with less than 1.54 culms were BB genotypes while those with more than 1.54 culms were TT genotypes). Stepping down through the markers reveals that gain-of-function (low tillering) was achieved in three genotypes (10564-2, 10704-1 and 10620-4) at markers txp542 or txp563. The data suggest that the breakpoint resides between txp563 and txa3676, since one recombinant (10568-2) exhibited a high tillering phenotype, while three others (10620-4, 10704-1 and 10564-2) exhibited low tillering phenotypes at this breakpoint. An auxin efflux carrier component 5 gene is located in the target region and is therefore a strong candidate (Table 4), since auxin is known to affect the growth of auxillary buds in plants.

TABLE 4

| Gene/ Marker Name | Physical LG | Physical Start Position | End position | Length | JGI annotation |
|---|---|---|---|---|---|
| txp563 | 3 | 65,208,189 | 65,208,485 | 296 | |
| Sb03g037190 | 3 | 65,209,678 | 65,211,603 | 1,925 | "similar to Pentatricopeptide (PPR) repeat-containing protein-like" |
| Sb03g037200 | 3 | 65,222,350 | 65,226,307 | 3,957 | "similar to Putative diphosphonucleotide phosphatase 1" |
| Sb03g037210 | 3 | 65,227,168 | 65,227,630 | 462 | "similar to Putative uncharacterized protein" |
| Sb03g037220 | 3 | 65,234,620 | 65,235,162 | 542 | "similar to Putative uncharacterized protein" |
| Sb03g037230 | 3 | 65,236,723 | 65,237,917 | 1,194 | "similar to Putative uncharacterized protein" |
| Sb03g037240 | 3 | 65,240,591 | 65,246,229 | 5,638 | "similar to Putative DNA-(Apurinic or apyrimidinic site) lyase" |
| Sb03g037250 | 3 | 65,246,632 | 65,250,387 | 3,755 | "similar to Os01g0801100 protein" |
| Sb03g037260 | 3 | 65,251,637 | 65,253,986 | 2,349 | "similar to Putative uncharacterized protein" |
| Sb03g037270 | 3 | 65,259,345 | 65,261,566 | 2,221 | "similar to Beta-1,3-glucanase precursor" |
| Sb03g037280 | 3 | 65,262,639 | 65,266,128 | 3,489 | "similar to Glycerol-3-phosphate dehydrogenase-like protein" |
| Sb03g037290 | 3 | 65,267,421 | 65,270,348 | 2,927 | "similar to Mucin-like protein" |
| Sb03g037293 | 3 | 65,272,234 | 65,272,633 | 399 | "similar to Os09g0292300 protein" |
| Sb03g037296 | 3 | 65,273,390 | 65,274,334 | 944 | "similar to Putative uncharacterized protein" |
| Sb03g037300 | 3 | 65,280,789 | 65,281,319 | 530 | "similar to Putative uncharacterized protein" |
| Sb03g037310 | 3 | 65,284,987 | 65,294,633 | 9,646 | "similar to Os01g0802000 protein" |
| Sb03g037330 | 3 | 65,295,725 | 65,296,295 | 570 | "weakly similar to Putative uncharacterized protein" |
| Sb03g037340 | 3 | 65,303,733 | 65,305,041 | 1,308 | "similar to Putative uncharacterized protein" |
| Sb03g037350 | 3 | 65,310,051 | 65,313,194 | 3,143 | "similar to Probable auxin efflux carrier component 5" |
| txp441 | 3 | 65,312,684 | 65,313,085 | 401 | |
| Sb03g037360 | 3 | 65,319,087 | 65,321,178 | 2,091 | "similar to Phosphate/phosphoenolpyruvate translocator protein-like" |
| Sb03g037360 | 3 | 65,319,633 | 65,321,178 | 1,545 | "similar to Phosphate/phosphoenolpyruvate translocator protein-like" |
| Sb03g037370 | 3 | 65,334,279 | 65,335,675 | 1,396 | "similar to Cystatin" |
| Sb03g037370 | 3 | 65,334,279 | 65,335,675 | 1,396 | "similar to Cystatin" |
| Sb03g037380 | 3 | 65,339,180 | 65,342,378 | 3,198 | "similar to Cytochrome P450" |
| Sb03g037390 | 3 | 65,353,300 | 65,355,651 | 2,351 | "similar to Putative nodulin MtN21 protein" |
| txp548 | 3 | 65,353,690 | 65,354,064 | 374 | |
| Sb03g037400 | 3 | 65,360,048 | 65,363,895 | 3,847 | "similar to 50S ribosomal protein L34" |
| Sb03g037400 | 3 | 65,361,649 | 65,363,895 | 2,246 | "similar to 50S ribosomal protein L34" |
| Sb03g037410 | 3 | 65,365,754 | 65,367,069 | 1,315 | "similar to Putative uncharacterized protein" |
| Sb03g037420 | 3 | 65,367,248 | 65,368,532 | 1,284 | "similar to Thylakoid lumenal 20 kDa protein-like" |
| Sb03g037423 | 3 | 65,372,022 | 65,374,178 | 2,156 | "similar to Putative uncharacterized protein" |
| Sb03g037426 | 3 | 65,377,633 | 65,377,797 | 164 | "Predicted protein" |
| Sb03g037430 | 3 | 65,379,179 | 65,380,287 | 1,108 | "Predicted protein" |
| Sb03g037440 | 3 | 65,382,179 | 65,384,675 | 2,496 | "weakly similar to Putative uncharacterized protein" |
| Sb03g037450 | 3 | 65,388,656 | 65,390,929 | 2,273 | "similar to Putative uncharacterized protein" |
| Sb03g037460 | 3 | 65,391,595 | 65,394,474 | 2,879 | "similar to Cyclin laZm" |
| Sb03g037470 | 3 | 65,395,511 | 65,401,947 | 6,436 | "similar to Os01g0805700 protein" |
| txp570 | 3 | 65,396,787 | 65,397,183 | 396 | |
| Sb03g037480 | 3 | 65,407,894 | 65,410,649 | 2,755 | "similar to Putative DNA-directed RNA polymerase II 23K chain" |
| Sb03g037480 | 3 | 65,407,894 | 65,410,649 | 2,755 | "similar to Putative DNA-directed RNA polymerase II 23K chain" |

TABLE 4-continued

| Gene/ Marker Name | Physical LG | Physical Start Position | End position | Length | JGI annotation |
|---|---|---|---|---|---|
| Sb03g037490 | 3 | 65,412,740 | 65,415,968 | 3,228 | "similar to Tubulin beta-2/beta-3 chain" |
| Sb03g037500 | 3 | 65,416,497 | 65,419,202 | 2,705 | "similar to Chromosome chr8 scaffold_29, whole genome shotgun sequence" |
| Sb03g037510 | 3 | 65,422,190 | 65,425,057 | 2,867 | "similar to F-box family protein-like" |
| Sb03g037520 | 3 | 65,432,183 | 65,433,007 | 824 | "similar to Putative uncharacterized protein P0702B09.7" |
| sPb-9429 | 3 | 65,448,961 | | | |
| Sb03g037530 | 3 | 65,453,690 | 65,457,006 | 3,316 | "similar to Las1-like family protein, expressed" |
| Sb03g037540 | 3 | 65,458,431 | 65,461,769 | 3,338 | "similar to Putative uncharacterized protein" |
| Sb03g037550 | 3 | 65,463,190 | 65,467,200 | 4,010 | "similar to Putative uncharacterized protein" |
| Sb03g037560 | 3 | 65,467,680 | 65,472,835 | 5,155 | "similar to Ocs-element binding factor 3.2" |
| Sb03g037570 | 3 | 65,485,324 | 65,487,344 | 2,020 | "similar to Putative calcium-dependent protein kinase" |
| Sb03g037575 | 3 | 65,498,061 | 65,503,236 | 5,175 | "weakly similar to Putative uncharacterized protein" |
| Sb03g037580 | 3 | 65,504,787 | 65,508,973 | 4,186 | "similar to Leucine-rich repeat protein" |
| Sb03g037590 | 3 | 65,513,699 | 65,516,568 | 2,869 | "similar to Dehydrogenase-like protein" |
| Sb03g037600 | 3 | 65,517,440 | 65,519,915 | 2,475 | "similar to Probable U3 small nucleolar RNA-associated protein 11" |
| Sb03g037610 | 3 | 65,520,796 | 65,524,603 | 3,807 | "similar to Chloroplast ribonuclease III domain protein" |
| Sb03g037620 | 3 | 65,524,940 | 65,528,396 | 3,456 | "similar to Putative uncharacterized protein" |
| Sb03g037630 | 3 | 65,528,969 | 65,531,465 | 2,496 | "similar to Novel calmodulin-like protein" |
| Sb03g037640 | 3 | 65,577,963 | 65,582,051 | 4,088 | "similar to Proteasome subunit alpha type-3" |
| Sb03g037645 | 3 | 65,584,698 | 65,588,296 | 3,598 | "similar to Proteasome subunit alpha type-3" |
| Sb03g037650 | 3 | 65,589,894 | 65,590,289 | 395 | "similar to Serine protease inhibitor-like protein" |
| Sb03g037660 | 3 | 65,611,172 | 65,614,571 | 3,399 | "similar to SET domain protein 113" |
| Sb03g037670 | 3 | 65,615,936 | 65,620,911 | 4,975 | "similar to Exostosin family protein-like" |
| txp581 | 3 | 65,634,826 | 65,636,402 | 1,576 | |

Table 4 is a list of genes located between markers txp581 and txp563. Note that a strong candidate for low tillering (auxin efflux carrier component 5) is located in an 18-gene block between markers txp563 and txp441.

Example 4

Reduced Tillering (Stg1 Fine-mapping Studies in the ROS)

Figure 5:
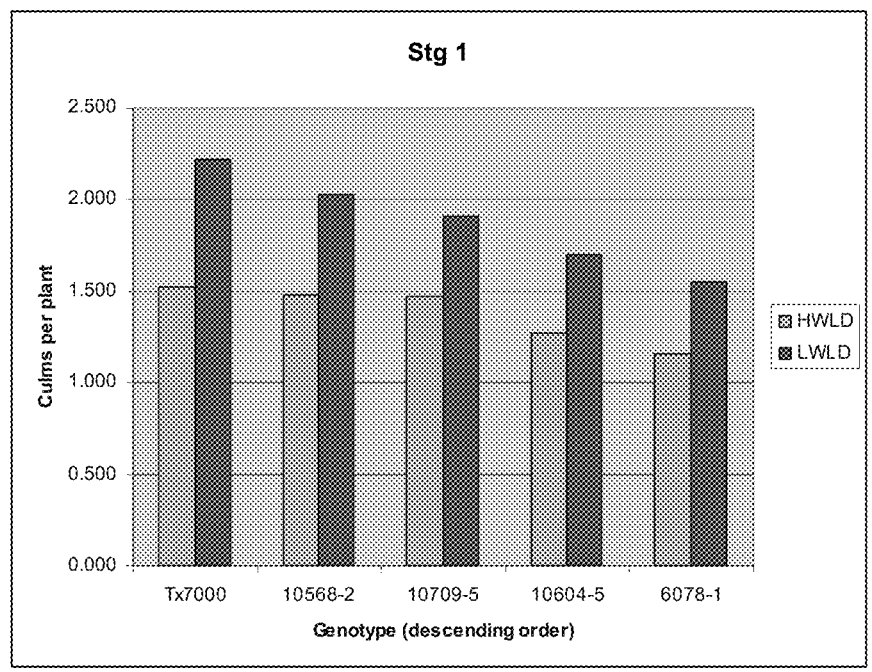
FIG. 5 is a graphical representation showing a histogram of culms per plant at 44 DAE for five genotypes grown under two water regimes. The genotypes comprise RTx7000 (recurrent parent), 6078-1 (donor parent), and three selections from the Stg1 fine-mapping population. HWLD=high water, low density (10 plants/$m^2$). LWLD=low water, low density (10 plants/$m^2$).

A subset of the Stg1 fine-mapping population was grown in the field at the Rain-Out Shelter (ROS) under high and low water conditions, with each water treatment split for high and low density. This created four water regimes with increasing levels of water deficit: HWLD (least stressed) <HWHD<LWLD<LWHD (most stressed). The number of culms per plant was measured at 44 days after emergence in each plot. Differences were most obvious in the Low Density (LD) treatment, since expression of tillering was maximized in this treatment. On average, RTx7000, 10568-2 and 10709-5 produced 27% more culms per plant than 6078-1 and 10604-5 under LWLD conditions (2.05 vs. 1.62; FIG. 5), and 23% more culms per plant under HWLD conditions (1.49 vs. 1.22). The 'low-tillering' gene mapped to a 152 gene block between txp563 and txp442 (the same region identified in the field fine-mapping studies; FIG. 6) containing the candidate gene (auxin efflux carrier component 5).

Example 5

Reduced Tillering (Stg1 Fine-mapping Studies in the Igloo)

Three additional fine-mapping studies were undertaken on the Stg1 population under controlled conditions in an igloo. In these studies, tillering was analyzed in more detail compared with the earlier field studies. The total number of tillers was counted and, more specifically, the number of tillers emerged from the axil of leaves 2 (T2), 3 (T3) and 4 (T4) were counted. Presence or absence of T2 was the best indicator of overall tillering potential for a given recombinant. T2 was also the best trait to use for fine-mapping the gene.

In this experiment, the total number of tillers was the sum of T2, T3 and T4, where T2 was the tiller emerging from the axil of leaf 2 (and so on for T3 and T4), including secondary tillers. Significant genotypic variation was observed for all of the traits relating to tillering in this study (Table 5), with heritabilities generally above 30.

TABLE 5

| trait | trait mean | P-value (Genotype) | Error variance | avSED | CV % | gen.var | Hsq |
|---|---|---|---|---|---|---|---|
| Tillering | | | | | | | |
| tillerno_max | 2.151 | 0.001 | 0.656 | 0.557 | 37.659 | 0.081 | 33.090 |
| presence_T2 | 0.408 | 0.000 | 0.204 | 0.316 | 110.676 | 0.038 | 42.715 |
| presence_T3 | 0.901 | 0.001 | 0.080 | 0.193 | 31.351 | 0.007 | 24.781 |
| presence_T4 | 0.831 | 0.015 | 0.132 | 0.237 | 43.787 | 0.004 | 10.651 |
| gleaf_T | 1.658 | 0.001 | 0.880 | 0.656 | 56.558 | 0.117 | 34.700 |
| stem_T | 0.801 | 0.003 | 0.226 | 0.332 | 59.334 | 0.027 | 32.261 |
| bio_T | 2.442 | 0.002 | 2.006 | 0.986 | 58.005 | 0.242 | 32.533 |
| bio.GLA_T_ratio | 50.259 | 0.010 | 39.356 | 4.716 | 12.482 | 4.510 | 31.429 |

Table 5 provides a summary of predicted means, P-value and heritability of tillering traits measured at the L11 harvest.

Figure 7:
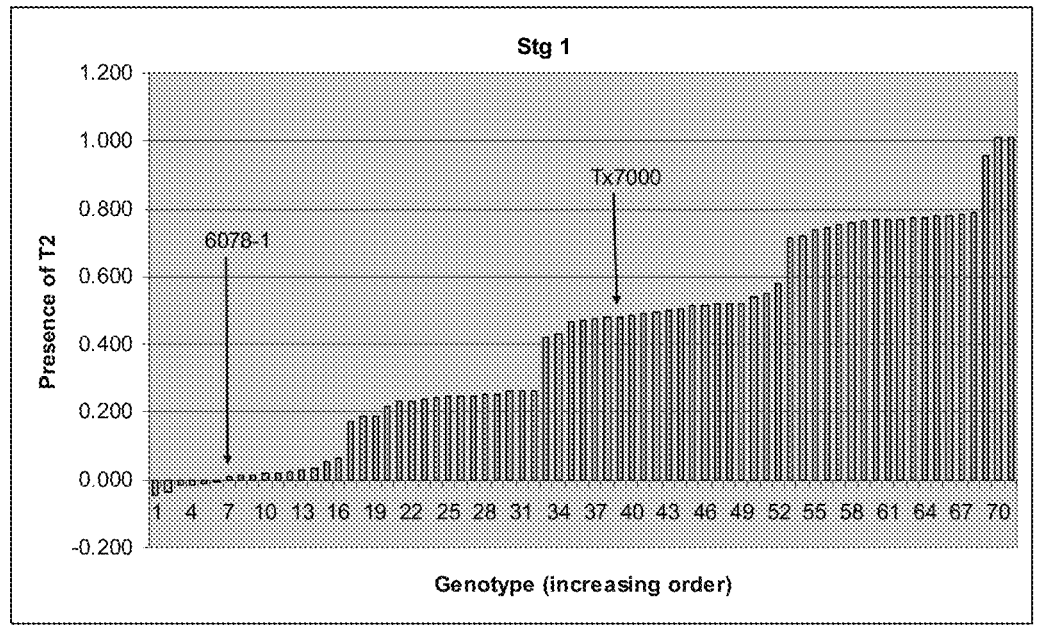
FIG. 7 is a graphical representation showing the phenotypic variation in the Stg1 fine-mapping population for presence of T2.

Separate analysis of the T2, T3 and T4 data found that 6078-1 produced no T2 tillers in any of the four replicates, while RTx7000 produced T2 tillers in 2 of 4 replicates (FIG. 7).

was significant (P<0.05) for all of the key tillering traits except for the presence of T4 (Table 6), suggesting a tillering gene(s) is located in this block. Note that the top of this block is the same breakpoint (between txa3676 and txp536) as already identified by the field fine-mapping studies, validating the previous result with a more specific phenotype (T2) under controlled conditions.

TABLE 6

| markerno | markername | markertype | cM | Tillerno_max (L11) | bio_T (L11) | gleaf_T (L11) |
|---|---|---|---|---|---|---|
| 1 | txa2506 | original | 125.2-127.5 | 0.82 | 0.86 | 0.78 |
| 2 | txp114 | both | 134.7-135.6 | 0.02 | 0.11 | 0.05 |
| 3 | txa2179 | original | 135.6-140 | 0.67 | 0.50 | 0.46 |
| 4 | CORN031 | original | 135.6-140 | 0.74 | 0.18 | 0.17 |
| 5 | TS196 | original | 140-142.5 | 0.74 | 0.18 | 0.17 |
| 6 | txp196 | new | 140-142.5 | 0.12 | 0.67 | 0.74 |
| 7 | txa2961 | original | 142.5 | 0.74 | 0.18 | 0.17 |
| 8 | BH245191 | both | 145.5-147.3 | 0.31 | 0.84 | 0.86 |
| 9 | BG411222 | original | 145.5-147.3 | 0.03 | 0.04 | 0.04 |
| 10 | txp439 | new | 145.5-147.3 | 0.52 | 0.67 | 0.75 |
| 11 | txp440 | new | 145.5-147.3 | 0.36 | 0.67 | 0.72 |
| 12 | txp542 | new | 145.5-147.3 | 0.58 | 0.27 | 0.25 |
| 13 | txp563 | new | 149.1-150.3 | 0.30 | 0.36 | 0.36 |
| 14 | txa3676 | original | 149.1-150.3 | 0.02 | 0.04 | 0.05 |
| 15 | txa2986 | original | 150.3 | 0.02 | 0.04 | 0.05 |
| 16 | txp581 | new | 150.3-151.9 | 0.03 | 0.03 | 0.01 |
| 17 | txp587 | new | 151.9-156.2 | 0.05 | 0.02 | 0.01 |
| 18 | txp446 | new | 151.9-156.2 | 0.04 | 0.01 | 0.00 |
| 19 | txp442 | original | 151.9-156.2 | 0.02 | 0.04 | 0.05 |
| 20 | txp38 | original | 158.3-161.4 | 0.18 | 0.09 | 0.11 |
| 21 | txa3390 | original | 158.3-161.4 | 0.31 | 0.14 | 0.15 |

| markerno | stem_T (L11) | GLA_T (L11) | presence_T2 (L11) | presence_T3 (L11) | presence_T4 (L11) |
|---|---|---|---|---|---|
| 1 | 0.98 | 0.65 | 0.02 | 0.52 | 0.03 |
| 2 | 0.23 | 0.13 | 0.02 | 0.17 | 0.66 |
| 3 | 0.59 | 0.36 | 0.37 | 0.21 | 0.28 |
| 4 | 0.22 | 0.13 | 0.35 | 0.37 | 0.31 |
| 5 | 0.22 | 0.13 | 0.35 | 0.37 | 0.31 |
| 6 | 0.83 | 0.95 | 0.06 | 0.79 | 0.80 |
| 7 | 0.22 | 0.13 | 0.35 | 0.37 | 0.31 |
| 8 | 0.97 | 0.94 | 0.14 | 0.64 | 0.88 |
| 9 | 0.03 | 0.02 | 0.29 | 0.06 | 0.05 |
| 10 | 0.66 | 0.79 | 0.13 | 0.90 | 0.84 |
| 11 | 0.56 | 0.77 | 0.03 | 0.86 | 0.81 |
| 12 | 0.14 | 0.27 | 0.04 | 0.80 | 0.71 |
| 13 | 0.32 | 0.24 | 0.04 | 0.88 | 0.85 |
| 14 | 0.03 | 0.02 | 0.03 | 0.08 | 0.39 |
| 15 | 0.03 | 0.02 | 0.03 | 0.08 | 0.39 |
| 16 | 0.06 | 0.03 | 0.02 | 0.62 | 0.63 |
| 17 | 0.04 | 0.03 | 0.04 | 0.38 | 0.74 |
| 18 | 0.01 | 0.00 | 0.03 | 0.45 | 0.42 |
| 19 | 0.03 | 0.02 | 0.03 | 0.08 | 0.39 |
| 20 | 0.08 | 0.18 | 0.03 | 0.09 | 0.33 |
| 21 | 0.14 | 0.22 | 0.04 | 0.16 | 0.21 |

P < 0.05
P < 0.10

Figure 8:
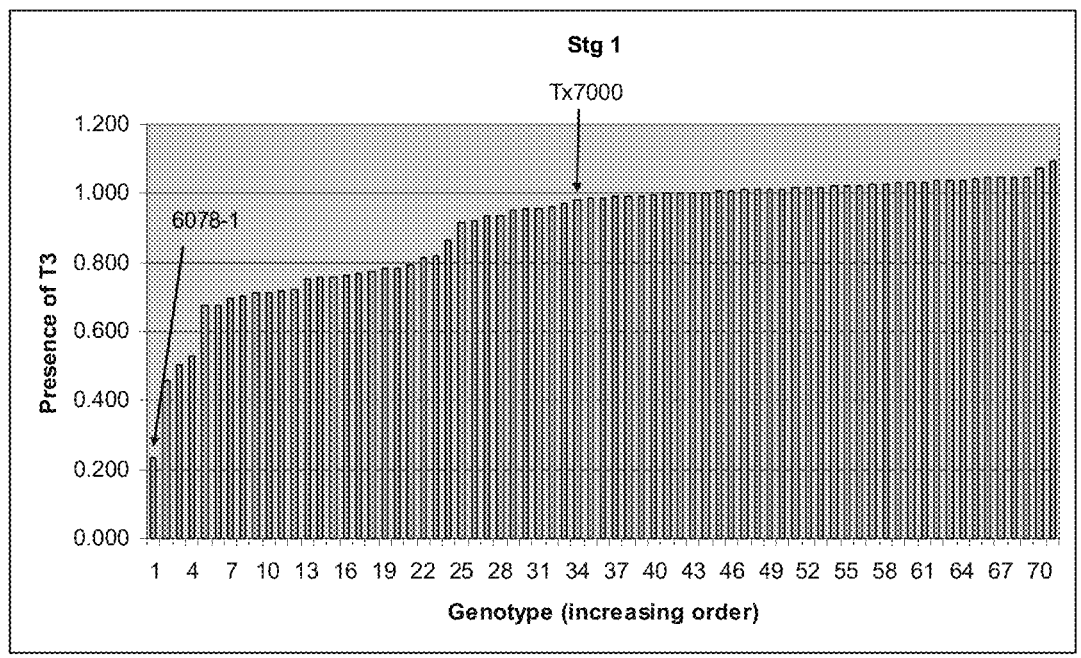
FIG. 8 is a graphical representation showing the phenotypic variation in the Stg1 fine-mapping population for presence of T3.

Differences were also apparent in T3 numbers 6078-1 produced a T3 tiller in 1 of 4 replicates, while RTx7000 produced a T3 tiller in all 4 replicates (FIG. 8).

T4 tiller numbers also varied among genotypes. 6078-1 produced a T4 tiller in 3 of 4 replicates, while RTx7000 produced a T4 in all 4 replicates. Hence the Stg1 introgression essentially prevented the growth of T2 and T3 tillers in a RTx7000 background.

A 'marker x trait' analysis identified a 7 cM region between txa3676 and txp442 containing about 60 genes that Table 6 is a summary of P-values for various tillering traits measured at the L11 harvest.

Figure 9:
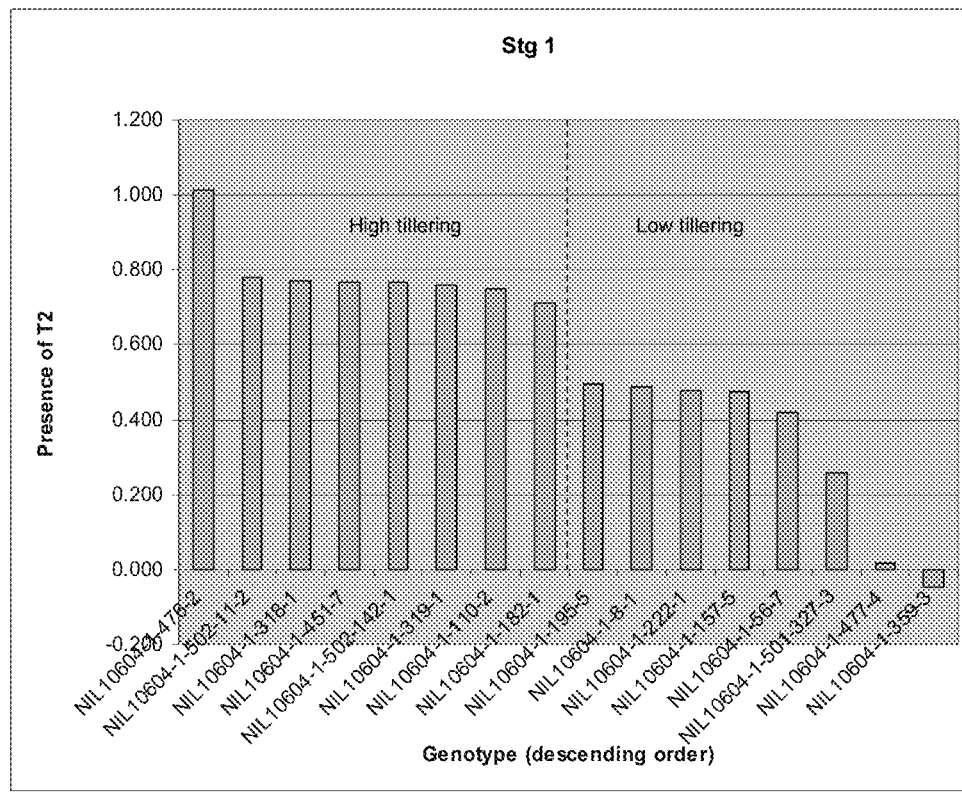
FIG. 9 is a tabulated representation showing a histogram of T2 presence for eight high-tillering and eight low-tillering recombinants from the Stg1 fine-mapping population.

A breakpoint analysis of those lines which, according to their genotype (BB or TT), 'step up' or 'step down' through the region of interest, was undertaken to further pinpoint the low-tillering gene. A very clear break was apparent, separating lines that produced a T2 tiller in 0-2 replicates (low tillering group; 8 recombinants) from those that produced a T2 tiller in 3-4 replicates (high tillering group; 8 recombinants) [Table 7, FIG. 9].

TABLE 7

| Genoname | presence_T2 (L11) | presence_T3 (L11) | presence_T4 (L11) | tillemo_max (L11) |
|---|---|---|---|---|
| NIL10604-1-476-2 | 1.013 | 0.714 | 0.795 | 2.551 |
| NIL10604-1-502-11-2 | 0.781 | 1.006 | 0.715 | 2.634 |
| NIL10604-1-318-1 | 0.770 | 0.956 | 0.920 | 2.628 |
| NIL10604-1-451-7 | 0.769 | 0.970 | 0.930 | 2.675 |
| NIL10604-1-502-142-1 | 0.768 | 0.993 | 0.956 | 2.809 |
| NIL10604-1-319-1 | 0.757 | 1.043 | 0.938 | 2.678 |
| NIL10604-1-110-2 | 0.752 | 1.034 | 0.972 | 2.761 |
| NIL10604-1-182-1 | 0.714 | 1.016 | 1.001 | 3.090 |
| NIL10604-1-195-5 | 0.498 | 0.914 | 0.467 | 2.016 |
| NIL10604-1-8-1 | 0.487 | 0.758 | 1.024 | 2.235 |
| NIL10604-1-222-1 | 0.481 | 0.695 | 0.917 | 2.071 |
| NIL10604-1-157-5 | 0.472 | 0.527 | 0.519 | 1.729 |
| NIL10604-1-56-7 | 0.419 | 1.026 | 0.899 | 2.296 |
| NIL10604-1-501-327-3 | 0.259 | 0.753 | 0.402 | 1.377 |
| NIL10604-1-477-4 | 0.017 | 1.049 | 1.038 | 2.066 |
| NIL10604-1-359-3 | −0.045 | 1.002 | 0.519 | 1.523 |

Table 7 shows the presence of tillers (T1-T3) and total tiller number for eight high-tillering recombinants and eight low-tillering recombinants from the Stg1 fine-mapping population.

Figure 10:
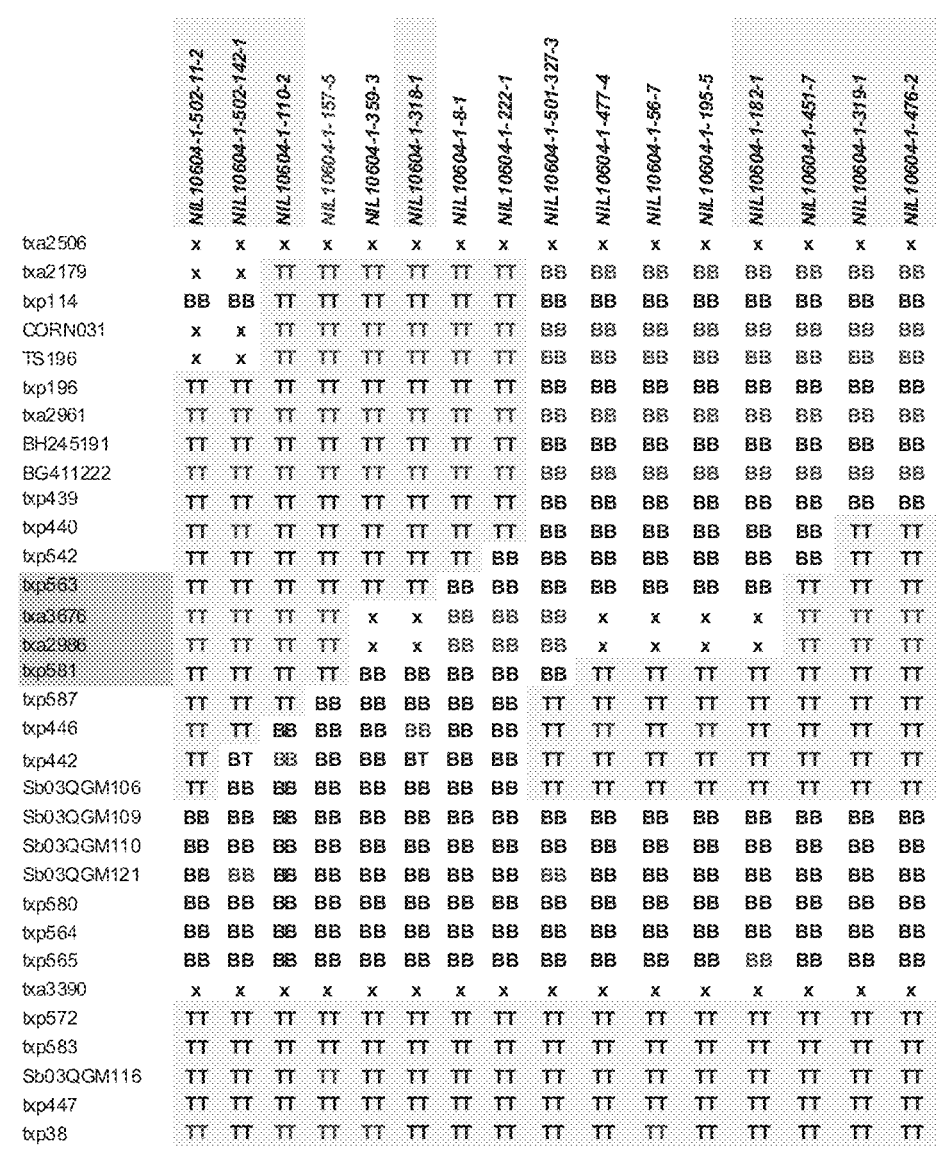

Stepping up through the markers in FIG. 10, gain-of-function (low tillering) is achieved in recombinant 10604-1-157-5 at marker txp587. This would mean the low-tillering gene(s) resides in a block extending down to (but not including) txp446 and up to (but not including) txp581. Stepping down through the markers, gain-of-function (low tillering) is achieved in three recombinants (10604-1-195-5, 10604-1-56-7, 10604-1-477-4) at one of three markers: txp563, txa3676 or txa2986 (missing marker data prevents a more exact location). However, if gain-of-function was not achieved until txa3676, the gene could only reside in a block extending down to (but not including) txa2986. Hence the region does not overlap with the region highlighted by 10604-1-157-5, suggesting that the genotyping or phenotyping is incorrect for this recombinant, Assuming 10604-1-157-5 is incorrect (for whatever reason), then all other recombinants map the gene to a block between txp563 and txp581 containing the candidate gene (auxin efflux carrier component 5).

A subset of lines was used in this experiment to validate the tillering region. More replicates per recombinant (20) were used to further reduce the error variance and increase the power of discrimination among lines. Preliminary results indicate the presence of a tillering gene between the markers txa3676 and txp536 (the same region as previously identified). Hence, five fine-mapping studies, comprising three field studies and two igloo studies, all indicate the presence of a low-tillering gene at the same location.

Figure 11:
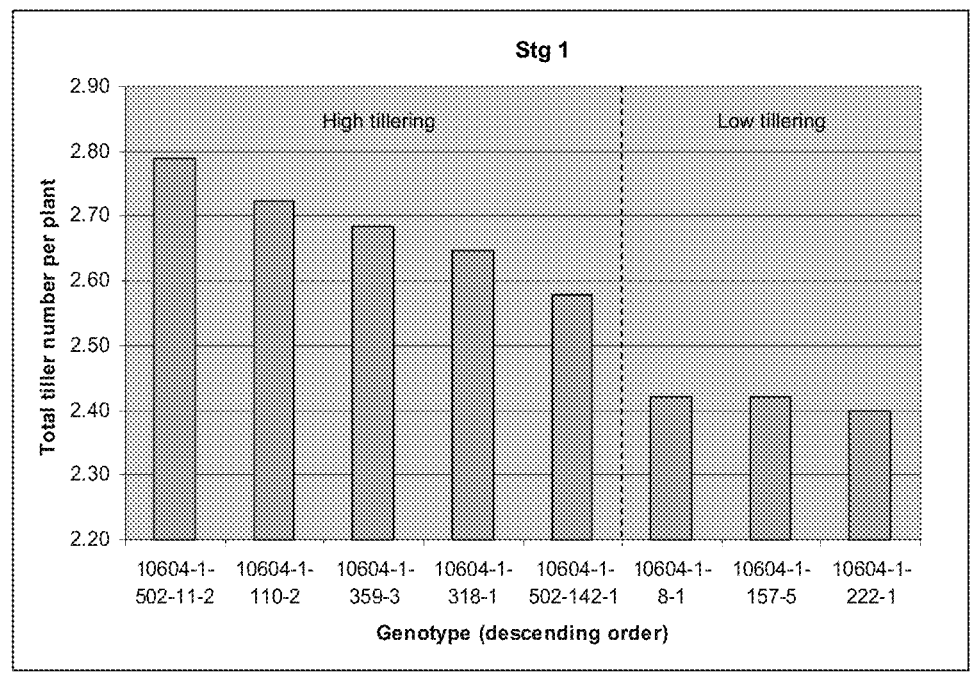
FIG. 11 is a tabulated representation showing a histogram of total tiller number per plant for five high-tillering and three low-tillering recombinants from the Stg1 fine-mapping population. A value of 2.5 was chosen as the arbitrary cut-off between high and low tillering.
Figure 13A:
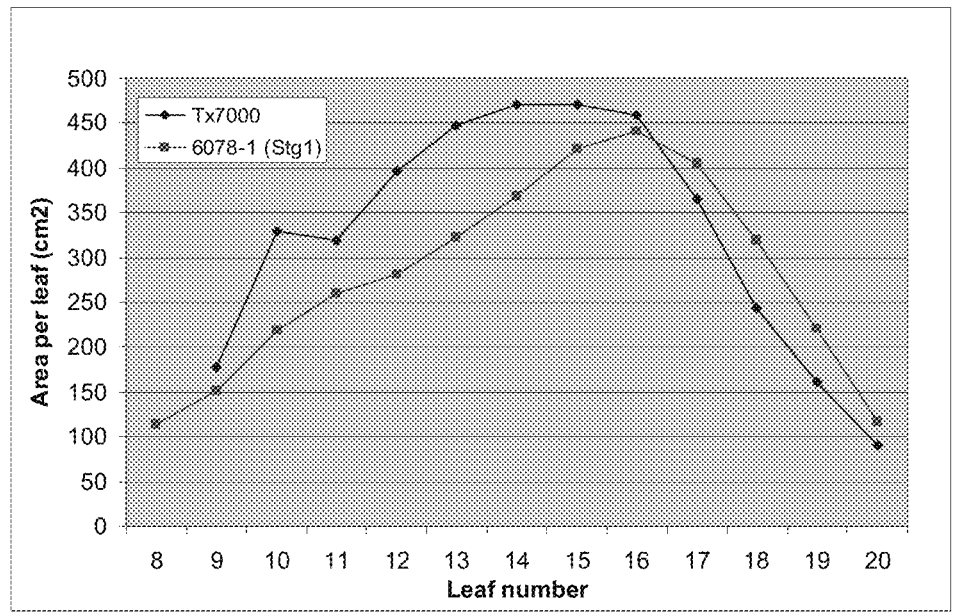
FIGS. 13A through D are graphical representations showing the leaf size distribution of mainstem and tillers for RTx7000 and 6078-1 (Stg1 NIL) grown in lysimeters under low and high VPD conditions.
Figure 13B:
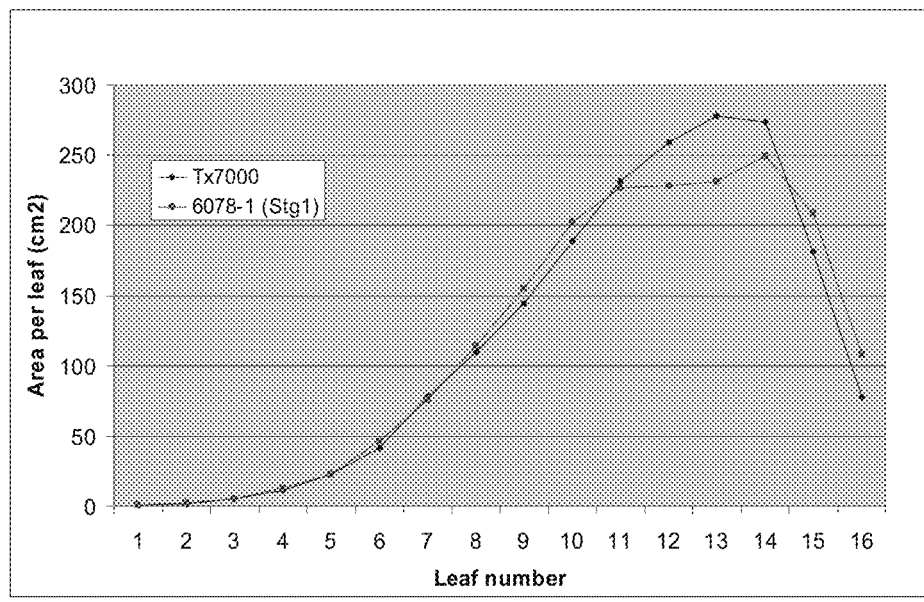
Figure 13C:
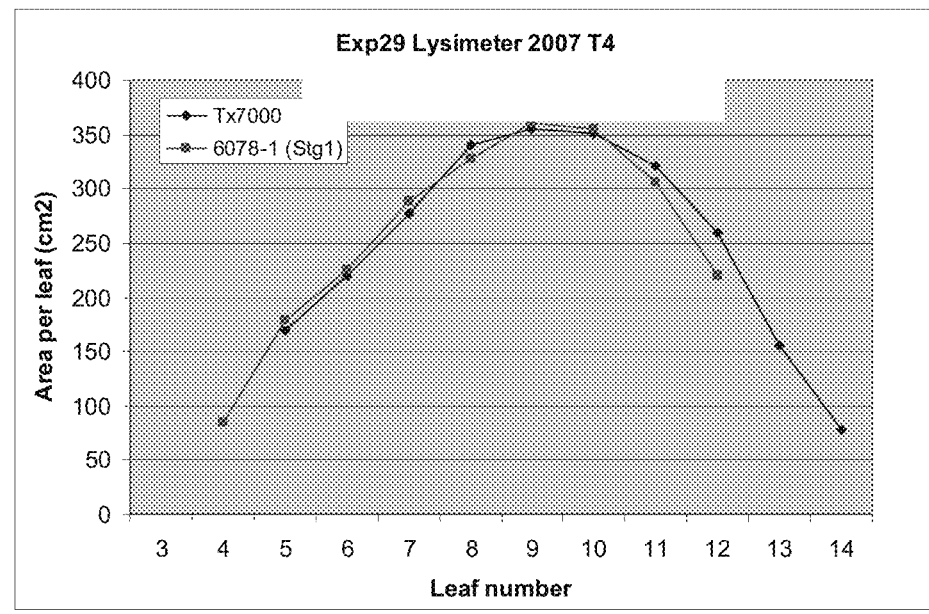
Figure 13D:
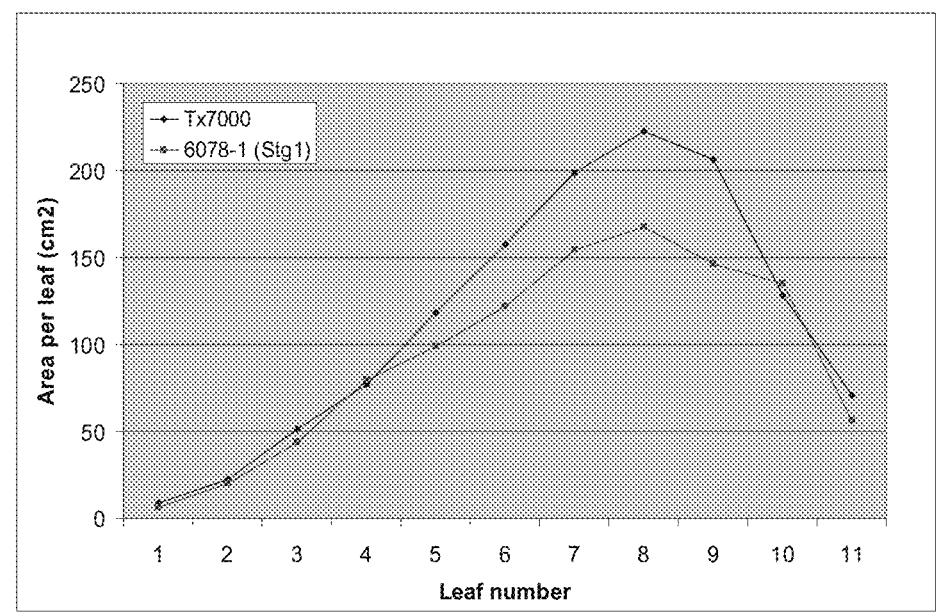

A breakpoint analysis of those lines which, according to their genotype (BB or TT), 'step up' or 'step down' through the region of interest, was undertaken to further pinpoint the low-tillering gene. A clear break was apparent, separating lines that produced a total tiller number >2.5 (high tillering group; 5 recombinants) from those that produced a total tiller number <2.5 (low tillering group; 3 recombinants) [Table 8, FIG. 11].

TABLE 8

| Genotype | T1 | T2 | T2.1 | T3 | T3.1 | T4 | Total tiller no |
|---|---|---|---|---|---|---|---|
| 10604-1-502-11-2 | 0.00 | 0.79 | 0.00 | 1.00 | 0.00 | 1.00 | 2.79 |
| 10604-1-110-2 | 0.11 | 0.67 | 0.00 | 1.00 | 0.00 | 1.00 | 2.72 |
| 10604-1-359-3 | 0.00 | 0.63 | 0.00 | 1.00 | 0.05 | 1.00 | 2.68 |
| 10604-1-318-1 | 0.06 | 0.59 | 0.00 | 1.00 | 0.00 | 1.00 | 2.65 |
| 10604-1-502-142-1 | 0.00 | 0.58 | 0.00 | 1.00 | 0.00 | 1.00 | 2.58 |
| 10604-1-8-1 | 0.00 | 0.53 | 0.00 | 1.00 | 0.00 | 1.00 | 2.42 |
| 10604-1-157-5 | 0.00 | 0.47 | 0.00 | 1.00 | 0.00 | 0.95 | 2.42 |
| 10604-1-222-1 | 0.00 | 0.45 | 0.00 | 1.00 | 0.00 | 1.00 | 2.40 |

Table 8 shows the presence of tillers (T1-T4), including secondary tillers, and total tiller number for five high-tillering recombinants and three low-tillering recombinants from the Stg1 fine-mapping population.

Stepping up through the markers in FIG. 12, gain-of-function (low tillering) is achieved in recombinant 10604-1-157-5 at marker txp587. However, stepping further up through marker txp581, and possibly txa2986 and txa3676, does still not confer function in 10604-1-359-3 or 10604-1-318-1, suggesting that either the genotyping or phenotyping of 10604-1-157-5 was erroneous. Gain-of-function is achieved at marker txp563 in 10604-1-8-1, suggesting that the low tillering gene resides in a block extending from txp563 up to (but not including) txp542 and down to (but not including) txa3676. This is the same region highlighted in the three field studies and in the previous igloo study. Hence, the PIN4 gene in Sorghum bicolor (designated herein "SbPIN4") is a strong candidate for the Stg1 low tillering gene.

Example 6

Smaller Leaves

Overall, introgressing the Stg1 region into RTx7000 reduced leaf size (length and width) under well-watered and water-limited conditions, indicating a constitutive gene action. However, the reduction in leaf size was generally greater under water-limited conditions indicating, to some extent, an adaptive (inducible) response in addition to the constitutive response. Hence Stg1 confers two mechanisms for reducing canopy size: a) reduced tillering, and b) reduced leaf size. Combined, these two mechanisms provide a fair 25 degree of plasticity for the plant to modify canopy architecture in response to environmental and/or management factors.

A series of lysimeter studies is particularly instructive in assessing leaf size patterns under varying levels of vapor pressure deficit (VPD) (FIGS. 13A through D). Although pots were regularly watered in both experiments, the canopy size differed between seasons, presumably due to seasonal differences in temperature and VPD, creating high (1.8 kPa) and low (1.3 kPa) VPD conditions. For the mainstem and the largest tiller (T3), the reduction in leaf size was significant under both high and low VPD conditions (FIGS. 13A through D), although the reduction commenced later under low VPD compared with high VPD in the mainstem (L12 vs L9) and T3 (L7 vs L5).

However for the remaining tillers (T4-T6), the leaf size distributions differed markedly between experiments. While there was no difference in leaf size between RTx7000 and 6078-1 under high VPD, the leaves of 6078-1 were significantly smaller under low VPD. This indicates an adaptive (inducible) response to leaf size reduction under certain environmental conditions for tillers T4-T6.

Example 7

Smaller Leaves (Rain-Out Shelter Studies)

Experiments were conducted under the Rain-Out Shelter (ROS) to assess the impact of the Stg1 region under two crop densities, thereby creating two levels of water deficit (high density=high stress; low density=low stress). In general, tillering was low or absent under ID (20 plants/m2) and normal under LD (10 plants/m2).

Canopy size was smaller in both years under the high density (HD) treatment, reflecting the greater water deficit generated by this treatment. In both years under the milder (LD) and more severe (HD) water deficits, leaf sizes were generally smaller in 6078-1 (Stg1) compared with RTx7000. The exception was where the leaf size distribution pattern was similar for 6078-1 and RTx7000 in the milder Water deficit (LD), yet leaves were significantly smaller in 6078-1 (up to 18% smaller) under greater water deficit (HD), suggesting an adaptive response by Stg1 plants to increasing water deficit. In fact, introgressing the Stg1 region into RTx7000 reduced the size of the four largest leaves (L10-L13) by an average of 16.5% in the more severe water deficit (HD). Since there was little tillering in either genotype in this treatment, reduced leaf size in 6078-1 should have markedly decreased canopy size and hence crop water use (assuming similar transpiration per unit leaf area).

Note that the leaf size reduction mechanism associated with Stg1 appears to operate in both the presence (LD) and absence of tillering (HD), but appears to be best expressed under HD where uniculm and high water deficit conditions generally occur.

Example 8

Smaller Leaves (Stg1 Fine-mapping Studies at Rain-Out Shelter)

A subset of the Stg1 fine-mapping population was grown in the field at the Rain-Out Shelter (ROS) under high and low water conditions, with each water treatment split for high and low density. This created four water regimes with increasing levels of water deficit: HWLD (least stressed) <HWHD<LWLD<LWHD (most stressed). The area of each fully-expanded mainstem leaf was measured for all genotypes in all treatments.

Figure 14:
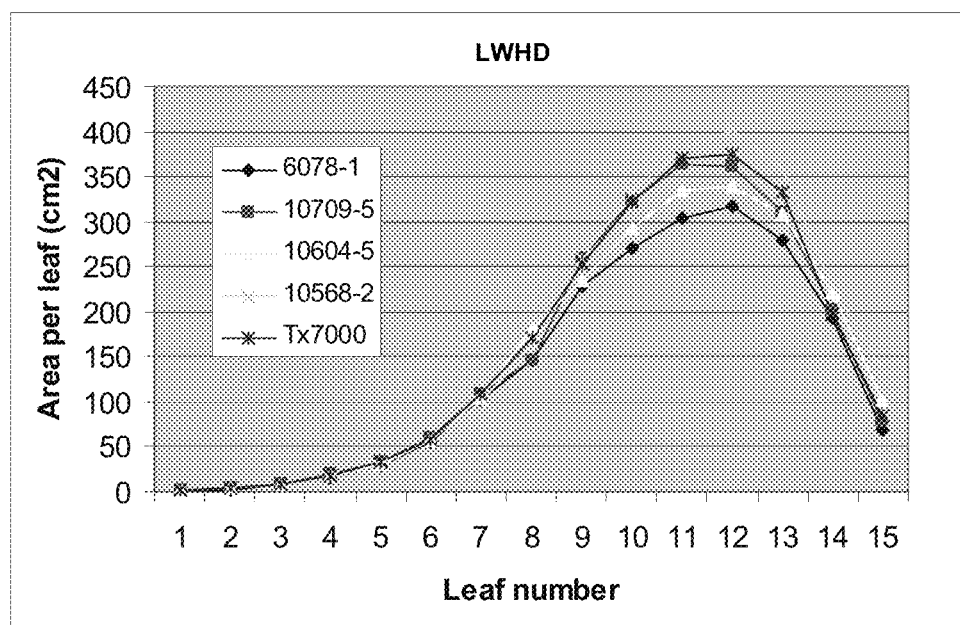
FIG. 14 is a graphical representation showing the mainstem leaf size distributions of RTx7000, 6078-1 (Stg1 NIL) and three recombinants from the Stg1 fine-mapping population grown under water-limited and high-density conditions in the field (HD=20 plants/m$^2$).

Introgressing the whole Stg1 region (6078-1) and, more specifically, the smaller region designated 10604-5, resulted in a reduction in the size of leaves 9-13 under low-water and high-density conditions (FIG. 14). For example compared with RTx7000, L11 was 9% and 16% smaller in 10604-5 and 6078-1, respectively. Since tillering was negligible in this treatment, differences in canopy size were essentially due to differences in leaf size.

Under low density conditions, leaf size distributions were affected by tillering, resulting in some crossovers compared with the high density treatment (see FIG. 14). However, note that 10604-5 produced smaller leaves 9-13 relative to 10709-5, 10568-2 and RTx7000 in both HD and LD treatments.

The "small leaf size" gene mapped to a 152 gene block between txp563 and txp442 (the same region identified for the low tillering gene) containing the candidate gene (auxin efflux carrier component 5), see FIG. 15.

Example 9

Smaller Leaves (Fine-mapping Studies in Igloo)

Figure 16:
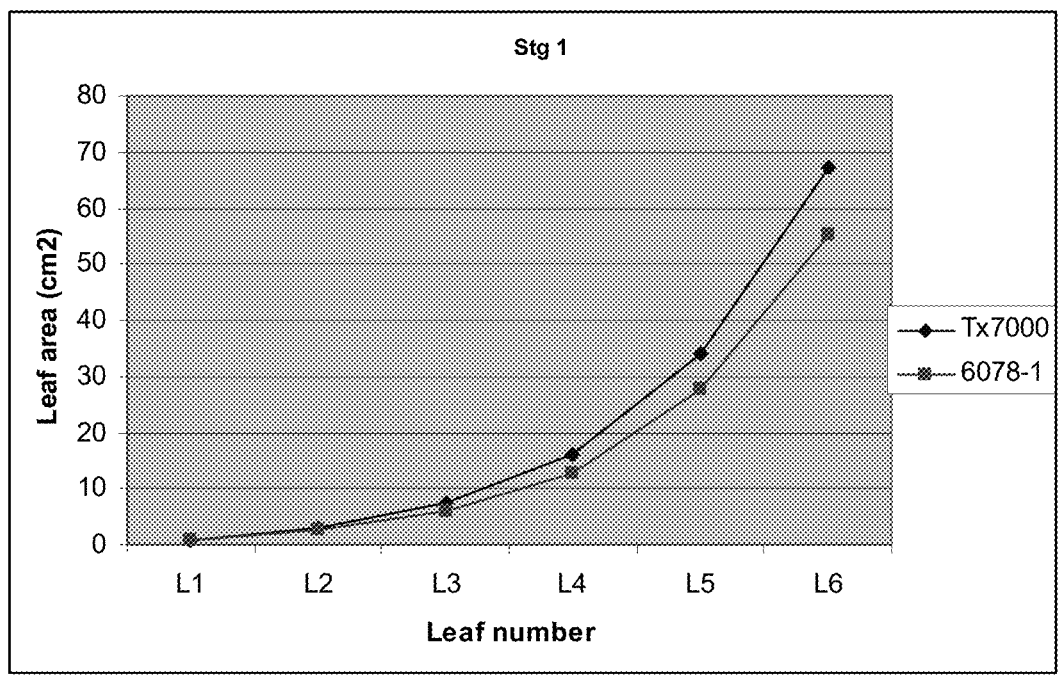
FIG. 16 is a graphical representation showing the leaf size distribution (L1-6) for the parents of the Stg1 fine-mapping population grown in an igloo.

Leaf area varied significantly (P<0.001) among genotypes with a heritability approaching 60 for leaves 4 and 5. Introgressing the Stg1 region into RTx7000 reduced the area of leaves 1-6 (FIG. 16). For example, L6 area was 22% higher in RTx7000 (67.4 cm2) than 6078-1 (55.3 cm2), although this difference was not significant at the P=0.05 level. The area of L6 ranged from 47.8 cm2 to 93.9 cm2 (LSD [0.05]=21), with a heritability of 42.

Figure 17:
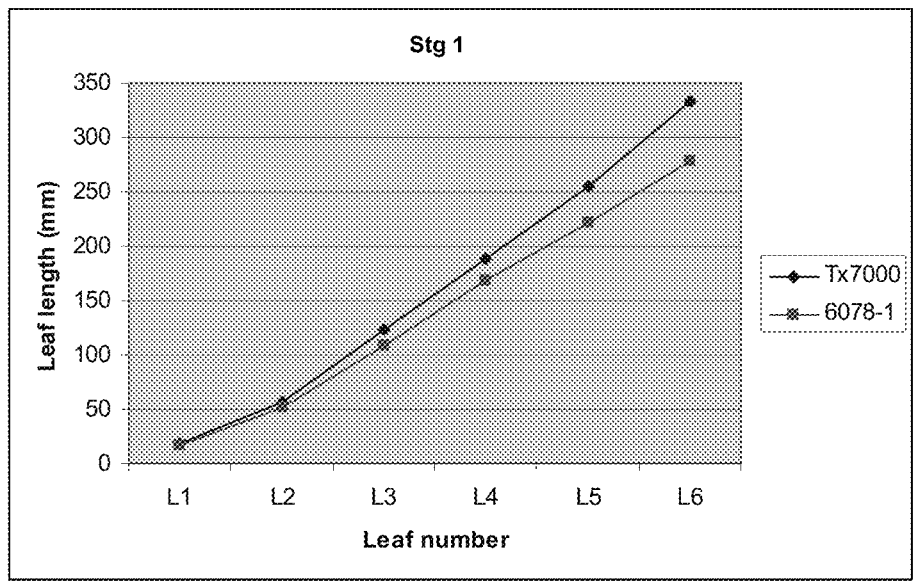
FIG. 17 is a graphical representation showing the leaf length distribution (L1-6) for the parents of the Stg1 fine-mapping population grown in an igloo.
Figure 18:
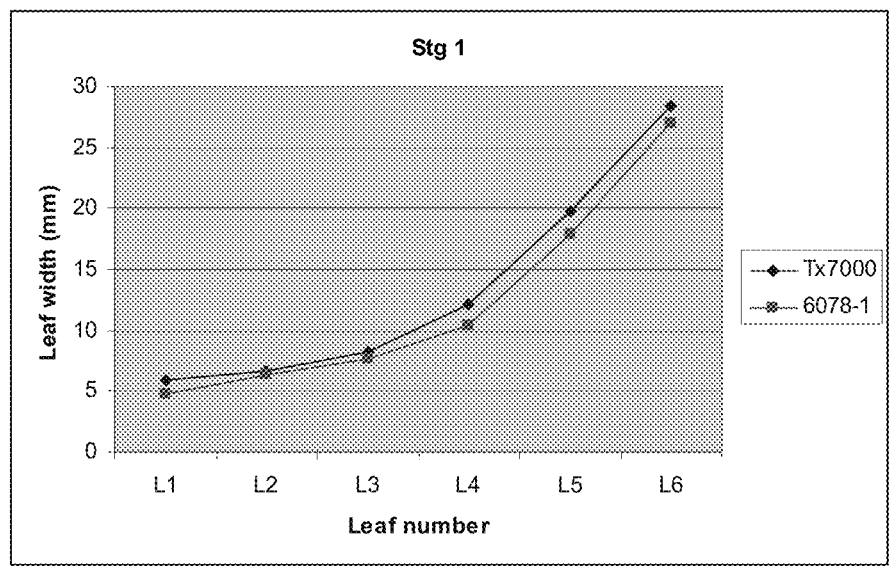
FIG. 18 is a graphical representation showing the leaf width distribution (L1-6) for the parents of the Stg1 fine-mapping population grown in an igloo.

Differences in leaf area were due more to differences in leaf length (FIG. 17) than leaf width (FIG. 18). While leaf area increased exponentially with leaf number (FIG. 21), leaf length increased linearly (FIG. 17). The relationship between leaf width and number was parabolic (FIG. 18). Hence the divergence in leaf area between 6078-1 and RTx7000 with increasing leaf number was due mainly to the divergence in leaf length between these genotypes. This suggests that the function of genes reducing leaf size is more likely associated with cell expansion (leaf length) than division (leaf width).

The allometric relationship in the Stg fine-mapping population between the area of leaf (n) and the area of leaf (n+1) indicates a significant change at about Leaf 8 (concurrent with floral initiation). Thereafter, increases in leaf size occurred at a lesser rate.

Figure 19:
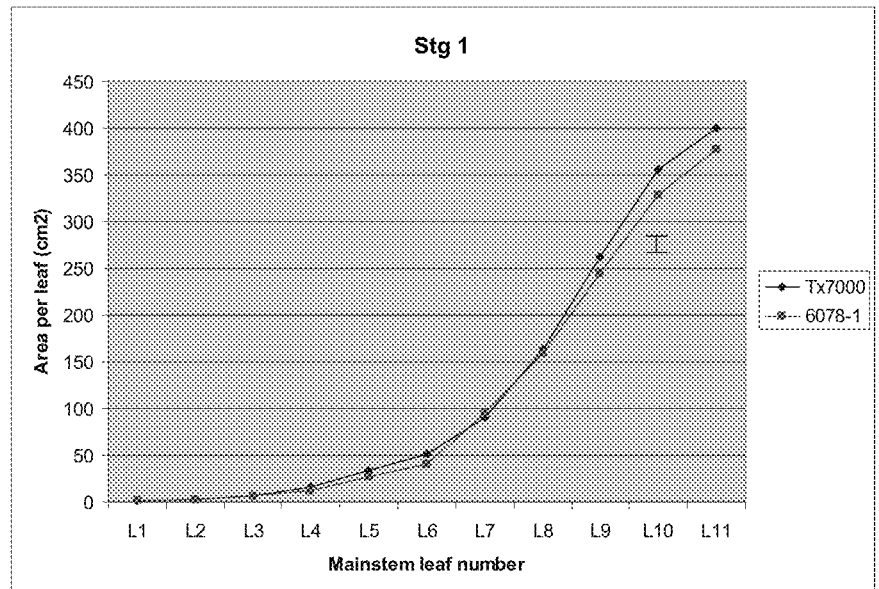
FIG. 19 is a graphical representation showing the leaf size distribution (I1-I1) for the parents of the Stg1 fine-mapping population grown in an igloo.

Introgressing the Stg1 region into RTx7000 reduced the area of leaves 9-11 (FIG. 19), as well as leaves 1-6 (discussed earlier). The area of L9 varied significantly (P=0.06) among genotypes, ranging from 234 to 300 cm2, with a heritability of 21 (Table 8). L9 area was 8% higher in RTx7000 (263 cm2) than 6078-1 (244 cm2) [FIG. 19]. Similar trends were apparent for leaves 10 and 11.

TABLE 9

| trait | trait mean | P-value (Genotype) | Error variance | avSED | CV % | gen.var | Hsq |
|---|---|---|---|---|---|---|---|
| Leaf size | | | | | | | |
| L6_GLA | 54.122 | 0.016 | 88.256 | 10.871 | 17.358 | 23.256 | 51.315 |
| L7_GLA | 103.157 | 0.317 | 213.237 | 14.083 | 14.156 | 16.947 | 24.122 |
| L8_GLA | 178.469 | 0.179 | 535.126 | 19.269 | 12.962 | 7.623 | 5.391 |
| L9_GLA | 266.844 | 0.060 | 673.230 | 18.676 | 9.724 | 45.684 | 21.348 |

TABLE 9-continued

| trait | trait mean | P-value (Genotype) | Error variance | avSED | CV % | gen.var | Hsq |
|---|---|---|---|---|---|---|---|
| L10_GLA | 342.756 | 0.506 | 1029.389 | | 9.361 | 1.177 | 0.455 |
| L11_GLA | 383.560 | 0.374 | 848.058 | | 7.592 | 3.098 | 1.440 |
| L11_DW | 1.955 | 0.522 | 0.058 | | 12.372 | 0.000 | 0.000 |
| SLW_L9_L11 | 50.083 | 0.030 | 17.372 | 3.073 | 8.322 | 0.956 | 18.041 |

Table 9 is a summary of predicted means, P-value and heritability of leaf size traits measured at the L11 harvest.

TABLE 10

| mark-erno | mark-ername | mark-ertype | cM | L1_GLA (L6) | L2_GLA (L6) | L7_GLA (L11) | L8_GLA (L11) | L9_GLA (L11) |
|---|---|---|---|---|---|---|---|---|
| 1 | txa2506 | original | 125.2-127.5 | 0.08 | 0.70 | 0.99 | 0.40 | 0.47 |
| 2 | txp114 | both | 134.7-135.6 | 0.31 | 0.15 | 0.06 | 0.41 | 0.03 |
| 3 | txa2179 | original | 135.6-140 | 0.38 | 0.61 | 0.67 | 0.66 | 0.50 |
| 4 | CORN031 | original | 135.6-140 | 0.63 | 0.57 | 0.66 | 0.87 | 0.67 |
| 5 | TS196 | original | 140-142.5 | 0.63 | 0.57 | 0.66 | 0.87 | 0.67 |
| 6 | txp196 | new | 140-142.5 | 0.85 | 0.02 | 0.06 | 0.21 | 0.02 |
| 7 | txa2961 | original | 142.5 | 0.63 | 0.57 | 0.66 | 0.87 | 0.67 |
| 8 | BH245191 | both | 145.5-147.3 | 0.67 | 0.28 | 0.02 | 0.30 | 0.02 |
| 9 | BG411222 | original | 145.5-147.3 | 0.74 | 0.92 | 0.22 | 0.32 | 0.15 |
| 10 | txp439 | new | 145.5-147.3 | 0.73 | 0.60 | 0.09 | 0.30 | 0.03 |
| 11 | txp440 | new | 145.5-147.3 | 0.82 | 0.73 | 0.01 | 0.27 | 0.06 |
| 12 | txp542 | new | 145.5-147.3 | 0.34 | 0.74 | 0.05 | 0.27 | 0.31 |
| 13 | txp563 | new | 149.1-150.3 | 0.16 | 0.57 | 0.45 | 0.21 | 0.79 |
| 14 | txa3676 | original | 149.1-150.3 | 0.50 | 0.30 | 0.43 | 0.20 | 0.10 |
| 15 | txa2986 | original | 150.3 | 0.50 | 0.30 | 0.43 | 0.20 | 0.10 |
| 16 | txp581 | new | 150.3-151.9 | 0.03 | 0.11 | 0.60 | 0.87 | 0.22 |
| 17 | txp587 | new | 151.9-156.2 | 0.13 | 0.29 | 0.49 | 0.91 | 0.07 |
| 18 | txp446 | new | 151.9-156.2 | 0.27 | 0.43 | 0.91 | 0.89 | 0.31 |
| 19 | txp442 | original | 151.9-156.2 | 0.50 | 0.30 | 0.43 | 0.20 | 0.10 |
| 20 | txp38 | original | 158.3-161.4 | 0.09 | 0.75 | 0.25 | 0.07 | 0.03 |
| 21 | txa3390 | original | 158.3-161.4 | 0.15 | 0.70 | 0.42 | 0.05 | 0.02 |

| mark-erno | mark-ername | mark-ertype | L10_GLA (L11) | L11_GLA (L11) | L6_DM (L6) | L11_DW (L11) | SLW_L6 (L6) | SLW_L9_L11 (L11) |
|---|---|---|---|---|---|---|---|---|
| 1 | txa2506 | original | 0.74 | 0.91 | 0.88 | 0.28 | 0.97 | 0.38 |
| 2 | txp114 | both | 0.08 | 0.01 | 0.57 | 0.47 | 0.82 | 0.05 |
| 3 | txa2179 | original | 0.50 | 0.97 | 0.92 | 0.64 | 0.90 | 0.56 |
| 4 | CORN031 | original | 0.43 | 1.00 | 0.52 | 0.61 | 0.70 | 0.69 |
| 5 | TS196 | original | 0.43 | 1.00 | 0.52 | 0.61 | 0.70 | 0.69 |
| 6 | txp196 | new | 0.32 | 0.38 | 0.34 | 0.45 | 0.07 | 0.06 |
| 7 | txa2961 | original | 0.43 | 1.00 | 0.52 | 0.61 | 0.70 | 0.69 |
| 8 | BH245191 | both | 0.60 | 0.66 | 0.22 | 0.72 | 0.03 | 0.22 |
| 9 | BG411222 | original | 0.21 | 0.88 | 0.26 | 0.95 | 0.35 | 0.93 |
| 10 | txp439 | new | 0.58 | 0.69 | 0.28 | 0.91 | 0.03 | 0.81 |
| 11 | txp440 | new | 0.06 | 0.63 | 0.07 | 0.78 | 0.02 | 0.66 |
| 12 | txp542 | new | 0.22 | 0.72 | 0.16 | 0.79 | 0.08 | 0.83 |
| 13 | txp563 | new | 0.98 | 0.28 | 0.63 | 0.73 | 0.56 | 0.55 |
| 14 | txa3676 | original | 0.03 | 0.69 | 0.29 | 0.22 | 0.22 | 0.16 |
| 15 | txa2986 | original | 0.03 | 0.69 | 0.29 | 0.22 | 0.22 | 0.16 |
| 16 | txp581 | new | 0.19 | 0.01 | 0.91 | 0.49 | 0.91 | 0.52 |
| 17 | txp587 | new | 0.23 | 0.05 | 0.93 | 0.78 | 0.81 | 0.38 |
| 18 | txp446 | new | 0.21 | 0.08 | 0.58 | 0.66 | 0.47 | 0.37 |
| 19 | txp442 | original | 0.03 | 0.69 | 0.29 | 0.22 | 0.22 | 0.16 |
| 20 | txp38 | original | 0.52 | 0.55 | 0.57 | 0.09 | 0.51 | 0.12 |
| 21 | txa3390 | original | 0.40 | 0.19 | 0.62 | 0.06 | 0.49 | 0.26 |

P <0.05
P <0.10

GLA=green leaf area. DW=dry weight. SLW_L9_L11=specific leaf weight.

Most of the variation in green leaf area at the Leaf 11 harvest was due to differences in tillering. However, leaves 9-11 were smaller in 6078-1 compared with RTx7000. These differences were significant (P<0.05) at txp114 (134.7-135.6 cM) and between markers txa3676 and txp442 (149.1-156.2 cM) [Table 10]. Note that 'low tillering' and 'small leaves' were both associated with the same region between markers txa3676 and txp442, indicating the possibility of a single gene controlling both canopy architecture traits.

Table 10 is a summary of P-values for various leaf size traits measured at the L11 harvest. GLA=green leaf area. DM=dry mass. DW=dry weight. SLW=specific leaf weight.

Example 10

Smaller Leaves (Fine-mapping Studies in Igloo)

Figure 20:
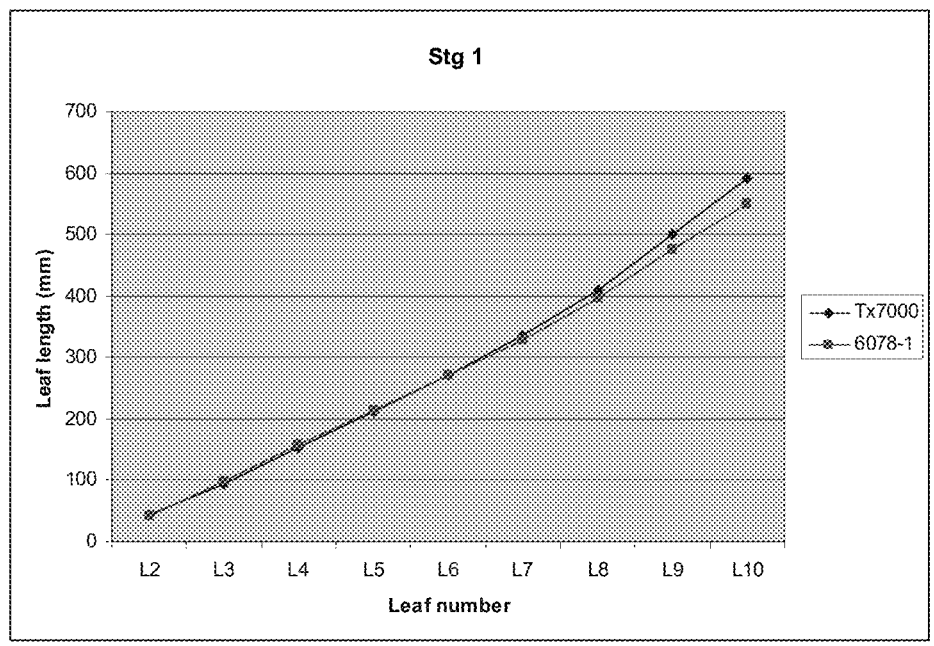
FIG. 20 is a graphical representation showing the leaf length distribution (L1-10) for the parents of the Stg1 fine-mapping population grown in an igloo.

Leaf number and length were linearly correlated for the parents of the Stg1 fine-mapping population (FIG. 20).

Introgressing Stg1 into RTx7000 resulted in a reduction in the length of leaves 8-10, with L10 being 7% shorter in 6078-1 than RTx7000 (550 vs. 592 mm).

For mapping purposes, the 'tails' of the Stg1 fine-mapping population were selected. Two genotypes exhibited particularly long leaves (10604-1-157-5 and 10604-1-318-1) and three genotypes exhibited particularly short leaves (10604-1-222-1, 10604-1-501-327-3 and 6078-1).

Gain-of-function (short leaf) is achieved in recombinant 10604-1-222-1 between markers txa2986 and txp542. This would mean the small-leaf gene(s) resides in a block extending down to (but not including) txp581 and up to (but not including) txp440. Hence the 'small leaf' gene maps to the same region as the 'low tillering' gene.

Figure 21:
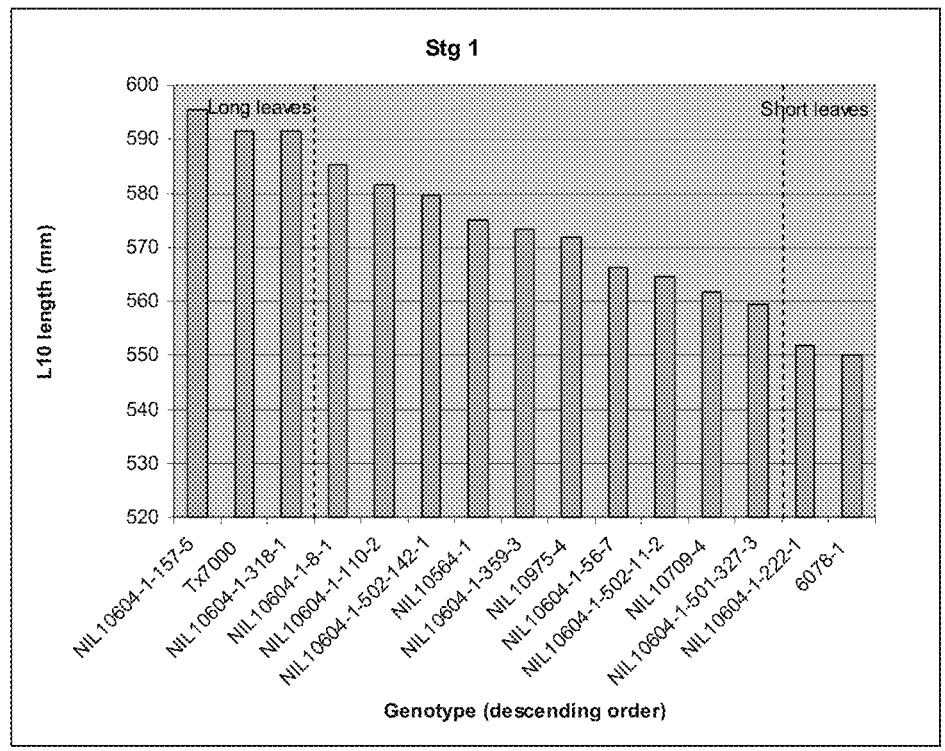
FIG. 21 is a tabulated representation showing a histogram of phenotypic variation for L10 length in a subset of the Stg1 fine-mapping population grown in an igloo.

For mapping purposes, the 'tails' of the Stg1 fine-mapping population were selected (FIG. 21). Three genotypes exhibited particularly long leaves (10604-1-157-5, 10604-1-318-1 and RTx7000) and two genotypes exhibited particularly short leaves (10604-1-222-1 and 6078-1).

Stepping up through the markers in FIG. 22, gain-of-function (short leaf) is achieved in recombinant 10604-1-222-1 between markers txa2986 and txp542. This would mean the small-leaf gene(s) resides in a block extending down to (but not including) txp581 and up to (but not including) txp440. Hence, once again, the 'small leaf' gene maps to the same region as the 'low tillering' gene. Note that leaf length in L9 and L10 map to the same region.

Multiple studies indicate that a gene (or genes) causing a low-tillering and small-leaf phenotype is located between markers txp563 and txa2986 (FIG. 23). An explanation is a single gene with multiple pleiotrophic effects. Enhanced availability of auxin would explain both the low tillering and small leaf size phenotypes observed in plants containing this region. An auxin efflux carrier component 5 gene is located in the target region and is therefore identified as a candidate.

Example 11

Figure 24:
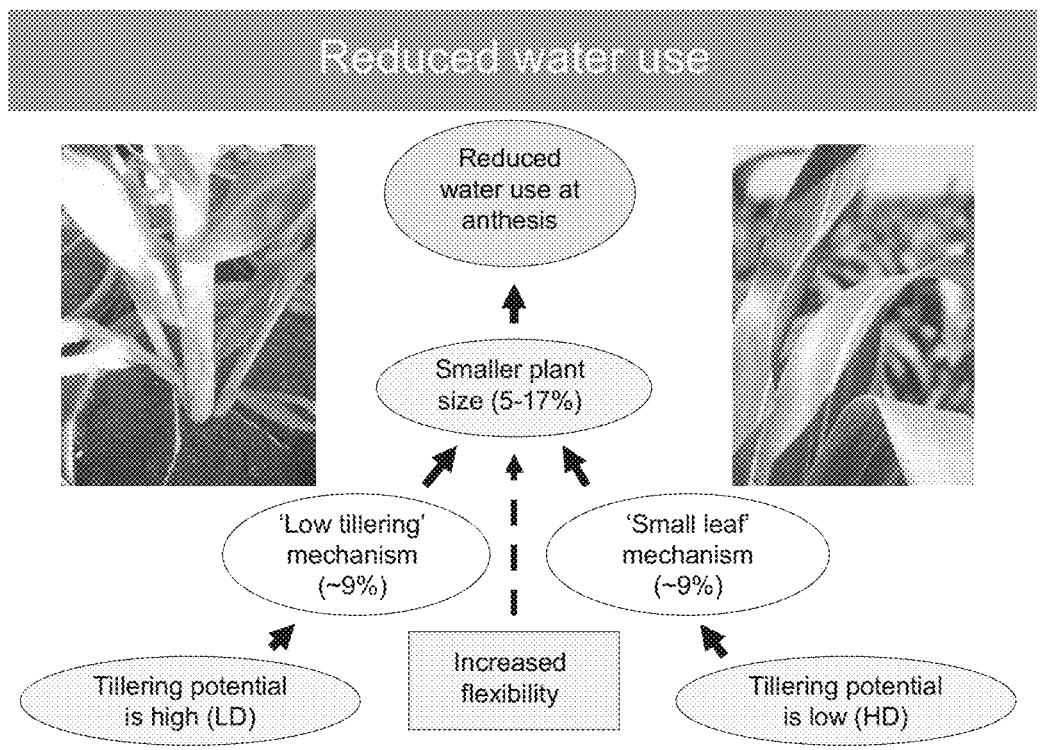
FIG. 24 is a diagrammatic representation showing that increased water availability at anthesis is achieved via reduced water use due to two mechanisms (reduced tillering and smaller leaves) in plants containing the Stg1 region.

Stay-green Enhances Canopy Architecture Plasticity Via Constitutive and Adaptive Responses Increased water availability at anthesis is achieved via reduced water use due to two mechanisms (reduced tillering and smaller leaves) in plants containing the Stg1 region FIG. 24). Both mechanisms, individually, appear to reduce canopy size by about 9%, on average. The 'low-tillering' mechanism dominates in low density environments when tillering potential is high. The 'small-leaf' mechanism dominates in high density environments when tillering potential is low. Combined, these two mechanisms provide crop plants with considerable plasticity to modify canopy architecture in response to the severity of water limitation.

Figure 25:
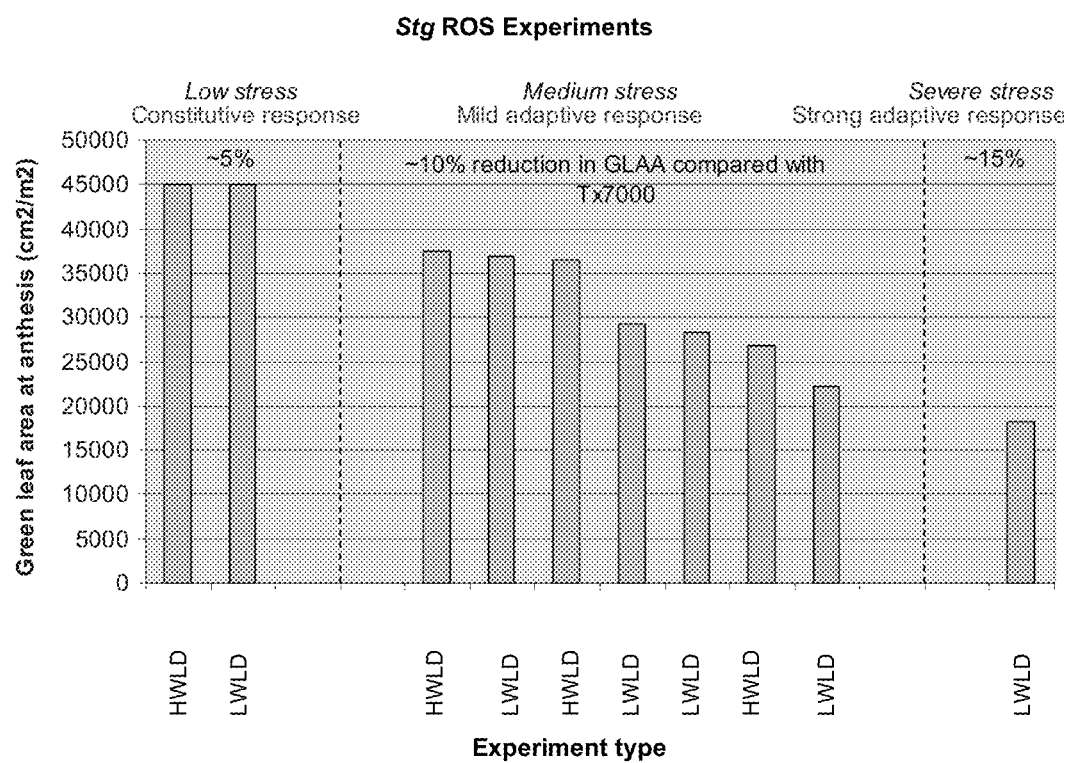
FIG. 25 is a tabulated representation showing that canopy size is modulated by both constitutive and adaptive responses controlled by a gene(s) in the Stg1 region.
Figure 26:
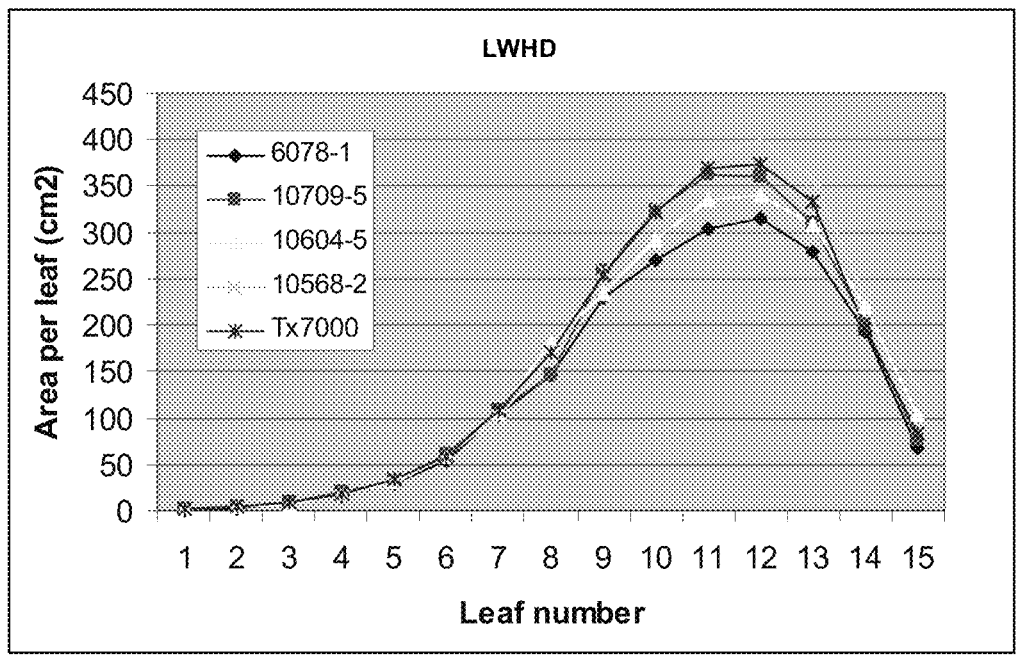
FIG. 26 is a graphical representation showing the mainstem leaf size distributions of RTx7000, 6078-1 (Stg1 NIL) and three recombinants from the Stg1 fine-mapping population grown under water-limited and high-density conditions in the field (HD=20 plants/m$^2$).

Stay-green exhibits both constitutive and adaptive responses (FIG. 25). Canopy size in Stg1 is reduced by about 5%, even when water is not limiting (constitutive response): Canopy size is further reduced (adaptive response) in a mild drought (~10%) and more severe drought (~15%). Low tillering is primarily a constitutive response, although smaller leaf size in tillers in response to increasing water deficit is an adaptive response. Small leaf size is both a constitutive and adaptive response.

Example 12

Link between Reduced Canopy Size (Via Reduced Tillering and Smaller Leaves) and Reduced Crop Water Use at Anthesis Reduced crop water use at anthesis can be caused by a) a smaller canopy size with equivalent transpiration per unit leaf area, b) an equivalent canopy size with lower transpiration per unit leaf area, or c) a smaller canopy size and lower transpiration per unit leaf area. ROS studies indicate that under high water stress conditions, the Stg1 region, and in particular the recombinant containing the Stg1 candidate gene (10604-5), exhibited lower crop water use due to a smaller canopy size rather than lower transpiration per unit leaf area. High correlations (r2=0.9) between canopy size and crop water use were observed in ROS and lysimeter studies.

(a) Water Savings due to Smaller Leaf Size

Figure 27:
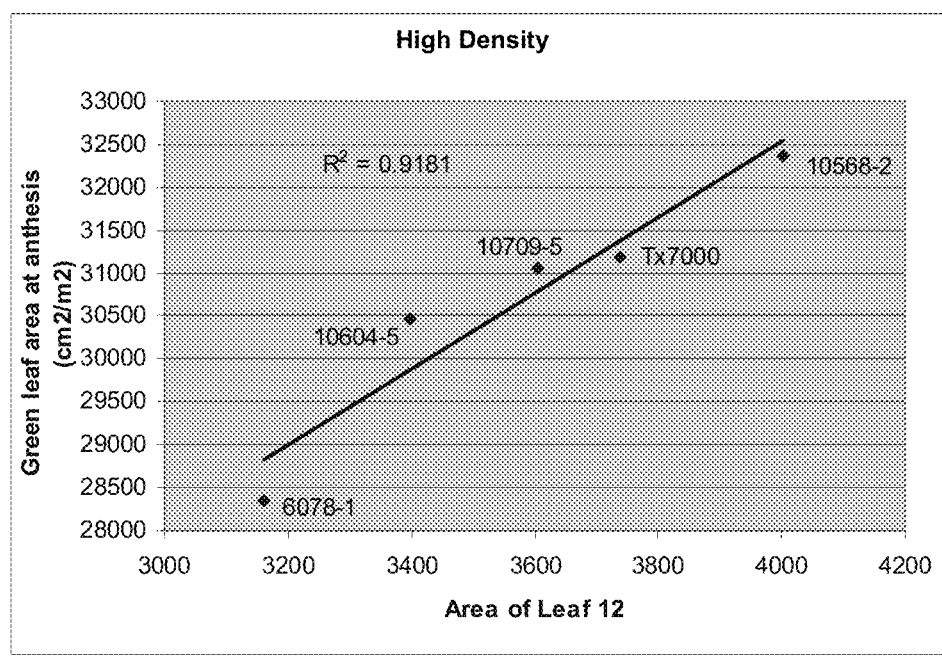
FIG. 27 is a graphical representation showing the relation between the area of leaf 12 and the total green leaf area at anthesis for the two parents (6078-1 and RTx7000) and three recombinants from the Stg1 fine-mapping population.
Figure 28:
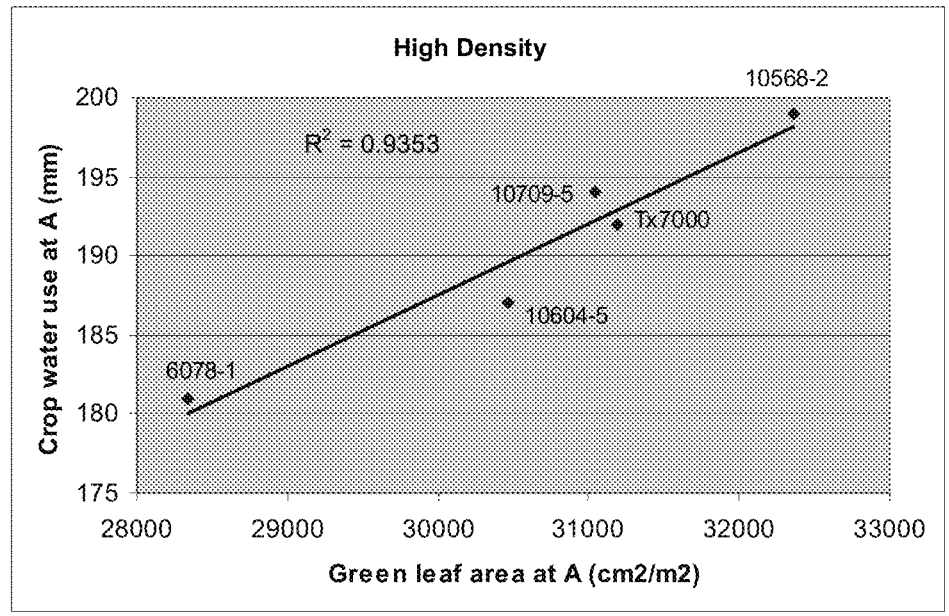
FIG. 28 is a graphical representation showing the relation between total green leaf area (cm$^2$/m$^2$) and crop water use (mm) at anthesis for the two parents (6078-1 and RTx7000) and three recombinants from the Stg1 fine-mapping population.

Tillering was negligible in this experiment due to the high crop density. Hence differences in canopy size were due to differences in leaf size (FIG. 27), as evidenced by the high correlation between the size of Leaf 12 and the total green leaf area at anthesis (FIG. 28).

Figure 29:
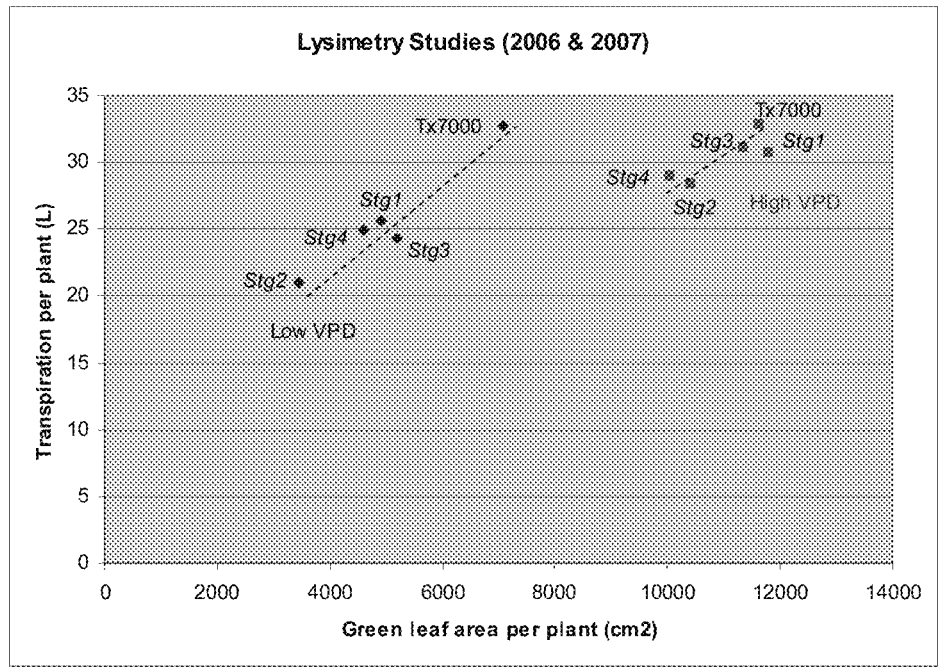
FIG. 29 is a graphical representation showing the relation between green leaf area and water use (T) in four Stg QTL and the recurrent parent (RTx7000) in lysimetry studies under two levels of VPD.

In turn, green leaf area at anthesis was highly correlated with crop water use at anthesis (FIG. 29). Relative to RTx7000, the two lines containing the Stg1 candidate gene (6078-1 and 10604-5) both exhibited smaller leaves (L10-L13), lower green leaf area at anthesis (GLAA), and lower crop water use at anthesis.

(b) Water Savings due to Reduced Transpiration per Unit Leaf Area (Lysimetry Studies)

Transpiration (T) is the product of leaf area (LA) and transpiration per leaf area (T/LA). Under high VPD conditions, LA was similar between Stg1 and RTx7000 (11795 vs 11628 cm2), yet T/LA was less in Stg1 than Tx7000 (2.60 vs 2.85), resulting in less water use per plant (T) in Stg1 than RTx7000 (30.7 vs 32.8 l). Hence water savings in Stg1 (in a high VPD environment) were achieved entirely by a reduction in T/LA, suggesting that this is a constitutive water conservation strategy conferred by Stg1. In this case, higher transpiration efficiency (TE) in Stg1 was a consequence of equivalent biomass and lower transpiration.

A broader analysis comparing the four Stg QTL (Stg1, Stg2, Stg3 and Stg4) with RTx7000 helps to put the Stg1 response in perspective. Under high VPD conditions, T/LA was positively correlated with T, However under low VPD conditions, T/LA was negatively correlated with T (r2=0.52). Green leaf area and transpiration were positively correlated under both low and high VPD conditions (FIG. 29). In both experiments, the Stg QTLs reduced green leaf area and transpiration compared with RTx7000.

(c) Water Savings due to Reduced Leaf Area

Transpiration (T) is the product of LA and T/LA. Under low VPD conditions, LA was 31% less in Stg1 than RTx7000 (4898 vs 7082 cm2). This was offset slightly by a 9% increase in T/LA in Stg1 compared with RTx7000 (5.15 vs 4.70). The net result was a 22% reduction in water use per plant (T) in Stg1 compared with RTx7000 (25.6 vs 32.7 l), primarily due to reduced canopy size. The increase in T/LA exhibited by Stg1 may itself be a drought adaptation mechanism, cooling the leaf and enabling photosynthesis to continue.

The plasticity in T/LA appears to be particularly important in the regulation of plant water status. Under high VPD conditions, reduced T/LA in Stg1 was the key mechanism for reducing T and increasing TE. Under low VPD conditions, increased T/LA in Stg1 may have contributed to maintenance of leaf function via cooling.

Lysimetry studies on a Stg1 fine-mapping subset provide additional insight into this region. Under high VPD conditions, LA per plant was less in 10604-5 (location of Stg1 candidate gene) than RTx7000 (10283 vs 11628 cm2), yet T/LA was equivalent in 10604-5 and RTx7000 (~2.86), resulting in less water use per plant in 10604-5 than RTx7000 (28.0 vs 32.8 l). Hence water savings in 10604-5 were achieved entirely by a reduction in canopy size.

Under low VPD conditions, LA per plant was less in all of the Stg1 lines compared with RTx7000, resulting in water savings in all Stg1 lines. Therefore it was difficult to fine-map this region, since all recombinants responded similarly to 6078-1.

(d) Simulation of Agronomy

Figure 64A:
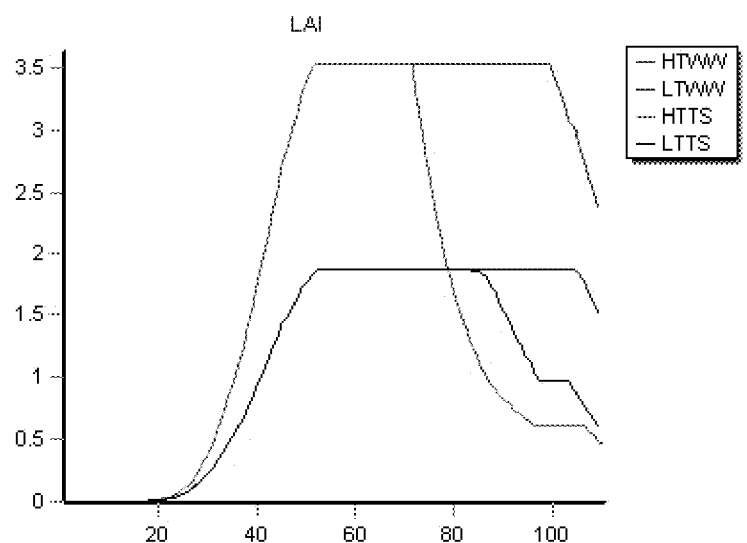
FIG. 64A through C are graphical representations showing results from running a sorghum crop simulation model using the generic variety Buster with the usual 2 tillers/plant (HT) versus a Buster with only 1 tiller/plant (LT) in a well-watered (WW) and a terminally stressed (TS) virtual environment. For both virtual environments the following parameters were chosen: planting density 5 plants/m2 with 1 m row spacing; soil depth=1800 mm; soil PAWC=324 mm; N non-limiting.
Figure 64B:
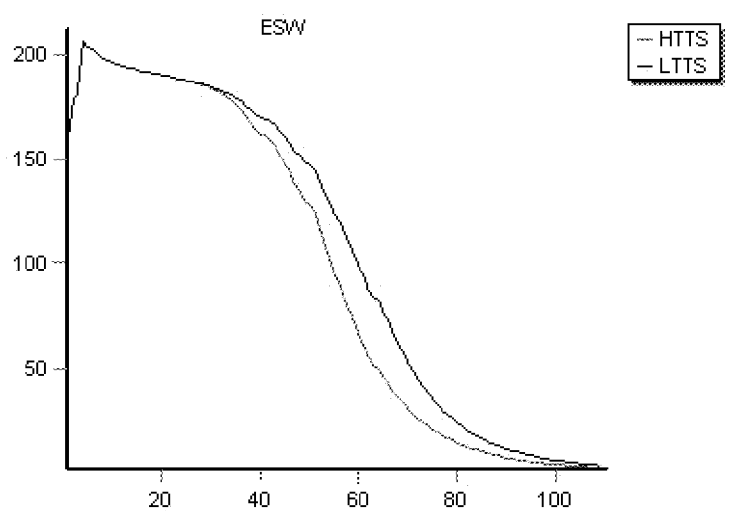
Figure 64C:
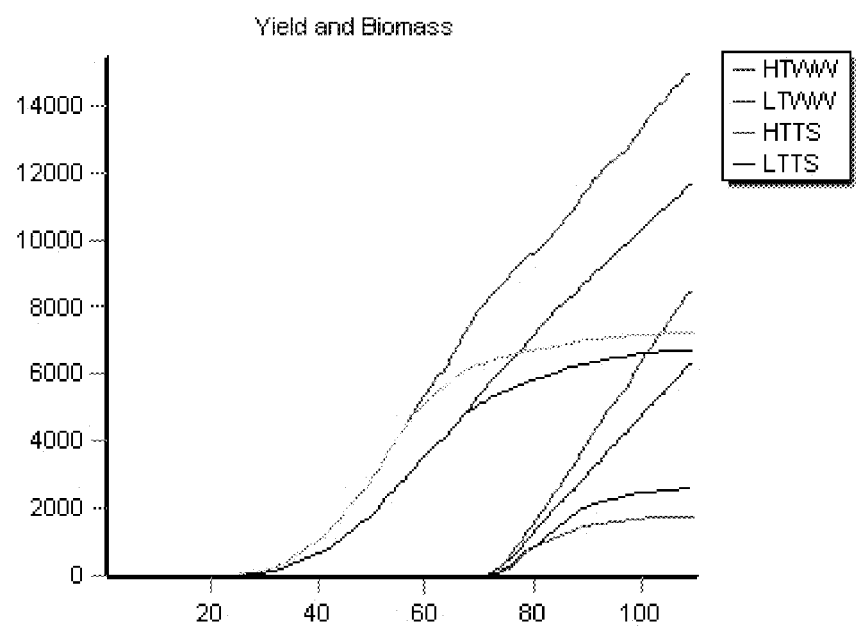

Buster planted at 5 plants/m2 with 1 m row spacing. Soil depth=1800 mm; soil PAWC=324 mm; N non-limiting. Results are shown in FIGS. 64A through C.

Treatments

HT High Tillering (2 tillers/plant)
LT Low Tillering (1 tiller/plant)
WW Well Watered (Start with 100% profile and rain fed)
TS Terminal Stress (Start with profile half full [162 mm] and no rain after establishment).

Example 13

Figure 30:
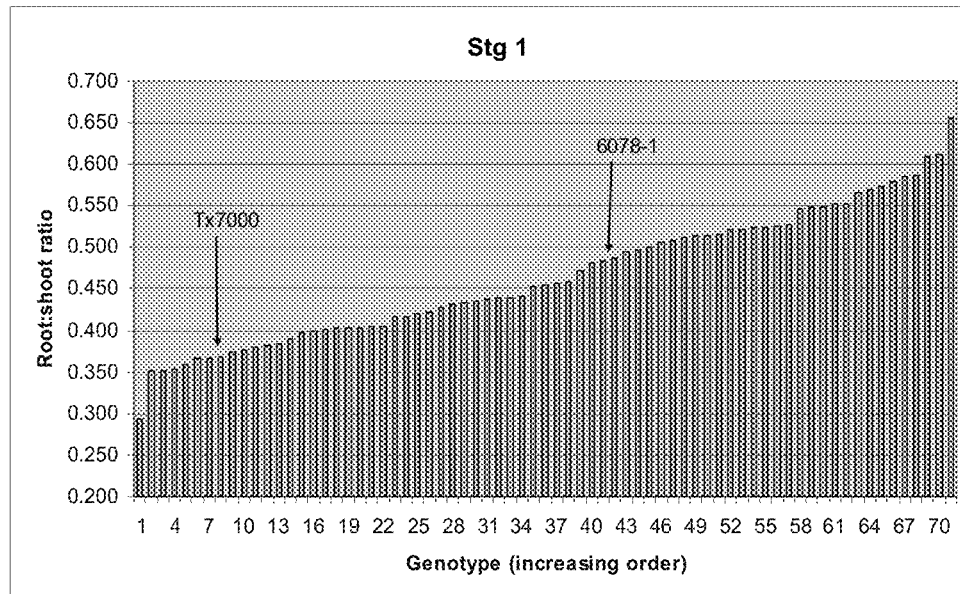
FIG. 30 is a graphical representation showing a histogram of phenotypic variation for the "root:shoot ratio" at L6 in the Stg1 fine-mapping population grown in an igloo.

Increased Water Availability at Anthesis may Also be Achieved Via Increased Water Accessibility due to Better Water Extraction and/or Deeper or Greater Lateral Spread of Roots in Plants Containing the Stg1 Region Root mass and root:shoot ratio (FIG. 30) were higher in Stg1 than RTx7000 at the Leaf 6 stage. There was considerable transgressive segregation for these traits in the Stg1 fine-mapping population. The relation between root mass and root:shoot ratio highlights the opportunity for further genetic advance in these traits.

Root mass per leaf area ratio can be used as a drought adaptation index at the seedling stage since it integrates the capacity of the plant to access water (root mass) with the capacity of the plant to utilise water (leaf area). A higher index indicates a greater capacity to access water per unit leaf area. Stg1 exhibited a higher root mass per leaf area ratio relative to RTx7000 due to both a higher root mass and a smaller leaf area.

In a Stg1 fine-mapping study, root harvest index (root: totalbio ratio) at the L6 stage mapped to txa3676 and txa2986, the same location as the Stg1 candidate gene (Table 11).

TABLE 11

| markerno | markername | markertype | cM | L1_GLA (L6) | L1_GLA (L6) | L1_GLA (L6) | L1_GLA (L6) | L1_GLA (L6) | L1_GLA (L6) | L1_GLA (L6) |
|---|---|---|---|---|---|---|---|---|---|---|
| 1 | txa2506 | original | 125.2-127.5 | 0.08 | 0.70 | 0.99 | 0.40 | 0.47 | 0.74 | 0.91 |
| 2 | txp114 | both | 134.7-135.6 | 0.31 | 0.15 | 0.06 | 0.41 | 0.03 | 0.08 | 0.01 |
| 3 | txa2179 | original | 135.6-140 | 0.38 | 0.61 | 0.67 | 0.66 | 0.50 | 0.50 | 0.97 |
| 4 | CORN031 | original | 135.6-140 | 0.63 | 0.57 | 0.66 | 0.87 | 0.67 | 0.43 | 1.00 |
| 5 | TS196 | original | 140-142.5 | 0.63 | 0.57 | 0.66 | 0.87 | 0.67 | 0.43 | 1.00 |
| 6 | txp196 | new | 140-142.5 | 0.85 | 0.02 | 0.06 | 0.21 | 0.02 | 0.32 | 0.38 |
| 7 | txa2961 | original | 142.5 | 0.63 | 0.57 | 0.66 | 0.87 | 0.67 | 0.43 | 1.00 |
| 8 | BH245101 | both | 145.5-147.3 | 0.67 | 0.28 | 0.02 | 0.30 | 0.02 | 0.60 | 0.66 |
| 9 | BG411222 | original | 145.6-147.3 | 0.74 | 0.92 | 0.22 | 0.32 | 0.15 | 0.21 | 0.88 |
| 10 | txp439 | new | 145.5-147.3 | 0.73 | 0.60 | 0.09 | 0.30 | 0.03 | 0.58 | 0.89 |
| 11 | txp440 | new | 145.5-147.3 | 0.82 | 0.73 | 0.01 | 0.27 | 0.06 | 0.06 | 0.63 |
| 12 | txp542 | new | 145.5-147.3 | 0.34 | 0.74 | 0.05 | 0.27 | 0.31 | 0.22 | 0.72 |
| 13 | txp563 | new | 149.1-150.3 | 0.16 | 0.57 | 0.45 | 0.21 | 0.79 | 0.98 | 0.28 |
| 14 | txa3876 | original | 149.1-150.3 | 0.50 | 0.30 | 0.43 | 0.20 | 0.10 | 0.03 | 0.69 |
| 15 | txa2986 | original | 150.3 | 0.50 | 0.30 | 0.43 | 0.20 | 0.10 | 0.03 | 0.69 |
| 16 | txp581 | new | 150.3-161.9 | 0.03 | 0.11 | 0.60 | 0.67 | 0.22 | 0.19 | 0.01 |
| 17 | txp587 | new | 151.9-155.2 | 0.13 | 0.29 | 0.49 | 0.91 | 0.07 | 0.23 | 0.05 |
| 18 | txp446 | new | 151.9-156.2 | 0.27 | 0.43 | 0.91 | 0.89 | 0.31 | 0.21 | 0.08 |
| 19 | txp442 | original | 151.9-158.2 | 0.50 | 0.30 | 0.43 | 0.20 | 0.10 | 0.03 | 0.69 |
| 20 | txp38 | original | 158.3-161.4 | 0.09 | 0.75 | 0.25 | 0.07 | 0.03 | 0.52 | 0.55 |
| 21 | txp3390 | original | 158.3-161.4 | 0.15 | 0.70 | 0.42 | 0.05 | 0.02 | 0.40 | 0.19 |

| markerno | L1_GLA (L6) | L1_GLA (L6) | SLW_L6 (L6) | SLW_L9_L11 (L11) | Tillerno_max (L11) | Bio_T (L11) | Gleaf_T (L11) | Stem_T (L11) | GLA_T (L11) | presence_T2 (L11) |
|---|---|---|---|---|---|---|---|---|---|---|
| 1 | 0.88 | 0.28 | 0.97 | 0.38 | 0.82 | 0.86 | 0.78 | 0.98 | 0.65 | 0.02 |
| 2 | 0.57 | 0.47 | 0.82 | 0.05 | 0.02 | 0.11 | 0.05 | 0.23 | 0.13 | 0.02 |
| 3 | 0.92 | 0.64 | 0.90 | 0.58 | 0.67 | 0.50 | 0.46 | 0.59 | 0.36 | 0.37 |
| 4 | 0.52 | 0.61 | 0.70 | 0.69 | 0.74 | 0.18 | 0.17 | 0.22 | 0.13 | 0.35 |
| 5 | 0.52 | 0.61 | 0.70 | 0.69 | 0.74 | 0.18 | 0.17 | 0.22 | 0.13 | 0.35 |
| 6 | 0.34 | 0.45 | 0.07 | 0.06 | 0.12 | 0.67 | 0.74 | 0.83 | 0.95 | 0.06 |
| 7 | 0.52 | 0.61 | 0.70 | 0.69 | 0.74 | 0.18 | 0.17 | 0.22 | 0.13 | 0.35 |
| 8 | 0.22 | 0.72 | 0.03 | 0.22 | 0.31 | 0.84 | 0.86 | 0.97 | 0.94 | 0.14 |
| 9 | 0.26 | 0.95 | 0.35 | 0.93 | 0.03 | 0.04 | 0.04 | 0.03 | 0.02 | 0.29 |
| 10 | 0.28 | 0.91 | 0.03 | 0.81 | 0.52 | 0.67 | 0.75 | 0.66 | 0.79 | 0.13 |
| 11 | 0.07 | 0.78 | 0.02 | 0.66 | 0.36 | 0.67 | 0.72 | 0.56 | 0.77 | 0.03 |
| 12 | 0.16 | 0.79 | 0.08 | 0.83 | 0.58 | 0.27 | 0.25 | 0.14 | 0.27 | 0.04 |
| 13 | 0.63 | 0.73 | 0.56 | 0.55 | 0.30 | 0.36 | 0.36 | 0.32 | 0.24 | 0.04 |
| 14 | 0.29 | 0.22 | 0.22 | 0.16 | 0.02 | 0.04 | 0.05 | 0.03 | 0.02 | 0.03 |
| 15 | 0.29 | 0.22 | 0.22 | 0.16 | 0.02 | 0.04 | 0.05 | 0.03 | 0.02 | 0.03 |
| 16 | 0.91 | 0.49 | 0.91 | 0.52 | 0.03 | 0.03 | 0.01 | 0.06 | 0.03 | 0.02 |
| 17 | 0.93 | 0.78 | 0.81 | 0.38 | 0.05 | 0.02 | 0.01 | 0.04 | 0.03 | 0.04 |
| 18 | 0.68 | 0.66 | 0.47 | 0.37 | 0.04 | 0.01 | 0.00 | 0.01 | 0.00 | 0.03 |
| 19 | 0.29 | 0.22 | 0.22 | 0.10 | 0.02 | 0.04 | 0.05 | 0.03 | 0.02 | 0.03 |
| 20 | 0.57 | 0.09 | 0.51 | 0.12 | 0.18 | 0.09 | 0.11 | 0.08 | 0.18 | 0.03 |
| 21 | 0.62 | 0.06 | 0.49 | 0.26 | 0.31 | 0.14 | 0.15 | 0.14 | 0.22 | 0.04 |

TABLE 11-continued

| markerno | presence_T3 (L11) | presence_T4 (L11) | totbio (L6) | rootbio (L6) | root.totbio_ratio (L6) | bio.totbio_ratio (L6) | remain_DM (L6) | bio.GLA_ratio (L11) |
|---|---|---|---|---|---|---|---|---|
| 1 | 0.52 | 0.03 | 0.83 | 0.86 | 0.32 | 0.31 | 0.50 | 0.80 |
| 2 | 0.17 | 0.66 | 0.82 | 0.72 | 0.55 | 0.56 | 0.69 | 0.34 |
| 3 | 0.21 | 0.28 | 0.98 | 0.89 | 0.25 | 0.24 | 0.94 | 0.90 |
| 4 | 0.37 | 0.31 | 0.79 | 0.85 | 0.43 | 0.42 | 0.80 | 1.00 |
| 5 | 0.37 | 0.31 | 0.79 | 0.85 | 0.43 | 0.42 | 0.80 | 1.00 |
| 6 | 0.79 | 0.80 | 0.99 | 0.76 | 0.40 | 0.41 | 0.93 | 0.09 |
| 7 | 0.37 | 0.31 | 0.79 | 0.85 | 0.43 | 0.42 | 0.80 | 1.00 |
| 8 | 0.64 | 0.88 | 0.81 | 0.73 | 0.63 | 0.84 | 0.73 | 0.32 |
| 9 | 0.06 | 0.05 | 0.74 | 0.71 | 0.68 | 0.68 | 0.83 | 0.91 |
| 10 | 0.90 | 0.84 | 0.61 | 0.50 | 0.43 | 0.44 | 0.61 | 0.85 |
| 11 | 0.86 | 0.81 | 0.15 | 0.17 | 0.39 | 0.40 | 0.15 | 0.74 |
| 12 | 0.80 | 0.71 | 0.03 | 0.03 | 0.25 | 0.26 | 0.04 | 0.92 |
| 13 | 0.88 | 0.85 | 0.49 | 0.48 | 0.37 | 0.37 | 0.66 | 0.03 |
| 14 | 0.08 | 0.39 | 0.28 | 0.24 | 0.04 | 0.04 | 0.37 | 0.81 |
| 15 | 0.08 | 0.39 | 0.28 | 0.24 | 0.04 | 0.04 | 0.37 | 0.81 |
| 16 | 0.62 | 0.63 | 0.74 | 0.68 | 0.58 | 0.60 | 0.77 | 0.57 |
| 17 | 0.38 | 0.74 | 0.71 | 0.76 | 0.66 | 0.67 | 0.63 | 0.80 |
| 18 | 0.45 | 0.42 | 0.76 | 0.94 | 0.89 | 0.90 | 0.60 | 0.77 |
| 19 | 0.08 | 0.39 | 0.28 | 0.24 | 0.04 | 0.04 | 0.37 | 0.81 |
| 20 | 0.09 | 0.33 | 0.10 | 0.14 | 0.70 | 0.71 | 0.10 | 0.48 |
| 21 | 0.16 | 0.21 | 0.15 | 0.23 | 0.92 | 0.91 | 0.13 | 0.84 |

$P < 0.05$
$P < 0.10$
Leaf area
Tillering
Biomass
Bio/GLA
SPAD

Table 11 is a summary of P-values for various leaf size, tillering and biomass traits measured at the L6 and L11 harvests.

Figure 31:
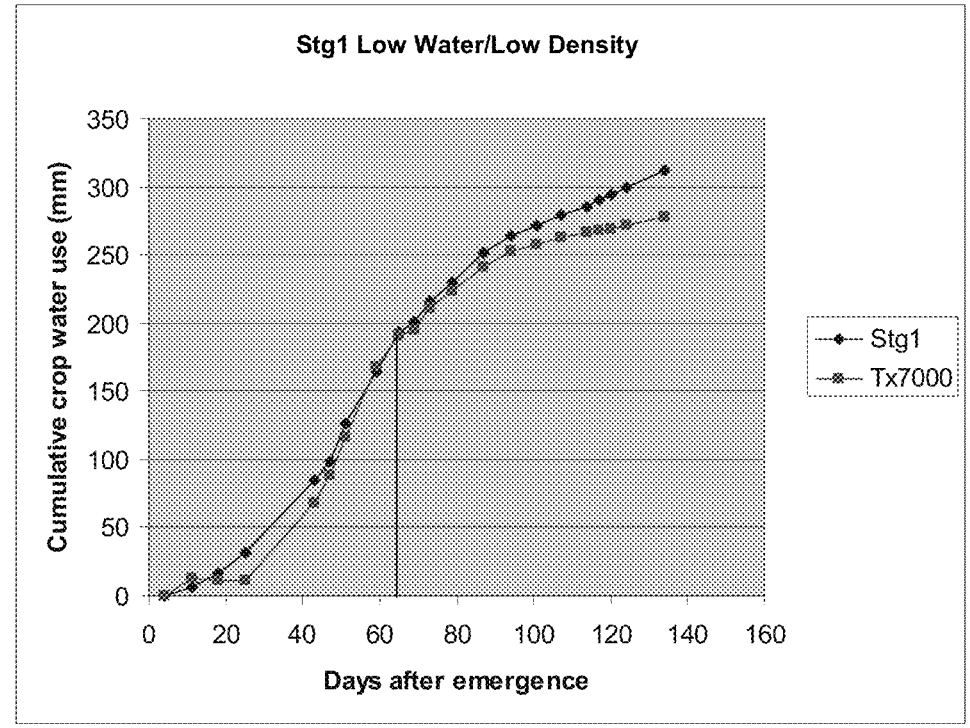
FIG. 31 is a graphical representation showing the temporal pattern of cumulative crop water use for RTx7000 and Stg1 grown under low-water and low-density (20 plants/m$^2$) conditions. The vertical lines marks anthesis.

The higher root mass per leaf area ratio exhibited by Stg1 at the L6 stage may explain why it used more water early in crop growth (20-50 DAE) compared with RTx7000 under the LWLD treatment (FIG. 31). It is not clear yet whether the increased water accessibility during grain filling exhibited by Stg1 compared with RTx7000 (FIG. 31) was due to better water extraction and/or greater root spread.

In a root chamber experiment at Gatton, Queensland, Australia (Van Oosterom et al. (2010) supra), the gravimetric lower limit of water extraction was 0.26% lower for A35 (stay-green) than AQL39 (senescent) hybrids. A35 contains the Stg1 region whereas AQL39 does not. Assuming a bulk density of 1.3 g cm-3 and a soil depth of 150 cm, this could potentially increase available water in the field by >5 mm throughout the life cycle of the crop.

Example 14

Stay-green Enhances Biomass per Unit Leaf Area at Anthesis. Assuming Root Mass is Equivalent (or at Least not Significantly Less), these Differences could be Explained by Differences in Transpiration per Unit Leaf Area and/or Transpiration Efficiency Mainstem biomass per unit leaf area (B/LA) at anthesis was ~24% higher in Stg1 than RTx7000 under low water stress (35.2 vs 26.2 g/m2/cm2) and high water stress (40.6 vs 31.4 g/m2/cm2) conditions (Table 12). Mainstem B/LA at anthesis was ~14% higher under high water stress than low water stress conditions for both Stg1 and RTx7000, i.e. B/LA increased with water deficit. Note that tiller B/LA was equivalent in Stg1 and RTx7000 under low and high water stress conditions.

TABLE 12

| Stg status | No of lines | Mainstem biomass per unit leaf area at anthesis (g/m²/cm²) × 1000 | | Tiller biomass per unit leaf area at anthesis (g/m²/cm²) × 1000 | | Total biomass per unit leaf area at anthesis (g/m²/cm²) × 1000 | |
|---|---|---|---|---|---|---|---|
| | | Low water stress | High water stress | Low water stress | High water stress | Low water stress | High water stress |
| Stg1 region | | | | | | | |
| 1 | 1 | 35.17 | 40.61 | 19.42 | 22.38 | 31.83 | 39.73 |
| 1, 2 | 2 | 31.70 | 34.70 | 18.40 | 19.77 | 28.02 | 33.16 |
| 1, 4 | 1 | 28.12 | 30.88 | 22.68 | 16.53 | 28.66 | 26.69 |
| No regions | | | | | | | |
| RTx 7000 | 7 | 26.21 | 31.36 | 18.04 | 20.61 | 21.20 | 25.81 |
| LSD (0.05) | | 6.70 | 6.70 | 5.90 | 5.90 | 5.96 | 5.96 |

Table 12 shows mainstem, tiller and total biomass per leaf area for RTx7000 (recurrent parent) and a number of near-isogenic lines containing various Stg1 introgressions grown under high and low water stress at Biloela, Queensland, Australia.

The detailed water use measurements suggest that the higher biomass per unit leaf area observed in Stg1 lines at Biloela was probably be due to higher transpiration per unit leaf area rather than TE.

Low Water Stress

Figure 53:
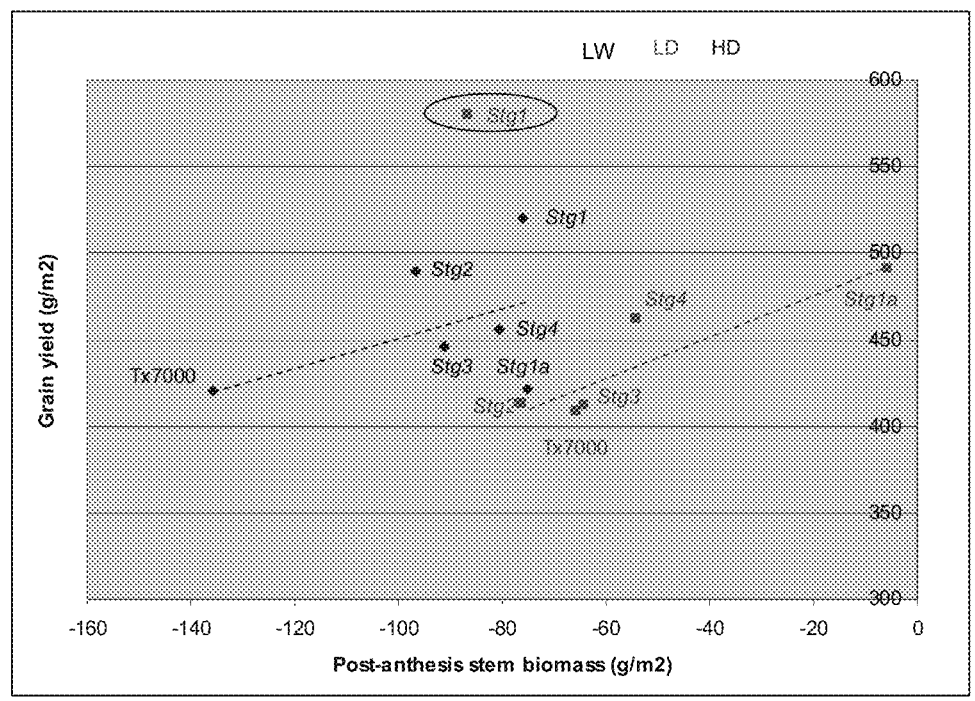
FIG. 53 is a graphical representation showing the relation between post-anthesis stem mass (PASM) and grain yield in four Stg QTL and the recurrent parent (RTx7000) grown under water-limited conditions at two crop densities (LD=10 plants/m$^2$; HD=20 plants/m$^2$) in an experiment grown in 2005.

Stg1 and RTx7000 displayed equivalent B/LA under low water stress. However, T was ~7% lower in Stg1, due to ~10% lower T/LA which, in turn, increased TE by ~9% (FIG. 53). Therefore, Stg1 maintained biomass but used less water compared with RTx7000.

High Water Stress

Under high water stress, B/LA was ~6% higher in Stg1 compared with RTx7000. B/LA was positively correlated with T/LA but not with TE. Hence, the higher B/LA displayed by Stg1 was due to higher T/LA. In general, B/LA was positively correlated with T/LA and negatively correlated with TE under high water stress.

In this case, Stg1 used ~22% less water than RTx7000 during the pre-anthesis period. Therefore, Stg1 would have significantly more water available to fill grain, despite lower biomass at anthesis.

Example 15

Figure 32:
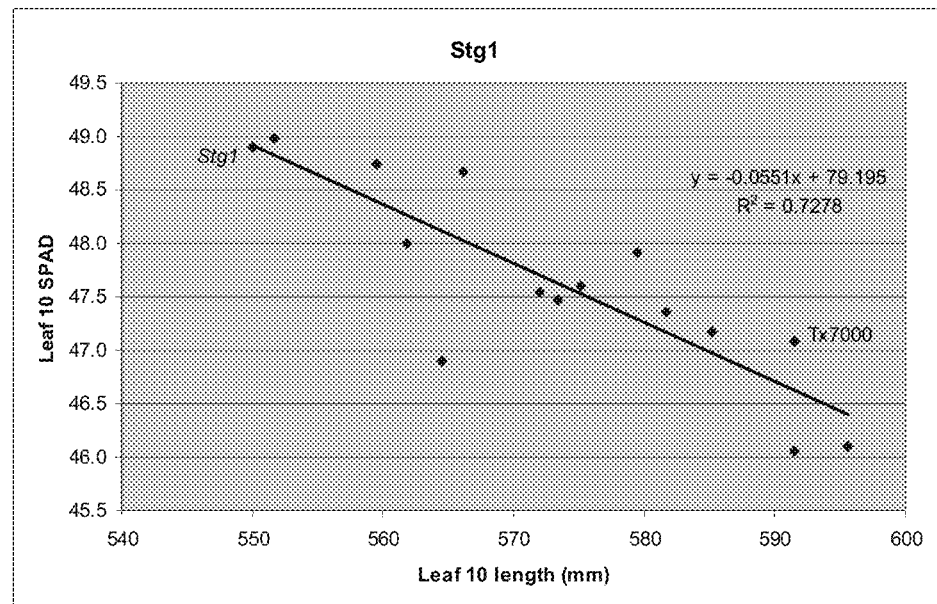
FIG. 32 is a graphical representation showing the relation between the length (mm) and greenness (SPAD) of leaf 10 in the Stg1 fine-mapping population grown in an igloo.

Increased TE Via Introgressing Stg1 may be due to a) Proportionally Higher Photosynthetic Capacity Compared with Stomatal Conductance, due to Smaller, Thinner and Greener Leaves, or b) a Decrease in Transpiration per Leaf Area while Maintaining Biomass per Leaf Area In the Stg1 fine-mapping population, the length and greenness (SPAD) of Leaf 10 were highly negatively correlated ($r2=0.72$, FIG. 32). Hence, decreasing the size of a leaf in this population increased the concentration of nitrogen in the leaf. Introgressing Stg1 into a RTx7000 background decreased L10 length by ~7% (from 592 to 550 mm) and increased L10 SPAD by ~4% (from 47.1 to 48.9).

Figure 33:
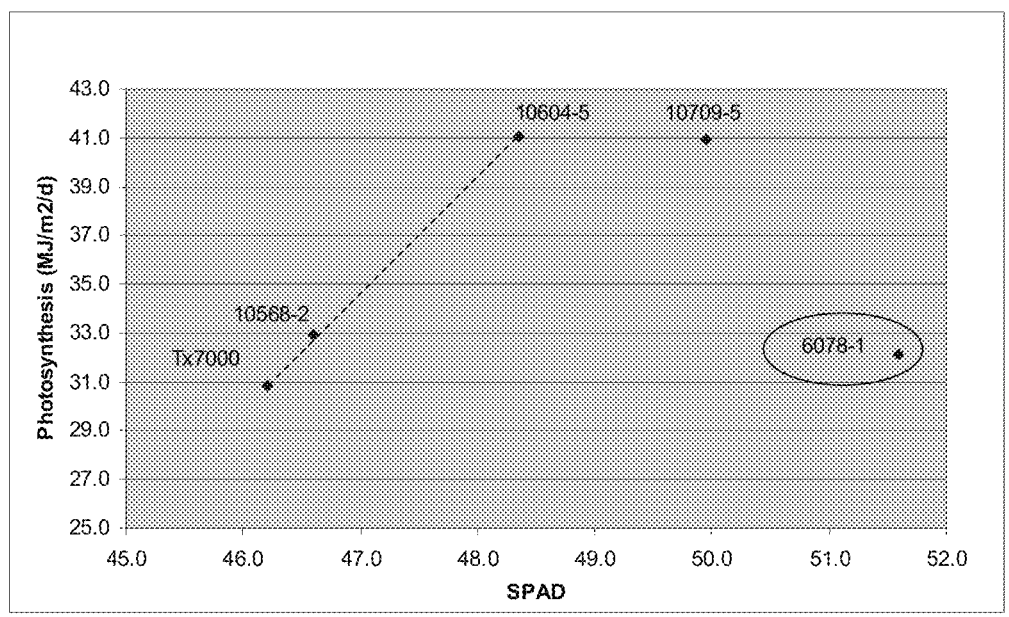
FIG. 33 is a graphical representation showing the relation between leaf greenness (SPAD) and leaf photosynthesis in a subset of lines from the Stg1 fine-mapping population, including the parents.

Greener leaves may increase photosynthetic capacity and therefore water use efficiency. In a subset of the Stg1 fine-mapping population, photosynthesis increased with SPAD value until reaching a plateau at a SPAD of ~48.5 (FIG. 33). However, the line (6078-1) with the highest SPAD value (51.6) exhibited a relatively low rate of photosynthesis (32.1 MJ/m2/d). This result is either a) anomalous, or b) indicates a real decline in photosynthesis at high SPAD values.

Figure 34:
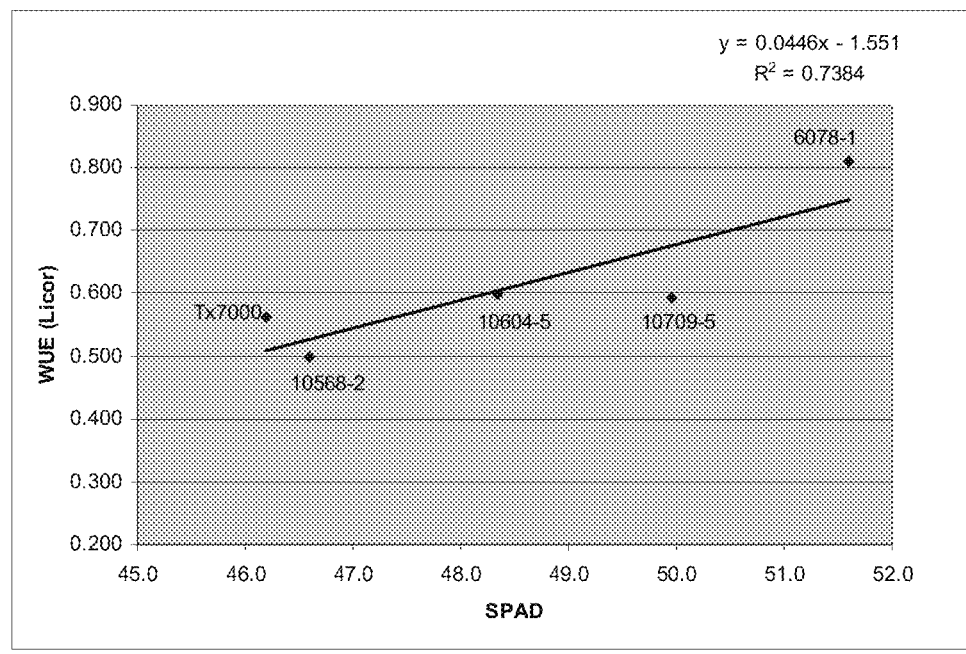
FIG. 34 is a graphical representation showing the relation between leaf greenness (SPAD) and WUE (Licor) in a subset of lines from the Stg1 fine-mapping population, including the parents.

Leaf greenness (SPAD) and WUE (based on an index calculated by Licor software) were positively correlated in a subset of the Stg1 fine-mapping population (FIG. 34). None of the Stg1 introgressions approached the value for 6078-1 (0.8), despite relatively high SPAD in the 10604-5 and 10709-5 NILs.

Figure 35:
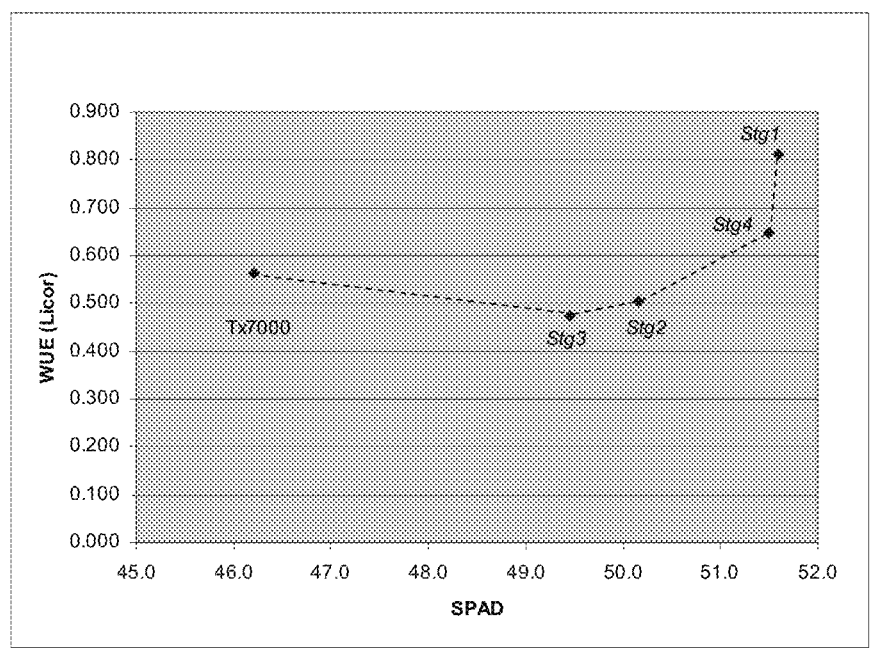
FIG. 35 is a graphical representation showing the relation between leaf greenness (SPAD) and WUE (Licor) in four Stg Nils (Stg1, Stg2, Stg3 and Stg4) and the recurrent parent (RTx7000).

Compared with RTx7000 and other Stg QTLs, Stg1 exhibited a greener leaf (higher SPAD value) and higher WUE (based on an index calculated by Licor software) [FIG. 35].

Example 16

Increased TE Via Introgressing Stg1 may be due to a) Proportionally Higher Photosynthetic Capacity Compared with Stomatal Conductance, due to Smaller, Thinner and Greener Leaves, or b) a Decrease in Transpiration per Leaf Area while Maintaining Biomass per Leaf Area Transpiration efficiency (TE) was negatively correlated with transpiration per leaf area (T/LA) under low and high VPD conditions (FIG. 36) in a set of Stg NILs, including the recurrent parent (RTx7000). However, the ranking of Stg NILs relative to RTx7000 interacted with VPD conditions. For example, T/LA in Stg1 was lower relative to RTx7000 under high VPD conditions, yet higher than RTx7000 under low VPD conditions.

Figure 36:
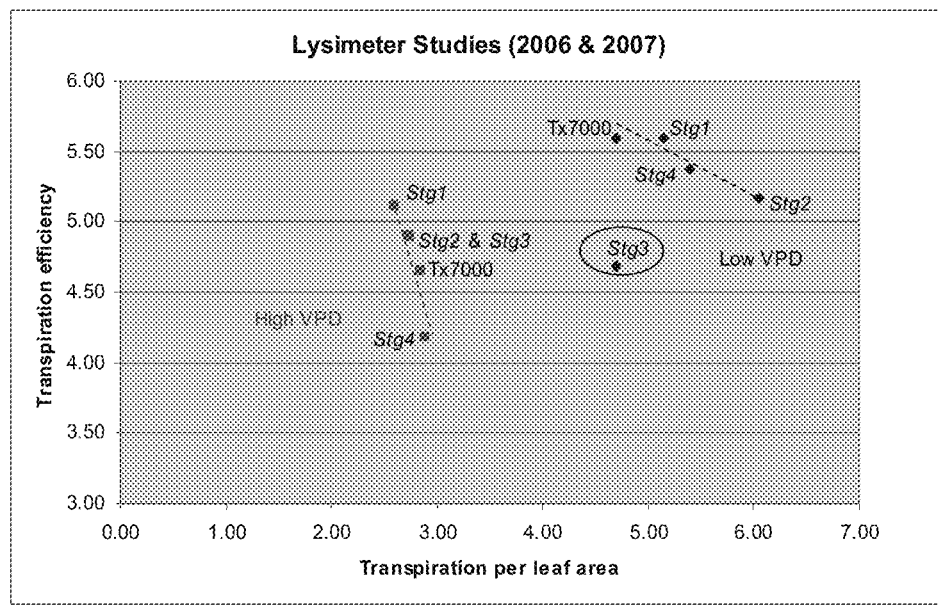
FIG. 36 is a graphical representation showing the relation between transpiration per leaf area and transpiration efficiency area in four Stg QTL and the recurrent parent (RTx7000) in lysimetry studies under two levels of VPD.

Under high VPD conditions, the slope of the negative correlation between T/LA and TE was steep, such that a slight decrease in T/LA from 2.9 mm/cm2 (Stg4) to 2.6 mm/cm2 (Stg1) resulted in a significant increase in TE from 4.2 g/m2/mm (Stg4) to 5.1 g/m2/mm (Stg1) [FIG. 36]. The gradient was less steep under low VPD conditions such that a sixfold greater decrease in T/LA was required per unit increase in TE compared with high VPD conditions (1.2 vs 0.2 units). Note that for an equivalent TE, Stg1 exhibited a higher T/LA than RTx7000 (5.1 vs 4.6 mm/cm2) under low VPD. This may provide a mechanism for Stg1 leaves to remain cooler under certain environmental conditions.

Example 17

Changes in Transpiration per Unit Leaf Area could be due to a) Number of Stomata, b) Stomatal Aperture, c) Changes in the Timing of Stomatal Opening and Closing Relative to VPD, and/or d) Number of Hair Base Cells (which Affects the Boundary Layer and Hence T/LA)

Introgressing Stg1 into RTx7000 variously affected T/LA, depending on VPD conditions. Relative to RTx7000, Stg1 increased T/LA by ~9% under low VPD and decreased T/LA by ~10% under high VPD. T/LA, inter alia, can be regulated by a) the number of stomata per unit leaf area, b) the size to the stomatal aperture, c) the timing of stomatal opening and closing, and/or d) the number of hair base cells (which affects the boundary layer and hence T/LA). Measurements of two of these four components (a and d) have been made. In one rainout shelter experiment, individual leaves were harvested from the high density treatment within the irrigated control, cuticles removed, and images taken of the cuticle surface. These images were used to determine a) the number of stomata per unit leaf area, b) the number of epidermal cells per unit leaf area, and c) the number of hair base cells per unit leaf area.

At the same time, transverse leaf sections were taken. Preliminary analysis of these data indicate that introgressing Stg1 into RTx7000 modified leaf anatomy. Differences in the morphology of leaves (e.g. Leaves 7 and 10) are apparent between RTx7000 and Stg1. In this case, there were more and smaller bundle sheaths surrounding the vascular bundle in Stg1. The increased number of cells in the bundle sheath might also contribute to increased photosynthetic assimilation (PNAS 2007) and hence TE.

Example 18

Figure 37:
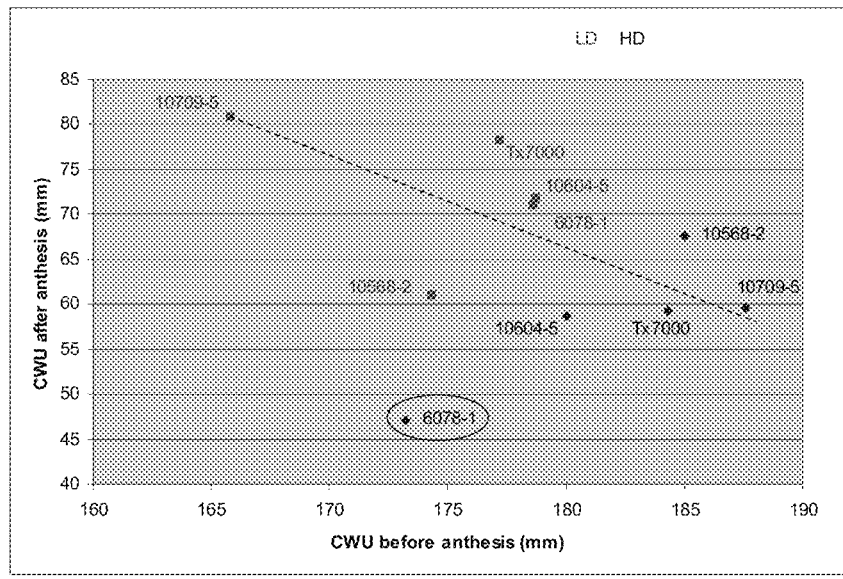
FIG. 37 is a graphical representation showing the relation between CWU (mm) before and after anthesis in a subset of lines from the Stg1 fine-mapping population, including the parents, grown under high density (HD) and low density (HD) conditions.

Increased Water Use During Grain Filling is Achieved Via (i) Increased Water Availability at Anthesis and (ii) Increased Water Accessibility (Better Water Extraction and Deeper or Greater Lateral Spread) during Grain Filling a) Increased Water Availability at Anthesis Crop water use (CWU) before anthesis was negatively correlated with CWU after anthesis in the ROS experiment (FIG. 37). For example, saving 20 mm of water before anthesis (165 vs 185 mm) enabled the utilization of an additional 20 mm after anthesis (80 mm vs 60 mm). So all of the water conserved before anthesis was utilized by the crop after anthesis. Overall, a 25% increase in water use after anthesis in this experiment resulted in a 25% increase in grain yield (400 vs 300 g/m2). This translated to 50 kg/ha of grain for every additional mm of water available. While this data supports the concept that increased water use during grain filling is achieved via increased water availability at anthesis, it does not tell us anything about increased water accessibility during grain filling.

b) Increased Water Accessibility during Grain Filling

Figure 38:
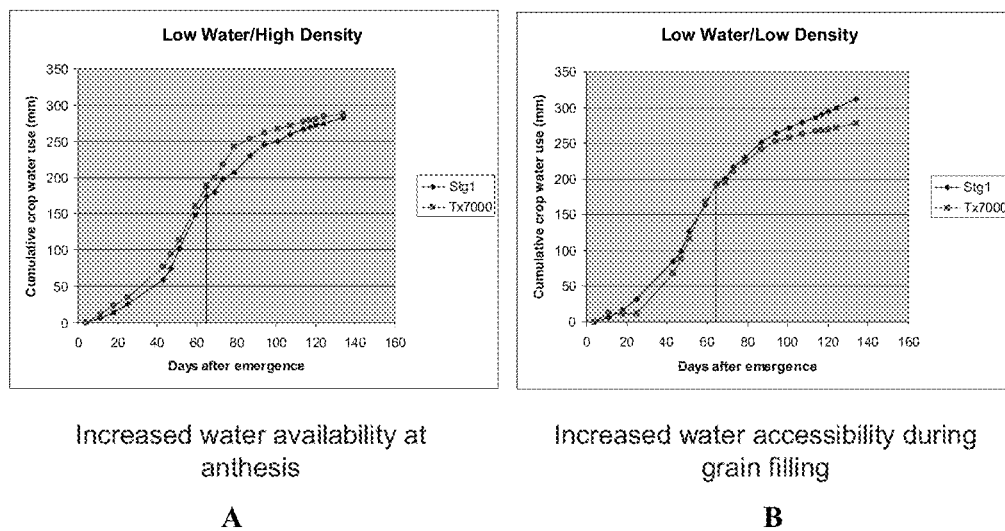
FIGS. 38A and B are graphical representations showing patterns of cumulative water use for Stg1 and RTx7000 grown under LWHD and conditions.

Increased water use during the grain filling period was exhibited by Stg1-under both low and high density treatments in the ROS experiment. This was due primarily to (i) increased water availability at anthesis under high density, and (ii) increased water accessibility during grain filling under low density (FIGS. 38a and b).

Figure 39:
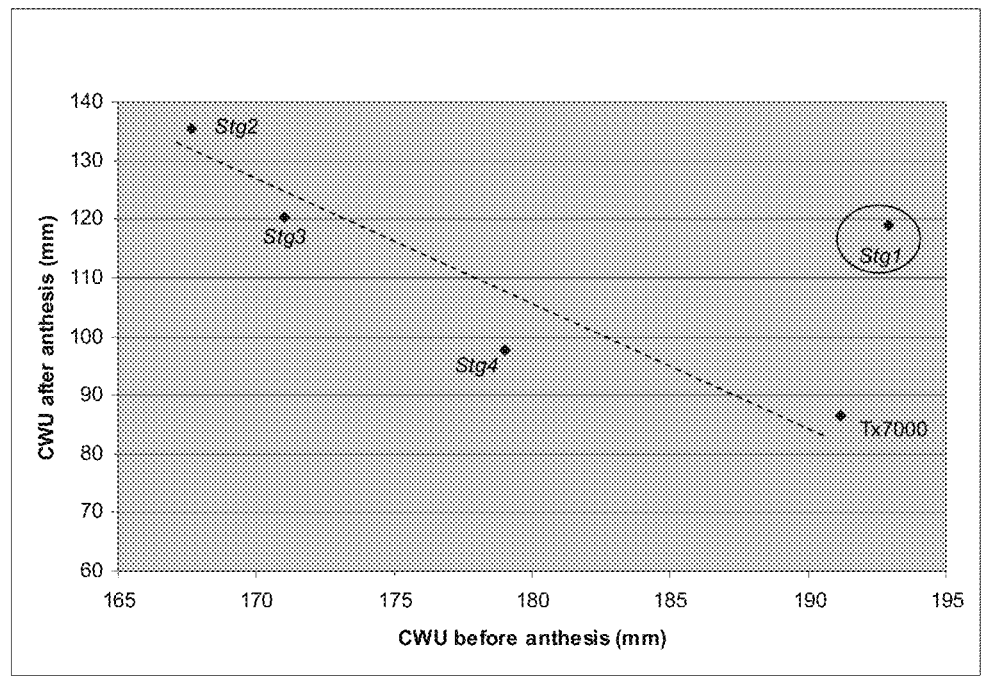
FIG. 39 is a graphical representation showing the relation between CWU (mm) before and after anthesis in four Stg QTL and the recurrent parent (RTx7000) grown under low water (LW) and low density (LD) conditions.

In a study of RTx7000 and four Stg NILs (Stg1, Stg2, Stg3 and Stg4), CWU before and after anthesis were negatively correlated in an ROS experiment under low density conditions (FIG. 39). In this case, saving ~25 mm of water before anthesis (168 vs 191 mm) contributed to the utilization of ~50 mm after anthesis (135 mm vs 86 mm), indicating that both increased water availability (~25 mm) and accessibility (~25 mm) were equally important. However, Stg1 was anomalous in this example, since high water use after anthesis was associated with high water use before anthesis. Explanations for this anomaly in Stg1 are a) an error in the pre-anthesis water data, b) an error in the post-anthesis water data, or c) no errors in water measurement (Stg1 simply responded differently to the other NILs). An examination of the biomass data reveals that, for some reason, Stg1 produced higher biomass before anthesis under LWLD compared with the other NILs, suggesting that the pre-anthesis water use patterns simply reflected biomass production in this experiment. Nonetheless, this example does provide evidence of increased water accessibility by Stg1 during the grain filling period.

Example 19

Link between Pre- and Post-anthesis Biomass Production

Under low density (LD), reducing pre-anthesis biomass by 23% (from 700 to 640 g/m2) increased post-anthesis biomass more than twofold (from ~200 to 425 g/m2). Under LD, Stg1 produced similar pre-anthesis biomass to RTx7000 (~610 g/m2), yet produced less post-anthesis biomass (265 vs 327 g/m2). However under HD, Stg1 and RTx7000 produced similar pre-anthesis biomass (~840 g/m2), yet Stg1 produced more post-anthesis biomass (195 vs 17 g/m2).

The relation between GLAA and the pre:post anthesis biomass ratio is critical in the Stg1 story. GLAA must be cut back to <3 to ensure the availability of adequate water for grain filling, and this is the critical role of the Stg1 gene. In this experiment, Stg1 reduced GLAA adequately to achieve a pre:post anthesis biomass ratio of <3 under ILD, but not HD. Under HD, note that introgressing Stg1 into RTx7000 reduced the GLAA from 31200 to 29300 cm2/m2, reducing the pre:post anthesis biomass ratio from 8.2 to 6.5 (but still not to <3). This highlights the importance of appropriate management strategies such as crop density in maximising limited water resources.

The negative relation between GLAA and post-anthesis stem mass is also critical to the Stg1 story. Lower GLAA, and hence reduced water use at anthesis, was associated with higher post-anthesis stem mass (a component of lodging resistance). Introgressing Stg1 into RTx7000 increased post-anthesis stem mass under both LD (marginal increase) and HD (significant increase) conditions.

The relation between the pre:post anthesis biomass ratio (PPBR) and post-anthesis biomass is instructive. The two density treatments provide a continuum in the range of PPBR from <2 to >8. Reducing PPBR from >8 to ~3 resulted in a gradual increase in post-anthesis biomass. However, further reducing PPBR below 3 resulted in a relatively sharp increase in post-anthesis biomass, presumably because more water was available during grain filling when the PPBR ratio fell below 3. Introgressing Stg1 into RTx7000 increased post-anthesis biomass under HD but not LD.

The relation between the pre:post anthesis biomass ratio (PPBR) and post-anthesis stem mass is equally instructive. Post-anthesis stem mass is a component of lodging resistance. Analysis of this component provides some understanding of how Stg introgressions affect lodging resistance. Reducing PPBR from >8 to ~4 resulted in a gradual increase in post-anthesis stem mass. However, further reducing PPBR below 4 resulted in a relatively sharp increase in post-anthesis stem mass. Introgressing Stg into RTx7000 increased post-anthesis stem mass under both LD (marginal increase) and HD (significant increase) conditions.

The relation between PPBR and grain yield was less clear in this experiment. While grain yield was higher in Stg1 than RTx7000 under both densities, the higher yield could only be explained by lower PPBR in Stg1 under HD.

Two Stg1 introgressions were examined in this experiment: a) 6078-1 (the whole Stg1 region), and b) 10946-5 (a recombinant covering about 1/3 of the Stg1 region between markers Sb03QGM116 and Sb03QGM106).

Figure 40:
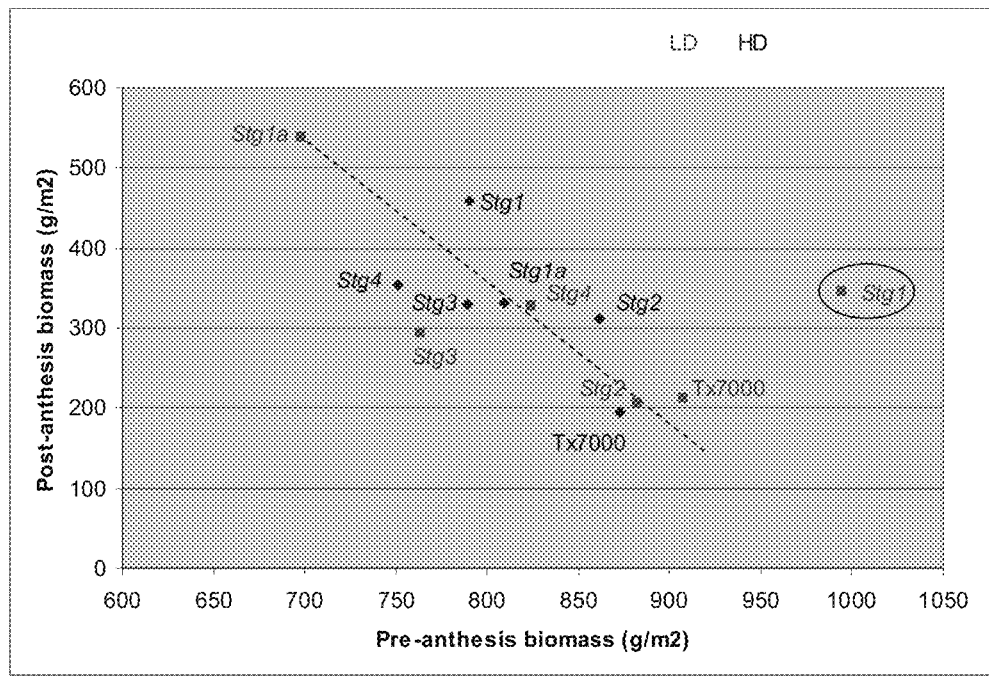
FIG. 40 is a graphical representation showing the relation between PPBR and PAB in four Stg QTL and the recurrent parent (RTx7000) grown under water-limited conditions at two crop densities (LD=10 plants/m2; HD=20 plants/m$^2$).

Reducing pre-anthesis biomass by 20% (from 920 to 735 g/m2) increased post-anthesis biomass by about 100% (from 200 to 400 g/m2) [FIG. 40]. In general, pre-anthesis biomass in RTx7000=Stg2>Stg3=Stg4>Stg1 and post-anthesis biomass in Stg1>Stg3=Stg4>Stg2>RTx7000. The data for Stg1 under LD was anomalous.

Figure 41:
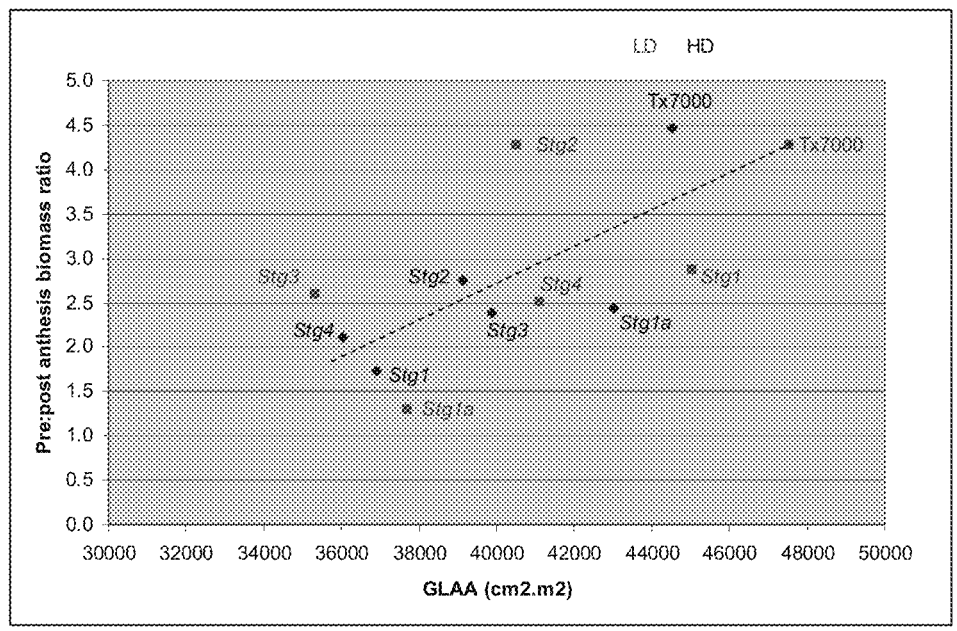
FIG. 41 is a graphical representation showing the relation between GLAA and PPBR in four Stg QTL and the recurrent parent (RTx7000) grown under water-limited conditions at two crop densities (LD=10 plants/m$^2$; HD=20 plants/m$^2$).

Canopy size, as evidenced by GLAA, largely determined the ratio of pre:post anthesis biomass (FIG. 41). Under both high and low density treatments, introgressing Stg1 into a RTx7000 background reduced GLAA which, in turn, reduced the ratio of pre:post anthesis biomass to <3, ensuring adequate water availability for grain filling under these water-limited conditions.

Figure 42:
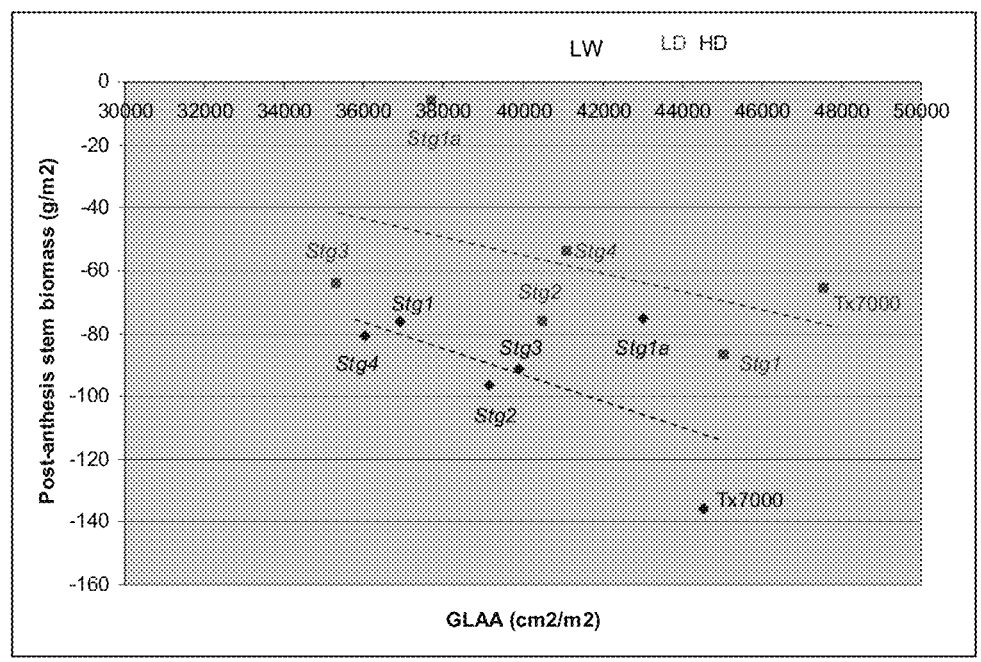
FIG. 42 is a graphical representation showing the relation between GLAA and PASB in four Stg QTL and the recurrent parent (RTx7000) grown under water-limited conditions at two crop densities (LD=10 plants/m$^2$; HD=20 plants/m$^2$).

Canopy size, as evidenced by GLAA, was a determinant of post-anthesis stem mass (PASM) [FIG. 42]. Under both high and low density treatments, introgressing Stg1 or Stg1a into a RTx7000 background reduced GLAA which, in turn, increased PASM. Approximately 40 g/m2 more stem reserves were utilized under HD compared with LD, reflecting the higher stress imposed by this treatment.

Figure 43:
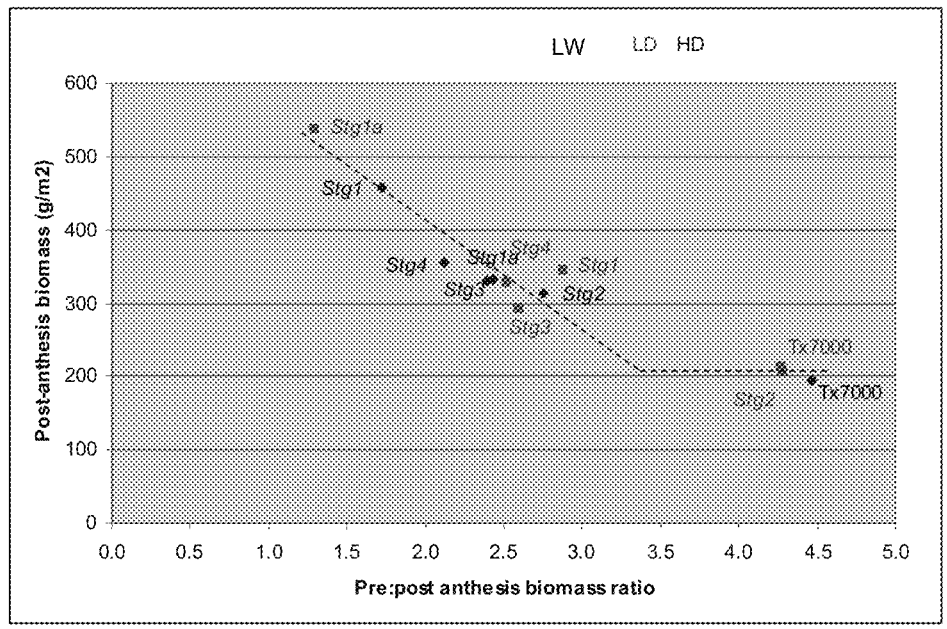
FIG. 43 is a graphical representation showing the relation between PPBR and PAB in four Stg QTL and the recurrent parent (RTx7000) grown under water-limited conditions at two crop densities (LD=10 plants/m2; HD=20 plants/m$^2$).

The relation between the pre:post anthesis biomass ratio (PPBR) and post-anthesis biomass (PAB) was strong (FIG. 43). The two density treatments provide a continuum in the range of PPBR from <1.5 to >4. Reducing PPBR from ~4.5 to ~3.5 had no impact on PAB. However, further reducing PPBR below ~3.5 resulted in a relatively sharp increase in PAB, presumably because more water was available during grain filling when the PPBR ratio fell below 3.5. Introgressing Stg1 into RTx7000 decreased PPBR below 3 under HD and LD, thereby increasing PAB under both density treatments.

Figure 44:
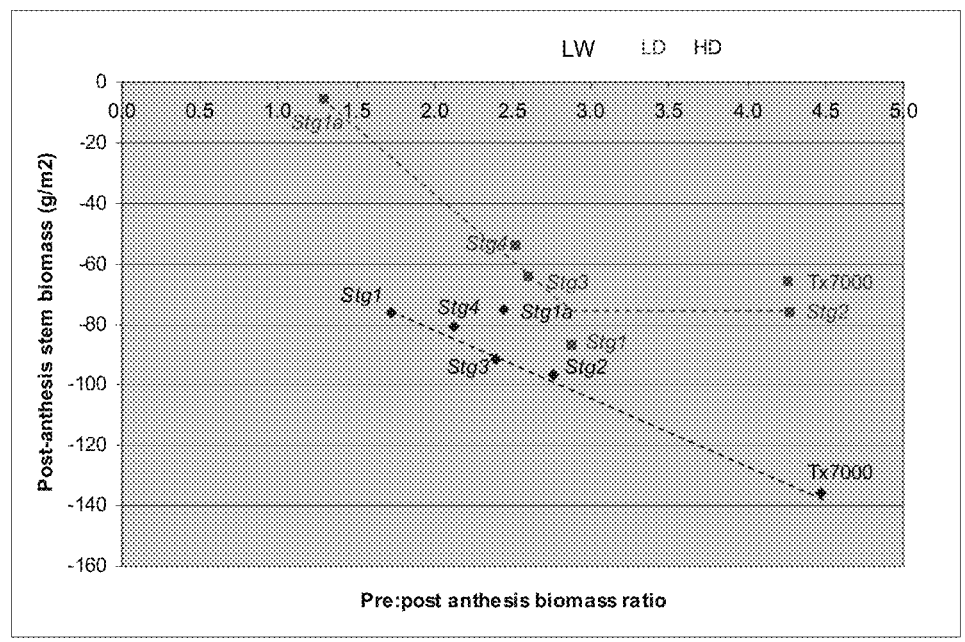
FIG. 44 is a graphical representation showing the relation between PPBR and PASM in four Stg QTL and the recurrent parent (RTx7000) grown under water-limited conditions at two crop densities (LD=10 plants/m$^2$; HD=20 plants/m$^2$).

The pre:post anthesis biomass ratio (PPBR) also affected lodging resistance (FIG. 44). In this case, post anthesis stem mass (PASM) is used as a surrogate for lodging resistance. Under high and low densities, PPBR was negatively correlated with post-anthesis stem biomass. That is, a high pre:post anthesis biomass ratio increased the amount of stem reserves remobilized during grain filling, thus reducing stem biomass and increasing the likelihood of lodging. Compared with RTx7000, Stg1a significantly reduced the amount of stem reserves mobilized under LD (~5 vs 65 g/m2) and HD (~80 vs 140 g/m2). Compared with RTx7000, Stg1 significantly reduced the amount of stem reserves mobilized under HD (~80 vs 140 g/m2), but not LD. The extent of stem reserves mobilized was greater under HD than LD, reflecting the greater water deficit under HD. For example, the difference in stem reserve mobilization between HD and LD was twofold in RTx7000 (about 140 vs 70 g/m2).

Figure 45:
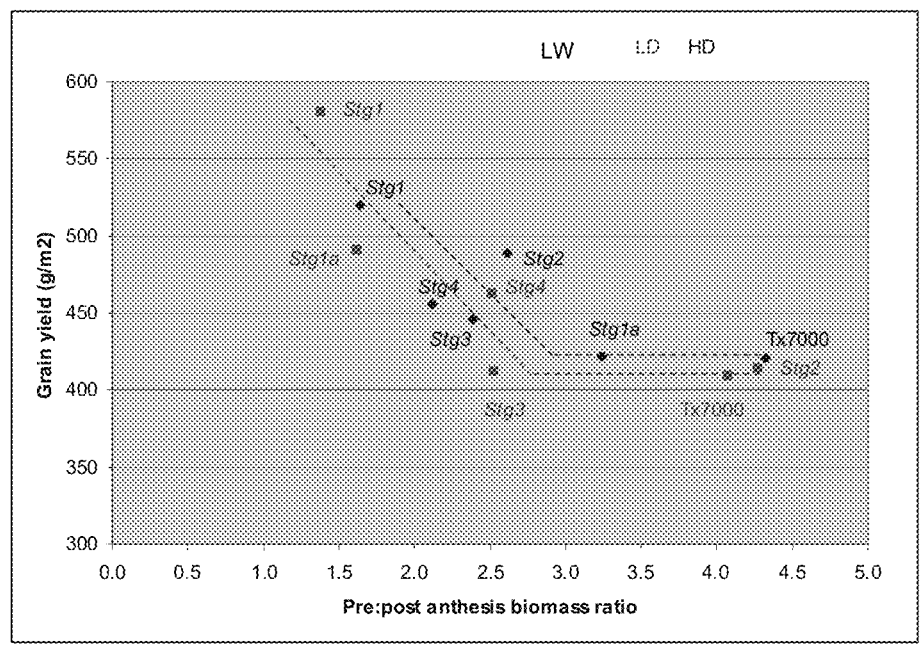
FIG. 45 is a graphical representation showing the relation between PPBR and grain yield in four Stg QTL and the recurrent parent (RTx7000) grown under water-limited conditions at two crop densities (LD=10 plants/m$^2$; HD=20 plants/m$^2$).

Grain yield remained low (at a benchmark of ~4.2 t/ha) until the pre:post anthesis biomass ratio fell below ~3 (HD) or ~2.5 (LD) [FIG. 45]. Below these critical values, grain yield increased significantly for each incremental reduction in these ratios, with the rate of increase in grain yield being slightly higher under LD than HD. This suggests that post-anthesis water availability was closely linked to pre-anthesis GLAA and biomass, and that a certain reduction in GLAA was required to ensure adequate water availability for grain filling. Under both densities, Stg1 reduced the pre:post anthesis biomass ratio below the critical levels, resulting in yield increases of 28% (LD) and 22% (HD), relative to RTx7000. These data provide a critical link between Stg1 gene action (reduced canopy size at anthesis) and grain yield under terminal drought. Note that the Stg1a introgression had some impact on reducing PPBR (HD and LD) and increasing grain yield (LD only) relative to RTx7000, but not to the same extent as Stg1. Hence there is not strong evidence from this experiment that the key Stg1 gene resides within the Stg1a region. This supports evidence presented earlier, since the strongest candidate for Stg1 (SbPIN4) is located above the Stg1a introgression.

Four Stg1 introgressions were examined in this experiment: a) 6078-1 (the whole Stg1 region between markers txa2179 and txp38), b) 10709-5 (a recombinant covering about 1/3 of the Stg1 region between markers Sb03QGM106 and txp38), c) 10604-5 (a recombinant covering about 3/4 of the Stg1 region between markers txa2506 and txp565), and d) 10568-2 (a recombinant covering almost 1/2 of the Stg1 region between markers txa2506 and txp563) [FIG. 46].

Under low density (LD), pre-anthesis biomass varied by only ~5% (from 522 to 552 g/m2) among genotypes, yet post-anthesis biomass varied almost twofold (from 173 to 313 g/m2). This suggests that the considerable differences in post-anthesis biomass were affected by something other than pre-anthesis biomass, e.g. differences in water accessibility. For example, 10709-5 and RTx7000 both produced ~550 g/m2 of pre-anthesis biomass, yet the Stg1 recombinant (10709-5) produced ~60% more post-anthesis biomass (310 vs 130 g/m2).

Under high density (HD), pre- and post-anthesis biomass were highly negatively correlated. Introgressing Stg1 into RTx7000 reduced pre-anthesis biomass by 9% and increased post-anthesis biomass by 23%.

Crop water use (CWU) at anthesis better discriminated between genotypes than did pre-anthesis biomass. Combining the HD and LD data, post-anthesis biomass (PAB) remained low (at a benchmark of ~150 g/m2) until the CWU at anthesis fell below ~180 mm. Below this critical value, PAB increased for each incremental reduction in CWU down to a level of 175 mm, with PAB plateauing at about 310 g/m2. Further reductions in CWU at anthesis below 175 mm did not result in additional PAB.

Canopy size, as evidenced by GLAA, largely determined the ratio of pre:post anthesis biomass (PPBR). Under both high and low density treatments, introgressing Stg1 (or particular recombinants such as 10709-5) into a RTx7000 background reduced GLAA which, in turn, reduced the ratio of pre:post anthesis biomass, thereby increasing water availability for grain filling under these water-limited conditions. The PPBR value for 6078-1 appears anomalous (too high) since this genotype is placed well above the GLAA/PPBR regression line.

Canopy size, as evidenced by GLAA, was a determinant of post-anthesis stem mass (PASM). Under the high density treatment, introgressing Stg1 (or Stg1 recombinants such as 10604-5 and 10709-5) into a RTx7000 background reduced GLAA which, in turn, increased PASM. Approximately, 60 g/m2 more stem reserves were utilized under HD compared with LD, reflecting the higher stress imposed by this treatment. Once again, the data for 6078-1 under LD appears anomalous.

The relation between the pre:post anthesis biomass ratio (PPBR) and post-anthesis biomass (PAB) was strong. The two density treatments provide a continuum in the range of PPBR from <2 to >5, although the slope of the regression was greater for LD than HD. Under HD, reducing PPBR from ~6 to ~3.5 resulted in a gradual increase in PAB from ~130 g/m2 (RTx7000) to ~180 g/m2 (10604-5). Further reducing PPBR below ~3 under LD resulted in a steeper increase in PAB, presumably because more water was available during grain filling when the PPBR ratio fell below three.

The pre:post anthesis biomass ratio (PPBR) also affected lodging resistance. In this case, post anthesis stem mass (PASM) is used as a surrogate for lodging resistance. Under high and low densities, PPBR was negatively correlated with post-anthesis stem biomass. That is, a high pre:post anthesis biomass ratio increased the amount of stem reserves remobilized during grain filling, thus reducing stem biomass and increasing the likelihood of lodging. Compared with RTx7000, Stg1 significantly reduced the amount of stem reserves mobilized under HD (~100 vs 160 g/m2). The extent of stem reserves mobilized was greater under HD than LD, reflecting the greater water deficit under HD. For example, the difference in stem reserve mobilization between HD and LD was more than twofold in RTx7000 (about 160 vs 60 g/m2). Interestingly, PASM increased with decreasing PPBR over the whole range of PPBR (1.5-6), whereas grain yield, and to a lesser extent PAB, only increased when PPBR fell below ~3. This suggests that relatively small water savings before anthesis were still able to improve lodging resistance, although greater water savings were required before grain yield responded.

Grain yield remained low (at a benchmark of ~3.1 t/ha) until the pre:post anthesis biomass ratio fell below ~3. Below this critical value, grain yield increased significantly for each incremental reduction in this ratio. Since none of the Stg1 introgressions reduced the PPBR to <3 under HD, no yield benefits were realized from Stg1 in this treatment. Under LD, some of the Stg1 introgressions reduced PPBR below the critical level, resulting in yield increases of 12% (10568-2) and 5% (10709-5), relative to RTx7000. These data provide a critical link between Stg1 gene action (reduced canopy size at anthesis) and grain yield under terminal drought.

Figure 47:
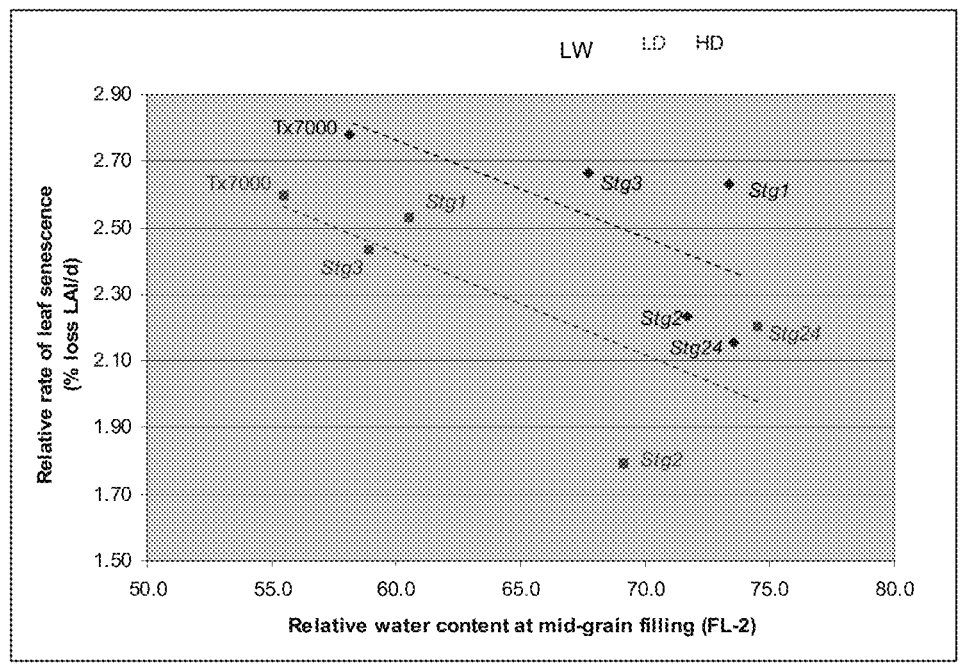
FIG. 47 is a graphical representation showing the relation between RWC at mid-grain filling (FL-2) and the relative rate of leaf senescence in various combinations of Stg QTL and the recurrent parent (RTx7000) grown under water-limited conditions at two crop densities (LD=10 plants/m$^2$; HD=20 plants/m$^2$).

CWU during grain filling remained low (at a benchmark of ~60 mm) until the pre:post anthesis biomass ratio fell below ~3.5 (FIG. 47). Below this critical value, CWU during grain filling increased significantly for each incremental reduction in this ratio. Since none of the Stg1 introgressions reduced the PPBR to <3.5 under HD, no increases in CWU during grain filling were realized from Stg1 recombinants in this treatment. Under LD, some of the Stg1 introgressions (and RTx7000) reduced PPBR below the critical level, increasing CWU during grain filling up to ~80 mm compared with the HD baseline (~60 mm).

Figure 48:
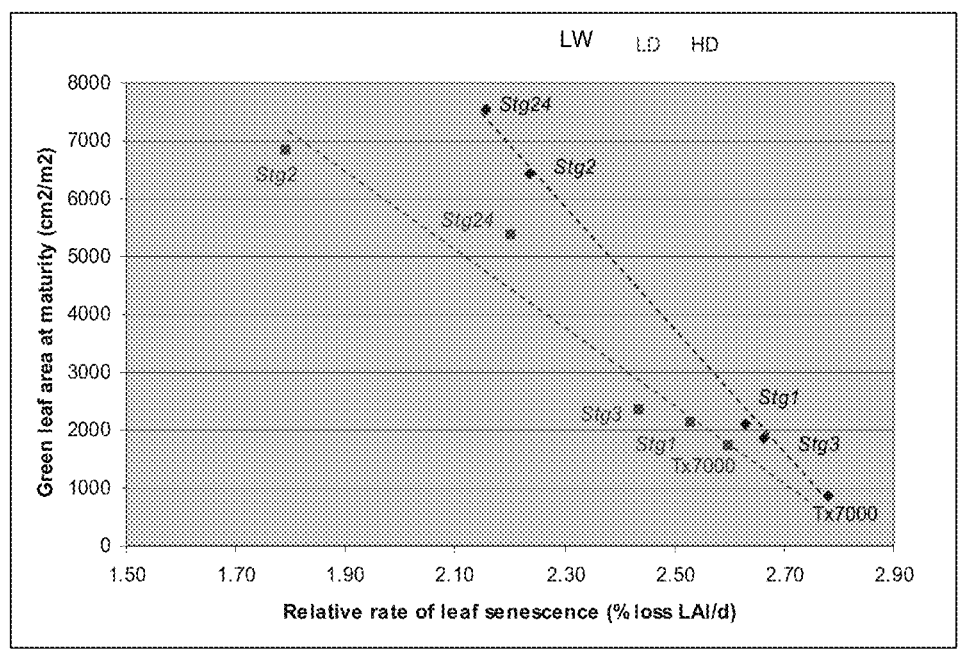
FIG. 48 is a graphical representation showing the relation between relative rate of leaf senescence and green leaf area at maturity in various Stg QTL and the recurrent parent (RTx7000) grown under water-limited conditions at two crop densities (LD=10 plants/m$^2$; HD=20 plants/m$^2$).

The relation between CWU during grain filling and grain yield was positive (FIG. 48). However, the correlation between these parameters was relatively low (r2=0.23), probably due to the highly variable nature of soil water measurements in the field.

Example 20

Delayed Leaf Senescence (Stay-green) is a Consequence of Higher Plant Water Status during Grain Filling (due to Increased Water Use)

Plant water status was determined on FL-2 (two leaves below the flag) at mid-grain filling using two methodologies: leaf water potential (LWP) and relative water content (RWC). LWP was measured in the field with a pressure bomb. Following determination of LWP in the field, a sample of the same leaf was placed on ice and, within a few minutes, taken to a laboratory some 300 m away for determination of RWC by standard methods.

The RWC of FL-2 was negatively correlated with the relative rate of leaf senescence at mid-grain filling under both high and low densities in a set of Stg NILs including the recurrent parent. Correlations for HD and LD were parallel, but offset by about 0.35 units of leaf senescence, i.e. for a given level of RWC, say 70, the relative rates of leaf senescence were 2.1 and 2.45 for LD and HD, respectively. Introgressing the Stg1 region into RTx7000 increased RWC at mid-grain filling (FL-2) and decreased the relative rate of leaf senescence under both HD and LD, although the impact was greater under HD.

Figure 49:
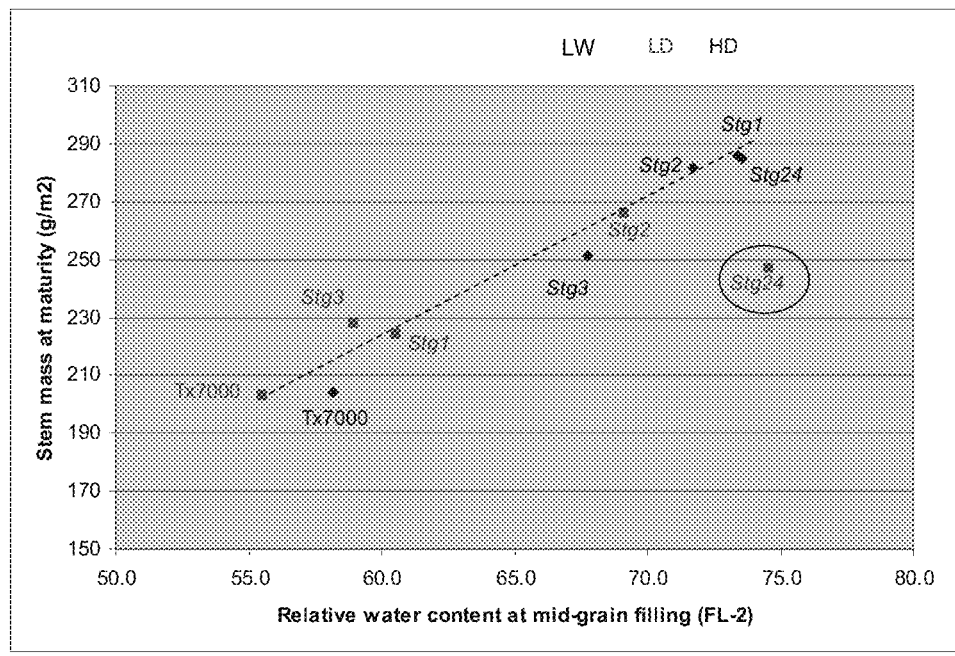
FIG. 49 is a graphical representation showing the relation between relative water content (RWC) at mid-grain filling (FL-2) and stem mass at maturity in various combinations of Stg QTL and the recurrent parent (RTx7000) grown under water-limited conditions at two crop densities (LD=10 plants/m$^2$; HD=20 plants/m$^2$).
Figure 50:
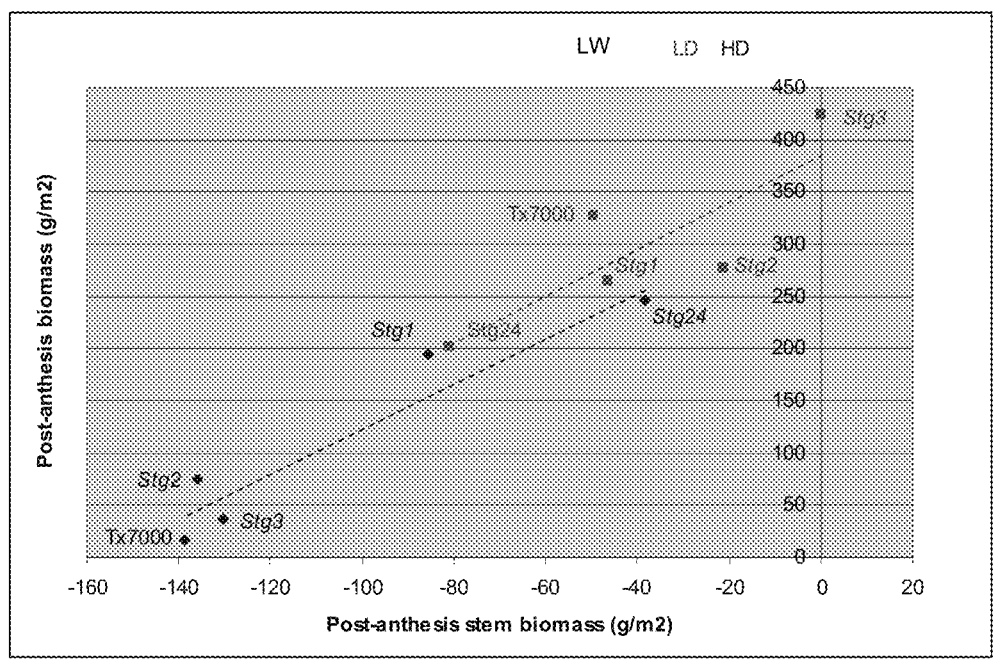
FIG. 50 is a graphical representation showing the relation between post-anthesis stem biomass and post-anthesis biomass in various combinations of Stg QTL and the recurrent parent (RTx7000) grown under water-limited conditions at two crop densities (LD=10 plants/m2; HD=20 plants/m$^2$) in an experiment grown in 2004.

In turn, the relative rate of leaf senescence was highly negatively correlated with green leaf area at maturity (GLAM) under HD and LD (FIG. 49), with higher rates of leaf senescence exhibited under HD. Stg1 produced more than twice as much GLAM as RTx7000 under HD (2106 vs 859 cm2/m2) and 19% more GLAM under LD (2145 vs. 1725 cm2/m2), see also FIG. 50.

Example 21

Increased Lodging Resistance is a Consequence of Higher Plant Water Status during Grain Filling (due to Increased Water Use)

Figure 51:
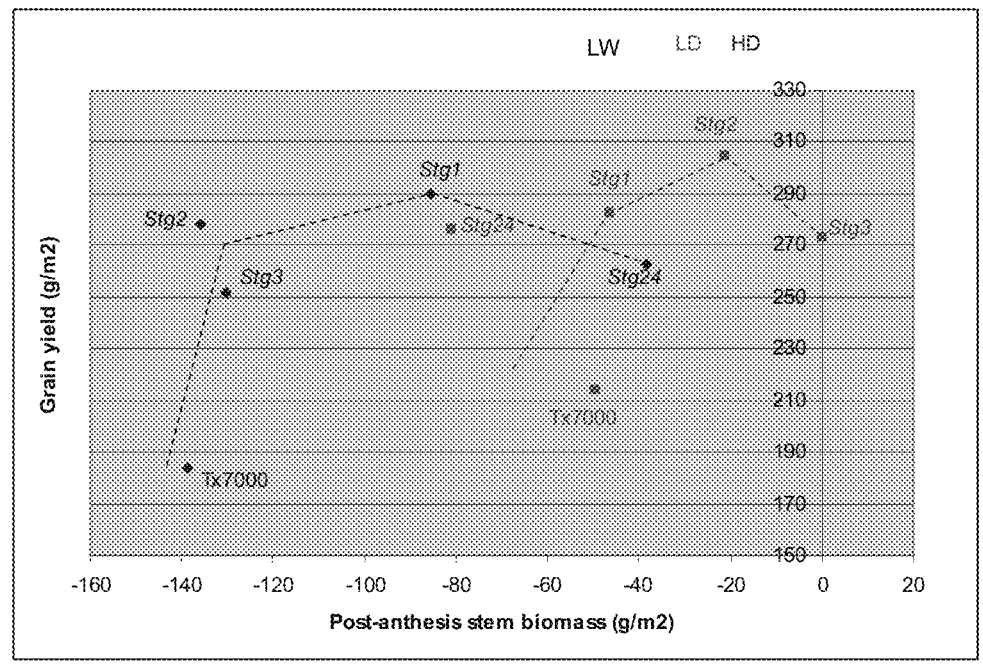
FIG. 51 is a graphical representation showing the relation between post-anthesis stem biomass and grain yield in various combinations of Stg QTL and the recurrent parent (RTx7000) grown under water-limited conditions at two crop densities (LD=10 plants/m$^2$; HD=20 plants/m$^2$) in an experiment grown in 2004.

Higher stem mass at maturity is a component of lodging resistance. RWC at mid-grain filling (FL-2) was highly negatively correlated with stem mass at maturity in a set of Stg NILs grown under water-limited conditions at two crop densities (FIG. 51). Introgressing Stg1 into RTx7000 increased RWC at mid-grain filling (FL-2) and stem mass at maturity under HD and LD, with a greater impact under HD. Relative to RTx7000, Stg1 increased stem mass at maturity by 9% under LD (224 vs. 203 g/m2) and 29% under HD (286 vs. 204 g/m2). Hence the benefit of Stg1, in terms of lodging resistance, increased with the level of water deficit.

Figure 52:
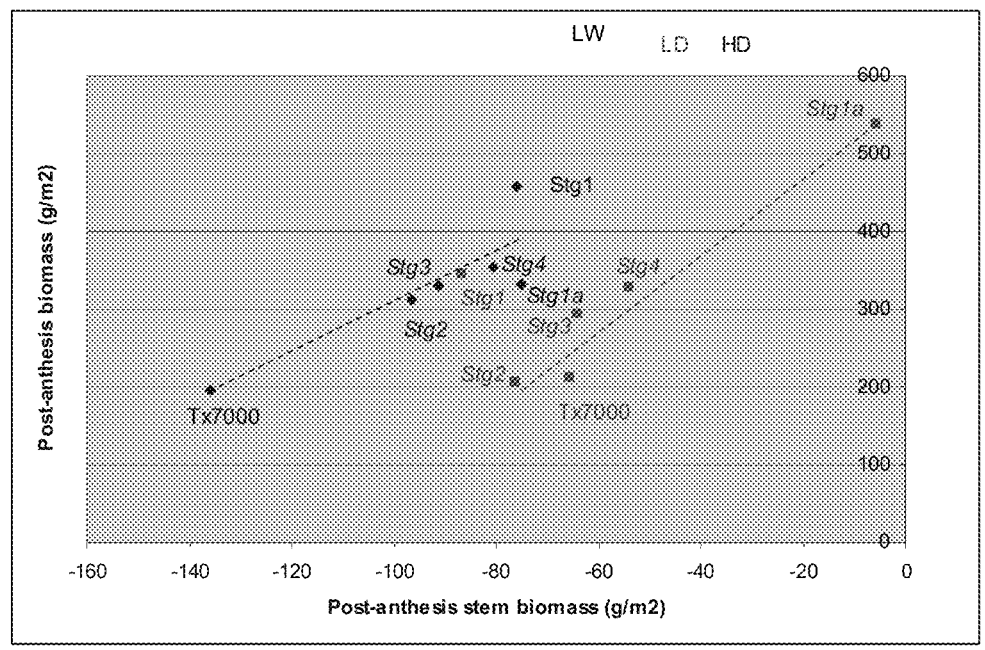
FIG. 52 is a graphical representation showing the relation between post-anthesis stem mass (PASM) and post-anthesis biomass (PAB) in four Stg QTL and the recurrent parent (RTx7000) grown under water-limited conditions at two crop densities (LD=10 plants/m$^2$; HD=20 plants/m$^2$) in an experiment grown in 2005.

Post-anthesis biomass is mainly comprised of a) post-anthesis stem mass (PASM), a measure of stem reserve mobilization and a component of lodging resistance, and b) grain yield. Grain-growers require that both grain yield and lodging resistance be maximized, i.e. they do not want one at the expense of the other. Post-anthesis stem mass was highly linearly correlated with PAB under HD and LD conditions (FIG. 52). While Stg1 had little impact on PASM under the milder drought (LD), the amount of dry mass translocated from the stem during grain filling was much less in Stg1 compared with RTx7000 (85 vs. 139 g/m2) under the more severe drought (HD). This resulted in greater stem mass at maturity in Stg1 relative to RTx7000 (286 vs. 204 g/m2) which, in turn, should have increased lodging resistance.

While the correlations between PASM and PAB were high under HD and LD (FIG. 51), the correlations between grain yield and PAB were low under both densities (FIG. 52). Introgressing Stg1 into RTx7000 increased grain yield under HD and LD, although PAB was only higher under HD. Note that the higher grain yield in Stg compared with RTx7000 (290 vs. 184 g/m2) under HD was achieved with significantly less stem reserves in Stg1 than RTx7000 (85 vs. 139 g/m2), indicating that carbon demand during grain filling was largely met by current photo-assimilation and stem reserves in Stg1 and RTx7000, respectively.

The potential trade-off between PASM and grain yield is highlighted in FIG. 53. Under HD, Stg1 achieved the highest grain yield of any introgression (290 g/m2) while keeping stem losses to 85 g/m2. Relative to RTx7000, Stg1 optimized the trade-off between PASM and grain yield. Further reductions in stem reserve utilization by Stg24 (38 g/m2) resulted in a lower grain yield (263 g/m2). Under LD, Stg1 also achieved a high grain yield relative to RTx7000 (282 vs. 214 g/m2) while utilising slightly less stem reserves (46 vs. 50 g/m2). Therefore under both densities, Stg1 attained higher grain yield and lodging resistance than RTx7000.

The relation between PASM and stem mass at maturity was relatively flat for the various Stg introgressions under HD and LD, although RTx7000 fell below the regression line in both cases. For a given level of stem reserve utilization (e.g. ~140 g/m2 under HD or 50 g/m2 under LD), introgressing a Stg region into RTx7000 significantly increased stem mass at maturity, suggesting that some other factor (e.g. stem strength) in addition to the amount of stem reserves utilized was important.

Figure 54:
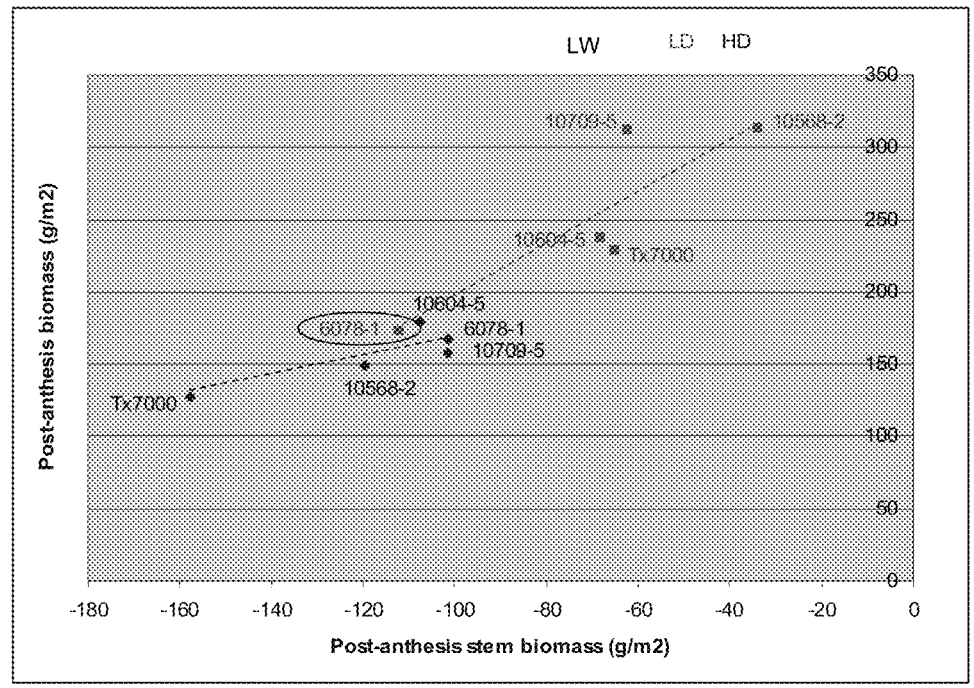
FIG. 54 is a graphical representation showing the relation between post-anthesis stem mass (PASM) and post-anthesis biomass (PAB) in various Stg1 fine-mapping lines and the recurrent parent (RTx7000) grown under water-limited conditions at two crop densities (LD=10 plants/m$^2$; HD=20 plants/m$^2$) in an experiment grown in 2006.

Post-anthesis stem mass (PASM) was highly linearly correlated with PAB under HD and LD conditions (FIG. 54). The HD and LD correlations were almost parallel, although offset by about 50 g/m2, i.e. for a given level of PAB, say 300 g/m2, PASM was ~50 g/m2 less in HD than LD (-100 vs. ~50 g/m2). This reflects the higher level of stress in the HD treatment. Under HD, both Stg1 and Stg1a utilized ~80 g/m2 of stem reserves compared with almost 140 g/m2 in RTx7000, yet Stg1 produced ~28% more PAB than Stg1a for equivalent stem reserve utilisation. Under LD, Stg1a and to a lesser extent Stg1, both increased PAB relative to RTx7000. However, while Stg1a used ~60 g/m2 less stem reserves than RTx7000, Stg1 used ~20 g/m2 more stem reserves than RTx7000.

Grain yield was positively correlated with PAB under HD and LD. Under HD, Stg1 outyielded RTx7000 by 24% although Stg1a was equivalent to RTx7000 in grain yield. Under LD, Stg1 and Stg1a outyielded RTx7000 by 42% and 20%, respectively.

Figure 55:
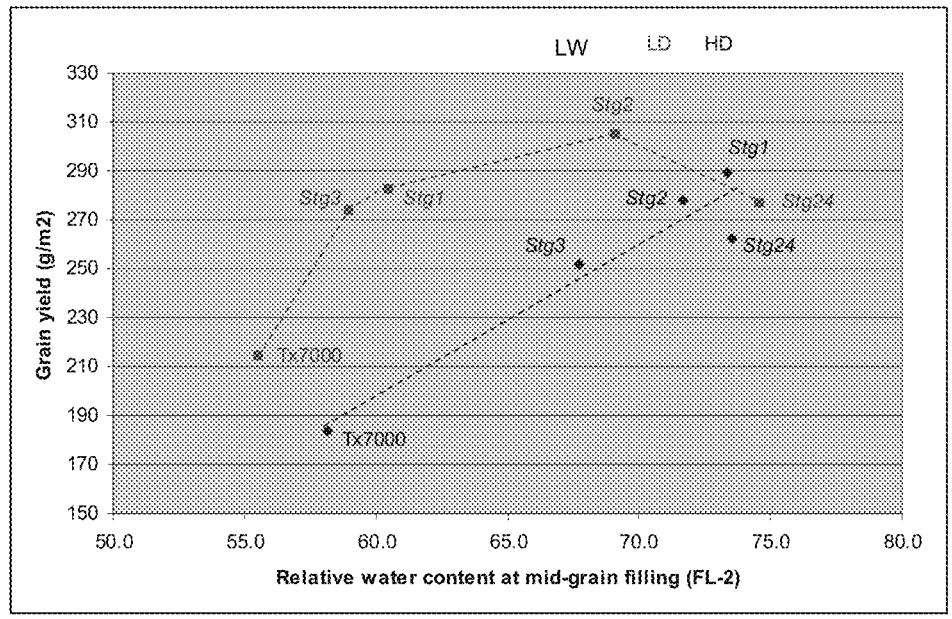
FIG. 55 is a graphical representation showing the relation between relative water content (RWC) at mid-grain filling (FL-2) and grain yield in various combinations of Stg QTL and the recurrent parent (RTx7000) grown under water-limited conditions at two crop densities (LD=10 plants/m2; HD=20 plants/m2) in an experiment grown in 2004.

In this experiment, there was no trade-off between PASM and grain yield, since the correlation between these parameters was positive and linear for both crop densities (FIG. 55). Under HD, Stg1 exhibited the highest stem mass and grain yield of all the Stg introgressions, highlighting that grain yield and lodging resistance are not mutually exclusive.

The relation between PASM and stem mass at maturity was positively correlated under HD and negatively correlated under LD. Under HD, PASM and stem mass at maturity were both significantly higher in Stg1 than RTx7000. Under LD, stem mass at maturity was higher in Stg1 than RTx7000 (314 vs. 271 g/m2), although Stg1 utilized more stem reserves compared with RTx7000 (87 vs 66 g/m2). Overall, Stg increased stem mass at maturity by 22% (HD) and 16% (LD) relative to RTx7000. Also, Stg1a utilized significantly less stem reserves than RTx7000 under both crop densities.

Figure 56:
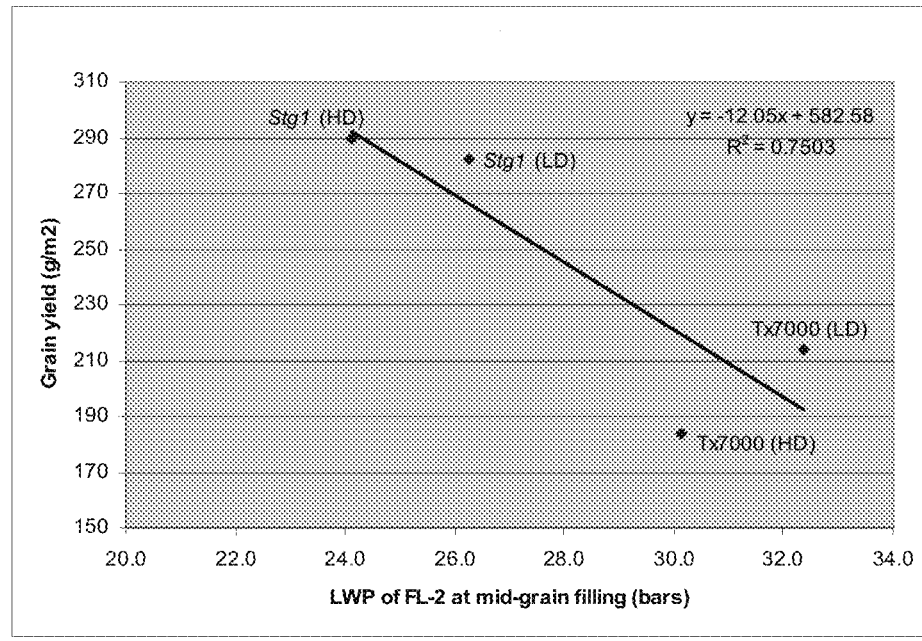
FIG. 56 is a graphical representation showing the relation between leaf water potential (LWP) of FL-2 at mid-grain filling (bars) and grain yield (g/m2) in the Stg1 QTL (6078-1) and the recurrent parent (RTx7000) grown under water-limited conditions at two crop densities (LD=10 plants/m2; HD=20 plants/m2).

Post-anthesis stem mass (PASM) was highly linearly correlated with PAB under HD and LD conditions (FIG. 56. Genetic variation in utilization of post-anthesis stem reserves ranged from ~30-110 g/m2 under LD, and from ~100-160 g/m2 under HD, reflecting the higher level of stress in the HD treatment. Under HD, the Stg1 parent (6078-1) and two of the Stg1 recombinants (10604-5 and 10709-5) utilized significantly less stem reserves compared with RTx7000 (~100 vs.160 g/m2), yet produced more PAB than RTx7000 (~170 vs. 130 g/m2). Under LD, only one of the Stg1 recombinants (10568-2) utilized significantly less stem reserves than RTx7000 (~30 vs. 60 g/m2), and produced more PAB than RTx7000 (~310 vs. 230 g/m2).

Grain yield was positively correlated with PAB under LD and negatively correlated under HD, although overall (combining HD and LD), the relationship was positive, with RTx7000 (HD) as an outlier.

In this experiment, there was no trade-off between PASM and grain yield, since the correlation between these parameters was positive and linear for both crop densities. Under HD, the Stg1 parent (6078-1) exhibited high stem mass and grain yield compared with the other Stg1 introgressions. RTx7000 was an anomaly under HD, exhibiting low stem mass and high grain yield. Under LD, 10709-5 and 10568-2 exhibited high stem mass and grain yield relative to RTx7000.

The relation between PASM and stem mass at maturity was positively correlated under both densities. Under HD, PASM and stem mass at maturity were both significantly higher in 6078-1 and 10709-5 than RTx7000. Under LD, only one Stg1 recombinant (10568-2) exceeded RTx7000 in PASM and stem mass at maturity.

Example 22

Higher Grain Yield is a Consequence of Higher Plant Water Status during Grain Filling Introgressing Stg1 into a RTx7000 background increased plant water status at mid-grain filling, as indicated by a) higher relative water content (RWC) in FL-2 under LD and HD lower leaf water potential (LWP) in FL-2 under LD and HD. Overall, plants were more stressed under LD than HD in this experiment, evidenced by lower RWC under LD. However, the beneficial impact of Stg1 on plant water status was more dramatic under HD, where RWC was 26% higher in Stg1 than RTx7000.

RWC at mid-grain filling in FL-2 was positively correlated with grain yield under HD and LD. At higher levels of plant water stress (RWC<73), grain yield was higher under LD than HD for a given level of RWC. RWC and grain yield were higher in Stg1 than RTx7000 under both crop densities. For example in Stg1 under HD, a 26% increase in RWC was associated with a 58% increase in grain yield, relative to RTx7000.

Figure 57:
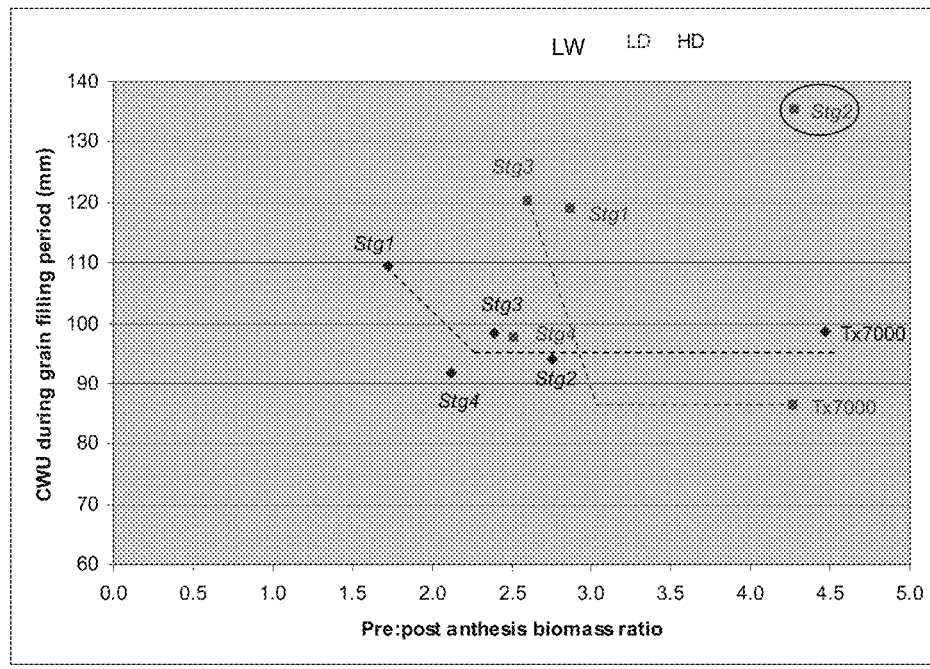
FIG. 57 is a graphical representation showing the relation between PPBR and CWU during grain filling in four Stg QTL and the recurrent parent (RTx7000) grown under water-limited conditions at two crop densities (LD=10 plants/m2; HD=20 plants/m2).

The leaf water potential (LWP) of FL-2 at mid-grain filling was negatively correlated with grain yield under HD and LD conditions (FIG. 57). Under both densities, Stg1 exhibited a lower LWP (less stressed) and higher grain yield relative to RTx7000. These data, together with the RWC data, provide strong evidence for a link between higher plant water status during grain filling and enhanced grain yield due to the Stg1 region.

Example 23

Higher Grain Yield and Larger Grain Size are Consequences of Increased Water Availability during Grain Filling Critical to the hypothesis on Stg function is the link between pre- and post-anthesis water use and, subsequently, the link between post-anthesis water use and grain yield. The Stg1 gene is of little value at the field level is there is no link between increased water availability during grain filling and either grain yield or grain size.

Figure 58:
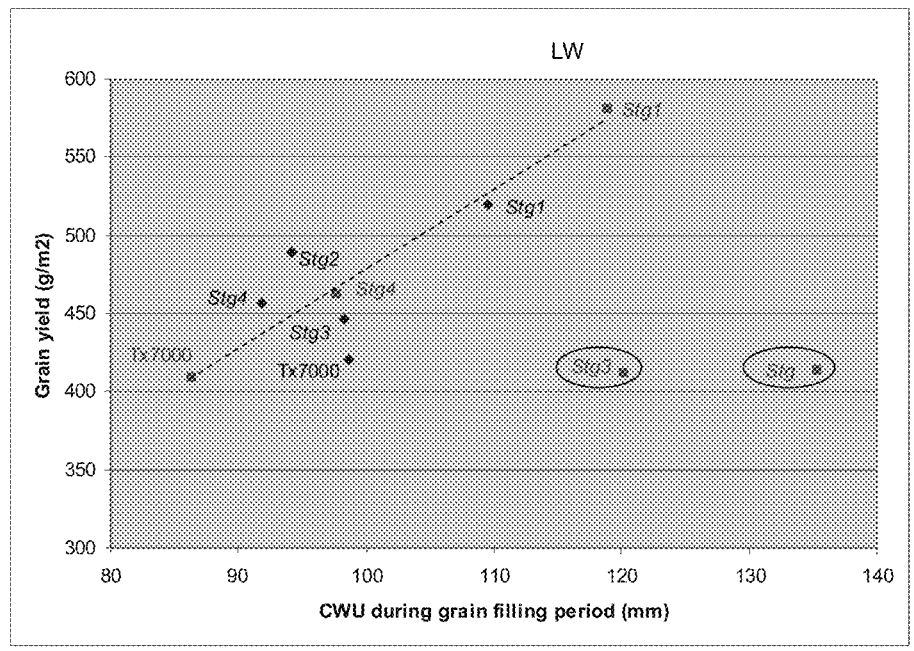
FIG. 58 is a graphical representation showing the relation between CWU during grain filling (mm) and grain yield (g/m2) in four Stg QTL and the recurrent parent (RTx7000) grown under water-limited conditions at two crop densities (LD=10 plants/m2; HD=20 plants/m2).

First, it is important to establish the link between the pre:post anthesis biomass ratio (PPBR) and crop water use (CWU) during grain filling. CWU during grain filling remained low (at a benchmark of ~85 and 95 mm for LD and HD, respectively) until the pre:post anthesis biomass ratio fell below ~3 and 2.5 for LD and HD, respectively (FIG. 58). Below this critical value, CWU during grain filling increased significantly for each incremental reduction in this ratio. Under both densities, Stg1 introgressions reduced the PPBR sufficiently to significantly increase CWU relative to RTx7000.

Second, it is important to show the link between CWU during grain filling and grain yield. In general, these parameters were positively associated in a ROS experiment, apart from two distinct outliers under LD (Stg2 and Stg3) [FIG. 59]. Introgressing Stg1 into RTx7000 increased both CWU during grain filling and grain yield under both crop densities.

Figure 59:
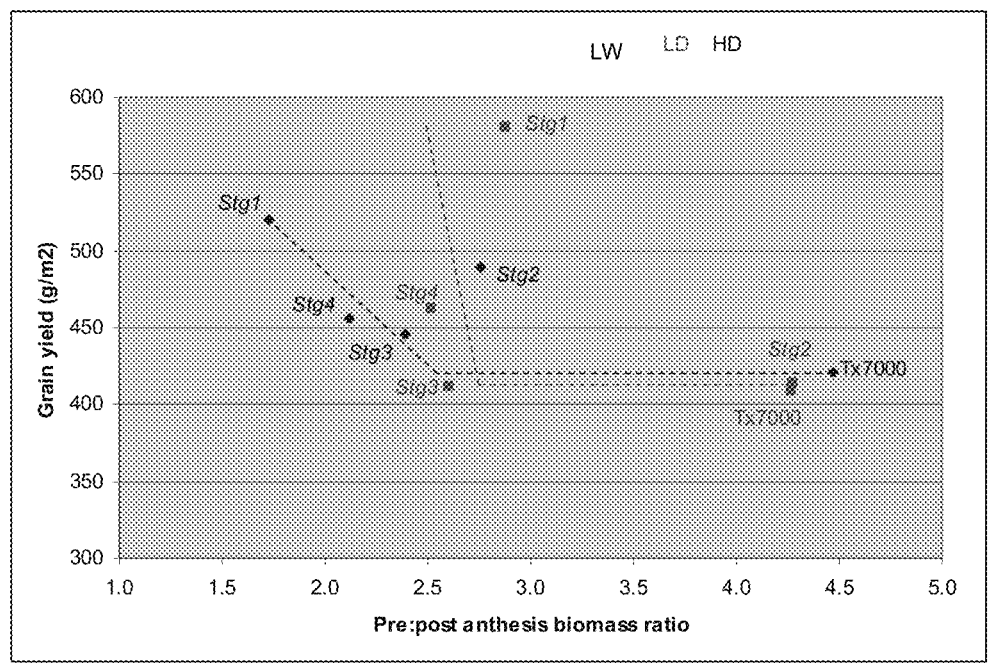
FIG. 59 is a graphical representation showing the relation between PPBR and grain yield in four Stg QTL and the recurrent parent (RTx7000) grown under water-limited conditions at two crop densities (LD=10 plants/m2; HD=20 plants/m2).

Finally, the link between PPBR and grain yield under water-limited conditions completes the picture (FIG. 59). Grain yield remained low (at a benchmark of ~410 g/m2) until the pre:post anthesis biomass ratio fell below ~2.7 (FIG. 59). Below this critical value, grain yield increased significantly for each incremental reduction in this ratio. Under both densities, Stg1 introgressions reduced the PPBR sufficiently to significantly increase grain yield relative to RTx7000. These data provide a critical link between Stg1 gene action (reduced canopy size at anthesis) and grain yield under terminal drought.

Figure 60:
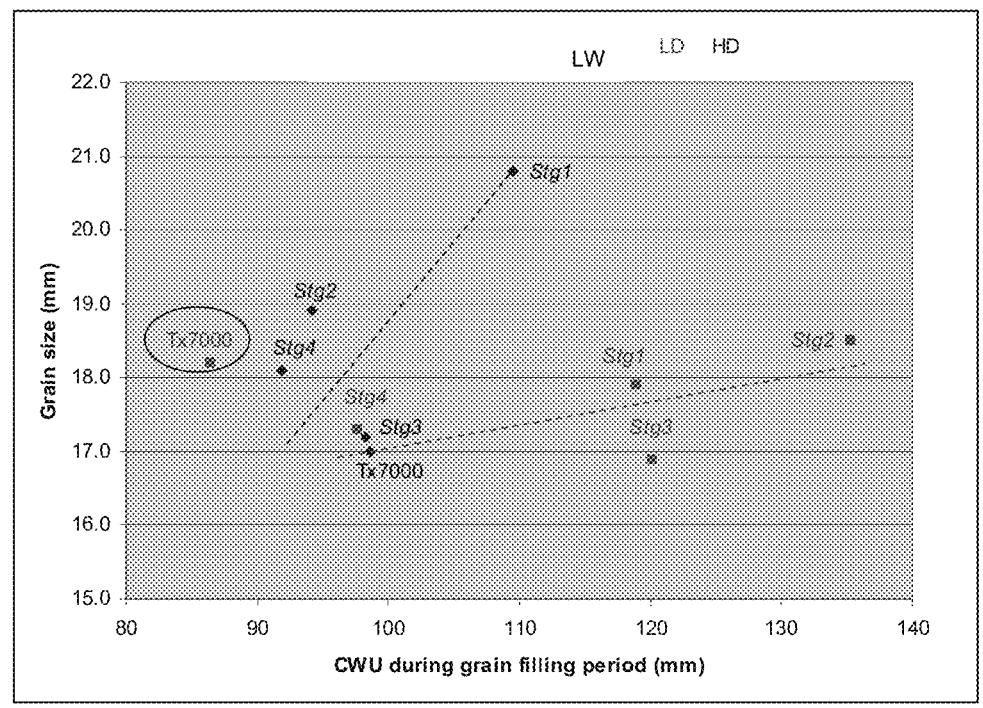
FIG. 60 is a graphical representation showing the relation between CWU during grain filling (mm) and grain size (mg) in four Stg QTL and the recurrent parent (RTx7000) grown under water-limited conditions at two crop densities (LD=10 plants/m2; HD=20 plants/m2).

CWU during grain filling was positively correlated with grain size under both HD and LD treatments (FIG. 60). Introgressing Stg1 into RTx7000 significantly increased grain size under HD, but not LD.

Figure 61:
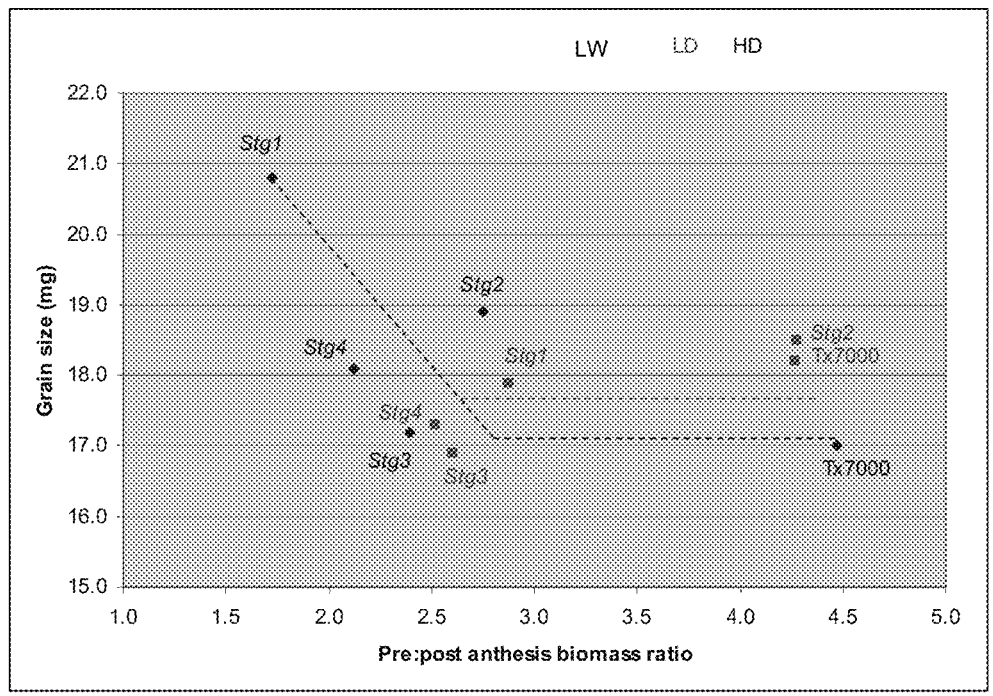
FIG. 61 is a graphical representation showing the relation between PPBR and grain size in four Stg QTL and the recurrent parent (RTx7000) grown under water-limited conditions at two crop densities (LD=10 plants/m2; HD=20 plants/m2).

The relation between PPBR and grain size under water-limited conditions highlights the importance of water conservation before anthesis as a determinant of grain size (FIG. 61). Grain size remained low (at a benchmark of ~17 and 17.5 mg for HD and LD, respectively) until the pre:post anthesis biomass ratio fell below ~2.7 (FIG. 61). Below this critical value, grain size increased significantly for each incremental reduction in this ratio. Under HD but not LD, Stg1 introgressions reduced the PPBR sufficiently to significantly increase grain size relative to RTx7000. These data provide a critical link between Stg1 gene action (reduced canopy size at anthesis) and grain size under terminal drought.

Figure 62:
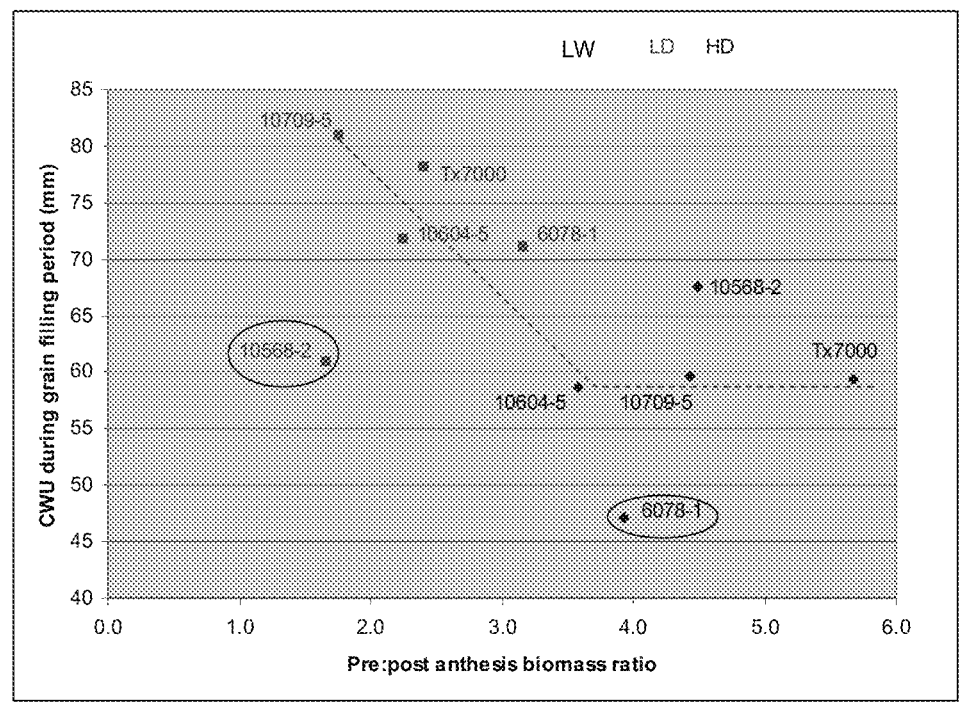
FIG. 62 is a graphical representation showing the relation between PPBR and CWU during grain filling in various Stg1 fine-mapping lines and the recurrent parent (RTx7000) grown under water-limited conditions at two crop densities (LD=10 plants/m2; HD=20 plants/m2).

CWU during grain filling remained low (at a benchmark of ~58 mm for HD) until the pre:post anthesis biomass ratio fell below ~3.5 (FIG. 62). Note that the PPBR Did not drop below the critical threshold in any genotype under HD, hence CWU during grain filling remained relatively low for all genotypes in this treatment. However, as genotypes fell below this critical value in the LD treatment, CWU during grain filling increased significantly for each incremental reduction in this ratio. Only one Stg1 recombinant (10709-5) increased CWU during grain filling relative to RTx7000.

Figure 63:
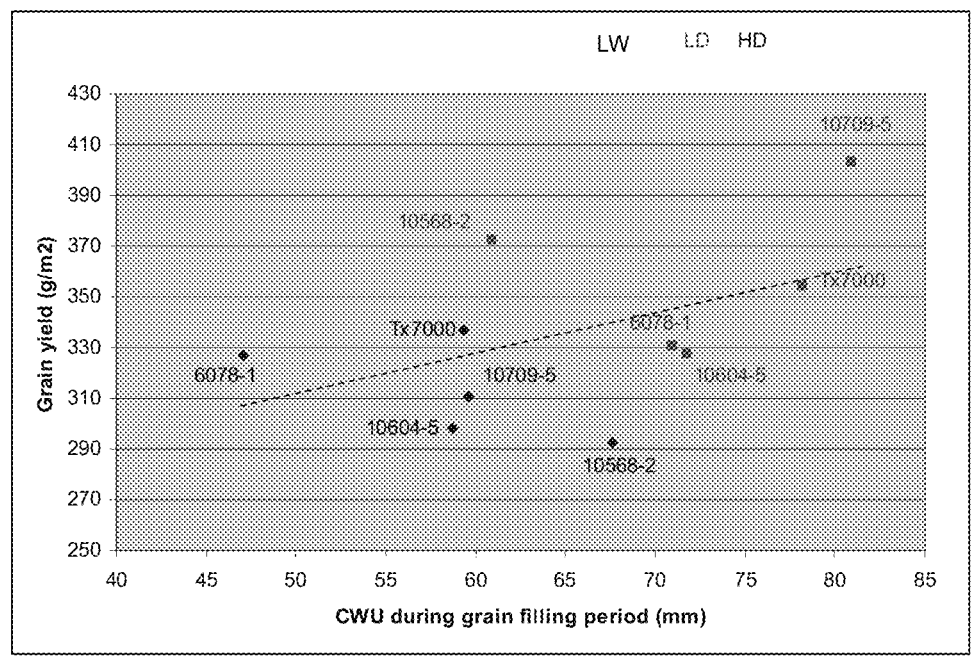
FIG. 63 is a graphical representation showing the relation between CWU during grain filling (mm) and grain yield (g/m2) in various Stg1 fine-mapping lines and the recurrent parent (RTx7000) grown under water-limited conditions at two crop densities (LD=10 plants/m2; HD=20 plants/m2).

In general, CWU during grain filling and grain yield were positively correlated using a combined data set from the HD and LD treatments, with genotypes using more water and producing more grain under LD (FIG. 63). However, the relation between these parameters was not very strong. Nor did particular Stg1 recombinants consistently out-yield RTx7000 in HD and LD treatments.

Example 24

QTL and PIN Gene Analysis

QTL Analysis

Stay-green QTL data were collected from 7 studies (Crasta el al. (1999) *Molecular and General Genetics* 262: 579-588; Hausmann et al. (2002) theroretical and *Applied Genetics* 106:133-142; Kebede et al. (2001) *Theoretical and Applied Genetics* 103:266-276; Srininvas et al. (2009) *Theor Appl Genet* 118:703-717; Subudhi et al. (2000) *Theor App Genet* 101:733-741; Tao et al. (2000) *Theor Appl Genet* 100:1225-1232; Xu el al. (2000) *Genome* 43:461-469). From the 7 studies, 47 individual QTL were identified and projected onto the sorghum consensus map (Mace et al. (2009) BMC Plant Biol. 9:13).

Where estimated Confidence Intervals (CI) of QTL for the same trait overlapped, those QTL were grouped into a meta QTL. Nine meta-QTL for stay-green were identified in this way. QTL for the same trait were classified as separate QTL if their CI had no region in common and mean QTL location were less than or equal to 15 cM away from each other.

Statistical Machine Learning (SML) QTL analysis (Bedo et al. (2008) *BMC Genetics* 9:35) was conducted on a set of over 500 entries on the DEEDI sorghum pyt males trial. 23 QTL identified with a probability <0.05 were also plotted onto the consensus map.

PIN Gene Analysis

All available PIN genes in rice and *Arabidopsis* were searched for via NCBI (ncbi.org). In total, sequence for 9 rice PIN genes (OsPIN1, OsPIN1b, OsPIN1c, OsPIN2, OsPIN3a, OsPIN3b, OsPIN4, OsPIN5, OsPIN6) and 3 Arabidopsis PIN genes (AtPIN1, AtPIN2, AtPIN4) were identified. All genes (protein sequence) were BLASTed against the sorghum WGS (gramene.org) and the top 100 hits were identified. The score (S value: a measure of the similarity of the query to the sequence shown), E-value (the probability due to chance, that there is another alignment with a similarity greater than the given S score), % ID and length of sequence homology for each of the 1200 hits were collated. The relationship between the 4 measures was analyzed and the S score was selected as the main measure to assess likelihood of sequence similarity. Following an analysis of the distribution of S score values, 3 S score categories were identified (>1000; >499 and <1000; <499) and a list of 11 sorghum genes with scores >499 (i.e. in the first 2 categories) was produced. See Table 13.

TABLE 13

| Sorghum Gene ID | Target gene | JGI Annotation |
|---|---|---|
| Sb02g029210 | OsPIN6 | "similar to Os09g0505400 protein" |
| Sb03g029320 | OsPIN3a | "similar to Probable auxin efflux carrier component 3a" |

TABLE 13-continued

| Sorghum Gene ID | Target gene | JGI Annotation |
|---|---|---|
| Sb03g032850 | OsPIN1 | "similar to Putative uncharacterized protein" |
| Sb03g037350 | OsPIN5 | "similar to Probable auxin efflux carrier component 5" |
| Sb03g043960 | OsPIN6 | "similar to Probable auxin efflux carrier component 6" |
| Sb04g028170 | OsPIN1 | "similar to Auxin efflux carrier component 1" |
| Sb05g002150 | OsPIN1b | "similar to Probable auxin efflux carrier component 1b" |
| Sb07g026370 | OsPIN4 | "similar to Probable auxin efflux carrier component 4" |
| Sb10g004430 | OsPIN1 | "similar to Putative auxin efflux carrier component 3b" |
| Sb10g008290 | OsPIN1c | "similar to Probable auxin efflux carrier component 1c" |
| Sb10g026300 | OsPIN2 | "similar to Probable auxin efflux carrier component 2" |

Comparisons

Figure 65:
FIG. 65 is a diagrammatical representation showing comparisons of PIN, SPL and CCD7/8 orthologs aligned with QTL for stay-green for the sorghum chromosomes 1 through 5.
Figure 65:
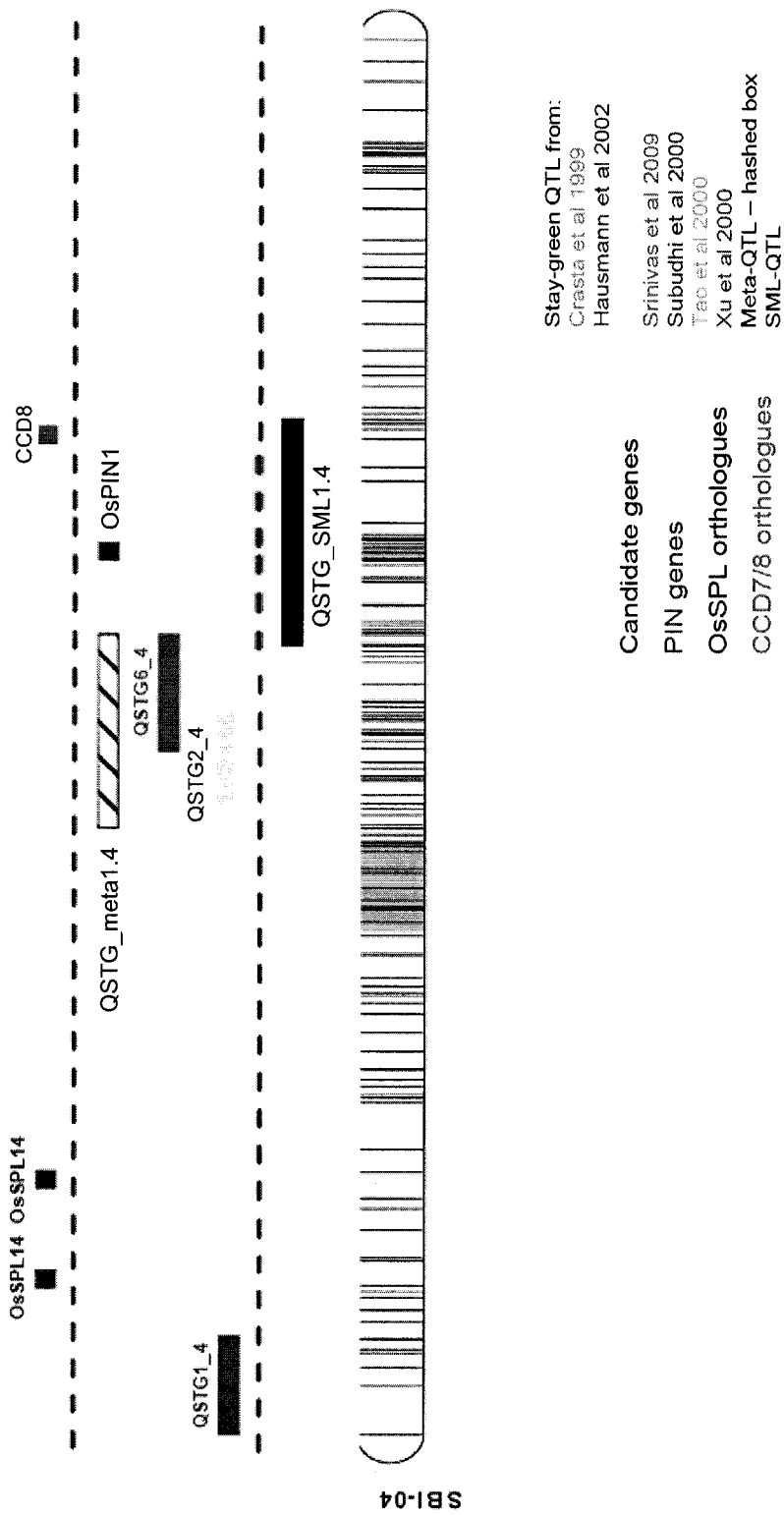
Figure 65:
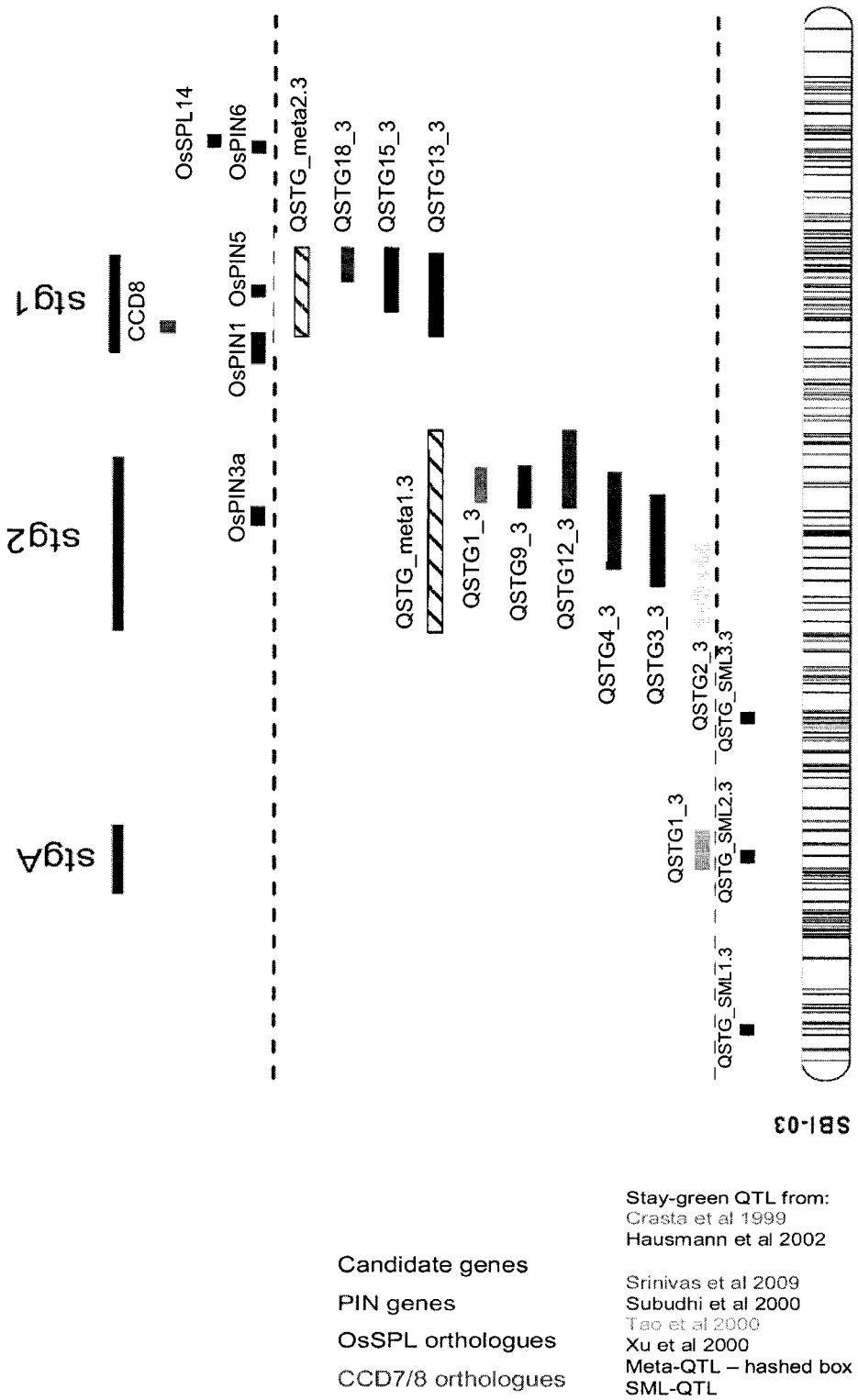
Figure 65:
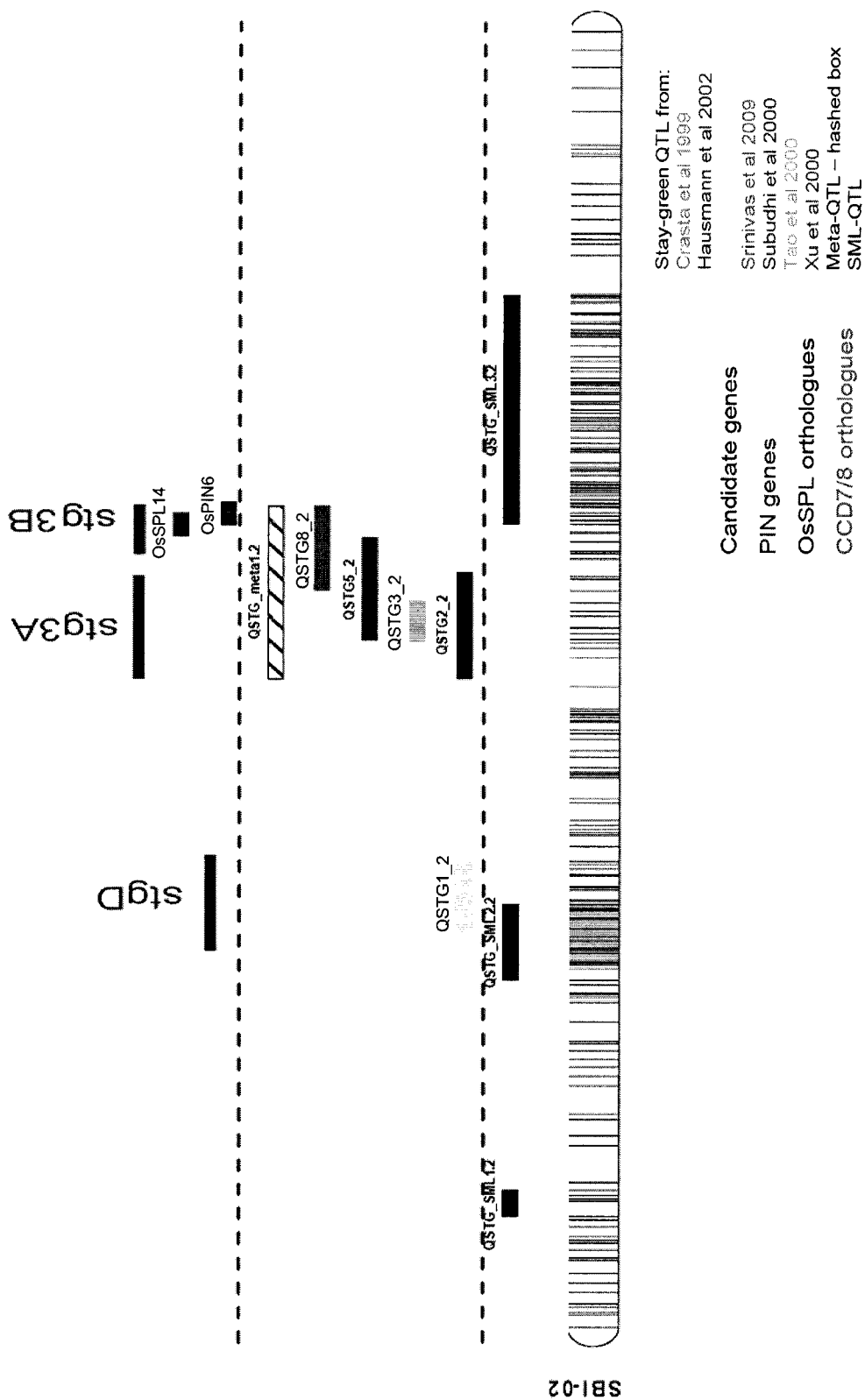
Figure 65:
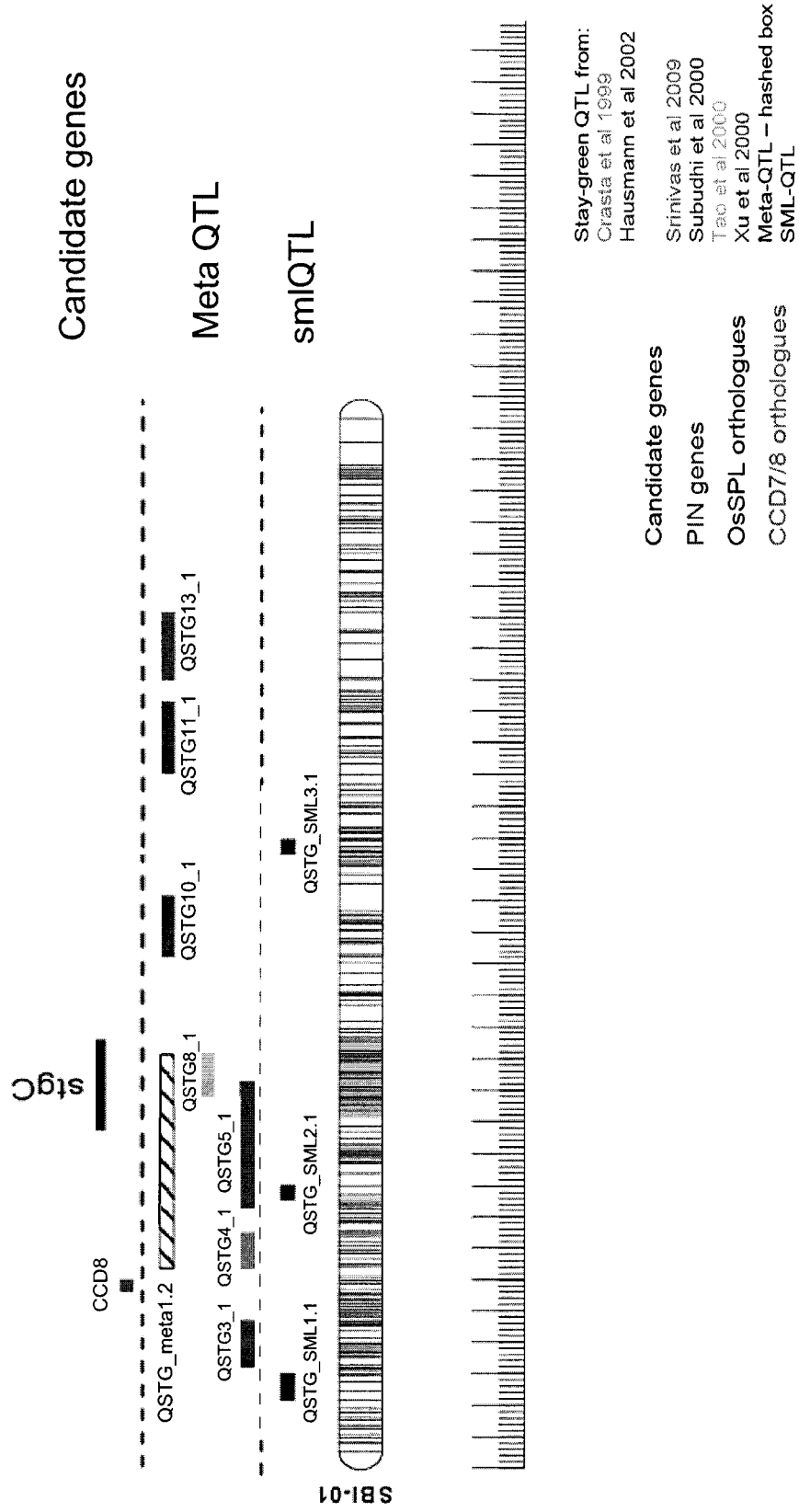
Figure 66:
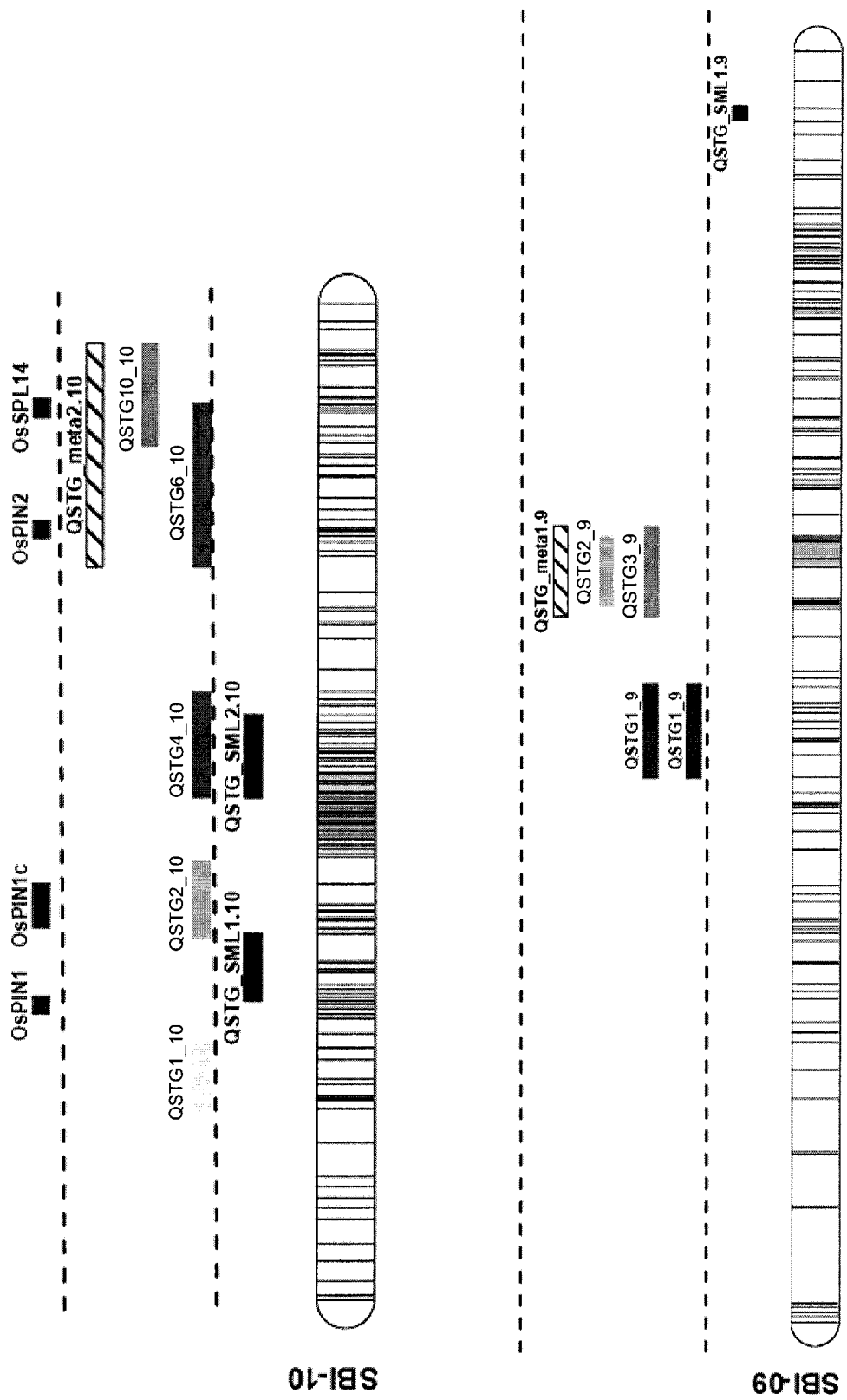
FIG. 66 is a diagrammatical representation showing comparisons of PIN, SPL and CCD7/8 orthologs aligned with QTL for stay-green for the sorghum chromosomes 6 through 10.
Figure 66:
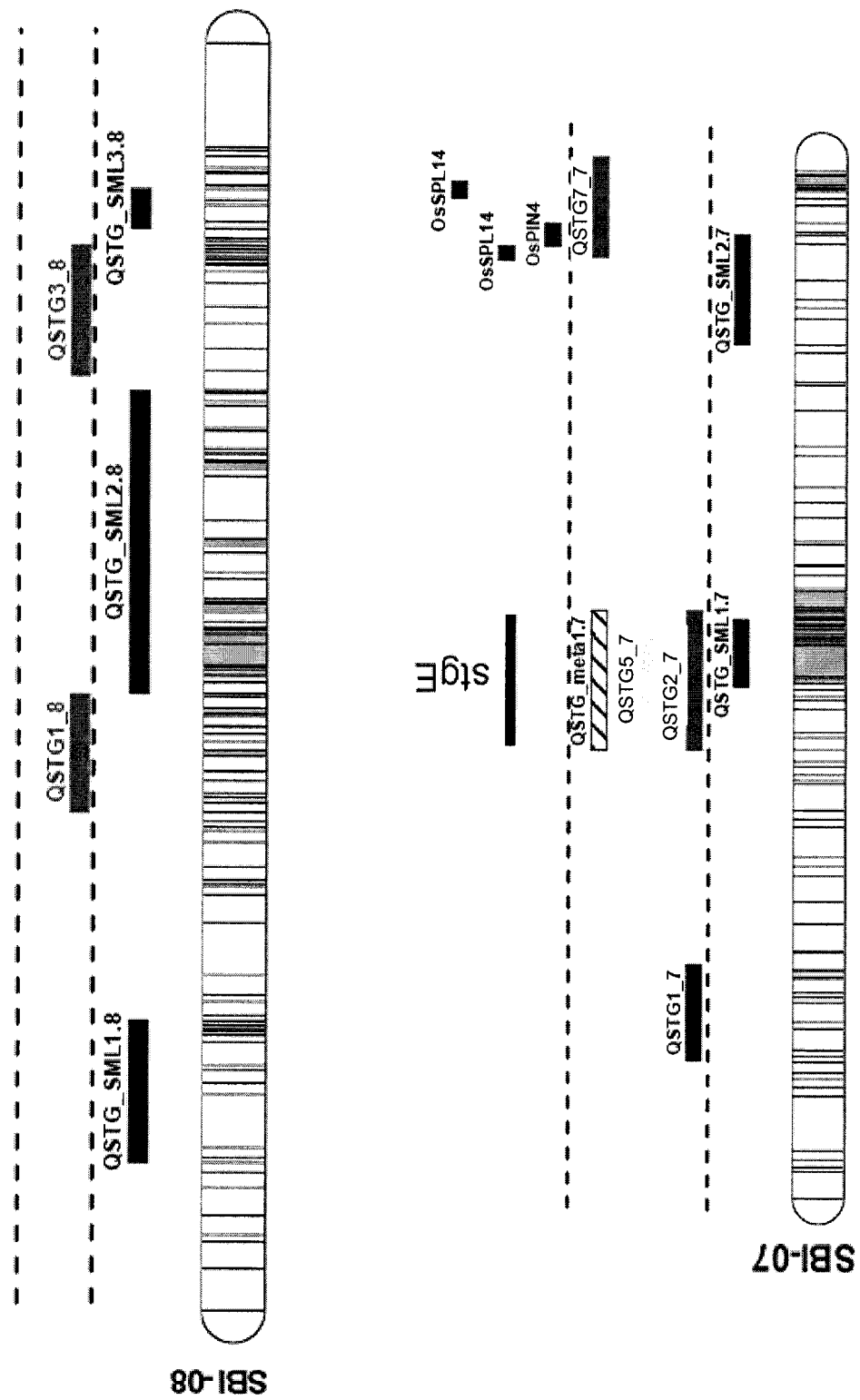
Figure 66:
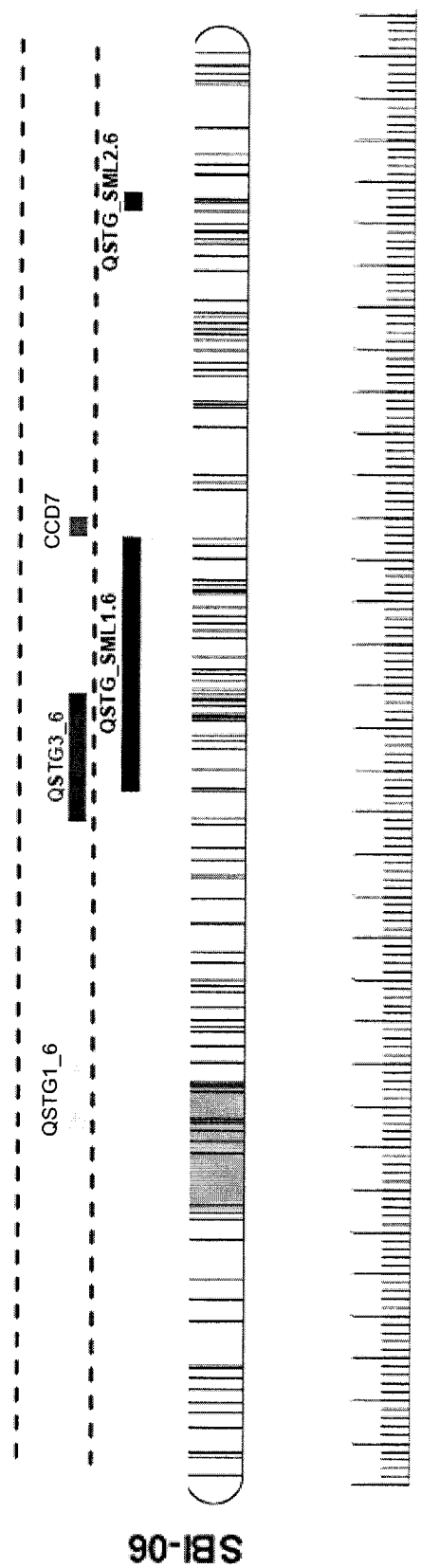
Figure 67A:
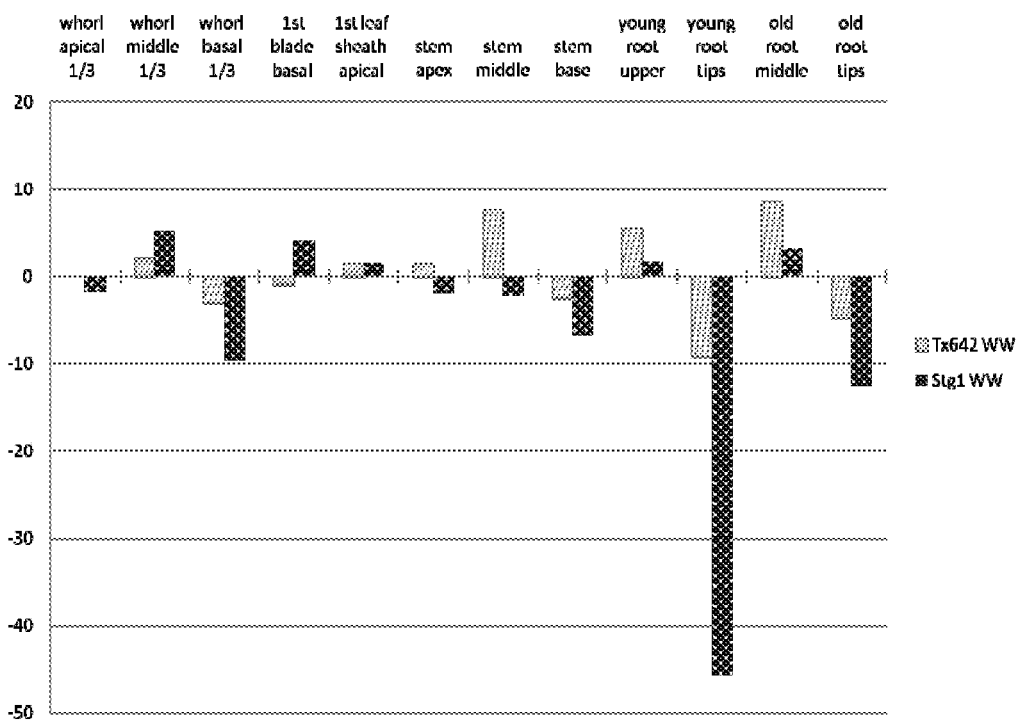
FIG. 67A is a graphical representation of differential expression of SbPIN4 (Stg1 candidate) under well-watered conditions. Under well-watered conditions, this gene is down-regulated in young root tips Tx642 and Stg1 NIL compared to Tx7000.
Figure 67B:
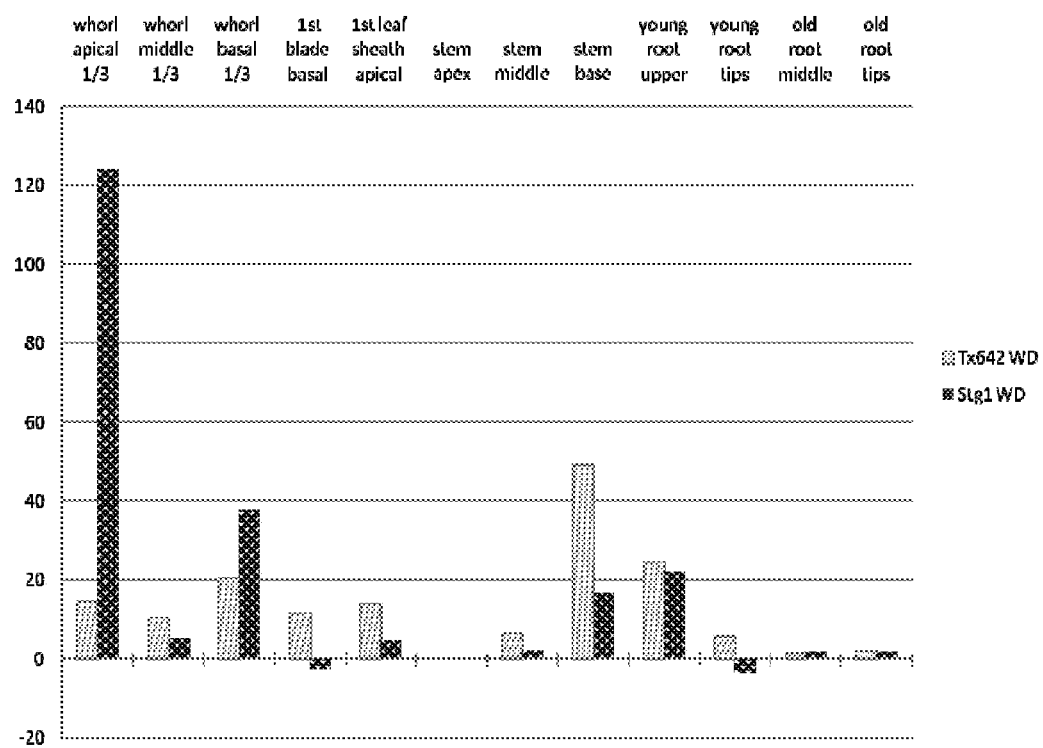
FIG. 67B is a graphical representation of differential expression of SbPIN4 (Stg1 candidate) under water-deficient conditions. Under water-deficient conditions, this gene is up-regulated in most tissues, but especially in expanding leaves of Tx642 and Stg1 NIL compared to Tx7000.
Figure 67C:
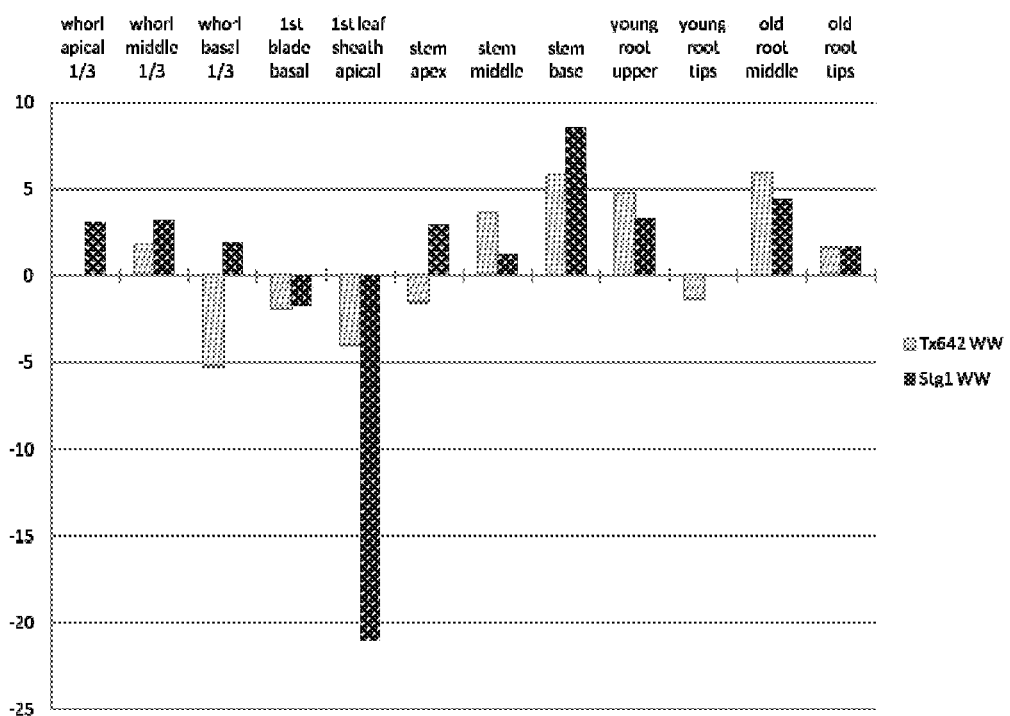
FIG. 67C is a graphical representation of differential expression of SbPIN2 (Stg2 candidate) under well-watered conditions. Under well-watered conditions, this gene is slightly up-regulated in stem and root tissues of Tx642 and Stg1 NIL compared to Tx7000.
Figure 67D:
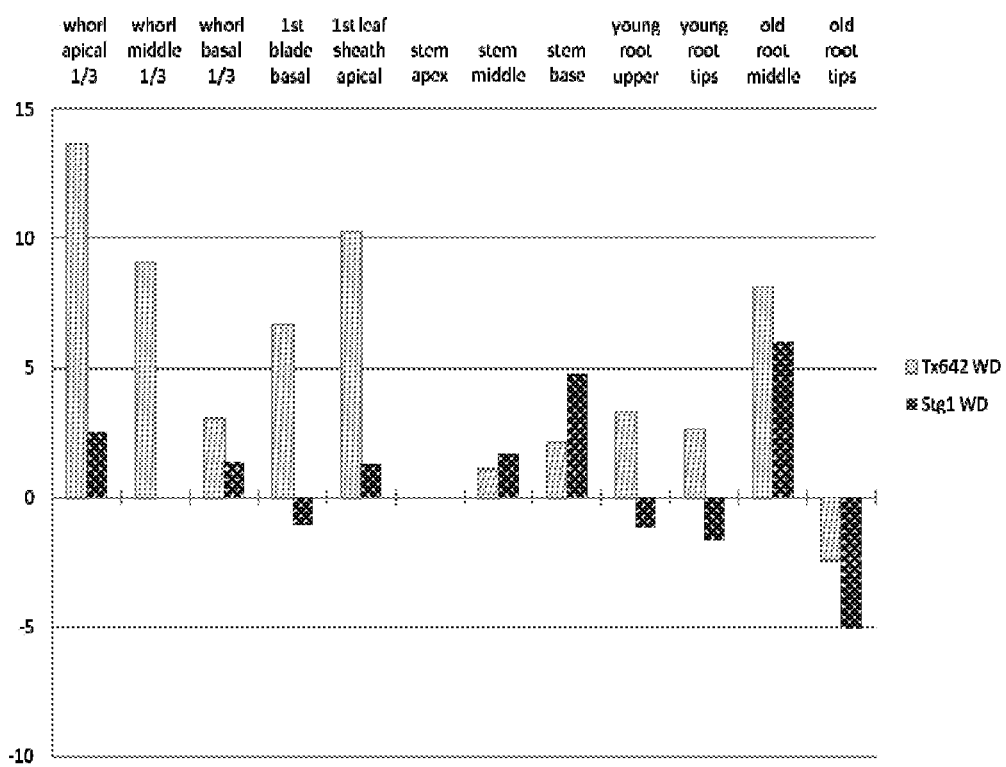
FIG. 67D is a graphical representation of a differential expression of SbPIN2 (Stage 2 candidate) under water-deficient conditions. Under water-deficient conditions, this gene is up-regulated in most tissues of Tx642 and Stg1 NIL compared to Tx7000.

Of the 11 PIN orthologues identified, 10 (90.9%) aligned, with known QTL for stay-green. Only one of the 11 sorghum PIN genes (Sb03g043960 on SBI-03, marked with a grey star on FIGS. 65 and 66) did not align to any reported QTL. Of the 79 QTL plotted (23 SML-QTL and 56 from the literature/meta-QTL), 30 (38%) aligned with the PIN orthologs.

Example 25

Analysis of PIN2, PIN3, PIN4 and PIN5

The stay-green source BTx642 (B35), and near-isogenic lines (NILs) containing the Stg1, Stg2, Stg4 QTLs, as well as the contrasting senescent line Tx7000 were grown in root pipes in a glasshouse.

The aim of the experiment was to measure expression levels of genes that are identified herein as stay-green gene candidates under well-watered conditions and after a drought stress has been imposed on the plants to see whether there were any differences in expression in the stay-green compared with the senescent plants.

The experiment was divided into two parts: an early drought stress (Exp1) and a late drought stress (Exp2).

Results from the early drought stress experiment are shown in Table 14.

TABLE 14

| Gene | GeneID | Rice Homologue | Stg QTL | Comment |
|---|---|---|---|---|
| SbPIN2 | Sb03g029320 | OsPIN3a | Stg2 | Stg2 Candidate |
| SbPIN3 | Sb03g032850 | OsPIN1 | Stg1 | Upper Stg1 QTL |
| SbPIN4 | Sb03g037350 | OsPIN5 | Stg1 | Stg1 Candidate |
| SbPIN5 | Sb03g043960 | OsPIN6 | Stg1 | Lower Stg1 QTL |

The main differences in expression of these PIN genes are summarized below (Table 15 and in FIGS. 67A through D).

TABLE 15

| Gene | Main Tissues | Response to WD | Differential Expression |
|---|---|---|---|
| SbPIN4 (Stg 1 candidate) | WW: low in leaves, high in roots WD: low in leaves, high in roots | Lower expression in most tissues | WW: Higher in Tx7000 vs BTx642 and Stg1 in roots (FIG. 1) WD: Higher in Stg1 and BTx642 vs Tx7000 in leaves. stems and upper roots (FIG. 2) |
| SbPIN2 (Stg2 candidate) | WW: high in leaves, low in roots WD: high in leaves, low in roots | Increase in roots, decrease in stems | WW: Higher in Stg2/BTx642 vs Tx7000 in stem and roots (FIG. 3) WD: higher in BTx642 and to lesser extent Stg2 vs Tx7000 in most tissues except old roots (FIG. 4) |
| SbPIN3 | Limited variation among tissues | Limited response to WD | WD: slightly higher in BTx642/Stg1 vs Tx7000 |
| SbPIN5 | WW: high in leaves, low in roots WD: high in leaves, low in roots | Increase in roots, not much change in leaves | WW: Higher in Stg1 (and to much lesser extent Tx642) vs Tx7000 in upper young roots especially WD: Higher in Stg1 (and to lesser extent) BTx642 vs Tx7000 in stem |

Emerging patterns were identified for SbPIN4 and SbPIN2, Stg1 and Stg2, respectively.

In both cases the expression of these genes was higher in stay-green lines compared to the senescent line in response to water deficit.

These two PIN genes showed differences in tissue specificity. SbPIN4 was generally (across all conditions) more highly expressed in roots and stems and less expressed in leaves, while SbPIN2 generally showed higher expression in leaves and stems and lower expression in roots).

Example 26

Determination of StgX Loci

Tables 1B and 1C provide examples of loci located at: Stg1: Fine-mapped region between txp563 and txp581 containing 60 annotated genes, Larger middle region between txp440 and txp580 containing 307 annotated genes, Candidates in tail between txp58,0 and txp38 containing 178 annotated genes; Stg2: Fine-mapped region between txp512 and txp2 containing 15 annotated genes, Larger region between txp31 and txp530 containing 241 annotated genes; Stg3a: Entire region between txp298 and sPb-2568 containing 520 annotated genes; Stg3b: Entire region between sPb-2568 and txp179 containing 291 annotated genes; Stg4: Entire region defined by txp283 and txp15 containing 306 annotated genes, How these various loci fit in various biochemical and physiology pathways is depicted in FIG. 68.

In an embodiment, the locus is in Stg1 selected from PIN5, GID1L2, P45098A1, indole-3-acetate and brassinosteroid insensitive.

In an embodiment, the locus is in Stg2 and is auxin efflux carrier component 3a (PIN3a).

In an embodiment, the locus is in Stg3a selected from leaf senescence protein-like (Sb02g023510), leaf senescence protein-like (Sb02g023520), RAMOSA1 C2H2 zinc-finger transcription factor (Sb02g024410), putative auxin-independent growth promoter (Sb02g024540), similar to dehydration-responsive protein-like (Sb02g024670), similar to glucose transporter (Sb02g024690), WRKY transcription factor 76 (Sb02g024760), glutamine synthetase-like protein (Sb02g025100), senescence-associated protein DH (Sb02g025180), putative alanine aminotransferase (Sb02g025480), auxin-induced protein-like (Sb02g025610), auxin-induced protein-like (Sb02g025620), putative far-red impaired response protein (Sb02g025670), similar to cytochrome P450 monooxygenase CYP92A1 (Sb02g025820), auxin-independent growth promoter (Sb02g025960), asparate aminotransferase (Sb02g026430), similar to abscisic acid 8'-hydroxylase 3 (Sb02g026600) similar to ethylene-binding protein-like (Sb02g026630) and putative auxin-induced protein family (Sb02g027150).

In an embodiment, the locus is in Stg3b selected from putative auxin-independent growth promoter (Sb02g027470), squamosa promoter-binding-like protein 17 (Sb02g028420), similar to Os09g0505400 (OsPIN9) protein (Sb02g029210), squamosa promoter-binding-like protein 17 (Sb02g029300) similar to auxin-induced protein-like (Sb02g029630).

In an embodiment, the locus is in Stg4 selected from brassinosteroid LRR receptor (Sb05g006842), brassinosteroid LRR receptor (Sb05g006860), putative far-red impaired response protein (Sb05g007130), cytochrome P450 84A1 (Sb05g007210), gibberellin receptor GID1L2 (Sb05g007270), gibberellin receptor GID1L2 (Sb05g007290), sucrose-phosphate synthase (Sb05g007310), aquaporin SIP1-1 (Sb05g007520), gibberellin 20 oxidase 2 (Sb05g008460), OsIAA29-auxin-responsive (Sb05g008510), OsIAA29-auxin-responsive (Sb05g008512), protein gibberellin receptor GID1L2 (Sb05g008610), similar to aminotransferase, putative (Sb05g009410), indole-3-acetic acid-amido (Sb05g010310), indole-3-acetic acid-amido (Sb05g010320), indole-3-acetic acid-amido (Sb05g010326), cytochrome P450 86A2 (Sb05g010360), cytochrome P450 51, putative (Sb05g011296), cytochrome P450 51, putative (Sb05g011430), triacylglycerol lipase, leaf senescence, jasmonic acid biosynthetic process_GO (Sb05g013160), growth regulator like (Sb05g015590), cytochrome P450 78A4 (Sb05g016750), similar to ABC transporter family protein, expressed (Sb05g017120) and squamosa promoter-binding-like protein 19 (Sb05g017510).

Those skilled in the art will appreciate that aspects described herein are susceptible to variations and modifications other than those specifically described. It is to be understood that those aspects include all such variations and modifications. Aspects herein described also include all of the steps, features, compositions and compounds referred to or indicated in this specification, individually or collectively, and any and all combinations of any two or more of the steps or features.

BIBLIOGRAPHY

Andrade et al. (2002) *Crop Sci.* 42:1173-1179
Bedo et al. (2008) *BMC Genetics* 9:35
Borrell et al. (2000a) *Crop Sci.* 40:1026-1037
Borrell et al. (2000b) *Crop Sci.* 40:1037-1048
Borrell and Hammer (2000) *Crop Sci.* 40:1295-1307
Christopher et al. (2008) *Aust. J, Agric. Res.* 59:354-364
Crasta et al. (1999) *Molecular and General Genetics* 262: 579-588
Domagalska and Leyser (2011) *Bat Rev iMol Cell Biol* 12:211-221
Forestan and Varotto (2009) *Plant Physiology*
Friml et al. (2003) *Current Opinion in Plant Biology* 6:7-12
Garud et al. (2002) *Int. Sorghum and Millets Newsl.* 43:63-65
Hammer et al. (1997) *Aust. J. Agric. Res.* 48:649-655
Hammer (2006) *Agric. Sci.* 19:16-22
Harris et al. (2007) *J. Exp. Bot.* 58:327-338
Hausmann et al. (2002) *Theoretical and Applied Genetics* 106:133-142
Henderson et al. (1998) *Aust. J. Plant Physiol.* 25:111-123
Henzell et al. (1997) *Australia Int. Sorghum and Millets Newsl.* 38:1-9
Jiao et al. (2010) *Nature Genetics* 42:541-544
Jordan et al. (2003) *Theor. Appl. Genet.* 106:559-567
Kashiwagi et al. (2006) *Plant Physiology and Biochemistry* 44:152-157
Kassahun et al. (2010) *Euphytica* 72:351-362
Kebede et al. (2001) *Theoretical and Applied Genetics* 103:266-276
Mace et al. (2009) *BMC Plant Biol.* 9:13
Manschadi et al. (2006) *Funct. Plant. Biol.* 33:823-837
Miura et al. (2010) *Nature Genetics* 42:545-549
Mortlock and Hammer (1999) *J. Crop Prod.* 2:265-286
Passioura (1977) *J. Aust. Inst. Agric. Sci.* 43:117-120
Rashotte et al. (2000) *Plant Cell* 13:1683-1697
Reddy et al. (2008) *Euphytica* 159:191-198
Rosenow et al. (1983) *Agric. Water Manag.* 7:207-222
Sadras and Connor (1991) *Field Crops Res.* 26:227-239
Spano et al. (2003) *J. Exp. Bot.* 54:1415-1420
Springer (2010) *Nature Genetics* 42:475-476
Srininvas et al (2009) *Theor Appl Genet* 118:703-717
Subudhi et al. (2000) *Theor Appl Genet* 101:733-741
Tao et al. (2000) *Theor Appl Genet* 100:1225-1232
Tenkouano et al. (1993) *Theor. Appl. Genet.* 85:644-648
Turner (2004) *J. Exp. Bot.* 55:2413-2425
Van Oosterom and Hammer (2008) *Field Crops Res.* 108: 259-268
Van Oosterom et al. (2010a) *Field Crops Res.* 115:19-28
Van Oosterom, et al. (2010b) *Field Crops Res.* 115:29-38
Wang eti al. (2009) *Molecular Plant* 2(4):823-831
Xin et al. (2009) *Field Crops Res.* 111:74-80
Xu et al. (2000) *Genome* 43:461-469
Zheng et al. (2009) *Plant Breed* 128:54-62

The invention claimed is:

1. A method for increasing water use efficiency in a *sorghum* plant, said method comprising:
    introducing into a sorghum plant by recombinant DNA technology a recombinant nucleic acid molecule comprising a nucleic acid sequence that encodes a *Sorghum bicolor* member of the auxin efflux carrier component 2 family (SbPIN2) protein
    wherein said nucleic acid sequence encoding the SbPIN2 protein consists essentially of a nucleic acid sequence corresponding to base pair 57449784 to base pair 57453744 of *Sorghum* Gene ID SBO3g029320 (Sb-PIN2), and
wherein expression of the nucleic acid molecule confers increased water use efficiency in the *sorghum* plant compared to a *sorghum* plant lacking the recombinant nucleic acid molecule.

2. The method of claim 1 wherein the increased water use efficiency includes enhanced canopy architecture plasticity.

3. The method of claim 1, further comprising introducing into the sorghum plant by recombinant DNA technology a recombinant nucleic acid molecule comprising a nucleic acid sequence that encodes an SbPIN, wherein said nucleic acid sequence encoding the SbPIN is selected from the group consisting of:
    (i) a nucleic acid sequence corresponding to base pair 64347327 to base pair 64350341 of *Sorghum* Gene ID Sb02g029210 (SbPIN1);
    (ii) a nucleic acid sequence corresponding to base pair 61297480 to base pair 61299969 of *Sorghum* Gene ID Sb03g032850 (SbPIN3);
    (iii) a nucleic acid sequence corresponding to base pair 65310051 to base pair 65313194 of *Sorghum* Gene ID Sb03g037350 (SbPIN4);
    (iv) a nucleic acid sequence corresponding to base pair 71204119 to base pair 71206483 of *Sorghum* Gene ID Sb03g043960 (SbPIN5);
    (v) a nucleic acid sequence corresponding to base pair 58261350 to base pair 58264959 of *Sorghum* Gene ID Sb04g028170 (SbPIN6);
    (vi) a nucleic acid sequence corresponding to base pair 2304407 to base pair 2307630 of *Sorghum* Gene ID Sb05g002150 (SbPIN7);
    (vii) a nucleic acid sequence corresponding to base pair 61560708 to base pair 61563133 of *Sorghum* Gene ID Sb07g026370 (SbPIN8);
    (viii) a nucleic acid sequence corresponding to base pair 3915101 to base pair 3917519 of *Sorghum* Gene ID Sb10g004430 (SbPIN9);
    (ix) a nucleic acid sequence corresponding to base pair 8438481 to base pair 3917519 of *Sorghum* Gene ID Sb10g008290 (SbPIN10); and
    (x) a nucleic acid sequence corresponding to base pair 55747009 to base pair 55751104 of *Sorghum* Gene ID Sb10g026300 (SbPIN11).

* * * * *